(12) United States Patent
Garcia-Echeverria et al.

(10) Patent No.: US 7,964,592 B2
(45) Date of Patent: Jun. 21, 2011

(54) 2,4-DI (PHENYLAMINO) PYRIMIDINES USEFUL IN THE TREATMENT OF NEOPLASTIC DISEASES, INFLAMMATORY AND IMMUNE SYSTEM DISORDERS

(75) Inventors: Carlos Garcia-Echeverria, Basel (CH); Takanori Kanazawa, Tsukuba (JP); Eiji Kawahara, Tsukuba (JP); Keiichi Masuya, Tsukuba (JP); Naoko Matsuura, Tsukuba (JP); Takahiro Miyake, Tsukuba (JP); Osamu Ohmori, Tsukuba (JP); Ichiro Umemura, Tsukuba (JP)

(73) Assignee: Novartis AG, Basel (CH)

( * ) Notice: Subject to any disclaimer, the term of this patent is extended or adjusted under 35 U.S.C. 154(b) by 1037 days.

(21) Appl. No.: 10/549,250

(22) PCT Filed: Mar. 12, 2004

(86) PCT No.: PCT/EP2004/002616
§ 371 (c)(1),
(2), (4) Date: May 18, 2006

(87) PCT Pub. No.: WO2004/080980
PCT Pub. Date: Sep. 23, 2004

(65) Prior Publication Data
US 2006/0247241 A1 Nov. 2, 2006

(30) Foreign Application Priority Data

Mar. 14, 2003 (GB) .................................. 0305929.2
Aug. 15, 2003 (GB) .................................. 0319227.5
Sep. 24, 2003 (GB) .................................. 0322370.8

(51) Int. Cl.
*C07D 239/48* (2006.01)
*A61K 31/506* (2006.01)

(52) U.S. Cl. .................. 514/227.5; 514/235.8; 514/249; 514/252.14; 514/275; 544/60; 544/122; 544/295; 544/323

(58) Field of Classification Search .................. 544/323, 544/60, 122, 295; 514/275, 227.5, 235.8, 514/249, 252.14
See application file for complete search history.

(56) References Cited

U.S. PATENT DOCUMENTS

| | | | |
|---|---|---|---|
| 3,361,749 A | 1/1968 | Matter et al. | |
| 3,432,493 A | 3/1969 | Short | |
| 5,958,935 A | 9/1999 | Davis et al. | |
| 6,048,866 A | 4/2000 | Hutchings et al. | |
| 6,093,716 A | 7/2000 | Davis et al. | |
| 6,114,333 A | 9/2000 | Davis et al. | |
| 6,235,746 B1 | 5/2001 | Davis | |
| 6,593,326 B1 | 7/2003 | Bradbury et al. | |
| 7,514,446 B2 | 4/2009 | Davis-Ward et al. | |
| 7,671,063 B2 | 3/2010 | Baenteli et al. | |
| 2006/0100227 A1 | 5/2006 | Baenteli et al. | |
| 2008/0132504 A1 | 6/2008 | Garcia-Echeverria et al. | |

FOREIGN PATENT DOCUMENTS

| | | |
|---|---|---|
| EP | 1 054 004 | 11/2000 |
| EP | 1 184 376 | 3/2002 |
| EP | 1184376 B1 | 2/2005 |
| WO | 97/19065 | 5/1997 |
| WO | 9841512 A1 | 9/1998 |
| WO | 99/50250 | 10/1999 |
| WO | 99/50250 A1 | 10/1999 |
| WO | 00/12485 | 3/2000 |
| WO | 00/12485 A1 | 3/2000 |
| WO | 00/39101 | 7/2000 |
| WO | 0125220 A1 | 4/2001 |
| WO | 01/60816 | 8/2001 |
| WO | 01/64654 | 9/2001 |
| WO | 01/64655 | 9/2001 |
| WO | 01/64656 | 9/2001 |
| WO | 01/65655 | 9/2001 |
| WO | 02056888 A2 | 7/2002 |
| WO | 03/018021 | 3/2003 |
| WO | 03/030909 | 4/2003 |
| WO | 03/063794 | 8/2003 |
| WO | 03/066601 | 8/2003 |
| WO | 03/066601 A1 | 8/2003 |
| WO | 03/078404 | 9/2003 |
| WO | 03/095448 | 11/2003 |
| WO | 03/095448 A1 | 11/2003 |
| WO | 2004/002964 | 1/2004 |
| WO | 2004056786 A1 | 7/2004 |
| WO | 2004/074244 | 9/2004 |
| WO | 2004/074244 A2 | 9/2004 |

(Continued)

OTHER PUBLICATIONS

Traxler, Protein Tyrosine Kinase Inhibitors in Cancer Treatment, Expert Opinion on Therapeutic Patents, 7(6):571-588, 1997.*

(Continued)

*Primary Examiner* — Deepak Rao
(74) *Attorney, Agent, or Firm* — Emily Tongco Wu; Genomics Institute of the Novartis Research Foundation

(57) ABSTRACT

Novel pyrimidine derivatives of formula I

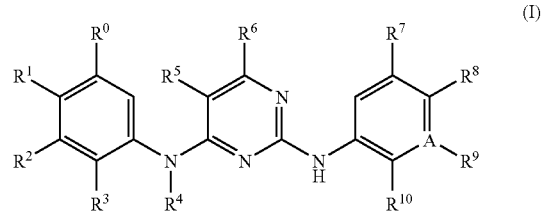

to process for their production, their use as pharmaceuticals and to pharmaceutical compositions comprising them.

17 Claims, No Drawings

FOREIGN PATENT DOCUMENTS

| | | |
|---|---|---|
| WO | 2004/080980 | 9/2004 |
| WO | 2004/080980 A1 | 9/2004 |
| WO | 2005/016894 | 2/2005 |
| WO | 2005026130 A1 | 3/2005 |
| WO | 2006068770 A1 | 6/2006 |

OTHER PUBLICATIONS

Simone, Oncology: Introduction, Cecil Textbook of Medicine, 20$^{th}$ Edition, vol. 1, pp. 1004-1010, 1996.*

Ghosh et al., "2,4-Bis(Arylamino)-5-methylpyrimidines as antimicrobial agents," Journal of Medicinal Chemistry, vol. 10, No. 5, p. 974 (1967).

Ghoneim et al., "Synthesis and evaluation of some 2-, 4- and 2,4-Di-Substituted-6-Methylpyrimidine Derivatives for Antimicrobial Activity," Journal of the Indian Chemical Society, vol. 63, No. 10, pp. 914-917 (1986).

Ghosh D., "2,4-Bis(arylamino)-6-methylpyrimidines as antimicrobial agents," Journal of the Indian Chemical Society, vol. 58, No. 5, pp. 512-513 (1981).

van Seventer et al., "Focal Adhesion Kinase Regulates B1, Integrin Dependent T Cell Migration Through an HEF1 Effector Pathway," Eur. J. Immunol. 31:1417-1427 (2001).

Wood et al., "A Novel and Potent Inhibitor of Vascular Endothelial Growth Factor Receptor Tyrosine Kinases, Impairs Vascular Endothelial Growth Factor-induced Responses and Tumor Growth after Oral Administration," Cancer Res. 60:2178-2189 (Apr. 15, 2000).

Dirks et al., "Expression and Functional Analysis of the Anaplastic Lymphoma Kinase (ALK) Gene In Tumor Cell Lines," Int. J. Cancer 100:49-56 (2002).

Traxler, Peter M., "Protein Tyrosine Kinase Inhibitors in Cancer Treatment", Expert Opinion on Therapeutic Patents, vol. 7, No. 6, pp. 571-588, 1997.

Simone et al., Oncology: Introduction, Cecil Textbook of Medicine, 20th Edition, vol. 1, pp. 1004-1010, 1997.

Basford et al., CAPLUS Abstract 41:763, pp. 7810-7812, 1947.

Coopman et al., "The Syk Tyrosine Kinase Suppresses Malignant Growth of Human Breast Cancer Cells", Nature, vol. 406, pp. 742-747, Aug. 17, 2000.

USPTO Final Office Action mailed Mar. 16, 2010, of pending U.S. Appl. No. 10/568,367 (U.S. Patent Publication No. 2008/0132504).

* cited by examiner

2,4-DI (PHENYLAMINO) PYRIMIDINES USEFUL IN THE TREATMENT OF NEOPLASTIC DISEASES, INFLAMMATORY AND IMMUNE SYSTEM DISORDERS

This application is a 371 of PCT/EP04/02616 filed Mar. 12, 2004.

The present invention relates to novel pyrimidine derivatives, to processes for their production, their use as pharmaceuticals and to pharmaceutical compositions comprising them.

More particularly the present invention provides in a first aspect, a compound of formula I

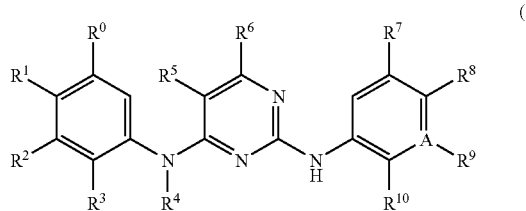

wherein
each of $R^0$, $R^1$, $R^2$, and $R^3$ independently is hydrogen, $C_1$-$C_8$alkyl, $C_2$-$C_8$alkenyl, $C_2$-$C_8$alkinyl, $C_3$-$C_8$cycloalkyl, $C_3$-$C_8$cycloalkyl$C_1$-$C_8$alkyl, $C_5$-$C_{10}$aryl$C_1$-$C_8$alkyl, hydroxy$C_1$-$C_8$alkyl, $C_1$-$C_8$alkoxy$C_1$-$C_8$alkyl, amino$C_1$-$C_8$alkyl, halo$C_1$-$C_8$alkyl, unsubstituted or substituted $C_5$-$C_{10}$aryl, unsubstituted or substituted 5 or 6 membered heterocyclyl comprising 1, 2 or 3 hetero atoms selected from N, O and S, hydroxy, $C_1$-$C_8$alkoxy, hydroxy$C_1$-$C_8$alkoxy, $C_1$-$C_8$alkoxy$C_1$-$C_8$alkoxy, halo$C_1$-$C_8$alkoxy, unsubstituted or substituted $C_5$-$C_{10}$aryl$C_1$-$C_8$alkoxy, unsubstituted or substituted heterocyclyloxy, or unsubstituted or substituted heterocyclyl$C_1$-$C_8$alkoxy, unsubstitued or substituted amino, $C_1$-$C_8$alkylthio, $C_1$-$C_8$alkylsulfinyl, $C_1$-$C_8$alkylsulfonyl, $C_5$-$C_{10}$arylsulfonyl, halogen, carboxy, $C_1$-$C_8$alkoxycarbonyl, unsubstitued or substituted carbamoyl, unsubstitued or substituted sulfamoyl, cyano or nitro;
or $R^0$ and $R^1$, $R^1$ and $R^2$, and/or $R^2$ and $R^3$ form, together with the carbon atoms to which they are attached, a 5 or 6 membered carbocyclic or heterocyclic ring comprising 0, 1, 2 or 3 heteroatoms selected from N, O and S;
$R^4$ is hydrogen or $C_1$-$C_8$alkyl;
each of $R^5$ and $R^6$ independently is hydrogen, $C_1$-$C_8$alkyl, $C_1$-$C_8$alkoxy$C_1$-$C_8$alkyl, halo$C_1$-$C_8$alkyl, $C_1$-$C_8$alkoxy, halogen, carboxy, $C_1$-$C_8$alkoxycarbonyl, unsubstitued or substituted carbamoyl, cyano, or nitro;
each of $R^7$, $R^8$, $R^9$, and $R^{10}$ independently is $C_1$-$C_8$alkyl, $C_2$-$C_8$alkenyl, $C_2$-$C_8$alkinyl, $C_3$-$C_8$cycloalkyl, $C_3$-$C_8$cycloalkyl$C_1$-$C_8$alkyl, $C_5$-$C_{10}$aryl$C_1$-$C_8$alkyl, hydroxy$C_1$-$C_8$alkyl, $C_1$-$C_8$alkoxy$C_1$-$C_8$alkyl, amino$C_1$-$C_8$alkyl, halo$C_1$-$C_8$alkyl, unsubstituted or substituted $C_5$-$C_{10}$aryl, unsubstituted or substituted 5 or 6 membered heterocyclyl comprising 1, 2 or 3 hetero atoms selected from N, O and S, hydroxy, $C_1$-$C_8$alkoxy, hydroxy$C_1$-$C_8$alkoxy, $C_1$-$C_8$alkoxy$C_1$-$C_8$alkoxy, halo$C_1$-$C_8$alkoxy, unsubstituted or substituted $C_5$-$C_{10}$aryl$C_1$-$C_8$alkoxy, unsubstituted or substituted heterocyclyloxy, or unsubstituted or substituted heterocyclyl$C_1$-$C_8$alkoxy, unsubstitued or substituted amino, $C_1$-$C_8$alkylthio, $C_1$-$C_8$alkylsulfinyl, $C_1$-$C_8$alkylsulfonyl, $C_5$-$C_{10}$arylsulfonyl, halogen, carboxy, $C_1$-$C_8$alkoxycarbonyl, unsubstitued or substituted carbamoyl, unsubstitued or substituted sulfamoyl, cyano or nitro; wherein $R^7$, $R^8$ and $R^9$ independently of each other can also be hydrogen;
or $R^7$ and $R^8$, $R^8$ and $R^9$, and/or $R^9$ and $R^{10}$ form together with the carbon atoms to which they are attached, a 5 or 6 membered carbocyclic or heterocyclic ring comprising 0, 1, 2 or 3 heteroatoms selected from N, O and S;
A is C or N, most preferably C;
and salts thereof.

The general terms used hereinbefore and hereinafter preferably have within the context of this disclosure the following meanings, unless otherwise indicated:

Where the plural form is used for compounds, salts, and the like, this is taken to mean also a single compound, salt, or the like.

Any asymmetric carbon atoms may be present in the (R)-, (S)- or (R,S)-configuration, preferably in the (R)- or (S)-configuration. The compounds may thus be present as mixtures of isomers or as pure isomers, preferably as enantiomer-pure diastereomers.

The invention relates also to possible tautomers of the compounds of formula I.

$C_1$-$C_8$alkyl denotes a an alkyl radical having from 1 up to 8, especially up to 4 carbon atoms, the radicals in question being either linear or branched with single or multiple branching; preferably, $C_1$-$C_8$alkyl is butyl, such as n-butyl, sec-butyl, isobutyl, tert-butyl, propyl, such as n-propyl or isopropyl, ethyl or methyl; especially methyl, propyl or tert-butyl.

$C_2$-$C_8$alkenyl denotes a an alkenyl radical having from 2 up to 8, especially up to 5 carbon atoms, the radicals in question being either linear or branched with single or multiple branching; preferably, $C_2$-$C_8$alkenyl is pentenyl, such as 3-methyl-2-buten-2-yl, butenyl, such as 1- or 2-butenyl or 2-buten-2-yl, propenyl, such as 1-propenyl or allyl, or vinyl.

$C_2$-$C_8$alkinyl denotes a an alkinyl radical having from 2 up to 8, especially up to 5 carbon atoms, the radicals in question being either linear or branched; preferably, $C_2$-$C_8$alkinyl is propinyl, such as 1-propinyl or propargyl, or acetylenyl.

$C_3$-$C_8$cycloalkyl denotes a cycloalkyl radical having from 3 up to 8 carbon atoms, such as cyclopropyl, cyclobutyl, cyclopentyl, cyclohexyl, cycloheptyl or cyclooctyl, preferably cyclopropyl, cyclopentyl or cyclohexyl.

$C_1$-$C_8$alkoxy is especially methoxy, ethoxy, isopropyloxy, or tert-butoxy.

Hydroxy$C_1$-$C_8$alkyl is especially hydroxymethyl, 2-hydroxyethyl or 2-hydroxy-2-propyl.

Hydroxy$C_1$-$C_8$alkoxy is especially 2-hydroxyethoxy or 3-hydroxypropoxy.

$C_1$-$C_8$alkoxy$C_1$-$C_8$alkoxy is especially 2-methoxyethoxy.

$C_1$-$C_8$alkoxy$C_1$-$C_8$alkyl is especially methoxymethyl, 2-methoxyethyl or 2-ethoxyethyl.

Halogen is preferably fluorine, chlorine, bromine, or iodine, especially fluorine, chlorine, or bromine.

Halo$C_1$-$C_8$alkyl is preferably chloro$C_1$-$C_8$alkyl or fluoro$C_1$-$C_8$alkyl, especially trifluoromethyl or pentafluoroethyl.

Halo$C_1$-$C_8$alkoxy is preferably chloro$C_1$-$C_8$alkoxy or fluoro$C_1$-$C_8$alkoxy, especially trifluoromethoxy.

$C_1$-$C_8$alkoxycarbonyl is especially tert-butoxycarbonyl, iso-propoxycarbonyl, methoxycarbonyl or ethoxycarbonyl.

Unsubstitued or substituted carbamoyl is carbamoyl substituted by one or two substituents selected from hydrogen, $C_1$-$C_8$alkyl, $C_2$-$C_8$alkenyl, $C_2$-$C_8$alkinyl, $C_3$-$C_8$cycloalkyl, $C_3$-$C_8$cycloalkyl$C_1$-$C_8$alkyl, $C_5$-$C_{10}$aryl$C_1$-$C_8$alkyl, hydroxy$C_1$-$C_8$alkyl, $C_1$-$C_8$alkoxy$C_1$-$C_8$alkyl, halo$C_1$-$C_8$alkyl, unsubstitued or substituted $C_5$-$C_{10}$aryl, or amino$C_1$-

$C_8$alkyl, or carbamoyl wherein the substituents and the nitrogen atom of the carbamoyl group represent a 5 or 6 membered heterocyclyl further comprising 0, 1 or 2 hetero atoms selected from N, O and S; and is preferably carbamoyl, methylcarbamoyl, dimethylcarbamoyl, propylcarbamoyl, hydroxyethyl-methyl-carbamoyl, di(hydroxyethyl)carbamoyl, dimethylaminoethylcarbamoyl, or pyrrolidinocarbonyl, piperidinocarbonyl, N-methylpiperazinocarbonyl or morpholinocarbonyl, especially carbamoyl or dimethylcarbamoyl.

Unsubstitued or substituted sulfamoyl is sulfamoyl substituted by one or two substituents selected from hydrogen, $C_1$-$C_8$alkyl, $C_2$-$C_8$alkenyl, $C_2$-$C_8$alkinyl, $C_3$-$C_8$cycloalkyl, $C_3$-$C_8$cycloalkyl$C_1$-$C_8$alkyl, $C_1$-$C_{10}$aryl$C_1$-$C_8$alkyl, hydroxy$C_1$-$C_8$alkyl, $C_1$-$C_8$alkoxy$C_1$-$C_8$alkyl, halo$C_1$-$C_8$alkyl, unsubstitued or substituted $C_5$-$C_{10}$aryl, or amino$C_1$-$C_8$alkyl, or sulfamoyl wherein the substituents and the nitrogen atom of the sulfamoyl group represent a 5 or 6 membered heterocyclyl further comprising 0, 1 or 2 hetero atoms selected from N, O and S; and is preferably sulfamoyl, methylsulfamoyl, propylsulfamoyl, cyclopropylmethyl-sulfamoyl, 2,2,2-trifluoroethylsulfamoyl, dimethylaminoethylsulfamoyl, dimethylsulfamoyl, hydroxyethyl-methylsulfamoyl, di(hydroxyethyl)sulfamoyl, or pyrrolidinosulfonyl, piperidinosulfonyl, N-methylpiperazinosulfonyl or morpholinosulfonyl, especially sulfamoyl or methylsulfamoyl.

Unsubstitued or substituted amino is amino substituted by one or two substituents selected from hydrogen, $C_1$-$C_8$alkyl, $C_2$-$C_8$alkenyl, $C_2$-$C_8$alkinyl, $C_3$-$C_8$cycloalkyl, $C_3$-$C_8$cycloalkyl$C_1$-$C_8$alkyl, $C_5$-$C_{10}$aryl$C_1$-$C_8$alkyl, hydroxy$C_1$-$C_8$alkyl, $C_1$-$C_8$alkoxy$C_1$-$C_8$alkyl, halo$C_1$-$C_8$alkyl, unsubstitued or substituted $C_5$-$C_{10}$aryl, amino$C_1$-$C_8$alkyl, acyl, e.g. formyl, $C_1$-$C_8$alkylcarbonyl, $C_5$-$C_{10}$arylcarbonyl, $C_1$-$C_8$alkylsulfonyl or $C_5$-$C_{10}$arylsulfonyl, and is preferably amino, methylamino, dimethylamino, propylamino, benzylamino, hydroxyethyl-methyl-amino, di(hydroxyethyl)amino, dimethylaminoethylamino, acetylamino, acetyl-methyl-amino, benzoylamino, methylsulfonylamino or phenylsulfonylamino, especially amino or dimethylamino.

Amino$C_1$-$C_8$alkyl is especially aminoethyl, methylaminoethyl, dimethylaminoethyl or dimethylaminopropyl.

Unsubstituted or substituted $C_5$-$C_{10}$aryl is, for example, phenyl, indenyl, indanyl, naphthyl, or 1,2,3,4-tetrahydronaphthalenyl, optionally substituted by $C_1$-$C_8$alkyl, $C_1$-$C_8$alkoxy$C_1$-$C_8$alkyl, halo$C_1$-$C_8$alkyl, hydroxy, $C_1$-$C_8$alkoxy, methylenedioxy, amino, substituted amino, halogen, carboxy, $C_1$-$C_8$alkoxycarbonyl, carbamoyl, sulfamoyl, cyano or nitro; preferably phenyl, tolyl, trifluoromethylphenyl, methoxyphenyl, dimethoxyphenyl, methylenedioxyphenyl, chlorophenyl or bromophenyl, whereby the substituents may be in ortho, meta or para position, preferably meta or para.

$C_5$-$C_{10}$aryloxy is especially phenoxy or methoxyphenoxy, e.g. p-methoxyphenoxy.

$C_5$-$C_{10}$aryl$C_1$-$C_8$alkyl is especially benzyl or 2-phenylethyl.

$C_5$-$C_{10}$aryl$C_1$-$C_8$alkoxy is especially benzyloxy or 2-phenylethoxy.

Unsubstitued or substituted 5 or 6 membered heterocyclyl comprising 1, 2 or 3 hetero atoms selected from N, O and S may be unsaturated, partially unsaturated or saturated, and further condensed to a benzo group or a 5 or 6 membered heterocyclyl group, and may be bound through a hetero or a carbon atom, and is, for example, pyrrolyl, indolyl, pyrrolidinyl, imidazolyl, benzimidazolyl, pyrazolyl, triazolyl, benzotriazolyl, tetrazolyl, pyridyl, quinolinyl, isoquinolinyl, 1,2,3,4-tetrahydroquinolinyl, piperidyl, pyrimidinyl, pyrazinyl, piperazinyl, purinyl, tetrazinyl, oxazolyl, isoxalyl, morpholinyl, thiazolyl, benzothiazolyl, oxadiazolyl, and benzoxadiazolyl. Substituents considered are $C_1$-$C_8$alkyl, hydroxy$C_1$-$C_8$alkyl, $C_1$-$C_8$alkoxy$C_1$-$C_8$alkyl, $C_1$-$C_8$alkoxy$C_1$-$C_8$alkoxy, halo$C_1$-$C_8$alkyl, hydroxy, amino, substituted amino, $C_1$-$C_8$alkoxy, halogen, carboxy, $C_1$-$C_8$alkylcarbonyl, $C_0$-$C_8$alkoxycarbonyl, carbamoyl, $C_1$-$C_8$alkylcarbamoyl, cyano, oxo, or unsubstitued or substituted 5 or 6 membered heterocyclyl as defined in this paragraph. 5 or 6 membered heterocyclyl preferably comprises 1 or 2 hetero atoms selected from N, O and S, and is especially indolyl, pyrrolidinyl, pyrrolidonyl, imidazolyl, N-methylimidazolyl, benzimidazolyl, S,S-dioxoisothiazolidinyl, piperidyl, 4-acetylaminopiperidyl, 4-methylcarbamoylpiperidyl, 4-piperidinopiperidyl, 4-cyanopiperidyl, piperazinyl, N-methylpiperazinyl, N-(2-hydroxyethyl)piperazinyl, morpholinyl, 1-aza-2,2-dioxo-2-thiacyclohexyl, or sulfolanyl.

In unsubstitued or substituted heterocyclyloxy, heterocyclyl has the meaning as defined above, and is especially N-methyl-4-piperidyloxy. In unsubstitued or substituted heterocyclyl$C_1$-$C_8$alkoxy, heterocyclyl has the meaning as defined above, and is especially 2-pyrrolidinoethoxy, 2-morpholinoethoxy, 3-morpholinopropoxy, 1-methyl-piperidin-3-ylmethoxy, 3-(N-methylpiperazino)propoxy or 2-(1-imidazolyl)ethoxy.

In a 5 or 6 membered carbocyclic or heterocyclic ring comprising 0, 1, 2 or 3 heteroatoms selected from N, O and S, and formed by two adjacent substituents together with the benzene ring, the ring may be further substituted, e.g. by $C_1$-$C_8$alkyl, $C_1$-$C_8$alkoxy, halo$C_1$-$C_8$alkyl, hydroxy, amino, substituted amino, $C_1$-$C_8$alkoxy, halogen, carboxy, $C_1$-$C_8$alkoxycarbonyl, carbamoyl, cyano, or oxo. The two adjacent substituents forming such a ring are preferably propylene, butylene, 1-aza-2-propylidene, 3-aza-1-propylidene, 1,2-diaza-2-propylidene, 2,3-diaza-1-propylidene, 1-oxapropylene, 1-oxapropylidene, methylenedioxy, difluoromethylenedioxy, 2-aza-1-oxopropylene, 2-aza-2-methyl-1-oxopropylene, 1-aza-2-oxopropylene, 2-aza-1,1-dioxo-1-thiapropylene or the corresponding butylene derivatives forming a 6 membered ring.

Salts are especially the pharmaceutically acceptable salts of compounds of formula I.

Such salts are formed, for example, as acid addition salts, preferably with organic or inorganic acids, from compounds of formula I with a basic nitrogen atom, especially the pharmaceutically acceptable salts. Suitable inorganic acids are, for example, halogen acids, such as hydrochloric acid, sulfuric acid, or phosphoric acid. Suitable organic acids are, for example, carboxylic, phosphonic, sulfonic or sulfamic acids, for example acetic acid, propionic acid, octanoic acid, decanoic acid, dodecanoic acid, glycolic acid, lactic acid, fumaric acid, succinic acid, adipic acid, pimelic acid, suberic acid, azelaic acid, malic acid, tartaric acid, citric acid, amino acids, such as glutamic acid or aspartic acid, maleic acid, hydroxymaleic acid, methylmaleic acid, cyclohexanecarboxylic acid, adamantanecarboxylic acid, benzoic acid, salicylic acid, 4-aminosalicylic acid, phthalic acid, phenylacetic acid, mandelic acid, cinnamic acid, methane- or ethane-sulfonic acid, 2-hydroxyethanesulfonic acid, ethane-1,2-disulfonic acid, benzenesulfonic acid, 2-naphthalenesulfonic acid, 1,5-naphthalenedisulfonic acid, 2-, 3- or 4-methylbenzenesulfonic acid, methylsulfuric acid, ethylsulfuric acid, dodecylsulfuric acid, N-cyclohexylsulfamic acid, N-methyl-, N-ethyl- or N-propyl-sulfamic acid, or other organic protonic acids, such as ascorbic acid.

For isolation or purification purposes it is also possible to use pharmaceutically unacceptable salts, for example picrates or perchlorates. For therapeutic use, only pharmaceutically acceptable salts or free compounds are employed (where applicable in the form of pharmaceutical preparations), and these are therefore preferred.

In view of the close relationship between the novel compounds in free form and those in the form of their salts, including those salts that can be used as intermediates, for example in the purification or identification of the novel compounds, any reference to the free compounds hereinbefore and hereinafter is to be understood as referring also to the corresponding salts, as appropriate and expedient.

The compounds of formula I have valuable pharmacological properties, as described hereinbefore and hereinafter.

In formula I the following significances are preferred independently, collectively or in any combination or sub-combination. In each of the following significances A is C or N preferably C:

(a) each of $R^0$ or $R^2$ independently is hydrogen, $C_1$-$C_8$alkyl, e.g. methyl, ethyl or isopropyl, hydroxy$C_1$-$C_8$alkyl, e.g. hydroxyethyl or hydroxybutyl, halo$C_1$-$C_8$alkyl, e.g. trifluoromethyl, unsubstituted or substituted $C_5$-$C_{10}$aryl, e.g. phenyl or methoxyphenyl, unsubstituted or substituted 5 or 6 membered heterocyclyl comprising 1 or 2 hetero atoms selected from N, O and S, e.g. morpholino, piperidino, piperazino or N-methylpiperazino, $C_1$-$C_8$alkoxy, e.g. methoxy, ethoxy or isopropoxy, halo$C_1$-$C_8$alkoxy, e.g. trifluoromethoxy, $C_5$-$C_{10}$aryloxy, e.g. phenoxy, unsubstituted or substituted heterocyclyloxy, e.g. 1-methyl-4-piperidyloxy, unsubstituted or substituted heterocyclyl$C_1$-$C_8$alkoxy, e.g. 2-(1-Imidazolyl)ethoxy, 3-morpholinopropoxy or 2-morpholinoethoxy, unsubstituted or substituted amino, e.g. methylamino, dimethylamino or acetylamino, $C_1$-$C_8$alkylsulfonyl, e.g. methylsulfonyl, halogen, e.g. fluoro or chloro, unsubstituted or substituted carbamoyl, e.g. cyclohexylcarbamoyl, piperidinocarbonyl, piperazinocarbonyl, N-methylpiperazinocarbonyl or morpholinocarbonyl, unsubstituted or substituted sulfamoyl, e.g. sulfamoyl, methylsulfamoyl or dimethylsulfamoyl; preferably hydrogen, piperazino, N-methylpiperazino or 1-methyl-4-piperidyloxy, in particular hydrogen;

(b) $R^1$ is hydrogen, $C_1$-$C_8$alkyl, e.g. methyl, ethyl or isopropyl, hydroxy$C_1$-$C_8$alkyl, e.g. hydroxyethyl or hydroxybutyl, halo$C_1$-$C_8$alkyl, e.g. trifluoromethyl, unsubstituted or substituted $C_5$-$C_{10}$aryl, e.g. phenyl or methoxyphenyl, unsubstituted or substituted 5 or 6 membered heterocyclyl comprising 1 or 2 hetero atoms selected from N, O and S, e.g. morpholino, piperidino, piperazino or N-methylpiperazino, $C_1$-$C_8$alkoxy, e.g. methoxy, ethoxy or isopropoxy, halo$C_1$-$C_8$alkoxy, e.g. trifluoromethoxy, $C_5$-$C_{10}$aryloxy, e.g. phenoxy, unsubstituted or substituted heterocyclyloxy, e.g. 1-methyl-4-piperidyloxy, unsubstituted or substituted heterocyclyl$C_1$-$C_8$alkoxy, e.g. 2-(1-imidazolyl)ethoxy, 3-morpholinopropoxy or 2-morpholinoethoxy, unsubstituted or substituted amino, e.g. methylamino, dimethylamino or acetylamino, $C_1$-$C_8$alkylsulfonyl, e.g. methylsulfonyl, halogen, e.g. fluoro or chloro, unsubstituted or substituted carbamoyl, e.g. cyclohexylcarbamoyl, piperidinocarbonyl, piperazinocarbonyl, N-methylpiperazinocarbonyl or morpholinocarbonyl, unsubstituted or substituted sulfamoyl, e.g. sulfamoyl, methylsulfamoyl or dimethylsulfamoyl; preferably hydrogen, piperazino, N-methylpiperazino, morpholino, 1-methyl-4-piperidinyloxy, 3-morpholinopropoxy or 2-morpholinoethoxy, in particular hydrogen;

(c) $R^3$ is hydrogen, $C_1$-$C_8$alkyl, e.g. methyl or ethyl, hydroxy$C_1$-$C_8$alkyl, e.g. hydroxyethyl or hydroxybutyl, halo$C_1$-$C_8$alkyl, e.g. trifluoromethyl, unsubstituted or substituted 5 or 6 membered heterocyclyl comprising 1 or 2 heteroatoms selected from N, O and S, e.g. 2-pyrrolidonyl or S,S-dioxoisothiazolidinyl, $C_1$-$C_8$alkoxy, e.g. methoxy, substituted amino, e.g. acetylamino, acetyl-methyl-amino, benzoylamino, methylsulfonylamino or phenylsulfonylamino, $C_1$-$C_8$alkylsulfonyl, e.g. methylsulfonyl, $C_5$-$C_{10}$arylsulfonyl, e.g. phenylsulfonyl, halogen, e.g. fluoro or chloro, carboxy, substituted or unsubstituted carbamoyl, e.g. carbamoyl, methylcarbamoyl or dimethylcarbamoyl, unsubstituted or substituted sulfamoyl, e.g. sulfamoyl, methylsulfamoyl, propylsulfamoyl, isopropylsulfamoyl, isobutylsulfamoyl, cyclopropylmethyl-sulfamoyl, 2,2,2-trifluoroethylsulfamoyl, dimethylsulfamoyl or morpholinosulfonyl; preferably sulfamoyl, methylsulfamoyl or propylsulfamoyl;

(d) each pair of adjacent substituents $R^0$ and $R^1$, or $R^1$ and $R^2$, or $R^2$ and $R^3$ are —CH$_2$—NH—O—, —CH$_2$—CH$_2$—NH—CO—, —CH$_2$—CO—NH—, —CH$_2$—CH$_2$—CO—NH—, —CH$_2$—NH—SO$_2$—, —CH$_2$—CH$_2$—NH—SO$_2$—, —CH$_2$—SO$_2$—NH—, —CH$_2$—CH$_2$SO$_2$—NH—, —CH$_2$—CH$_2$—SO$_2$—, —CH$_2$—CH$_2$—CH$_2$—SO$_2$—, —O—CH$_2$—O—, or —O—CF$_2$—O—, and such pairs wherein hydrogen in NH is replaced by $C_1$-$C_8$alkyl; preferably the pair of adjacent substituents $R^0$ and $R^1$, or $R^1$ and $R^2$ being —O—CH$_2$—O—, and the pair of adjacent substituents $R^2$ and $R^3$ being —CH$_2$—NH—CO— or —CH$_2$—NH—SO$_2$—.

(e) $R^4$ is hydrogen or $C_1$-$C_8$alkyl, e.g. methyl; preferably hydrogen;

(f) $R^5$ is hydrogen; $C_1$-$C_8$alkyl, e.g. methyl or ethyl, halogen, e.g. chloro or bromo, halo$C_1$-$C_8$alkyl, e.g. trifluoromethyl, cyano or nitro; preferably hydrogen, methyl, ethyl, chloro, bromo, trifluoromethyl or nitro; in particular chloro or bromo;

(g) $R^6$ is hydrogen;

(h) each of $R^7$ and $R^9$ independently is hydrogen, $C_1$-$C_8$alkyl, e.g. methyl, ethyl or isopropyl, hydroxy$C_1$-$C_8$alkyl, e.g. hydroxyethyl or hydroxybutyl, halo$C_1$-$C_8$alkyl, e.g. trifluoromethyl, unsubstituted or substituted $C_5$-$C_{10}$aryl, e.g. phenyl or methoxyphenyl, unsubstituted or substituted 5 or 6 membered heterocyclyl comprising 1 or 2 hetero atoms selected from N, O and S, e.g. morpholino, piperidino, piperazino or N-methylpiperazino, $C_1$-$C_8$alkoxy, e.g. methoxy, ethoxy or isopropoxy, halo$C_1$-$C_8$alkoxy, e.g. trifluoromethoxy, $C_5$-$C_{10}$aryloxy, e.g. phenoxy, unsubstituted or substituted heterocyclyloxy, e.g. 1-methyl-4-piperidyloxy, unsubstituted or substituted heterocyclyl$C_1$-$C_8$alkoxy, e.g. 2-(1-imidazolyl)ethoxy, 3-morpholinopropoxy or 2-morpholinoethoxy, unsubstituted or substituted amino, e.g. methylamino, dimethylamino or acetylamino, $C_1$-$C_8$alkylsulfonyl, e.g. methylsulfonyl, halogen, e.g. fluoro or chloro, unsubstituted or substituted carbamoyl, e.g. cyclohexylcarbamoyl, piperidinocarbonyl, piperazinocarbonyl, N-methylpiperazinocarbonyl or morpholinocarbonyl, unsubstituted or substituted sulfamoyl, e.g. sulfamoyl, methylsulfamoyl or dimethylsulfamoyl; preferably hydrogen, methyl, isopropyl, trifluoromethyl, phenyl, methoxyphenyl, piperidino, piperazino, N-methylpiperazino, morpholino, methoxy, ethoxy, isopropoxy, phenoxy, 3-morpholinopropoxy, 2-morpholinoethoxy, 2-(1-imidazolyl)ethoxy, dimethylamino, fluoro, morpholinocarbonyl, piperidinocarbonyl, piperazinocarbonyl or cyclohexylcarbamoyl;

(i) $R^8$ is hydrogen, $C_1$-$C_8$alkyl, e.g. methyl, ethyl or isopropyl, hydroxy$C_1$-$C_8$alkyl, e.g. hydroxyethyl or hydroxybutyl, halo$C_1$-$C_8$alkyl, e.g. trifluoromethyl, $C_5$-$C_{10}$aryl, e.g. phenyl or methoxyphenyl, unsubstituted or substituted 5 or 6 membered heterocyclyl comprising 1 or 2 hetero atoms selected from N, O and S, e.g. morpholino, piperidino, piperazino or N-methylpiperazino, $C_1$-$C_8$alkoxy, e.g. methoxy, ethoxy or isopropoxy, halo$C_1$-$C_8$alkoxy, e.g. trifluoromethoxy, $C_5$-$C_{10}$aryloxy, e.g. phenoxy, unsubstituted or substituted heterocyclyloxy, e.g. 1-methyl-4-piperidyloxy, unsubstituted or substituted heterocyclyl$C_1$-$C_8$alkoxy, e.g. 2-(1-imidazolyl)ethoxy, 3-morpholinopropoxy or 2-morpholinoethoxy, unsubstituted or substituted amino, e.g. methylamino or dimethylamino, $C_1$-$C_8$alkylsulfonyl, e.g. methylsulfonyl, halogen, e.g. fluoro or chloro, unsubstituted or substituted carbamoyl, e.g. cyclohexylcarbamoyl, piperidinocarbonyl, piperazinocarbonyl, N-methylpiperazinocarbonyl or morpholinocarbonyl, unsubstituted or substituted sulfamoyl, e.g. sulfamoyl, methylsulfamoyl or dimethylsulfamoyl, cyano, or nitro; preferably hydrogen, methyl, piperidino, piperazino, N-methylpiperazino, morpholino, methoxy, ethoxy, trifluoromethoxy, phenoxy, 1-methyl piperidyloxy, 3-morpholinopropoxy, 2-morpholinoethoxy, 3-(N-methylpiperazino)-propoxy, methylamino, fluoro, chloro, sulfamoyl or nitro;

(j) $R^{10}$ is $C_1$-$C_8$alkyl, e.g. methyl, ethyl or butyl, hydroxy$C_1$-$C_8$alkyl, e.g. hydroxyethyl or hydroxybutyl, halo$C_1$-$C_8$alkyl, e.g. trifluoromethyl, $C_1$-$C_8$alkoxy, e.g. methoxy or ethoxy, unsubstituted or substituted heterocyclyl$C_1$-$C_8$alkoxy, e.g. 2-(1-imidazolyl)ethoxy, unsubstituted or substituted amino, e.g. methylamino or dimethylamino, halogen, e.g. fluoro or chloro; carboxy, carbamoyl, or unsubstituted or substituted sulfamoyl, e.g. sulfamoyl, methylsulfamoyl or dimethylsulfamoyl; preferably methyl, butyl, methoxy, ethoxy, 2-(1-imidazolyl)ethoxy, methylamino, dimethylamino or fluoro; and (k) each pair of adjacent substituents $R^7$ and $R^8$, or $R^8$ and $R^9$ or $R^9$ and $R^{10}$, are —NH—CH=CH—, —CH=CH—NH—, —NH—N=CH—, —CH=N—NH—, —CH$_2$—CH$_2$—CH$_2$—, —CH$_2$—CH$_2$—CH$_2$—CH$_2$—, —CH$_2$—CH$_2$—O—, —CH=CH—O—, —O—CH$_2$—O—, or —O—CF$_2$—O—; preferably the pair of adjacent substituents $R^7$ and $R^8$ or $R^8$ and $R^9$ being —O—CH$_2$—O— or the pair of adjacent substituents $R^9$ and $R^{10}$ being —NH—CH=CH—, —CH=N—NH—, —CH$_2$—CH$_2$—CH$_2$—, —CH$_2$—CH$_2$—CH$_2$—CH$_2$— or —O—CF$_2$—O—.

More preferred are the following meanings, independently, collectively or in any combination or sub-combination:

(a') each of $R^0$ or $R^2$ independently is hydrogen, $C_1$-$C_8$alkyl, e.g. methyl, ethyl or isopropyl, halo$C_1$-$C_8$alkyl, e.g. trifluoromethyl, unsubstituted or substituted 5 or 6 membered heterocyclyl comprising 1 or 2 hetero atoms selected from N, O and S, e.g. morpholino, piperidino, piperazino or N-methylpiperazino, $C_1$-$C_8$alkoxy, e.g. methoxy, ethoxy or isopropoxy, unsubstituted or substituted heterocyclyloxy, e.g. 1-methyl-4-piperidyloxy, unsubstituted or substituted heterocyclyl$C_1$-$C_8$alkoxy, e.g. 2-(1-imidazolyl)ethoxy, 3-morpholinopropoxy or 2-morpholinoethoxy, unsubstituted or substituted amino, e.g. methylamino, dimethylamino or acetylamino, halogen, e.g. fluoro or chloro; preferably hydrogen, piperazino, N-methylpiperazino or 1-methyl-4-piperidyloxy, in particular hydrogen;

(b') $R^1$ is hydrogen, $C_1$-$C_8$alkyl, e.g. methyl, ethyl or isopropyl, halo$C_1$-$C_8$alkyl, e.g. trifluoromethyl, unsubstituted or substituted 5 or 6 membered heterocyclyl comprising 1 or 2 hetero atoms selected from N, O and S, e.g. morpholino, piperidino, piperazino or N-methylpiperazino, $C_1$-$C_8$alkoxy, e.g. methoxy, ethoxy or isopropoxy, unsubstituted or substituted heterocyclyloxy, e.g. 1-methyl-4-piperidyloxy, unsubstituted or substituted heterocyclyl$C_1$-$C_8$alkoxy, e.g. 2-(1-imidazolyl)ethoxy, 3-morpholinopropoxy or 2-morpholinoethoxy, unsubstituted or substituted amino, e.g. methylamino, dimethylamino or acetylamino, halogen, e.g. fluoro or chloro; preferably hydrogen, piperazino, N-methylpiperazino, morpholino, 1-methyl-4-piperidinyloxy, 3-morpholinopropoxy or 2-morpholinoethoxy, in particular hydrogen;

(c') $R^3$ is hydrogen, $C_1$-$C_8$alkyl, e.g. methyl or ethyl, halo$C_1$-$C_8$alkyl, e.g. trifluoromethyl, unsubstituted or substituted 5 or 6 membered heterocyclyl comprising 1 or 2 heteroatoms selected from N, O and S, e.g. 2-pyrrolidonyl or S,S-dioxoisothiazolidinyl, $C_1$-$C_8$alkoxy, e.g. methoxy, substituted amino, e.g. acetylamino, acetyl-methyl-amino, benzoylamino, methylsulfonylamino or phenylsulfonylamino, $C_1$-$C_8$alkylsulfonyl, e.g. methylsulfonyl, $C_5$-$C_{10}$arylsulfonyl, e.g. phenylsulfonyl, halogen, e.g. fluoro or chloro, carboxy, substituted or unsubstituted carbamoyl, e.g. carbamoyl, methylcarbamoyl or dimethylcarbamoyl, unsubstituted or substituted sulfamoyl, e.g. sulfamoyl, methylsulfamoyl, propylsulfamoyl, isopropylsulfamoyl, isobutylsulfamoyl, cyclopropylmethyl-sulfamoyl, 2,2,2-trifluoroethylsulfamoyl, dimethylsulfamoyl or morpholinosulfamoyl; preferably sulfamoyl, methylsulfamoyl or propylsulfamoyl;

(d') each pair of adjacent substituents $R^0$ and $R^1$, or $R^1$ and $R^2$, or $R^2$ and $R^3$ are —CH$_2$—NH—CO—, —CH$_2$—NH—SO$_2$—, —CH$_2$CH$_2$—SO$_2$—, —O—CH$_2$—O—, or —O—CF$_2$—O—, and such pairs wherein hydrogen in NH is replaced by $C_1$-$C_8$alkyl; preferably the pair of adjacent substituents $R^0$ and $R^1$, or $R^1$ and $R^2$ being —O—CH$_2$—O—, and the pair of adjacent substituents $R^2$ and $R^3$ being —CH$_2$—NH—CO— or —CH$_2$—NH—SO$_2$—.

(e') $R^4$ is hydrogen;

(f') $R^5$ is hydrogen, halogen, e.g. chloro or bromo, halo$C_1$-$C_8$alkyl, e.g. trifluoromethyl, or nitro; preferably hydrogen, chloro, bromo, trifluoromethyl or nitro; in particular chloro or bromo;

(g') $R^6$ is hydrogen;

(h') each of $R^7$ and $R^9$ independently is hydrogen, $C_1$-$C_8$alkyl, e.g. methyl, ethyl or isopropyl, halo$C_1$-$C_8$alkyl, e.g. trifluoromethyl, unsubstituted or substituted $C_5$-$C_{10}$aryl, e.g. phenyl or methoxyphenyl, unsubstituted or substituted 5 or 6 membered heterocyclyl comprising 1 or 2 hetero atoms selected from N, O and S, e.g. morpholino, piperidino, piperazino or N-methylpiperazino, $C_1$-$C_8$alkoxy, e.g. methoxy, ethoxy or isopropoxy, unsubstituted or substituted heterocyclyloxy, e.g. 1-methyl-4-piperidyloxy, unsubstituted or substituted heterocyclyl$C_1$-$C_8$alkoxy, e.g. 2-(1-imidazolyl)ethoxy, 3-morpholinopropoxy or 2-morpholinoethoxy, unsubstituted or substituted amino, e.g. methylamino, dimethylamino or acetylamino, halogen, e.g. fluoro or chloro, unsubstituted or substituted carbamoyl, e.g. cyclohexylcarbamoyl, piperidinocarbonyl, piperazinocarbonyl, N-methylpiperazinocarbonyl or morpholinocarbonyl, unsubstituted or substituted sulfamoyl, e.g. sulfamoyl, methylsulfamoyl or dimethylsulfamoyl; preferably hydrogen, methyl, isopropyl, trifluoromethyl, phenyl, o-, m- or p-methoxyphenyl, piperidino, piperazino, N-methylpiperazino, morpholino, methoxy, ethoxy, isopropoxy, phenoxy, 3 morpholinopropoxy, 2-morpholinoethoxy, 2-(1-imidazolyl)ethoxy, dimethylamino, fluoro, morpholinocarbonyl, piperidinocarbonyl, piperazinocarbonyl or cyclohexylcarbamoyl;

(i') R$^8$ is hydrogen, C$_1$-C$_8$alkyl, e.g. methyl, ethyl or isopropyl, haloC$_1$-C$_8$alkyl, e.g. trifluoromethyl, C$_5$-C$_{10}$aryl, e.g. phenyl or methoxyphenyl, unsubstituted or substituted 5 or 6 membered heterocyclyl comprising 1 or 2 hetero atoms selected from N, O and S, e.g. morpholino, piperidino, piperazino or N-methylpiperazino, C$_1$-C$_8$alkoxy, e.g. methoxy, ethoxy or isopropoxy, haloC$_1$-C$_8$alkoxy, e.g. trifluoromethoxy, C$_5$-C$_{10}$aryloxy, e.g. phenoxy, unsubstituted or substituted heterocyclyloxy, e.g. 1-methyl-4-piperidyloxy, unsubstituted or substituted heterocyclylC$_1$-C$_8$alkoxy, e.g. 2-(1-imidazolyl)ethoxy, 3-morpholinopropoxy or 2-morpholinoethoxy, unsubstituted or substituted amino, e.g. methylamino or dimethylamino, halogen, e.g. fluoro or chloro, unsubstituted or substituted sulfamoyl, e.g. sulfamoyl, methylsulfamoyl or dimethylsulfamoyl, or nitro; preferably hydrogen, methyl, piperidino, piperazino, N-methylpiperazino, morpholino, methoxy, ethoxy, trifluoromethoxy, phenoxy, 1-methyl-4-piperidyloxy, 3-morpholinopropoxy, 2-morpholinoethoxy, 3-(N-methylpiperazino)-propoxy, methylamino, fluoro, chloro, sulfamoyl or nitro;

(j') R$^{10}$ is C$_1$-C$_8$alkyl, e.g. methyl, ethyl or butyl, haloC$_1$-C$_8$alkyl, e.g. trifluoromethyl, C$_1$-C$_8$alkoxy, e.g. methoxy or ethoxy, unsubstituted or substituted heterocyclylC$_1$-C$_8$alkoxy, e.g. 2-(1-imidazolyl)ethoxy, unsubstituted or substituted amino, e.g. methylamino or dimethylamino, halogen, e.g. fluoro or chloro; preferably methyl, butyl, methoxy, ethoxy, 2-(1-imidazolyl)ethoxy, methylamino, dimethylamino or fluoro; and (k') each pair of adjacent substituents R$^7$ and R$^8$, or R$^8$ and R$^9$ or R$^9$ and R$^{10}$, are —NH—CH=CH—, —CH=CH—NH—, —NH—N=CH—, —CH=N—NH—, —CH$_2$—CH$_2$—CH$_2$—, —CH$_2$—CH$_2$—CH$_2$CH$_2$—, —O—CH$_2$—O—, or —O—CF$_2$—O—; preferably the pair of adjacent substituents R$^7$ and R$^8$ or R$^8$ and R$^9$ being —O—CH$_2$—O— or the pair of adjacent substituents R$^9$ and R$^{10}$ being —NH—CH=CH—, —CH=N—NH—, —CH$_2$—CH$_2$—CH$_2$—, —CH$_2$—CH$_2$—CH$_2$—CH$_2$— or —O—CF$_2$—O—.

Most preferred as compounds of the formula I are those wherein the substituents have the meaning given in the Examples.

The present invention also provides a process for the production of a compound of formula I, comprising reacting a compound of formula II

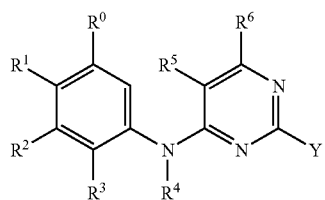

(II)

wherein R$^0$, R$^1$, R$^2$, R$^3$, R$^4$, R$^5$, and R$^6$ are as defined above, and Y is a leaving group, preferably halogen such as bromide, iodine, or in particular chloride;

with a compound of formula III

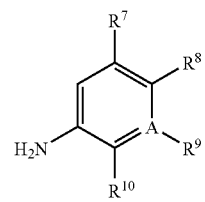

(III)

wherein R$^7$, R$^8$, R$^9$ and R$^{10}$ are as defined above;
and, if desired, converting a compound of formula I, wherein the substituents have the meaning as defined above, into another compound of formula I as defined;
and recovering the resulting compound of formula I in free from or as a salt, and, when required, converting the compound of formula I obtained in free form into the desired salt, or an obtained salt into the free form.

The reaction can be carried out in a manner known per se, the reaction conditions being dependent especially on the reactivity of the leaving group Y and the reactivity of the amino group in the aniline of formula III, usually in the presence of a suitable solvent or diluent or of a mixture thereof and, if necessary, in the presence of an acid or a base, with cooling or, preferably, with heating, for example in a temperature range from approximately −30° C. to approximately +150° C., especially approximately from 0° C. to +100° C., preferably from room temperature (approx. +20° C.) to +80° C., in an open or closed reaction vessel and/or in the atmosphere of an inert gas, for example nitrogen.

If one or more other functional groups, for example carboxy, hydroxy or amino, are or need to be protected in a compound of formula II or III, because they should not take part in the reaction, these are such groups as are usually used in the synthesis of peptide compounds, cephalosporins and penicillins, as well as nucleic acid derivatives and sugars.

The protecting groups may already be present in precursors and should protect the functional groups concerned against unwanted secondary reactions, such as substitution reaction or solvolysis. It is a characteristic of protecting groups that they lend themselves readily, i.e. without undesired secondary reactions, to removal, typically by solvolysis, reduction, photolysis or also by enzyme activity, for example under conditions analogous to physiological conditions, and that they are not present in the end-products. The specialist knows, or can easily establish, which protecting groups are suitable with the reactions mentioned hereinabove.

Salts of a compound of formula I with a salt-forming group may be prepared in a manner known per se. Acid addition salts of compounds of formula I may thus be obtained by treatment with an acid or with a suitable anion exchange reagent.

Salts can usually be converted to compounds in free form, e.g. by treating with suitable basic agents, for example with alkali metal carbonates, alkali metal hydrogencarbonates, or alkali metal hydroxides, typically potassium carbonate or sodium hydroxide.

Stereoisomeric mixtures, e.g. mixtures of diastereomers, can be separated into their corresponding isomers in a manner known per se by means of suitable separation methods. Diastereomeric mixtures for example may be separated into their individual diastereomers by means of fractionated crystallization, chromatography, solvent distribution, and similar procedures. This separation may take place either at the level of a starting compound or in a compound of formula I itself. Enantiomers may be separated through the formation of diastereomeric salts, for example by salt formation with an enantiomer-pure chiral acid, or by means of chromatography, for example by HPLC, using chromatographic substrates with chiral ligands.

It should be emphasized that reactions analogous to the conversions mentioned in this chapter may also take place at the level of appropriate intermediates.

The compounds of formula I, including their salts, are also obtainable in the form of hydrates, or their crystals can include for example the solvent used for crystallization (present as solvates).

The compound of formula II used as starting materials may be obtained by reacting a compound of formula IV

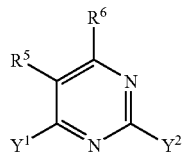

(IV)

with a compound of formula V

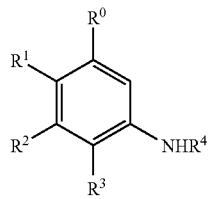

(V)

wherein $R^1$, $R^2$, $R^3$, $R^4$, $R^5$ and $R^6$ are as defined above, and $Y^1$ and $Y^2$ are identical or different leaving groups as defined above for Y. The reaction conditions are those mentioned above for the reaction of a compound of formula II with a compound of formula III.

The compounds of formula IV and V are known or may be produced in accordance with known procedures.

The compounds of formula I and their pharmaceutically acceptable salts exhibit valuable pharmacological properties when tested in vitro in cell-free kinase assays and in cellular assays, and are therefore useful as pharmaceuticals. In particular, the compounds of the invention are inhibitors of Focal Adhesion Kinase, and are useful as pharmaceuticals to treat conditions caused by a malfunction of signal cascades connected with Focal Adhesion Kinase, in particular tumors as described hereinbelow.

Focal Adhesion Kinase (FAK) is a key enzyme in the integrin-mediated outside-in signal cascade (D. Schlaepfer et al., Prog Biophys Mol Biol 1999, 71, 435-478). Interaction between cells and extracellular matrix (ECM) proteins is transduced as intracellular signals important for growth, survival and migration through cell surface receptors, integrins. FAK plays an essential role in these integrin-mediated outside-in signal cascades. The trigger in the signal transduction cascade is the autophosphorylation of Y397. Phosphorylated Y397 is a SH2 docking site for Src family tyrosine kinases. The bound c-Src kinase phosphorylates other tyrosine residues in FAK. Among them, phsophorylated Y925 becomes a binding site for the SH2 site of Grb2 small adaptor protein. This direct binding of Grb2 to FAK is one of the key steps for the activation of down stream targets such as the Ras-ERK2/MAP kinase cascade.

The inhibition of endogenous FAK signalling results in reduced motility and in some cases induces cell death. On the other hand, enhancing FAK signalling by exogenous expression increases cell motility and transmitting a cell survival signal from ECM. In addition FAK is overexpressed in invasive and metastatic epithelial, mesenchymal, thyroid and prostate cancers. Consequently, an inhibitor of FAK is likely to be a drug for anti-tumor growth and metastasis. The compounds of the invention are thus indicated, for example, to prevent and/or treat a vertebrate and more particularly a mammal, affected by a neoplastic disease, in particular breast tumor, cancer of the bowel (colon and rectum), stomach cancer and cancer of the ovary and prostate, non-small cell lung cancer, small cell lung cancer, cancer of liver, melanoma, bladder tumor and cancer of head and neck.

The relation between FAK inhibition and immuno-system is described e.g. in G. A. van Seventer et al., Eur. J. Immunol. 2001, 31, 1417-1427. Therefore, the compounds of the invention are, for example, useful to prevent and/or treat a vertebrate and more particularly a mammal, affected by immune system disorders, diseases or disorders mediated by T lymphocytes, B lymphocytes, mast cells and/or eosinophils e.g. acute or chronic rejection of organ or tissue allo- or xenografts, atherosclerosis, vascular occlusion due to vascular injury such as angioplasty, restenosis, hypertension, heart failure, chronic obstructive pulmonary disease, CNS disease such as Alzheimer disease or amyotrophic lateral sclerosis, cancer, infectious disease such as AIDS, septic shock or adult respiratory distress syndrome, ischemia/reperfusion injury e.g. myocardial infarction, stroke, gut ischemia, renal failure or hemorrhage shock, or traumatic shock. The agent of the invention are also useful in the treatment and/or prevention of acute or chronic inflammatory diseases or disorders or autoimmune diseases e.g. rheumatoid arthritis, osteoarthritis, systemic lupus erythematosus, Hashimoto's thyroiditis, multiple sclerosis, myasthenia gravis, diabetes (type I and II) and the disorders associated with therewith, respiratory diseases such as asthma or inflammatory liver injury, inflammatory glomerular injury, cutaneous manifestations of immunologically-mediated disorders or illnesses, inflammatory and hyperproliferative skin diseases (such as psoriasis, atopic dermatitis, allergic contact dermatitis, irritant contact dermatitis and further eczematous dermatitises, seborrhoeic dermatitis), inflammatory eye diseases, e.g. Sjoegren's syndrome, keratoconjunctivitis or uveitis, inflammatory bowel disease, Crohn's disease or ulcerative colitis.

Compounds of the invention are active in a FAK assay system as described in the Examples, and show an inhibition $IC_{50}$ in the range of 1 nM to 100 nM. Particularly active are the compounds Example No. 3-12 and No. 3-17 described hereinbelow showing $IC_{50}$ vales in the range of 1 to 5 nM.

Some of the compounds of the invention exhibit also ZAP-70 (zeta chain-associated protein of 70 kD) protein tyrosine kinase inhibiting activity. ZAP-70 protein tyrosine kinase interaction of the agents of the invention may be demonstrated by their ability to prevent phosphorylation of e.g. LAT-11 (linker for activation of T cell) by human ZAP-70 protein tyrosine kinase in aqueous solution, as described in the Examples. The compounds of the invention are thus also indicated for the prevention or treatment of disorders or diseases where ZAP-70 inhibition inhibition play a role.

Compounds of the invention are active in a ZAP-70 assay system as described in the Examples, and show an inhibition $IC_{50}$ in the range of 1 μM to 10 μM, e.g. the compounds Example No. 2 and No. 3-2 described hereinbelow.

Compounds of the present invention are also good inhibitors of the IGF-IR (insulin like growth factor receptor 1) and are therefore useful in the treatment of IGF-1R mediated diseases for example such diseases include proliferative diseases, such as tumours, like for example breast, renal, prostate, colorectal, thyroid, ovarian, pancreas, neuronal, lung, uterine and gastrointestinal tumours as well as osteosarcomas and melanomas. The efficacy of the compounds of the invention as inhibitors of IGF-IR tyrosine kinase activity can be demonstrated using a cellular "Capture ELISA". In this assay the activity of the compounds of the invention against Insulin-like growth factor I (IGF-I) induced autophosphorylation of the IGF-IR is determined.

The compounds of the present invention also exhibit powerful inhibition of the tyrosine kinase activity of anaplastic lymphoma kinase (ALK) and the fusion protein of NPM-ALK. This protein tyrosine kinase results from a gene fusion of nucleophosmin (NPM) and the anaplastic lymphoma kinase (ALK), rendering the protein tyrosine kinase activity of ALK ligand-independent. NPM-ALK plays a key role in signal transmission in a number of hematopoetic and other human cells leading to hematological and neoplastic diseases, for example in anaplastic large-cell lymphoma (ALCL) and non-Hodgkin's lymphomas (NHL), specifically in ALK+NHL or Alkomas, in inflammatory myofibroblastic tumors (IMT) and neuroblastomas. (Duyster J et al. 2001 Oncogene 20, 5623-5637). In addition to NPM-ALK, other gene fusions have been identified in human hematological and neoplastic diseases; mainly TPM3-ALK (a fusion of nonmuscle tropomyosin with ALK).

The inhibition of ALK tyrosine kinase activity can be demonstrated using known methods, for example using the recombinant kinase domain of the ALK in analogy to the VEGF-R kinase assay described in J. Wood et al. Cancer Res. 60, 2178-2189 (2000). In vitro enzyme assays using GST-ALK protein tyrosine kinase are performed in 96-well plates as a filter binding assay in 20 mM Tris.HCl, pH=7.5, 3 mM $MgCl_2$, 10 mM $MnCl_2$, 1 mM DTT, 0.1 µCi/assay (=30 µl) [$\gamma$-$^{33}$P]-ATP, 2 µM ATP, 3 µg/ml poly (Glu, Tyr 4:1) Poly-EY (Sigma P-0275), 1% DMSO, 25 ng ALK enzyme. Assays are incubated for 10 min at ambient temperature. Reactions are terminated by adding 50 µl of 125 mM EDTA, and the reaction mixture is transferred onto a MAIP Multiscreen plate (Millipore, Bedford, Mass., USA), previously wet with methanol, and rehydrated for 5 min with $H_2O$. Following washing (0.5% $H_3PO_4$), plates are counted in a liquid scintillation counter. $IC_{50}$ values are calculated by linear regression analysis of the percentage inhibition. Compared with the control without inhibitor, the compounds of formula I inhibit the enzyme activity by 50% ($IC_{50}$), for example in a concentration of from 0.001 to 0.5 µM, especially from 0.01 to 0.1 µM.

The compounds of formula I potently inhibit the growth of human NPM-ALK overexpressing murine BaF3 cells (DSMZ Deutsche Sammlung von Mikroorganismen und Zellkulturen GmbH, Braunschweig, Germany). The expression of NPM-ALK is achieved by transfecting the BaF3 cell line with an expression vector pCIneo™ (Promega Corp., Madison Wis., USA) coding for NPM-ALK and subsequent selection of G418 resistant cells. Non-transfected BaF3 cells depend on IL-3 for cell survival. In contrast NPM-ALK expressing BaF3 cells (named BaF3-NPM-ALK hereinafter) can proliferate in the absence of IL-3 because they obtain proliferative signal through NPM-ALK kinase. Putative inhibitors of the NPM-ALK kinase therefore abolish the growth signal and result in antiproliferative activity. The antiproliferative activity of putative inhibitors of the NPM-ALK kinase can however be overcome by addition of IL-3 which provides growth signals through an NPM-ALK independent mechanism. [For an analogous cell system using FLT3 kinase see E Weisberg et al. Cancer Cell; 1, 433-443 (2002)]. The inhibitory activity of the compounds of formula I is determined, briefly, as follows: BaF3-NPM-ALK cells (15,000/microtitre plate well) are transferred to 96-well microtitre plates. The test compounds [dissolved in dimethyl sulfoxide (DMSO)] are added in a series of concentrations (dilution series) in such a manner that the final concentration of DMSO is not greater than 1% (v/v). After the addition, the plates are incubated for two days during which the control cultures without test compound are able to undergo two cell-division cycles. The growth of the BaF3-NPM-ALK cells is measured by means of Yopro™ staining [T Idziorek et al. J. Immunol. Methods; 185: 249-258 (1995)]: 25 µl of lysis buffer consisting of 20 mM sodium citrate, pH 4.0, 26.8 mM sodium chloride, 0.4% NP40, 20 mM EDTA and 20 mM is added to each well. Cell lysis is completed within 60 min at room temperature and total amount of Yopro bound to DNA is determined by measurement using the Cytofluor II 96-well reader (PerSeptive Biosystems) with the following settings: Excitation (nm) 485/20 and Emission (nm) 530/25.

$IC_{50}$ values are determined by a computer-aided system using the formula:

$$IC_{50}=[(ABS_{test}-ABS_{start})/(ABS_{control}-ABS_{start})]\times 100.$$
(ABS=absorption)

The $IC_{50}$ value in those experiments is given as that concentration of the test compound in question that results in a cell count that is 50% lower than that obtained using the control without inhibitor. The compounds of formula I exhibit inhibitory activity with an $IC_{50}$ in the range from approximately 0.01 to 1 µM.

The antiproliferative action of the compounds of formula I can also be determined in the human KARPAS-299 lymphoma cell line (DSMZ Deutsche Sammlung von Mikroorganismen und Zellkulturen GmbH, Braunschweig, Germany) [described in W G Dirks et al. Int. J. Cancer 100, 49-56 (2002)] using the same methodology described above for the BaF3-NPM-ALK cell line. The compounds of formula I exhibit inhibitory activity with an $IC_{50}$ in the range from approximately 0.01 to 1 µM.

The action of the compounds of formula I on autophosphorylation of the ALK can be determined in the human KARPAS-299 lymphoma cell line by means of an immunoblot as described in W G Dirks et al. Int. J. Cancer 100, 49-56 (2002). In that test the compounds of formula I exhibit an $IC_{50}$ of approximately from 0.001 to 1 µM.

Among the compounds of formula I, 2-[5-chloro-2-(2-methoxy-4-morpholin-4-yl-phenylamino)-pyrimidin-4-ylamino]-N-methyl-benzamide is an especially potent ALK inhibitor, in that this compound inhibits the growth of the BaF3-NPM-ALK cells with an $IC_{50}$ of 97 nM. Further specifically preferred compounds that inhibit the tyrosine kinase activity of anaplastic lymphoma kinase (ALK) are the compounds described hereinafter in the examples 7A and 7B, as well as 7-2, 7-15, 7-36, 7-39, 7-44 and 7-52, respectively, all of which are having an $IC_{50}$ within the range from <0.5 to 200 nM.

For the above uses in the treatment of neoplastic diseases and immune system disorders the required dosage will of course vary depending on the mode of administration, the particular condition to be treated and the effect desired. In general, satisfactory results are indicated to be obtained systemically at daily dosages of from about 0.1 to about 100 mg/kg body weight. An indicated daily dosage in the larger mammal, e.g. humans, is in the range from about 0.5 mg to about 2000 mg, conveniently administered, for example, in divided doses up to four times a day or in retard form.

The compounds of the invention may be administered by any conventional route, in particular parenterally, for example in the form of injectable solutions or suspensions, enterally, preferably orally, for example in the form of tablets or capsules, topically, e.g. in the form of lotions, gels, ointments or creams, or in a nasal or a suppository form. Pharmaceutical compositions comprising a compound of the invention in association with at least one pharmaceutical acceptable carrier or diluent may be manufactured in conventional manner by mixing with a pharmaceutically acceptable carrier or diluent. Unit dosage forms for oral administration contain, for example, from about 0.1 mg to about 500 mg of active substance. Topical administration is e.g. to the skin. A further form of topical administration is to the eye.

The pharmaceutical compositions of the present invention are prepared in a manner known per se, for example by means of conventional mixing, granulating, coating, dissolving or lyophilizing processes.

Preference is given to the use of solutions of the active ingredient, and also suspensions or dispersions, especially isotonic aqueous solutions, dispersions or suspensions which, for example in the case of lyophilized compositions comprising the active ingredient alone or together with a carrier, for example mannitol, can be made up before use. The pharmaceutical compositions may be sterilized and/or may comprise excipients, for example preservatives, stabilizers, wetting agents and/or emulsifiers, solubilizers, salts for regulating osmotic pressure and/or buffers and are prepared in a manner known per se, for example by means of conventional dissolving and lyophilizing processes. The said solutions or suspensions may comprise viscosity-increasing agents, typically sodium carboxymethylcellulose, carboxymethylcellulose, dextran, polyvinylpyrrolidone, or gelatins, or also solubilizers, e.g. Tween 80® (polyoxyethylene(20)sorbitan mono-oleate).

Suspensions in oil comprise as the oil component the vegetable, synthetic, or semisynthetic oils customary for injection purposes. In respect of such, special mention may be made of liquid fatty acid esters that contain as the acid component a long-chained fatty acid having from 8 to 22, especially from 12 to 22, carbon atoms, for example lauric acid, tridecylic acid, myristic acid, pentadecylic acid, palmitic acid, margaric acid, stearic acid, arachidic acid, behenic acid or corresponding unsaturated acids, for example oleic acid, elaidic acid, erucic acid, brassidic acid or linoleic acid, if desired with the addition of antioxidants, for example vitamin E, β-carotene or 3,5-di-tert-butyl-4-hydroxytoluene. The alcohol component of these fatty acid esters has a maximum of 6 carbon atoms and is a monovalent or polyvalent, for example a mono-, di- or trivalent, alcohol, for example methanol, ethanol, propanol, butanol or pentanol or the isomers thereof, but especially glycol and glycerol. As fatty acid esters, therefore, the following are mentioned: ethyl oleate, isopropyl myristate, isopropyl palmitate, "Labrafil M 2375" (polyoxyethylene glycerol), "Labrafil M 1944 CS" (unsaturated polyglycolized glycerides prepared by alcoholysis of apricot kernel oil and consisting of glycerides and polyethylene glycol ester), "Labrasol" (saturated polyglycolized glycerides prepared by alcoholysis of TCM and consisting of glycerides and polyethylene glycol ester; all available from Gattefossé, France), and/or "Miglyol 812" (triglyceride of saturated fatty acids of chain length $C_8$ to $C_{12}$ from Hüls AG, Germany), but especially vegetable oils such as cottonseed oil, almond oil, olive oil, castor oil, sesame oil, soybean oil and more especially groundnut oil.

The manufacture of injectable preparations is usually carried out under sterile conditions, as is the filling, for example, into ampoules or vials, and the sealing of the containers.

Pharmaceutical compositions for oral administration can be obtained, for example, by combining the active ingredient with one or more solid carriers, if desired granulating a resulting mixture, and processing the mixture or granules, if desired or necessary, by the inclusion of additional excipients, to form tablets or tablet cores.

Suitable carriers are especially fillers, such as sugars, for example lactose, saccharose, mannitol or sorbitol, cellulose preparations, and/or calcium phosphates, for example tricalcium phosphate or calcium hydrogen phosphate, and also binders, such as starches, for example corn, wheat, rice or potato starch, methylcellulose, hydroxypropyl methylcellulose, sodium carboxymethylcellulose, and/or polyvinylpyrrolidone, and/or, if desired, disintegrators, such as the above-mentioned starches, also carboxymethyl starch, crosslinked polyvinylpyrrolidone, alginic acid or a salt thereof, such as sodium alginate. Additional excipients are especially flow conditioners and lubricants, for example silicic acid, talc, stearic acid or salts thereof, such as magnesium or calcium stearate, and/or polyethylene glycol, or derivatives thereof.

Tablet cores can be provided with suitable, optionally enteric, coatings through the use of, inter alia, concentrated sugar solutions which may comprise gum arabic, talc, polyvinylpyrrolidone, polyethylene glycol and/or titanium dioxide, or coating solutions in suitable organic solvents or solvent mixtures, or, for the preparation of enteric coatings, solutions of suitable cellulose preparations, such as acetylcellulose phthalate or hydroxypropylmethylcellulose phthalate. Dyes or pigments may be added to the tablets or tablet coatings, for example for identification purposes or to indicate different doses of active ingredient.

Pharmaceutical compositions for oral administration also include hard capsules consisting of gelatin, and also soft, sealed capsules consisting of gelatin and a plasticizer, such as glycerol or sorbitol. The hard capsules may contain the active ingredient in the form of granules, for example in admixture with fillers, such as corn starch, binders, and/or glidants, such as talc or magnesium stearate, and optionally stabilizers. In soft capsules, the active ingredient is preferably dissolved or suspended in suitable liquid excipients, such as fatty oils, paraffin oil or liquid polyethylene glycols or fatty acid esters of ethylene or propylene glycol, to which stabilizers and detergents, for example of the polyoxyethylene sorbitan fatty acid ester type, may also be added.

Pharmaceutical compositions suitable for rectal administration are, for example, suppositories that consist of a combination of the active ingredient and a suppository base. Suitable suppository bases are, for example, natural or synthetic triglycerides, paraffin hydrocarbons, polyethylene glycols or higher alkanols.

For parenteral administration, aqueous solutions of an active ingredient in water-soluble form, for example of a water-soluble salt, or aqueous injection suspensions that contain viscosity-increasing substances, for example sodium carboxymethylcellulose, sorbitol and/or dextran, and, if desired, stabilizers, are especially suitable. The active ingredient, optionally together with excipients, can also be in the form of a lyophilizate and can be made into a solution before parenteral administration by the addition of suitable solvents.

Solutions such as are used, for example, for parenteral administration can also be employed as infusion solutions.

Preferred preservatives are, for example, antioxidants, such as ascorbic acid, or microbicides, such as sorbic acid or benzoic acid.

The compounds of the invention may be administered as the sole active ingredient or together with other drugs useful against neoplastic diseases or useful in immunomodulating regimens. For example, the agents of the invention may be used in accordance with the invention in combination with pharmaceutical compositions effective in various diseases as described above, e.g. with cyclophosphamide, 5-fluorouracil, fludarabine, gemcitabine, cisplatinum, carboplatin, vincristine, vinblastine, etoposide, irinotecan, paclitaxel, docetaxel, rituxan, doxorubicine, gefitinib, or imatinib; or also with cyclosporins, rapamycins, ascomycins or their immunosuppressive analogs, e.g. cyclosporin A, cyclosporin G, FK-506, sirolimus or everolimus, corticosteroids, e.g. prednisone, cyclophosphamide, azathioprene, methotrexate, gold salts, sulfasalazine, antimalarials, brequinar, leflunomide, mizoribine, mycophenolic acid, mycophenolate, mofetil, 15-deoxyspergualine, immuno-suppressive monoclonal antibodies, e.g. monoclonal antibodies to leukocyte receptors, e.g. MHC, CD2, CD3, CD4, CD7, CD25, CD28, CD40, CD45, CD58, CD80, CD86, CD152, CD137, CD154, ICOS, LFA-1, VLA-4 or their ligands, or other immunomodulatory compounds, e.g. CTLA4Ig.

In accordance with the foregoing, the present invention also provides:

(1) A compound of the invention for use as a pharmaceutical;
(2) a compound of the invention for use as a FAK inhibitor, an ALK inhibitor and/or ZAP-70 inhibitor, for example for use in any of the particular indications hereinbefore set forth;
(3) a pharmaceutical composition, e.g. for use in any of the indications herein before set forth, comprising a compound of the invention as active ingredient together with one or more pharmaceutically acceptable diluents or carriers;
(4) a method for the treatment of any particular indication set forth hereinbefore in a subject in need thereof which comprises administering an effective amount of a compound of the invention or a pharmaceutical composition comprising same;
(5) the use of a compound of the invention for the manufacture of a medicament for the treatment or prevention of a disease or condition in which FAK, ALK and/or ZAP-70 activation plays a role or is implicated;
(6) the method as defined above under (4) comprising co-administration, e.g. concomitantly or in sequence, of a therapeutically effective amount of a compound of the invention and one or more further drug substances, said further drug substance being useful in any of the particular indications set forth hereinbefore;
(7) a combination comprising a therapeutically effective amount of a compound of the invention and one or more further drug substances, said further drug substance being useful in any of the particular indications set forth hereinbefore;
(8) use of a compound of the invention for the manufacture of a medicament for the treatment or prevention of a disease which responds to inhibition of the anaplastic lymphoma kinase;
(9) the use according to (8), wherein the disease to be treated is selected from anaplastic large-cell lymphoma, non-Hodgkin's lymphomas, inflammatory myofibroblastic tumors and neuroblastomas;
(10) the use according to (8) or (9), wherein the compound is 2-[5-chloro-2-(2-methoxy-4-morpholin-4-yl-phenylamino)-pyrimidin-4-ylamino]-N-methyl-benzamide or a pharmaceutically acceptable salt thereof, or any of the the compounds described hereinafter in the examples or a pharmaceutically acceptable salt of any one of these;
(11) a method for the treatment of a disease which responds to inhibition of the anaplastic lymphoma kinase, especially a disease selected from anaplastic large-cell lymphoma, non-Hodgkin's lymphomas, inflammatory myofibroblastic tumors and neuroblastomas, comprising administering an effective amount of a compound of the invention, especially 2-[5-chloro-2-(2-methoxy-4-morpholin-4-yl-phenylamino)-pyrimidin-4-ylamino]-N-methyl-benzamide, or a pharmaceutically acceptable salt thereof.

Additionally preferred a compound according to the present invention that is useful as herein before described is a compound specifically mentioned in the examples.

Additional specifically preferred compounds according to the present invention that are useful either as FAK inhibitor, as ALK inhibitor or for inhibition of both and which may be prepared essentially according to the methods described hereinbefore are the following:

2-[5-chloro-2-(2-methoxy-4-morpholin-4-yl-phenylamino)-pyrimidin-4-ylamino]-N-methyl-benzamide, $N^2$-(4-[1,4']Bipiperidinyl-1'-yl-2-methoxy-phenyl)-5-chloro-$N^4$-[2-(propane-1-sulfonyl)-phenyl]-pyrimidine-2,4-diamine, 2-{5-Chloro-2-[2-methoxy-4-(4-methyl-piperazin-1-yl)-phenylamino]-pyrimidin-4-ylamino}-N-isopropyl-benzenesulfonamide, 2-[5-Bromo-2-(2-methoxy-5-morpholin-4-yl-phenylamino)-pyrimidin-4-ylamino]-N-methyl-benzenesulfonamide 2-{2-[5-(1-Acetyl-piperidin-4-yloxy)-2-methoxy-phenylamino]-5-bromo-pyrimidin-4-ylamino}-N-methyl-benzenesulfonamide, N-[5-Bromo-2-(2,5-dimethoxy-phenylamino)pyrimidin-4-yl]-N-(4-morpholin-4-yl-phenyl)-methanesulfonamide, 5-Bromo-N-4-(4-fluoro-phenyl)-N*2*-(2-methoxy-4-morpholin-4-yl-phenyl)pyrimidine-2,4-diamine, 2-[5-Chloro-2-(2-methoxy-4-piperazin-1-yl-phenylamino)-pyrimidin-4-ylamino]-N-methyl-benzenesulfonamide, 2-[5-Bromo-2-(5-fluoro-2-methoxy-phenylamino)-pyrimidin-4-ylamino]-N-methyl-benzenesulfonamide, 2-[5-Chloro-2-(5-fluoro-2-methoxy-phenylamino)-pyrimidin-4-ylamino]-N-isobutyl-benzenesulfonamide, and 2-{5-Chloro-2-[2-methoxy-5-(4-methyl-piperazin-1-ylmethyl)-phenylamino]-pyrimidin-4-ylamino}-N-methyl-benzenesulfonamide.

The invention also provides a compound of formula 2-{5-Chloro-2-[4-(3-methylamino-pyrrolidin-1-yl)-phenylamino]-pyrimidin-4-ylamino}-N-isopropyl-benzenesulfonamide The following Examples serve to illustrate the invention without limiting the invention in its scope.

EXAMPLES

Abbreviations

AcOH=acetic acid, ALK=anaplastic lymphoma kinase, ATP=adenosine 5'-triphosphate, brine=saturated sodium chloride solution, BSA=bovine serum albumin, DIAD=diisopropyl azodicarboxylate, DIPCDI=N,N'-diisopropylcarbodiimid, DMAP=4-dimethylaminopyridine, DMF=N,N-dimethylformamide, DTT=1,4-dithio-D,L-threitol, EDTA=ethylene diamine tetraacetic acid, Et=ethyl, EtOAc=ethyl acetate, EtOH=ethanol, Eu-PT66=LANCE™ europium-W1024-labelled anti-phosphotyrosine antibody (Perkin Elmer), FAK=Focal Adhesion Kinase, FRET=fluorescence resonance energy transfer, HEPES=N-2-hydroxyethyl-piperazine-N'-2-ethanesulfonic acid, HOAt=1-hydroxy-7-azabenzotriazole, Me=methyl, RT-PCR=reverse transcription polymerase chain reaction, SA-(SL)APC=Streptavidin conjugated to SuperLight™ allophycocyanin (Perkin Elmer), subst.=substituted, TBTU=O-(benzotriazol-1-yl)-N,N,N',N'-tetramethylammonium tetrafluoroborate, THF=tetrahydrofuran.

Example 1

2-[2-(2,5-Dimethoxy-phenylamino)-5-nitro-pyrimidin-4-ylamino]-N-methyl-benzenesulfonamide

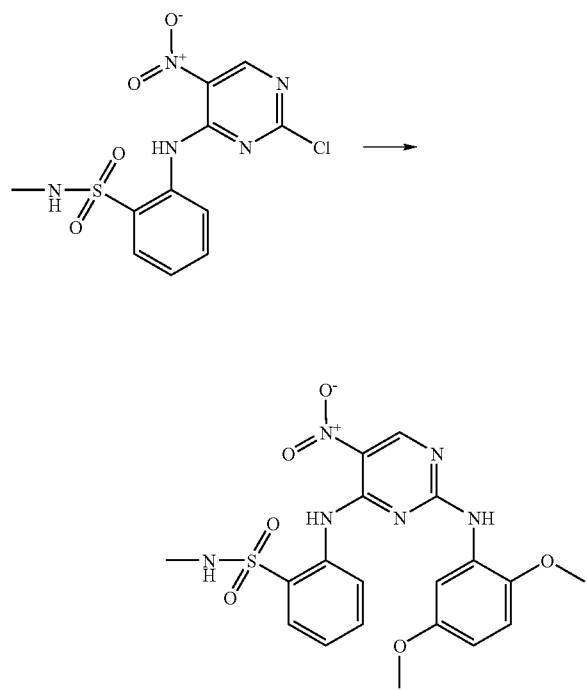

To a solution of 2-(2-chloro-5-nitro-pyrimidin-4-ylamino)-N-methyl-benzenesulfonamide (100 mg, 0.29 mmol) in EtOH (3 mL), 2,5-dimethoxyaniline (49 mg, 0.32 mmol) is added at room temperature. The mixture is heated at 78° C. for 5 h. The solvent is evaporated, and the mixture is purified by reverse phase HPLC to give the title product in.

Rf=0.47 (n-hexane:ethyl acetate=1:1). ¹H-NMR (400 MHz, CDCl₃), δ (ppm): 2.36 (d, 3H), 3.57 (s, 3H), 3.73 (s, 3H), 6.72 (d, 1H), 6.99 (d, 1H), 7.17 (s, 1H), 7.35 (t, 1H), 7.4-7.6 (m, 1H), 7.63 (d, 1H), 7.81 (d, 1H), 8.0-8.2 (m, 1H), 9.13 (s, 1H), 9.41 (br.s, 1H), 11.0 (s, 1H).

Preparation of 2-(2-chloro-5-nitro-pyrimidin-4-ylamino)-N-methyl-benzenesulfonamide 2,4-Dichloro-5-nitro-pyrimidine (1.94 g, 10 mmol) and 2-amino-N-methyl-benzenesulfonamide (1.86 g, 10 mmol) are dissolved in CHCl₃ (30 mL). The reaction mixture is heated at 61° C. for 2 h. The solvent is evaporated and the residue is washed with ether to give the title product.

Rf=0.5 (n-hexane:ethyl acetate=1:1). ¹H-NMR (400 MHz, CDCl₃), δ (ppm): 2.67 (d, 3H), 4.6-4.7 (m, 2H), 7.41 (dd, 1H), 7.7 (dd, 1H), 8.04 (d, 1H), 8.15 (d, 1H), 9.21 (s, 1H), 11.2 (s, 1H).

Example 2

2-[5-Bromo-2-(2,4-dimethoxy-phenylamino)-pyrimidin-4-ylamino]-N-methyl-benzenesulfonamide

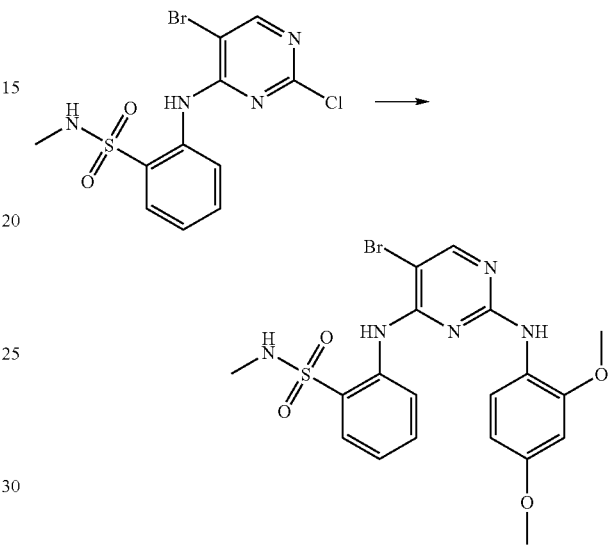

To a solution of 2-(5-bromo-2-chloro-pyrimidin-4-ylamino)-N-methyl-benzenesulfonamide (300 mg, 0.79 mmol), 2,4-dimethoxyaniline (181.5 mg, 1.18 mmol) in ethanol (3 mL), 1 N hydrochloric acid (0.03 mL) is added and stirred under reflux condition for 5 hours. The reaction mixture is cooled to room temperature, poured into water and extracted twice with ethyl acetate. The organic layer is successively washed with water and brine, dried over magnesium sulfate, and evaporated in vacuo. The residue is purified with silica gel column chromatography (n-hexane:ethyl acetate=5:1 to 1:1) to afford the title compound.

¹H-NMR (CDCl₃), δ (ppm): 8.95 (s, 1H), 8.44 (d, 1H), 8.20 (s, 1H), 7.98 (dd, 1H), 7.58 (ddd, 1H), 7.22-7.32 (m, 1H), 6.51 (d, 1H), 6.40 (d, 1H), 4.56-4.48 (m, 1H), 3.86 (s, 3H), 3.81 (s, 3H), 2.64 (d, 3H). Rf (n-hexane:ethyl acetate=1:1): 0.31.

Preparation of 2-(5-bromo-2-chloro-pyrimidin-4-ylamino)-N-methyl-benzenesulfonamide A solution of 5-bromo-2,4-dichloropyrimidine (684 mg, 3.0 mmol) and 2-amino-N-methyl-benzenesulfonamide (559 mg, 3.0 mmol) in N,N-dimethylformamide (10 mL) containing potassium carbonate (830 mg, 6.0 mmol) is stirred at room temperature for 23 hours. Saturated aqueous ammonium chloride is added and the mixture is poured into water and extracted twice with ethyl acetate. The organic layer is washed with brine, dried over sodium sulfate, and evaporated in vacuo. The residue is purified with silica gel column chromatography (n-hexane-ethyl acetate gradient) to afford the title compound as a slightly yellow solid.

¹H-NMR (CDCl₃), δ (ppm): 2.67 (d, 3H), 4.79 (q, 1H), 7.26 (s, 1H), 7.29 (ddd, 1H), 7.66 (ddd, 1H), 7.95 (dd, 1H), 8.37 (s, 1H), 8.48 (d, 1H), 9.52 (s, 1H). Rf (n-hexane:ethyl acetate=10:3): 0.33.

Example 3

The following 2-[5-bromo-2-(subst. phenylamino)-pyrimidin-4-ylamino]-N-methyl-benzenesulfonamides are prepared from 2-(5-bromo-2-chloro-pyrimidin-4-ylamino)-N-methyl-benzenesulfonamide and the corresponding aniline following the procedure of Example 2:

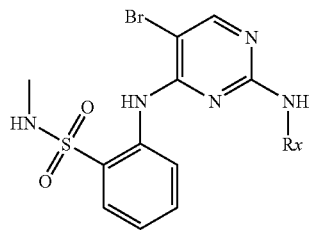

| ExplNo. | Rx | Rf (solvent) or MS | $^1$H-NMR (400 MHz), δ (ppm) |
|---|---|---|---|
| 3-1 | | 0.48 (n-hexane: AcOEt = 1:1) | CDCl$_3$: 2.64(d, 3H), 4.48-4.40(m, 1H), 6.78(d, 1H), 6.87(bs, 1H), 6.99(dd, 1H), 6.82(8, 1H), 7.54(ddd, 1H), 7.79(d, 1H), 7.97(dd, 1H), 8.28(s, 1H), 8.32(dd, 1H), 9.07(s, 1H) |
| 3-2 | | 0.58 (n-hexane: AcOEt = 1:1) | CDCl$_3$: 2.25(s, 3H), 2.33(s, 3H), 2.63(d, 3H), 4.53-4.45(m, 1H), 6.61(bs, 1H), 6.99(dd, 1H), 7.04(s, 1H), 7.18(ddd, 1H), 7.43(ddd, 1H), 7.56(d, 1H), 7.92(dd, 1H), 8.19(s, 1H), 8.41(dd, 1H), 9.08(s, 1H) |
| 3-3 | | 0.36 (n-hexane: AcOEt = 1:1) | CDCl$_3$: 2.23(s, 3H), 2.62(d, 3H), 3.69(s, 3H), 4.53-4.44(m, 1H), 6.62(dd, 1H), 6.69(bs, 1H), 7.10(d, 1H), 7.19(dd, 1H), 7.48(d, 1H), 7.51(dd, 1H), 7.93(dd, 1H), 8.22(s, 1H), 8.44(dd, 1H), 9.09(s1, 1H) |
| 3-4 | | 0.41 (n-hexane: AcOEt = 1:1) | CDCl$_3$: 2.32(s, 3H), 2.63(d, 3H), 4.45-4.44(m, 1H), 6.85(d, 1H), 6.91(d, 1H), 7.00(bs, 1H), 7.28-7.24(m, 1H), 7.57(dd, 1H), 7.99(dd, 1H), 8.25(s, 1H), 8.39(d, 1H), 9.00(bs, 1H) |
| 3-5 | | 0.39 (n-hexane: AcOEt = 1:1) | CDCl$_3$: 2.33(s, 3H), 2.63(d, 3H), 3.87(s, 3H), 4.46-4.44(m, 1H), 6.66(d, 1H), 6.71(s, 1H), 7.48(bs, 1H), 7.63-7.59(m, 1H), 7.97(dd, 1H), 8.05(d, 1H), 8.23 (s, 1H), 8.44(d, 1H), 8.92(bs, 1H) |
| 3-6 | | 0.27 (n-hexane: AcOEt = 3:1) | CDCl$_3$: 2.63(d, 3H), 3.90(s, 3H), 4.45-4.40(m, 1H), 6.90–6.86(m, 2H), 7.00-6.96(m, 1H), 7.23–7.17 (m, 3H), 7.45(dd, 1H), 7.50-7.60(m, 2H), 7.97(dd, 1H), 8.22(d, 1H), 8.26 (S, 1H), 8.43(d, 1H), 8.94(bs, 1H) |
| 3-7 | | 0.34 (n-hexane: AcOEt = 3:1) | CDCl$_3$: 2.30(s, 3H), 2.63(d, 3H), 4.44-4.43(m, 1H), 6.68 (bs, 1H), 7.00-6.68(m, 1H), 7.23-7.17(m, 2H), 7.46–7.43(m, 1H), 7.76(d, 1H), 7.93(dd, 1H), 8.22 (s, 1H), 8.40(d, 1H), 9.01(bs, 1H) |

-continued

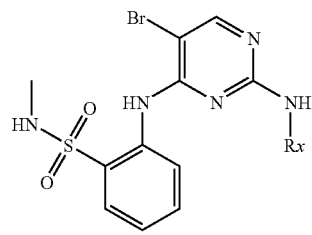

| ExplNo. | Rx | Rf (solvent) or MS | ¹H-NMR (400 MHz), δ (ppm) |
|---|---|---|---|
| 3-8 | | 0.12 (n-hexane: AcOEt = 3:1) | CDCl₃: 2.62(d, 3H), 2.81(s, 3H), 4.07-3.98(m, 1H), 4.52-4.45(m, 1H), 6.37(bs, 1H), 6.77-6.73 (m, 2H), 7.12(dd, 1H), 7.24-7.20(m, 1H), 7.30-7.27(m, 1H), 7.35(dd, 1H), 7.88(dd, 1H), 8.18 (S, 1H), 8.41(d, 1H), 9.19(bs, 1H) |
| 3-9 | | 0.28 (n-hexane: AcOEt = 3:1) | CDCl₃: 2.62(d, 3H), 3.94(s, 3H), 4.49–4.43(m, 1H), 6.99-6.90 (m, 3H), 7.18-7.23(m, 1H), 7.31-7.24(m, 3H), 7.63(bs, 1H), 7.93-7.86(m, 1H), 8.28-8.23(m, 1H), 8.28 (s, 1H), 8.45(bs, 1H), 8.89(bs, 1H) |
| 3-10 | | 0.23 (n-hexane: AcOEt = 3:1) | CDCl₃: 0.91(t, 3H), 1.37 (dd, 2H), 1.64-1.55(m, 2H), 2.64-2.60(m, 2H), 4.45-4.40(m, 1H), 6.69(bs, 1H), 7.23–7.10(m, 1H), 7.46-7.38(m, 1H), 7.73(d 1H), 7.92(d, 1H), 8.21(s, 1H), 8.38-8.46(m, 1H), 9.09(bs, 1H) |
| 3-11 | | 0.12 (n-hexane: AcOEt = 3:1) | CDCl₃: 2.63(d, 3H), 4.15-4.10(m, 1H), 6.58(bs, 1H), 7.31-7.10(m, 4H), 7.53-7.49(m, 1H), 7.71(d 1H), 7.95 (d, 1H), 8.30–8.23(m, 1H), 8.26(s, 1H), 8.45(d, 1H), 9.03(bs, 1H) |
| 3-12 | | 0.4 (n-hexane: AcOEt = 3:1) | CDCl₃: 2.09 (dd, 2H), 2.63 (d, 3H), 2.85(t, 2H), 2.96 (t, 2H), 4.46-4.43 (m, 2H), 6.73 (bs, 1H), 6.99 (d, 1H), 7.09 (dd, 1H), 7.25-7.20(m, 1H), 7.52 (dd, 1H), 7.74 (d 1H), 7.92 (dd, 1H), 8.22 (s, 1H), 8.42 (d, 1H), 9.02 (bs, 1H) |
| 3-13 | | 0.33 (AcOEt) | CDCl₃: 2.63 (d, 3H), 4.63–4.64 (m, 1H), 7.11(d, 2H), 7.18(dd, 1H), 7.42-7.34(m, 1H), 1.58-7.55(m, 1H), 7.96(d, 1H), 8.07(s, 1H), 8.19-8.10(m, 1H), 8.24(s, 1H), 9.15(s, 1H), 11.6-11.4(m, 1H) |
| 3-14 | | 0.28 (n-hexane: AcOEt = 3:1) | CDCl₃: 2.63(d, 3H), 3.88(s, 3H), 3.89(s, 3H), 4.47-4.41(m, 1H), 6.60(d, 1H), 6.92(dd, 1H), 7.64(dd, 1H), 7.66-7.61(m, 1H), 7.89(d, 1H), 7.98(dd, 1H), 8.26(s, 1H), 8.43(d, 1H), 8.95(s, 1H) |
| 3-15 | | 0.30 (n-hexane: AcOEt = 3:1) | CDCl₃: 2.63(d, 3H), 3.66(s, 3H), 3.85(s, 3H), 4.45-4.44(m, 1H), 6.48(dd, 1H), 6.79(d, 1H), 7.64(dd, 1H), 7.97(dd, 2H), 8.26(s, 1H), 8.44(d, 1H), 8.96(s, 1H) |

-continued

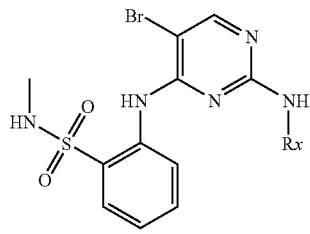

| ExplNo. | Rx | Rf (solvent) or MS | ¹H-NMR (400 MHz), δ (ppm) |
|---|---|---|---|
| 3-16 | 3,4,5-trimethylphenyl (Me, Me, Me) | 0.22 (n-hexane: AcOEt = 3:1) | CDCl₃: 2.17(s, 3H), 2.22(s, 3H), 2.64(s, 3H), 2.63(d, 3H), 4.46-4.44(m, 1H), 6.57(bs, 1H), 7.00(s, 1H), 7.17(dd, 1H), 7.44-7.40(m, 1H), 7.44(s, 1H), 7.93(dd, 1H), 8.19(s, 1H), 8.43(d, 1H), 9.06(s, 1H) |
| 3-17 | 4,5-dimethyl-2-methoxy-phenyl with OMe | 0.46 (AcOEt) | CDCl₃: 2.22(s, 3H), 2.63(d, 3H), 3.68(s, 3H), 3.89(s, 3H), 4.52-4.47(m, 1H), 6.51(s, 1H), 6.74(s, 1H), 7.12(s, 1H), 7.16-7.12(m, 1H), 7.40(dd, 1H), 7.91(dd, 1H), 8.19(s, 1H), 8.42(d, 1H), 9.12(s, 1H) |
| 3-18 | 3-methyl-4-isopropylphenyl | 0.35 (n-hexane: AcOEt = 3:1) | CDCl₃: 1.16(d, 6H), 2.25(s, 3H), 2.62(d, 3H), 2.77(t, 1H), 4.49-4.48(m, 1H), 7.00(s, 1H), 7.15(d, 1H), 7.41-7.37(m, 1H), 7.49(d, 2H), 7.54(dd, 1H), 7.92(dd, 1H), 8.21(s, 1H), 8.32(d, 1H), 9.02(s, 1H) |
| 3-19 | 4-methyl-3-methoxy-morpholinophenyl | 0.23 (n-hexane: AcOEt = 1:1) | CDCl₃: 2.63(d, 3H), 3.13-3.10(m, 4H), 3.87(s, 3H), 3.89-3.86(m, 4H), 4.91-4.93(m, 1H), 6.41(dd, 1H), 6.52(d, 1H), 7.24-7.22(m, 1H), 7.32(s, 1H), 7.57(dd, 1H), 7.96(dd, 1H), 8.01(d, 1H), 8.14(s, 1H), 8.44(d, 1H), 8.98(s, 1H) |
| 3-20 | 3,4-dimethyl-morpholinophenyl | 0.36 (n-hexane: AcOEt = 1:1) | CDCl₃: 2.22(s, 3H), 2.64(d, 3H), 3.00-3.2.97(m, 4H), 3.76-3.74(m, 4H), 4.54-4.50(m, 1H), 6.64(d, 1H), 6.66(dd, 1H), 7.11(d, 1H), 7.18(dd, 1H), 7.37(d, 1H), 7.46(dd, 1H), 7.93(dd, 1H), 8.22(s, 1H), 8.42(d, 1H), 9.09(s, 1H) |
| 3-22 | 3,4-dimethyl-morpholinocarbonylphenyl | 0.27 (AcOEt) | CDCl₃: 2.33(s, 3H), 2.65(d, 3H), 3.60-3.45(m, 8H), 4.53-4.49(m, 1H), 6.74(s, 1H), 7.11(d, 1H), 7.22-7.18(m, 1H), 7.58-7.54(m 1H), 7.94(dd, 1H), 8.00(d, 1H), 8.22(s, 1H), 8.37(d, 1H), 9.13(s, 1H) |

-continued

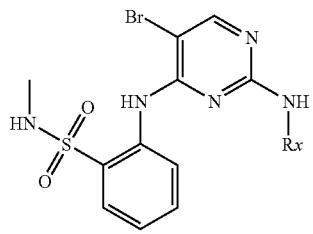

| ExplNo. | Rx | Rf (solvent) or MS | ¹H-NMR (400 MHz), δ (ppm) |
|---|---|---|---|
| 3-23 | 3-methyl-4-methyl-N-cyclohexylbenzamide | 0.38 (AcOEt) | CDCl₃: 1.24–1.08(m, 2H), 1.46-1.32(m, 2H), 1.76-1.67(m, 2H), 1.98-1.90(m, 2H), 2.33(s, 3H), 2.64(d, 3H), 3.95-3.90(m, 1H), 4.49-4.47(m, 1H), 5.89-5.80(m, 1H), 6.66(s, 1H), 7.15(dd, 1H), 7.48-7.31(m, 2H), 7.91(dd, 1H), 8.12(s, 1H), 8.23(s, 1H), 8.41(d, 1H), 9.18(s, 1H) |
| 3-24 | 3-methyl-4-methyl-piperazinylcarbonyl-benzene | 0.11 (AcOEt) | CDCl₃: 2.35(s, 3H), 2.71(s, 3H), 3.07-2.73(m, 2H), 3.86-3.31(m, 6H), 6.85(s, 1H), 7.10(d, 1H), 7.24-7.19(m, 1H), 7.52-7.48(m, 1H), 7.66-7.59(m, 2H), 7.93(d, 1H), 8.06(s, 1H), 8.27-8.21(m, 1H), 8.23(s, 1H), 9.11(s, 1H) |
| 3-25 | 3,4-dimethyl-4'-methoxybiphenyl | 0.5 (n-hexane: AcOEt = 1:1) | CDCl₃: 2.52(d, 3H), 2.62(s, 3H), 4.36-4.32(m, 1H), 6.74(s, 1H), 6.87(d, 2H), 7.00-6.91(m, 2H), 7.00-6.97(m, 2H), 7.38(dd, 2H), 7.86(dd, 1H), 7.98(s, 1H), 8.23(s, 1H), 8.28(d, 1H), 9.04(s, 1H) |
| 3-26 | 3,4-dimethyl-piperidinyl-benzene | 0.45 (n-hexane: AcOEt = 1:1) | CDCl₃: 1.62-1.34(m, 6H), 2.13(s, 3H), 2.56(d, 3H), 3.01-2.87(m, 4H), 4.54-4.38(m, 1H), 6.59(s, 1H), 6.69-6.59(m, 1H), 7.02(d, 1H), 7.10-7.07(m, 1H), 7.37(dd, 1H), 7.84(dd, 1H), 8.15(s, 1H), 8.34(d, 1H), 9.01(s, 1H) |
| 3-27 | 3,4-dimethyl-2'-methoxybiphenyl | 0.45 (n-hexane: AcOEt = 1:1) | CDCl₃: 2.32(s, 3H), 2.58(d, 3H), 3.75(s, 3H), 4.37-4.44(m, 1H), 6.77-6.73(m, 1H), 6.89-6.82(m 1H), 6.97-6.91(m, 2H), 6.96(d, 1H), 7.20(dd, 1H), 7.25-7.24(m, 1H), 7.33-7.29(m, 1H) |

-continued

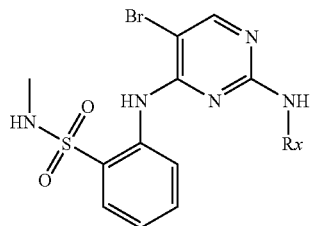

| ExplNo. | Rx | Rf (solvent) or MS | ¹H-NMR (400 MHz), δ (ppm) |
|---|---|---|---|
| 3-28 | 3-methyl-4-methyl-3'-methoxybiphenyl group (with OMe) | 0.35 (n-hexane: AcOEt = 1:1) | CDCl₃: 2.34(s, 3H), 2.64(d, 3H), 3.81(s, 3H), 4.57-4.50(m, 1H), 6.76(bs, 1H), 6.91-6.84(m, 41H), 7.04(d, 1H), 7.83(dd, 1H), 8.06(d, 1H), 8.19(dd, 1H), 8.23(s, 1H), 9.00(s, 1H) |
| 3-29 | 3-methyl-4-ethoxybiphenyl | 0.45 (n-hexane: AcOEt = 1:1) | CDCl₃: 1.50(t, 3H), 2.62 (d, 3H), 4.17(dd, 2H), 4.51-4.44(m, 1H), 6.95-6.89(m, 2H), 6.94(d, 1H), 7.16 (dd, 1H), 7.31-7.23(m, 5H), 7.67(s, 1H), 7.11(dd, 1H), 7.23(d, 2H), 7.65(s, 1H), 7.88(dd, 1H), 8.28-8.23(m, 1H), 8.28(s, 1H), 8.43(s, 1H), 8.89(s, 1H) |
| 3-30 | 3-methyl-4-ethoxy-4'-methoxybiphenyl | 0.45 (n-hexane: AcOEt = 1:1) | CDCl₃: 1.49(t, 3H), 2.63(d, 3H), 3.85(s, 3H), 4.16(dd, 2H), 4.55-4.48(m, 1H), 6.81(dd, 1H), 6.95-6.91(m, 3H), 7.11(dd, 1H), 7.23(d, 2H), 7.65(s, 1H), 7.90-7.88(m, 1H), 8.28-8.26(m, 1H), 8.27(s, 1H), 8.39(s, 1H), 8.90(s, 1H) |
| 3-31 | 5-methyl-1,2,3,4-tetrahydronaphthalene | 0.29 (n-hexane: AcOEt = 1:1) | ¹H-NMR: (CDCl₃) 1.83-1.72 (4H, m), 2.63 (3H, d), 2.66–2.62(2H, m), 2.80(2H, t), 4.41-4.44(1H, m), 6.64 (1H, br.s), 6.92 (1H, d), 7.09 (1H, dd), 7.18 (1H, dd), 7.45 (1H, dd), 7.59 (1H, dd), 7.92 (1H, d), 8.20 (1H, s), 8.42 (1H, d), 9.08 (1H, br.s). |
| 3-32 | 3-methyl-4-methoxy-morpholinyl phenyl | 0.3 (n-hexane: AcOEt = 1:1) | DMSO-d₆: 2.43 (s, 3H), 2.80-2.82(m, 4H), 3.61-3.64 (m, 4H), 3.75(s,3H), 6.62(dd, 1H), 6.93(d, 1H), 7.46(d, 1H), 7.54(dd, 1H), 7.77(dd, 2H), 8.14(bs, 1H), 8.32(s, 1H), 8.38-8.30(m, 1H), 9.14(bs, 1H) |
| 3-33 | 4-methyl-3-methoxy-(1-methylpiperidin-4-yloxy)phenyl | 0.61 (MeOH: CH2Cl2 = 1:1) | DMSO-d₆: 1.59-1.68(m, 2H), 1.88-1.98(m, 2H), 2.13-2.25(m,2H), 2.19(s, 3H), 2.43 (s, 3H), 2.60-2.70(m, 2H), 3.75 (s, 3H), 4.32-4.40(m, 1H), 6.51 (dd, 1H), 6.64(d, 1H), 7.20(dd, 1H), 7.39 (d, 1H), 7.75(dd, 1H), 7.70-7.78(s, 1H), 8.22(s, 1H), 8.26(s, 1H), 8.38-8.41(m, 1H), 9.22(s, 1H) |

-continued

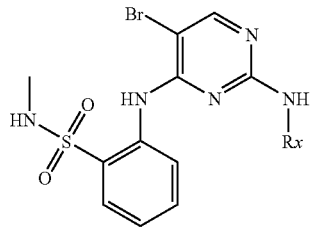

| ExplNo. | Rx | Rf (solvent) or MS | $^1$H-NMR (400 MHz), δ (ppm) |
|---|---|---|---|
| 3-34 | (3-methyl-4-methoxyphenyl)-4-acetylpiperazine | 0.17 (AcOEt) | CDCl$_3$: 2.11(s, 3H), 2.68(d, 3H), 2.76-2.83(m, 2H), 2.89-2.97(m, 2H), 3.47-3.55(m, 2H), 3.58-3.66(m, 2H), 3.86(s, 3H), 4.70-4.78(m, 1H), 6.53(dd, 1H), 6.81(d, 1H), 7.23(dd, 1H), 7.54-7.62(m, 2H), 7.97(dd, 1H), 8.02-8.03(m, 1H), 8.29(s, 1H), 8.40(d, 1H), 8.99(bs, 1H) |
| 3-35 | 2-(4-(3-methyl-4-methoxyphenoxy)ethyl)morpholine | 0.22 (AcOEt only) | DMSO-d$_6$: 2.40-2.48(m, 7H), 2.63(t, 2H), 3.50-3.58(m, 4H), 3.77(s, 3H), 3.91(t, 2H), 6.60(dd, 1H), 6.93(d, 1H), 7.28(dd, 1H), 7.56(d, 1H), 7.60(dd, 1H), 7.75-7.80(m, 1H), 7.80(dd, 1H), 8.10(s, 1H), 8.35(s, 1H), 8.40(d, 1H), 9.21(s, 1H) |
| 3-36 | 2,4-difluorotoluene | 0.4 (n-hexane: AcOEt = 1:1) | DMSO-d$_6$: 2.43(s, 3H), 7.03-7.08(m, 1H), 7.21-7.23(m, 1H), 7.25-7.36(m, 1H), 7.47-7.57(m, 2H), 7.74-7.77(m, 2H), 8.28(s, 1H), 8.35(d, 1H), 9.09(s, 1H), 9.24(s, 1H) |
| 3-37 | 2-chloro-4-fluorotoluene | 0.4 (n-hexane: AcOEt = 1:1) | CDCl$_3$: 2.64(d, 3H), 4.53-4.54(m, 1H), 6.88-6.93(m, 1H), 7.14-7.28(m, 3H), 7.54-7.58(m, 1H), 7.95-7.98(m, 1H), 8.16-8.21(m, 1H), 8.24(s, 1H), 8.33-8.36(m, 1H), 9.05(s, 1H) |
| 3-38 | 4-chloro-2-methyl-5-fluorobenzene | 0.42 (n-hexane: AcOEt = 1:1) | CDCl$_3$: 2.64(d, 3H), 4.46-4.47(m, 1H), 6.63-6.68(m, 1H), 1.30-7.32(m, 2H), 7.55(s, 1H), 7.64-7.68(m, 1H), 7.97-7.99(m, 1H), 8.20-8.39(m, 3H), 9.03(s, 1H) |

-continued

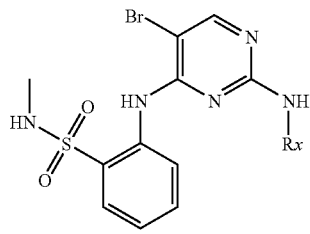

| ExplNo. | Rx | Rf (solvent) or MS | $^1$H-NMR (400 MHz), δ (ppm) |
|---|---|---|---|
| 3-39 | (4-methyl-3-methoxyphenyl)-4-methylpiperazine | 562, 564 [M + 1]+ | CDCl3: 2.37(s, 3H), 2.58-2.64(m, 7H), 3.15-3.18(m, 4H), 3.87(s, 3H), 4.60-4.65(m, 1H), 6.43(dd, 1H), G.44-6.54(m, 1H), 7.22(d, 1H), 7.30(s, 1H), 7.57(dd, 1H), 7.94-7.99(m, 2H), 8.18(s, 1H), 8.45(d, 1H), 8.95(s, 1H) |
| 3-40 | (4-methyl-3-methoxyphenyl)-4-cyanopiperidine | 572, 574 [M + 1]+ | DMSO-d6: 1.79-1.88(m, 2H), 1.98-2.02(m, 2H), 2.43(s, 3H), 3.02-3.08(m, 3H), 3.28-3.39(m, 2H), 3.76(s, 3H), 6.47(dd, 1H), 6.65(d, 1H), 7.22(dd, 1H), 7.39(d, 1H), 7.45-7.50(m, 1H), 7.74-7.77(m, 2H), 8.18(s, 1H), 8.22(s, 1H), 8.41-8.44(m, 1H), 9.21 (bs, 1H) |
| 3-41 | (4-methyl-3-methoxyphenyl)-thiomorpholine | 565, 567 [M + 1]+ | DMSO-d6: 2.44(d, 3H), 2.69-2.71(m, 4H), 3.49-3.52(m, 4H), 3.76(s, 3H), 6.45(dd, 1H), 6.62(d, 1H), 7.23(ddd, 1H), 7.38(d, 1H), 7.46-7.50(m, 1H), 7.72-7.77(m, 2H), 8.19(s, 1H), 8.22(s, 1H), 8.42-8.45(m, 1H), 9.22(s, 1H) |
| 3-42 | (4-methyl-3-methoxyphenyl)-N,N-bis(2-methoxyethyl)amine | 595, 597 [M + 1]+ | DMSO-d6: 2.44(s, 3H), 3.31(s, 6H), 3.48-3.53(m, 8H), 3.72(s, 3H), 6.24(dd, 1H), 6.37(d, 1H), 7.18-7.21(m, 2H), 7.40-7.55(m, 1H), 7.72-7.76(m, 2H), 8.17-8.19(m, 2H), 8.40-8.50(m, 1H), 9.23(s, 1H) |

-continued
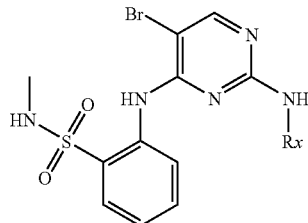
| ExplNo. | Rx | Rf (solvent) or MS | ¹H-NMR (400 MHz), δ (ppm) |
|---|---|---|---|
| 3-43 | (4-methyl-3-methoxyphenyl-piperidine-4-carboxamide) | 590, 592 [M + 1]+ | DMSO-d6: 1.64-1.71(m, 2H), 1.75-1.82(m, 2H), 2.21-2.28(m, 1H), 2.43(d, 3H), 2.62-2.67(m, 2H), 3.68-3.74(m, 2H), 3.76(s, 3H), 6.45(dd, 1H), 6.63(d, 1H), 6.75-6.81(m, 1H), 7.20(ddd, 1H), 7.25-7.30(m, 1H), 7.35(d, 1H), 7.45-7.52Cm, 1H), 7.70-7.77(m, 2H), 8.18(s, 1H), 8.21(s, 1H), 8.40-8.47(m, 1H), 9.22(s, 1H) |
| 3-44 | (4-methyl-3-methoxyphenyl-thiomorpholine 1,1-dioxide) | 597, 599 [M + 1]+ | DMSO-d6: 2.44(s, 3H), 3.12-3.17(m, 4H), 3.68-3.85(m, 4H), 3.79(s, 3H), 6.55(dd, 1H), 6.71(d, 1H), 7.19-7.25(m, 1H), 7.43(d, 1H), 7.46-7.53(m, 1H), 7.73-7.78(m, 2H), 8.19-8.22(m, 1H), 8.22(s, 1H), 8.38-8.45(m, 1H), 9.20(bs, 1H) |
| 3-45 | (4-methylindole-1-propyl-morpholine) | 600, 602 [M + 1]+ | DMSO-d6: 1.85-1.95(m, 2H), 2.19(t, 2H), 2.25-2.35(m, 4H), 2.43(s, 3H), 3.52-3.64(m, 4H), 4.19(t, 2H), 6.65(d, 1H), 7.05(dd, 1H), 7.20(d, 1H), 7.23(ddd, 1H), 7.27(d, 1H), 7.40-7.46(m, 1H), 7.42(d, 1H), 7.70-7.75(m, 1H), 7.76(dd, 1H), 8.32(s, 1H), 8.45(d, 1H), 9.22(s, 1H), 9.23(s, 1H) |

-continued

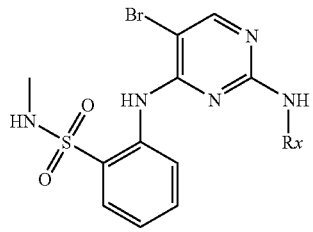

| ExplNo. | Rx | Rf (solvent) or MS | ¹H-NMR (400 MHz), δ (ppm) |
|---|---|---|---|
| 3-46 | (4-acetylpiperazin-1-yl, 3-methoxy-4-methylphenyl) | 590, 592 [M + 1]+ | DMSO-d6: 2.05(s, 3H), 2.44(s, 3H), 3.08-3.17(m, 4H), 3.55-3.63(m, 4H), 3.77(s, 3H), 6.48(dd, 1H), 6.67(d, 1H), 7.23(dd, 1H), 7.41(d, 1H), 7.45-7.52(m, 1H), 7.76(dd, 1H), 7.72-7.78(m, 1H), 8.19(s, 1H), 8.22(s, 1H), 8.40-8.47(m, 1H), 9.22(bs, 1H) |
| 3-47 | (piperazin-1-yl, 3-methoxy-4-methylphenyl) | 548, 550 [M + 1]+ | DMSO-d6: 2.43(s, 3H), 2.82-2.87(m, 4H), 2.99-3.15(m, 4H), 3.76(s, 3H), 6.43(dd, 1H), 6.61(d, 1H), 7.22(dd, 1H), 7.36(d, 1H), 7.43-7.51(m, 1H), 7.75(dd, 1H), 8.17(s, 1H), 8.21(s, 1H), 8.38-8.45(m, 1H), 9.12-9.28(m, 1H) |
| 3-48 | (imidazol-1-yl, 3-methoxy-4-methylphenyl) | MS 530, 532 | CDCl3: 2.65(d, 3H), 3.96(s, 3H), 4.40-4.48(m, 1H), 6.85-6.88(m, 2H), 7.22(d, 1H), 7.25-7.31(m, 1H), 7.56-7.65(m, 3H), 7.79(s, 1H), 8.00(dd, 1H), 8.29(s, 1H), 8.39(dd, 1H), 9.00(s, 1H). |
| 3-49 | (4-methylpiperazin-1-yl carbonyl, 4-methoxy-3-methylphenyl) | Rf (AcOEt: MeOH = 9:1) 0.20 | CDCl₃: 2.18-2.50(m, 4H), 2.28(s, 3H), 2.65(d, 3H), 3.10-3.75(m, 4H), 3.93(s, 3H), 4.50-4.61(m, 1H), 6.89(d, 1H), 7.06(dd, 1H), 7.59-7.67(m, 2H), 7.93-7.97(m, 1H), 8.26(s, 1H), 8.37-8.43(m, 2H), 9.02(s, 1H). |

-continued

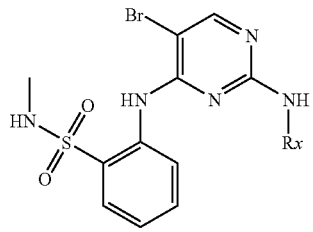

| ExplNo. | Rx | Rf (solvent) or MS | ¹H-NMR (400 MHz), δ (ppm) |
|---|---|---|---|
| 3-50 | 3-methyl-2,6-dimethoxypyridin-4-yl | Rf 0.4 (Hexane/AcOEt = 1/1) | CDCl₃: 2.63(d, 3H), 3.90(s, 3H), 4.00(s, 3H), 4.39-4.47(m, 1H), 6.23(d, 1H), 7.00(s, 1H), 7.22-7.25(m, 1H), 7.57(dd, 1H), 7.96(dd, 1H), 8.22(s, 1H), 8.25(d, 1H), 8.37(d, 1H), 8.96(s, 1H) |
| 3-51 | 3,4-dimethyl-N-(2-hydroxyethyl)-N-propylaniline | MS 535, 537 | CDCl3: 1.17(t, 3H), 1.71-1.79(m, 1H), 2.28(s, 3H), 2.62(d, 3H), 3.41(q, 2H), 3.46(t, 2H), 3.79(q, 2H), 4.41-4.48(m, 1H), 6.43(a, 1H), 6.10-6.18(m, 2H), 7.15(dd, 1H), 7.33(d, 1H), 7.35-7.42(m, 1H), 7.90(dd, 1H), 8.16(s, 1H), 8.45(d, 1H), 9.07(s, 1H). |
| 3-52 | 4-chloro-2-methyl-anisole | Rf | CDCl3: 2.66(d, 3H), 3.91(s, 3H), 4.41-4.47(m, 1H), 6.80(d, 1H), 6.92(dd, 1H), 7.26-7.35(m, 1H), 7.54(s, 1H), 7.76(dd, 1H), 8.00(dd, 1H), 8.27-8.32(m, 2H), 8.38(dd, 1H), 8.97(s, 1H). |
| 3-53 | 2,3-dimethyl-N,N-dimethylaniline | MS 491, 493 | CDCl₃: 2.26(s, 3H), 2.62(d, 3H), 2.68(s, 6H), 4.72(q, 1H), 6.78(s, 1H), 6.89(dd, 1H), 7.12(d, 1H), 7.15(d, 1H), 7.40-7.47(m, 2H), 7.91(dd, 1H), 8.40(s, 1H), 8.41(dd, 1H), 9.11(s, 1H). |
| 3-54 | 3,4-dimethyl-4'-pyridyl biphenyl | MS 525, 527 | CDCl₃: 2.04(s, 3H), 2.65(d, 3H), 4.42-4.48(m, 1H), 6.79(s, 1H), 6.96-7.00(m, 2H), 7.28-7.34(m, 4H), 7.87-7.91(m, 1H), 8.18(s, 1H), 8.23-8.26(m, 2H), 8.53(d, 2H), 9.07(s, 1H). |
| 3-55 | 2-methyl-1,4-diethoxybenzene | Rf (Hexane:AcOEt = 3:1) 0.19 | CDCl₃: 1.34(t, 3H), 1.44(t, 3H), 2.63(d, 3H), 3.81(q, 2H), 4.06(q, 2H), 4.46(q, 1H), 6.43(dd, 1H), 6.76(d, 1H), 7.63-7.69(m, 2H), 7.94(d, 1H), 7.98(dd, 1H), 8.42(d, 1H), 8.93(s, 1H). |

-continued

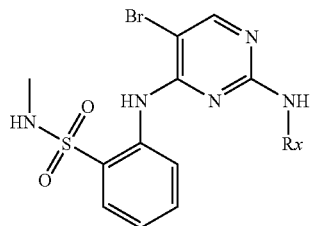

| ExplNo. | Rx | Rf (solvent) or MS | ¹H-NMR (400 MHz), δ (ppm) |
|---|---|---|---|
| 3-56 | | MS 570, 572 | CDCl₃: 2.63(d, 3H), 3.85(s, 3H), 3.93(s, 3H), 4.52 (q, 1H), 6.78-6.83(m, 2H), 6.93(d, 2H), 6390-7.02 (m, 1H), 7.11-7.15(m, 1H), 7.21-7.27(m, 1H), 7.61 (s, 1H), 7.87-7.92(m, 1H), 8.26(s, 1H), 8.20-8.30(m, 1H), 8.38-8.41(m, 1H), 8.92(s, 1H). |
| 3-57 | | Rf (Hexane: AcOEt = 3:1) 0.16 | CDCl₃: 1.44(t, 3H), 2.65(d, 3H), 2.79-2.89(m, 4H), 3.65-3.74(m, 4H), 4.07(q, 2H), 4.52(q, 4H), 6.48 (dd, 1H), 6.80(d, 1H), 7.20-7.25(m, 1H), 7.55-7.67 (m, 2H), 7.92-7.98(m, 2H), 8.29(s, 1H), 8.43(d, 1H), 8.95(s, 1H). |
| 3-58 | | Rf 0.17 (Hexane/AcOEt = 1/1) | CDCl₃: 1.46(t, 3H), 2.63(d, 3H), 3.08-3.13(m, 4H), 3.83-3.90(m, 4H), 4.09(q, 2H), 4.46(q, 1H), 6.39 (dd, 1H), 6.51(d, 1H), 7.21-7.28(m, 1H), 7.37(s, 1H), 7.58(dd, 1H), 7.97(dd, 1H), 8.03(d, 1H), 8.21(s, 1H), 8.46(d, 1H), 8.94(s, 1H). |
| 3-59 | | MS 538, 540 | CDCl₃: 2.63(d, 3H), 3.44(s, 3H), 3.65(s, 3H), 3.69-3.73(m, 2H), 4.10-4.15(m, 2H), 4.40(q, 1H), 6.45 (dd, 1H), 6.85 Cd, 1H), 7.19-7.25(m, 1H), 7.61(dd, 1H), 7.88(s, 1H), 7.93-7.97(m, 2H), 8.27(s, 1H), 8.46(d, 1H), 8.95(s, 1H). |
| 3-60 | | Rf (AcOEt) 0.54 | CDCl₃: 2.63(d, 3H), 3.67(s, 3H), 4.18(t, 2H), 4.38-4.49(m, 3H), 6.46(dd, 1H), 6.81(d, 1H), 7.60-7.69 (m, 2H), 7.92-7.99(m, 2H), 8.27(s, 1H), 8.49(d, 1H), 9.00(s, 1H). |
| 3-61 | | Rf (Hexane: AcOEt = 2:1) 0.46 | (Hexane: CDCl₃: 1.44(t, 3H), 2.63(d, 3H), 3.64(s, 3H), 4.07(q, 2H), 4.47(q, 1H), 6.45(dd, 1H), 6.78(d, 1H), 7.21-7.28(m, 1H), 7.40-7.48(m, 2H), 7.93-7.99(m, 2H), 8.26(s, 1H), 8.44(d, 1H), 8.96(s, 1H). |

-continued

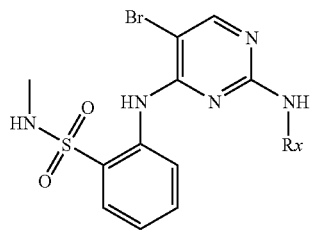

| ExplNo. | Rx | Rf (solvent) or MS | $^1$H-NMR (400 MHz), δ (ppm) |
|---|---|---|---|
| 3-62 | | Rf (Hexane:AcOEt = 3:1) 0.31 | CDCl$_3$: 1.36(d, 6H), 2.63(d, 3H), 3.63(s, 3H), 4.41-4.52(m, 2H), 6.45(dd, 1H), 6.81(d, 1H), 7.21-7.26 (m, 1H), 7.59-7.68(m, 2H), 7.91-7.98(m, 2H), 8.26 (s, 1H), 8.45(d, 1H), 8.96(s, 1H). |
| 3-63 | | Rf (Hexane:AcOEt = 3:1) 0.40 | CDCl$_3$: 1.07(t, 3H), 1.84(m, 2H), 6.63(d, 3H), 3.64 (s, 3H), 3.96(t, 2H), 4.40-4.49(m, 1H), 6.46(dd, 1H), 6.79(d, 1H), 7.20-7.27(m, 1H), 7.58-7.66(m, 2H), 7.94-7.97(m, 2H), 8.26(s, 1H), 8.45(d, 1H), 8.97(s, 1H). |
| 3-64 | | Rf (Hexane:AcOEt = 3:1) 0.19 | CDCl$_3$: 2.62(d, 3H), 6.68(s, 6H), 3.84(s, 3H), 4.41-4.48(m, 1H), 6.36(dd, 1H), 6.80(d, 1H), 7.17-7.24 (m, 1H), 7.51-7.62(m, 2H), 7.83(s, 1H), 7.95(dd, 1H), 8.27(s, 1H), 8.3*9-8.45(m, 1H), 8.91(s, 1H). |
| 3-65 | | Rf (Hexane:AcOEt = 1:1) 0.12 | CDCl$_3$: 2.66(d, 3H), 3.97(s, 3H), 4.47-4.55(m, 1H), 6.96-7.10(m, 3H), 7.21-7.24(m, 1H), 7.66(s, 1H), 7.93(dd, 1H), 8.25(d, 1H), 8.31(s, 1H), 8.47(d, 2H), 8.59(s, 1H), 8.96(s, 1H). |
| 3-66 | | MS 541, 543 | CDCl$_3$: 2.65(d, 3H), 3.96(s, 3H), 4.61-4.71(m, 1H), 6.89-7.05(m, 3H), 7.16(dd, 1H), 7.15-7.23(m, 1H), 7.60(d, 1H), 7.65(s, 1H), 7.89(d, 1H), 8.21(d, 1H), 8.28(d, 1H), 8.51(br. s, 2H), 8.57(s, 1H), 8.93(s, 1H). |
| 3-67 | | MS 541, 543 | CDCl$_3$: 2.65(d, 3H), 3.96(s, 3H), 4.51(q, 1H), 6.90-7.06(m, 3H), 7.11-7.16(m, 1H), 7.38(d, 1H), 7.50-7.61(m, 2H), 7.62-7.67(m, 1H), 7.89(dd, 1H), 8.29 (s, 1H), 8.34(d, 1H), 8.53(d, 1 H), 8.79(br.s, 1H), 8.94(s, 1H). |

-continued
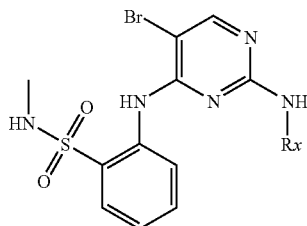
| ExplNo. | Rx | Rf (solvent) or MS | $^1$H-NMR (400 MHz), δ (ppm) |
|---|---|---|---|
| 3-68 | 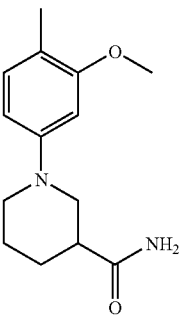 | LC-MS 590 | CDCl$_3$: 1.45-1.59(m, 2H), 1.70-1.78(m, 1H), 1.82-1.90(m, 1H), 2.38-2.50(m, 1H), 2.43(s, 3H), 2.62-2.77(m, 2H), 3.56-3.70(m, 2H), 3.76(s, 3H), 6.46 (dd, 1H), 6.63(d, 1H), 6.82-6.88(br, 1H), 7.22(dd, 1H), 7.31-7.40(m, 2H), 7.43-7.51(m, 1H), 7.50-7.80 (m, 2H), 8.14-8.20 Cbr, 1 H), 8.21(s, 1H), 8.39-8.48 (m, 1H), 9.16-9.26(br, 1) |
| 3-69 | 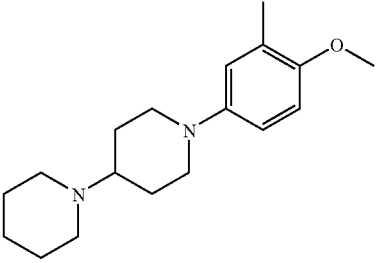 | 0.34 (CH2Cl2: MeOH = 9:1) | CDCl$_3$: 1.58-1.82(br, 7H), 1.88-2.03(br, 3H), 2.44-2.45(m, 5H), 3.42-3.52(m, 3H), 3.75(s, 3H), 6.66(dd, 1H), 6.92(d, 1H), 7.28(dd, 1H), 7.44(br, 1H), 7.51 (dd, 1H), 7.79-7.81(m, 2H), 8.18(s, 1H), 8.32(s, 1H), 8.35-8.37(m, 1H), 9.17(s, 1H) |
| 3-70 | 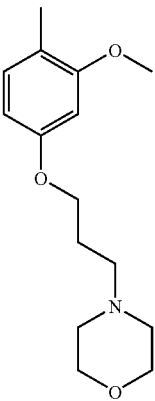 | Ms: 607, 609 | DMSO-d6: 1.84-1.92(m, 2H), 2.34-2.41(m, 4H), 2.41-2.45(m, 3H), 2.44(t, 2H), 3.58(t, 4H), 3.75(s, 3H), 4.02(t, 2H), 6.48(dd, 1H), 6.63(d, 1H), 7.21(dd, 1H), 7.41(d, 1H), 7.46(dd, 1H), 7.72-7.78(m, 1H), 7.76(dd, 1H), 8.22(s, 1H), 8.25(s, 1H), 8.40(d, 1H), 9.22(s, 1H) |

-continued
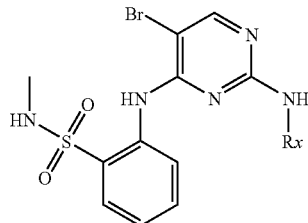
| ExplNo. | Rx | Rf (solvent) or MS | $^1$H-NMR (400 MHz), δ (ppm) |
|---|---|---|---|
| 3-71 | | Ms: 591, 593 | DMSO-d6: 1.84-1.92(m, 2H), 2.14(s, 3H), 2.35-2.4 (m, 4H), 2.43(t, 2H), 2.44(d, 3H), 3.58(t, 4H), 4.01(t, 2H), 6.77(dd, 1H), 6.82(d, 1H), 7.17(dd, 1H), 7.20(d, 1H), 7.3-7.39(m, 1H), 7.71-7.77(m, 2H), 8.2(s, 1H), 8.35-8.44(m, 1H), 8.71(s, 1H), 9.27(s, 1H) |
| 3-72 | | Ms: 620, 622 | DMSO-d6: 1.82-1.9(m, 2H), 2.13-2.17(m, 3H), 2.25-2.47(m, 13H), 3.75(s, 3H), 4.01(t, 2H), 6.47(dd, 1H), 6.63(d, 1H), 7.19-7.24(m, 1H), 7.41(d, 1H), 7.43-7.5(m, 1H), 7.70-7.79(m, 2H), 8.22(s, 1H), 8.25(brs, 1H), 8.37-8.44(m, 1H), 9.22(s, 1H) |
| 3-73 | | Ms: 607, 609 | DMSO-d6: 1.78(t, 2H), 2.32-2.36(m, 4H9, 2.35-2.38 (m, 3H), 3.54-3.59(m, 4H), 3.74(t, 3H), 3.78(s, 3H), 6.38-6.42(m, 1H), 6.85(d, 1H), 6.86-6.95(m, 1H), 7.33-7.43(m, 2H), 7.63-7.68(m, 1H), 7.85-8.15(m, 3H), 8.64-8.8(m, 1H). |

-continued
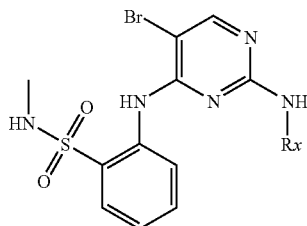
| ExplNo. | Rx | Rf (solvent) or MS | $^1$H-NMR (400 MHz), δ (ppm) |
|---|---|---|---|
| 3-74 | | Ms: 605, 607 | DMSO-d6: 1.47-1.67(m, 2H), 1.84-2.01(m, 2H), 2.03 (s, 3H), 2.41-2.46(m, 3H), 3.23-3.39(m, 2H), 3.65-3.73(m, 1H), 3.81(s, 3H), 3.8-3.88(m, 1H), 4.58-4.65 (m, 1H), 6.55(dd, 1H), 6.68(d, 1H), 7.2-7.26(m, 1H), 7.43(d, 1H), 7.42-7.51(m, 1H), 7.7-7.8(m, 2H), 8.23 (s, 1H), 8.26(brs, 1H), 8.37-8.44(m, 1H), 922(brs, 1H) |
| 3-75 | | Ms: 605, 607 | DMSO-d6: 1.38-1.6(m, 2H), 1.74-1.9(m, 2H), 2.0(s, 3H), 2.42-2.47(m, 3H), 3.12-3.3(m, 2H), 3.55-3.65 (m, 1H), 3.7-3.8(m, 1H), 3.78(s, 3H), 4.27-4.34(m, 1H), 6.65(dd, 1H), 6.94(d, 1H), 7.24-7.3(m, 1H), 7.53-7.63(m, 2H), 7.74-7.83(m, 2H), 8.09(brs, 1H), 8.35(s, 1H), 8.38(d, 1H), 9.19(brs, 1H) |
| 3-76 | | Ms: 577, 579 | DMSO-d6: 1.51-1.61(m, 2H), 1.79-1.87(m, 2H), 2.03-2.11(m, 2H), 2.14(s, 3H), 2.42-2.47(m, 3H), 2.52-2.6(m, 2H), 3.77(s, 3H), 4.02-4.09(m, 1H), 6.6 (dd, 1H), 6.92(d, 1H), 7.24-7.3(m, 1H), 7.52-7.6(m, 2H), 7.74-7.82(m, 2H), 8.08(brs, 1H), 8.34(s, 1H), 8.4(d, 1H), 9.2(brs, 1H) |
| 3-77 | | Rf: 0.4 (n-hexane: AcOEt = 7:3) | DMSO-d6: 2.41-2.45(m, 3H), 6.89-6.96(m, 1H), 6.69(bs, 1H), 7.24-7.33(m, 2H), 7.51-7.57(m, 1H), 7.63-7.7(m, 1H), 7.73-7.78(m, 1H), 7.79(dd, 1H), 8.37(s, 1H), 8.41(d, 1H), 9.21(brs, 1H), 9.24(brs, 1H) |

-continued
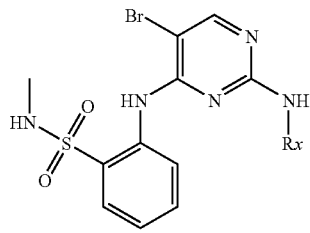
| ExplNo. | Rx | Rf (solvent) or MS | ¹H-NMR (400 MHz), δ (ppm) |
|---|---|---|---|
| 3-78 | | Ms: 563, 565 | DMSO-d6: 1.33-1.43(m, 2H), 1.79-1.86(m, 2H), 2.43-2.46(m, 3H), 2.46-2.53(m, 2H), 2.87-2.94(m, 2H), 3.77(s, 3H), 4.07-4.14(m, 1H), 6.59(dd, 1H), 6.91(d, 1H), 7.23-7.28(m, 1H), 7.53-7.59(m, 2H), 7.79(dd, 1H), 8.03(brs, 1H), 8.32(s, 1H), 8.38(d, 1H), 8.7-9.5(brs, 1H) |
| 3-79 | | Ms: 563, 565 | DMSO-d6: 1.41-1.51(m, 2H), 1.88-1.95(m, 2H), 2.41-2.45(m, 3H), 2.54-2.63(m, 2H), 2.92-3.0(m, 2H), 3.75(s, 3H), 4.35-4.43(m, 1H), 6.50(dd, 1H), 6.63(d, 1H), 7.18-7.23(m, 1H), 7.40(d, 1H), 7.42-7.48(m, 1H), 7.75(dd, 1H), 8.21(s, 1H), 8.22-8.25(m, 1H), 8.37-8.42(m, 1H), 8.9-9.5(brs, 1H) |
| 3-80 | | Ms: 482, 484 | DMSO-d6: 2.4-2.46(m, 3H), 3.79(s, 3H), 6.72(ddd, 1H), 6.99(dd, 1H), 7.21-7.26(m, 1H), 7.47-7.53(m, 1H), 7.59-7.64(m, 1H), 7.76(dd, 1H), 8.25(s, 1H), 8.29-8.37(m, 2H), 8.8-9.6(m, 1H) |
| 3-81 | | Ms: 482, 484 | DMSO-d6: 2.41-2.49(m, 3H), 3.82(s, 3H), 6.80(ddd, 1H), 7.01(dd, 1H), 7.3-7.35(m, 1H), 7.56-7.63(m, 1H), 7.7-7.8(m, 1H), 7.82(dd, 1H), 7.85(dd, 1H), 8.16(s, 1H), 8.35(dd, 1H), 9.18(brs, 1H) |
| 3-82 | | Ms: 563, 565 | DMSO-d6: 1.73-1.82(m, 1H), 2.23-2.34(m, 4H), 2.34-2.42(m, 3H), 2.42-2.46(m, 3H), 2.59(dd, 1H), 2.62-2.68(m, 1H), 2.80(dd, 1H), 3.75(s, 1H), 4.85-4.91(m, 1H), 6.42(dd, 1H), 6.57(d, 1H), 7.19-7.24(m, 1H), 7.41(d, 1H), 7.43-7.51(m, 1H), 7.68-7.79(m, 2H), 8.22(s, 1H), 8.23(s, 1H), 8.37-8.43(m, 1H), 9.21(brs, 1H). |

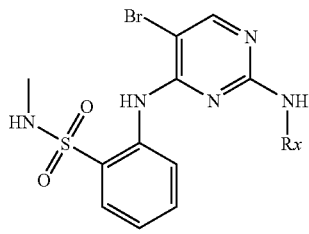

| ExplNo. | Rx | Rf (solvent) or MS | $^1$H-NMR (400 MHz), δ (ppm) |
|---|---|---|---|
| 3-83 | (2-methyl-1-(4-methyl-3-methoxyphenyl)imidazole) | MS 544, 546 | 2.36(s, 3H), 2.65(d, 3H), 3.93(s, 3H), 4.46-4.51(m, 1H), 6.75-6.80(m, 2H), 6.97-7.04(m, 2h), 7.25-7.30 (m, 1H), 7.56-7.66(m, 2H), 7.98(dd, 1H), 8.29(s, 1H), 8.36-8.44(m, 2H), 9.01(s, 1H). |
| 3-84 | (4-(4-methylpiperazin-1-yl)-2-methyl-1-methoxyphenyl) | MS 562, 564 | CDCl3: 2.32(s, 3H), 2.39-2.47(m, 4H), 2.64(d, 3H), 2.89-2.97(m, 4H), 3.85(s, 3H), 4.54-4.52(m, 1H), 6.52(dd, 1H), 6.79(d, 1H), 7.22(m, 1H), 7.52-7.64 (m, 2H), 7.94-7.99(m, 2H), 8.25(s, 1H), 8.42(d, 1H), 8.93(s, 1H). |

Example 4

2-[5-Bromo-2-(subst. phenylamino)-pyrimidin-4-ylamino]-N-propyl-benzenesulfonamides These compounds are prepared in analogy to Example 2 using 2-(5-bromo-2-chloro-pyrimidin-4-ylamino)-N-propyl-benzenesulfonamide and the corresponding aniline to give compounds No. 4-1 to 4-31 having the substituent Rx as listed under Example 3 for compounds No. 3-1 to 3-31.

Preparation of 2-(5-bromo-2-chloro-pyrimidin-4-ylamino)-N-propyl-benzenesulfonamide To a solution of 5-bromo-2,4-dichloropyrimidine (90 μL, 0.70 mmol) and 2-amino-N-propyl-benzenesulfonamide (100 mg, 0.47 mmol), sodium hydride (54.2 mg, 0.56 mmol) in DMSO (1.0 mL) is added and the resulting solution is stirred at 80° C. for 3.0 h. The mixture is poured into water and extracted with ethyl acetate three times. The organic layer is washed with water and then brine, dried over sodium sulfate, and evaporated in vacuo. The residue is purified with silica gel column chromatography (n-hexane:ethyl acetate=5: 1) to afford the title compound as a slightly yellow solid.

$^1$H-NMR (δ, ppm): 0.89 (t, 3H), 1.41 (q, 2H), 3.56 (t, 2H), 4.92 (br.s, 2H), 6.71 (dd, 1H), 6.77 (dd, 1H), 7.33 (dd, 1H), 7.54 (dd, 1H), 8.79 (s, 1H)

Rf (hexane:ethyl acetate=1:1): 0.64.

Example 5

2-[5-Trifluoromethyl-2-(subst. phenylamino)-pyrimidin-4-ylamino]-N-methyl-benzenesulfonamides These compounds are prepared in analogy to Example 2 using 2-(2-chloro-5-trifluoromethyl-pyrimidin-4-ylamino)-N-methyl-benzenesulfonamide and the corresponding aniline to give compounds No. 5-1 to 5-31 having the substituent Rx as listed under Example 3 for compounds No. 3-1 to 3-31.

Preparation of 2-(2-chloro-5-trifluoromethyl-pyrimidin-4-ylamino)-N-methyl-benzenesulfonamide To a solution of 2,4-dichloro-5-trifluoromethyl-pyrimidine (386 mg, 1.79 mmol) in acetonitrile (10 mL), 2-amino-N-methyl-benzenesulfonamide (333 mg, 1.79 mmol) and 1,8-diaza[5.4.0]-bicyclo-7-undecene (280 μL, 1.88 mmol) are added successively at ambient temperature. After stirring for 15 h at room temperature, dichloromethane (30 mL) is added to the mixture, and the solution is washed with saturated aqueous sodium hydrogen carbonate and saturated aqueous sodium chloride, dried over magnesium sulfate, and evaporated in vacuo. The resulting solid is purified by flash chromatography.

$^1$H NMR (CDCl$_3$) δ: 3.73(s, 3H), 6.67-6.69(m, 1H), 6.72-6.73(m, 1H), 7.27-7.31(m, 1H), 7.78 (dd, 1H), 8.60(s, 1H). Rf (hexane:ethyl acetate=1:1): 0.28.

Example 6

2-[5-Bromo-2-(2,3-[difluoromethylenedioxy]phenylamino)-pyrimidin-4-ylamino]-benzenesulonamide

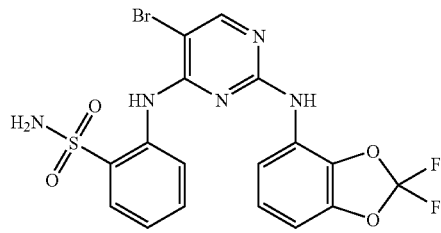

This compound is obtained as a side product formed by N-demethylation on reaction of 2-(5-bromo-2-chloropyrimidin-4-ylamino)-N-methyl-benzenesulfonamide with 2,3-(difluoromethylenedioxy)aniline following the procedure of Example 2. It may also be prepared by reaction of 2-(5-bromo-2-chloropyrimidin-4-ylamino)benzenesulfonamide with 2,3-(difluoromethylenedioxy)aniline.

Rf (n-hexane:ethyl acetate=1:1): 0.46.

$^1$H-NMR: (CDCl$_3$) 4.83 (bs, 2H), 6.77 (dd, 1H), 6.86 (s, 1H), 6.97 (dd, 1H), 7.31-7.24 (m, 1H), 7.57 (dd, 1H), 7.81 (d, 1H), 8.02 (dd, 1H), 8.28 (d, 1H), 8.29 (s, 1H), 8.88 (s, 1H).

Preparation of 2-(5-bromo-2-chloropyrimidin-4-ylamino)benzenesulfonamide: To a solution of 5-bromo-2,4-dichloropyrimidine (300 mg, 1.32 mmol) and 2-amino-benzenesulfonamide (340 mg, 1.97 mmol) in 2-propanol (3 mL), concentrated hydrochloric acid (0.06 mL) is added and the mixture is stirred at 90° C. for 4.5 hours. The mixture is poured into aqueous sodium hydrogen carbonate and extracted with ethyl acetate three times. The organic layer is washed with water, dried over sodium sulfate, and evaporated in vacuo. The residue is purified by column chromatography (hexane:ethyl acetate=2:1) to afford the title compound.

Rf (hexane:ethyl acetate=1:1): 0.55. $^1$H-NMR (400 MHz, CDCl3) δ: 4.78 (br.s, 2H), 7.22 (dd, 1H), 7.61 (ddd, 1H), 7.95 (dd, 1H), 8.35 (s, 1H), 8.35 (d, 1H), 9.18 (s, 1H).

Example 7A

2-[5-Chloro-2-(2-methoxy-4-morpholin-4-yl-phenylamino)-pyrimidin-4-ylamino]-N-methyl-benzamide

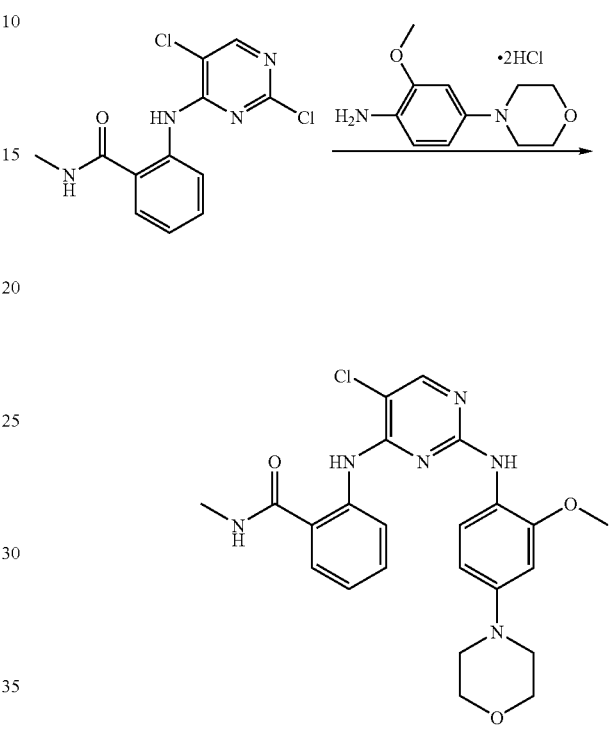

To a suspension of 2-(2,5-dichloro-pyrimidin-4-ylamino)-N-methyl-benzamide (5.05 g, 17.0 mmol) in 90 mL of 2-methoxyethanol are added 2-methoxy-4-morpholinoaniline dihydrochloride (4.56 g, 16.2 mmol) and 17.0 mL of 1N ethanolic solution of hydrogen chloride (17.0 mmol). After the reaction mixture is stirred at 110° C. for 4 hours and cooled to room temperature, the mixture is neutralized with 1N aqueous NaOH solution and extracted with EtOAc (100 mL×3). The organic layer is washed with brine, dried over Na$_2$SO$_4$ and concentrated under reduced pressure. The resulting black solid is washed with EtOH (90 mL), then purified with silica gel column chromatography (CH$_2$Cl$_2$ to CH$_2$Cl$_2$:AcOEt=1:2) to give 2-[5-chloro-2-(2-methoxy-4-morpholin-4-yl-phenylamino)-pyrimidin-4-ylamino]-N-methyl-benzamide as a pale yellow solid.

$^1$H-NMR (400 MHz, DMSO-d6,δ): 2.80 (d, 3H, J=4.52 Hz), 3.10-3.20 (m, 4H), 3.78 (s, 3H), 3.70-3.80 (m, 4H), 6.49 (dd, 1H, J=8.56, 2.52 Hz), 6.66 (d, 1H, J=2.52 Hz), 7.08 (dd, 1H, J=8.04, 8.04 Hz), 7.44 (d, 1H, J=8.56 Hz), 7.71 (dd, 1H, J=8.04, 1.48 Hz), 8.10 (s, 1H), 8.13 (s, 1H), 8.59 (d, 1H, J=8.04 Hz) 8.68-8.75 (m, 1H), 11.59 (S, 1H). MS m/z 469, 471 (M+1)$^+$.

The following 2-[5-Chloro-2-(substituted phenylamino)-pyrimidin-4-ylamino]-N-methyl-benzamide are prepared from 2-(2,5-Dichloro-pyrimidin-4-ylamino)-N-methyl-benzamide and the corresponding aniline following the procedure of Example 7A.

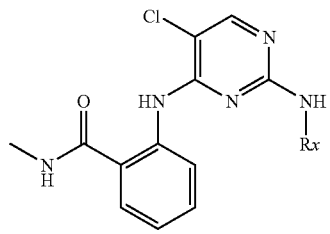
| Expl No. | Rx | Rf (solvent) or MS | NMR (400 MHz), δ (ppm) |
|---|---|---|---|
| 7-1 | | MS: m/z 550, 552 (M + 1) | DMSO-d6: 1.44-1.33(m, 2H), 1.64-1.45(m, 6H), 1.73-1.89(m, 2H), 2.34-2.44(m, 1H), 2.43-2.55(m, 4H), 2.55(t, 2H), 2.80(d, 3H), 3.75(s, 3H), 3.72-3.75 (m, 2H), 6.48(dd, 1H), 6.62(d, 1H), 7.06(dd, 1H), 7.32(dd, 1H), 7.39(d, 1H), 7.71(dd, 1H), 8.09(s, 1H), 8.60(d, 1H), 8.70(d, 1H), 11.58(s, 1H) |
| 7-2 | | 0.3 (MeOH: AcOEt = 5:95) | CDCl₃: 1.70-1.97(m, 4H), 2.62-2.79(m, 1H), 3.04(d, 3H), 3.02-3.18(m, 2H), 3.23-3.33(m, 2H), 3.88(s, 3H), 5.39-5.47(m, 1H), 6.15-6.24(m, 1H), 6.55-6.62(m, 2H), 6.74-6.82(m 1H), 7.09(dd, 1H), 7.23-7.32(m, 1H), 7.46-7.52(m, 2H), 8.09(s, 1H), 8.15(d, 1H), 8.68(d, 1H) 11.0(bs, 1 |
| 7-3 | | MS (ESI) m/z 482, 484 (M + 1)⁺ | DMSO-d6: 2.24(s, 3H), 2.45-2.55(m, 4H), 2.80(d, 3H, J=4.52 Hz), 3.12-3.17(m, 4H), 3.76(s, 3H), 6.48 (dd, 1H, J=8.56, 2.52 Hz), 6.63(d, 1H, J=2.52 Hz), 7.05-7.10(m, 1H), 7.27-7.35(m, 1H), 7.40(d, 1H, J= 8.56 Hz), 7.69-7.72(m, 1H), 8.09(S, 1H), 8.12(s, 1H), 8.55-8.65(m, 1H), 8.67-8.75(m, 1H), 11.59(s, 1H) |

-continued

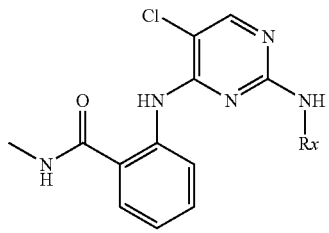

| Expl No. | Rx | Rf (solvent) or MS | NMR (400 MHz), δ (ppm) |
|---|---|---|---|
| 7-4 | (4-methyl-3-methoxyphenyl ether with 2-morpholinoethyl) | 0.46 (MeOH: CH₂Cl₂ = 1:4) | DMSO-d6: 2.48-2.55(m, 4H), 2.71(t, 2H), 2.80(d, 3H), 3.58-3.61(m, 4H), 3.76(s, 3H), 4.11(t, 2H), 6.52(dd, 1H), 6.66(d, 1H), 7.06(dd, 1H), 7.32(dd, 1H), 7.46(d, 1H), 7.71(dd, 1H), 8.11(s, 1H), 8.19(s, 1H), 8.54-8.60(m, 1H), 8.60-8.75(m, 1H), 11.6(s, 1H) |
| 7-5 | (4-methyl-3-methoxyphenyl ether with 1-methylpiperidin-4-yl) | m/z 497, 499 (M + 1)⁺ | DMSO-d6: 1.60-1.70(m, 2H), 1.90-1.98(m, 2H), 2.13-2.25(m, 2H), 2.19(s, 3H), 2.60-2.67(m, 2H), 2.80(d, 3H, J=4.52 Hz), 3.75(s, 3H), 4.30-4.40(m, 1H), 6.54(dd, 1H, J=8.56, 2.0 Hz), 6.65(d, 1H, J= 2.0 Hz), 7.04-7.09(m, 1H), 7.25-7.35(m, 1H), 7.43(d, 1H, J=8.56 Hz), 7.68-7.73(m, 1H), 8.10(s, 1H), 8.18 (s, 1H) 8.52-8.59(m, 1H), 8.68-8.75(m, 1H), 11.57(s, 1H) |
| 7-6 | (3-methyl-4-methoxyphenyl with morpholine) | 0.25 (n-hexane: AcOEt = 1:2) | CDCl₃: 2.95(m, 4H), 3.03(d, 3H), 3.75(m, 4H), 3.86 (s, 3H), 6.21-6.19(br, 1H), 6.49(dd, 1H), 6.50(d, 1H), 7.09-7.05(m, 1H), 7.50(dd, 1H), 8.08(d, 1H), 8.13 (s, 1H), 8.68(d, 1H), 11.07(s, 1H) |
| 7-7 | (4-methyl-3-methoxyphenyl with N-acetylpiperazine) | MS m/z 510, 512 (M + 1) | DMSO-d6: 2.06(s, 3H), 2.80(d, 3H), 3.11(t, 2H), 3.16(t, 2H), 3.60(dd, 4H), 3.77(s, 3H), 6.51(dd, 1H), 6.68(d, 1H), 7.08(dd, 1H), 7.33(dd, 1H), 7.46(d, 1H), 7.71(d, 1H), 8.10(s, 1H), 8.12(s, 1H), 8.59-8.61 (m, 1H), 8.70-8.71(m, 1H), 11.59(s, 1H) |

-continued

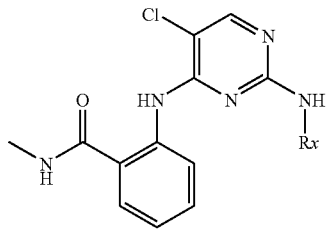

| Expl No. | Rx | Rf (solvent) or MS | NMR (400 MHz), δ (ppm) |
|---|---|---|---|
| 7-8 | (4-methyl-3-methoxyphenyl)-piperidin-4-ol | 0.48 (MeOH: AcOEt = 5:95) | CDCl₃: 1.46(d, 1H), 1.68-1.82(m, 2H), 2.02-2.09(m, 2H), 2.83-2.96(m, 2H), 3.03(d, 3H), 3.44-3.53(m, 2H), 3.82-3.92(m, 1H), 3.87(s, 3H), 6.15-6.23(m, 1H), 6.51 (d, 1H), 6.56(bs, 1H), 7.07(dd, 1H), 7.48(d, 2H), 8.08(s, 1H), 8.08-8.10(m, 1H), 8.69(d, 1H), 11.0(bs, 1H) |
| 7-9 | (4-methyl-3-methoxyphenyl)-4-(2-ethoxyethoxy)piperidine | 0.4 (n-hexane: AcOEt = 1:1) | CDCl₃: 1.22(t, 3H), 1.73-1.85(m, 2H), 2.00-2.09(m, 2H), 2.81-2.90(m, 2H), 3.03(d, 3H), 3.41-3.56(m, 3H), 3.56(dd, 2H), 3.58-3.62(m, 2H), 3.64-3.68(m, 2H), 3.86(s, 3H), 6.15-6.24(m, 1H), 6.50(dd, 1H), 6.56(d, 1H), 7.07(dd, 1H), 7.24-7.30(m, 1H), 7.45-7.52(m, 2H), 8.08(s, 1H), 8.06-8.08(m, 1H), 8.69(d, 1H), 11.0(bs, 1H) |
| 7-10 | (4-methyl-3-methoxyphenyl)-4-(2-methoxyethoxy)piperidine | 0.4 (n-hexane: AcOEt = 1:1) | CDCl₃: 1.73-1.85(m, 2H), 2.01-2.10(m, 2H), 2.82-2.90(m, 2H), 3.03(d, 3H), 3.41(s, 3H), 3.45-3.51(m, 2H), 3.56-3.58(m, 2H), 3.65-3.68(m, 2H), 3.86(s, 3H), 6.14-6.22(m, 1H), 6.50(dd, 1H), 6.56(d, 1H), 7.07(dd, 1H), 7.23-7.30(m, 1H), 7.44-7.52(m, 2H), 8.08(s, 1H), 8.06-8.08(m, 1H), 8.69(d, 1H), 11.0(bs, 1H) |
| 7-11 | (4-methyl-3-methoxyphenyl)-3-(dimethylamino)pyrrolidine | 0.54 (MeOH: CH₂Cl₂ = 1:4) | DMSO-d6: 1.78-1.89(m, 1H), 2.13-2.22(m, 1H), 2.22(s, 6H), 2.77-2.87(m, 1H), 2.79(d, 3H), 3.04-3.10(m, 1H), 3.23-3.50(m, 3H), 3.75(s, 3H), 6.11(dd, 1H), 6.22(d, 1H), 7.05(dd1H), 7.21-7.32(m, 1H), 7.26(d, 1H), 7.70(d, 1H), 8.06(s, 1H), 8.08(s, 1H), 8.57-8.66(m, 1H), 8.66-8.73(m, 1H), 11.6(s, 1H) |

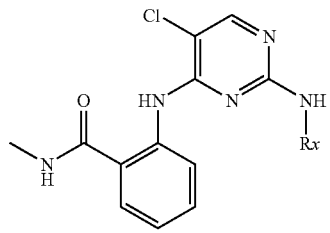
| Expl No. | Rx | Rf (solvent) or MS | NMR (400 MHz), δ (ppm) |
|---|---|---|---|
| 7-12 | | 0.27 (MeOH: CH$_2$Cl$_2$ = 1:1) | DMSO-d6: 1.77-1.87(m, 1H), 2.09-2.18(m, 1H), 2.35(s, 3H), 2.79(d, 1H), 3.02-3.07(m, 1H), 3.23-3.50(m, 4H), 3.74(s, 3H), 6.09(dd, 1H), 6.20(d, 1H), 7.04(dd, H), 7.22-7.32(m, 1H), 7.26(d, 1H), 7.70(d, 1H), 8.05(s, 1H), 8.08(s, 1H), 8.57-8.67(m, 1H), 8.67-8.73(m, 1H), 11.6(s, 1H) |
| 7-13 | | 0.23 (MeOH: AcOEt = 5:95) | CDCl$_3$: 1.62-1.74(m, 3H), 1.76-1.85(m, 2H), 2.00-2.09(m, 2H), 2.20-2.31(m, 1H), 2.64-2.69(m, 2H), 2.79(d, 3H), 3.56-4.04(m, 2H), 4.04(s, 3H), 6.49(dd, 1H), 6.63(d, 1H), 6.78(bs, 1H), 7.07(dd, 1H), 7.28-7.38(m, 1H), 7.39(d, 1H), 7.71(d, 1H), 8.09-8.11(m, 2H), 8.09(s, 1H), 8.60(d, 1H), 8.71(d, 1H), 11.6(bs, 1H) |
| 7-14 | | 0.30 (MeOH: CH$_2$Cl$_2$ = 4:1) | DMSO-d6: 1.61-1.46(m, 2H), 1.92-1.82(m, 2H), 2.14 (s, 3H), 2.41-2.23(m, 5H), 2.60-2.45(m, 4H), 2.67(t, 2H), 2.79(d, 3H), 3.75(s, 3H), 3.71-3.75(m, 2H), 6.48(dd, 1H), 6.63(d, 1H), 7.10-7.03(m, 1H), 7.34-7.27(m, 1H), 7.43-7.35(m, 1H), 7.71(dd, 1H), 8.09(s, 1H), 8.11(bs, 1H), 8.65-8.56(m, 1H), 8.75-8.67(m, 1H), 11.6(s, 1H) |

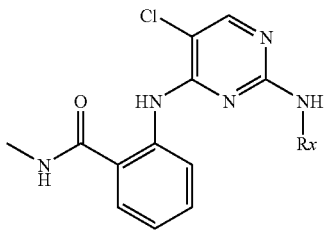
| Expl No. | Rx | Rf (solvent) or MS | NMR (400 MHz), δ (ppm) |
|---|---|---|---|
| 7-15 | | MS (ESI) m/z 524, 526 (M + 1)⁺ | DMSO-d6: 2.19-2.37(m, 4H), 2.65-2.85(m, 3H), 2.80(d, 3H, J=4.5 Hz), 3.15-3.21(m, 1H), 3.48-3.59 m, 2H), 3.61-3.67(m, 1H), 3.72-3.81(m, 1H), 3.76 (s, 3H), 6.47(dd, 1H, J=8.6, 2.5 Hz), 6.65(d, 1H, J= 2.5 Hz), 7.04-7.10(m, 1H), 7.28-7.35(m, 1H), 7.42(d, 1H, J=8.6 Hz), 7.69-7.74(m, 1H), 8.09(s, 1H), 8.12 (s, 1H), 8.55-8.63(m, 1H), 8.68-8.73(m, 1H), 11.60 (s, 1H) |
| 7-16 | | MS (ESI) m/z 524, 526 (M + 1)⁺ | DMSO-d6: 2.19-2.37(m, 4H), 2.65-2.85(m, 3H), 2.80 (d, 3H, J=4.5 Hz), 3.15-3.21(m, 1H), 3.48-3.59(m, 2H), 3.61-3.67(m, 1H), 3.72-3.81(m, 1H), 3.76(s, 3H), 6.47(dd, 1H, J=8.6, 2.5 Hz), 6.65(d, 1H, J= 2.5 Hz), 7.04-7.10(m, 1H), 7.28-7.35(m, 1H), 7.42(d, 1H, J=8.6 Hz), 7.69-7.74(m, 1H), 8.09(s, 1H), 8.12 (s, 1H), 8.55-8.63(m, 1H), 8.68-8.73(m, 1H), 11.60 (s, 1H) |
| 7-17 | | MS 510 | DMSO-d6: 0.98(t, 3H), 1.81-1.71(m, 3H), 1.95-1.84 (m, 3H), 2.68-2.63(m, 1H), 2.80(d, 3H), 3.12-3.08(m, 4H), 3.28(d, 2H), 3.76(s,3H), 6.50(dd, 1H), 6.64(d, 1H), 6.86(bs, 1H), 7.07(dd, 1H), 7.46-7.19(m, 3H), 7.71(d, 1H), 8.09(s, 1H), 8.15-8.10(m, 1H), 8.66-8.58(m, 1H), 8.77-8.70(m, 1H), 11.6(s, 1H) |
| 7-18 | | MS 510 | DMSO-d6: 0.98(t, 3H), 1.81-1.71(m, 3H), 1.95-1.84 (m, 3H), 2.68-2.63(m, 1H), 2.80(d, 3H), 3.12-3.08(m, 4H), 3.28(d, 2H), 3.76(s,3H), 6.50(dd, 1H), 6.64(d, 1H), 6.86(bs, 1H), 7.07(dd, 1H), 7.46-7.19(m, 3H), 7.71(d, 1H), 8.09(s, 1H), 8.15-8.10(m, 1H), 8.66-8.58(m, 1H), 8.77-8.70(m, 1H), 11.6(s, 1H) |

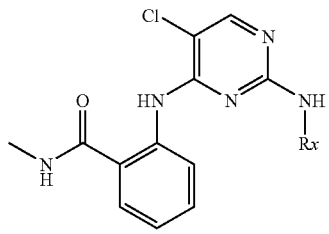

| Expl No. | Rx | Rf (solvent) or MS | NMR (400 MHz), δ (ppm) |
|---|---|---|---|
| 7-19 | (4-methoxy-3-methylphenyl)-piperidin-1-yl-4-methylpiperazine | 0.16 (CH2Cl2:MeOH = 9:1) | 1.40-1.53(m, 2H), 1.72-1.80(m, 2H), 2.18(s, 3H), 2.19-2.44(m, 5H), 2.80(d, 3H), 3.46(m, 2H), 3.74(s, 3H), 6.65(dd, 1H), 6.91(d, 1H), 7.07-7.10(m, 1H), 7.36-7.40(m, 1H), 7.45-7.49(m, 1H), 7.73(dd, 1H), 8.12(s, 1H), 8.18(S, 1H), 8.61(d, 1H), 8.72-8.77(m, 1H), 11.68(s, 1H) |
| 7-20 | (1-methylpiperidin-4-yl)methoxy-3-methoxy-4-methylphenyl | Ms: 511 | 1.25-1.37(m, 2H), 1.62-1.79(m, 3H), 1.81-1.9(m, 2H), 2.16(s, 3H), 2.75-2.85(m, 5H), 3.76(s, 3H), 3.8-3.88(m, 2H), 6.45-6.55(m, 1H), 6.6-6.67(m, 1H), 7.02-7.12(m, 1H), 7.25-7.35(m, 1H), 7.4-7.5(m, 1H), 7.67-7.78(m, 1H), 8.1(s, 1H), 8.19(brs, 1H) 8.5-8.62(m, 1H), 8.66-8.8(m, 1H), 11.6(s, 1H) |
| 7-21 | 2-(4-methylpiperazin-1-yl)ethoxy-3-methoxy-4-methylphenyl | Ms: 526 | 2.17(s, 3H), 2.29-2.39(m, 3H), 2.45-2.56(m, 4H), 2.7 (t, 2H), 3.76(s, 3H), 4.09(t, 2H), 6.52(dd, 1H), 6.66 (d, 1H), 7.06(dd, 1H), 7.31(dd, 1H), 7.45(d, 1H), 7.71(dd, 1H), 8.1(S, 1H), 8.19(s, 1H), 8.5-8.6(m, 1H), 8.67-8.75(m, 1H), 11.6(s, 1H) |
| 7-22 | 4-methoxy-3-methylphenyl-4-methylpiperazine | Ms: 482 | 2.24(s, 3H), 2.42-2.5(m, 4H), 2.8(d, 3H), 2.94-3.0 (m, 4H), 3.74(5, 3H), 6.65(dd, 1H), 6.93(d, 1H), 7.07-7.14(m, 1H), 7.34-7.4(m, 1H), 7.45(d, 1H), 7.73(dd, 1H), 8.14(s, 1H), 8.18(s, 1H), 8.61(dd, 1H), 8.7-8.77(m, 1H), 11.7(s, 1H) |

-continued

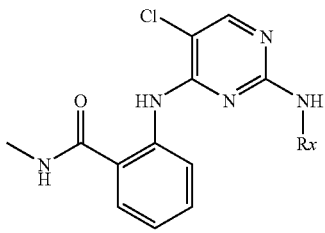

| Expl No. | Rx | Rf (solvent) or MS | NMR (400 MHz), δ (ppm) |
|---|---|---|---|
| 7-23 | (3-methylamino-pyrrolidin-1-yl)(4-methoxy-3-methylphenyl) group | Ms: 482 | 1.67-1.76(m, 1H), 2.0-2.1(m, 1H), 2.25-2.31(m, 3H), 2.8(d, 3H), 2.85-2.91(m, 1H), 3.04-3.12(m, 1H), 3.14-3.3(m, 3H), 3.7(s, 3H), 6.26(dd, 1H), 6.91(d, 1H), 7.01-7.04(m, 1H), 7.07(dd, 1H), 7.32(dd, 1H), 7.72(d, 1H), 8.14(s, 1H), 8.17(s, 1H), 8.63(d, 1H), 8.7-8.78(m, 1H), 11.6(s, 1H) |
| 7-24 | 4-piperidinyl-piperidine-methoxymethylphenyl group | Ms: 550 | 1.35-1.57(m, 8H), 1.7-1.78(m, 2H), 2.81(d, 3H), 3.46-3.52(m, 2H), 3.74(s, 3H), 6.65(dd, 1H), 6.91(d, 1H), 7.05-7.12(m, 1H), 7.34-7.42(m, 1H), 7.46(d, 1H), 7.73(dd, 1H), 8.11(s, 1H), 8.18(s,1H), 8.62(dd, 1H), 8.71-8.78(m, 1H), 11.7(s, 1H) |
| 7-25 | 4-pyrrolidinyl-piperidine-methoxymethylphenyl group | 536 [M + 1]+ | DMSO-d6: 1.48-1.58(m, 2H), 1.65-1.72(m, 4H), 1.90-1.97(m, 2H), 2.07-2.14(m, 1H), 2.49-2.55(m, 4H), 2.70-2.77(m, 2H), 2.79(d, 3H), 3.60-3.65(m, 2H), 3.75(s, 3H), 6.48(dd, 1H), 6.63(d, 1H), 7.03-7.09(m, 1H), 7.28-7.34(m, 1H), 7.39(d, 1H), 7.71(dd, 1H), 8.09(s, 1H), 8.11(s, 1H), 8.55-8.65(m, 1H), 8.69-8.73(m, 1H), 11.59(s, 1H) |
| 7-26 | piperazin-1-yl-methoxymethylphenyl group | 468 [M + 1]+ | DMSO-d6: 2.80(d, 3H), 2.84-2.89(m, 4H), 3.04-3.08(m, 4H), 3.76(s, 3H), 6.47(dd, 1H), 6.62(dd, 1H), 7.04-7.10(m, 1H), 7.28-7.35(m, 1H), 7.40(d, 1H), 7.69-7.73(m, 1H), 8.09(s, 1H), 8.12(s, 1H), 8.55-8.63(m, 1H), 8.68-8.73(m, 1H), 11.59(s, 1H) (an aliphatic NH is hidden) |

-continued
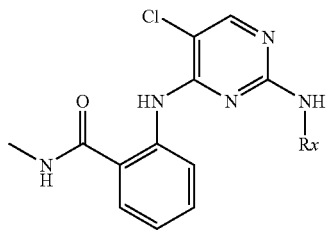
| Expl No. | Rx | Rf (solvent) or MS | NMR (400 MHz), δ (ppm) |
|---|---|---|---|
| 7-27 | 4-methyl-1H-indole | 393 [M + 1]+ | DMSO-d6: 2.80(d, 3H), 6.64-6.67(m, 1H), 7.01-7.08(m, 2H), 7.15(d, 1H), 7.24-7.29(m, 2H), 7.44(d, 1H), 7.69-7.73(m, 1H), 8.20(s, 1H), 8.65-8.73(m, 2H), 9.15(s, 1H), 11.06(s, 1H), 11.63(s, 1H) |
| 7-28 | 1,4-dimethylindole | 407 [M + 1]+ | DMSO-d6: 2.81(d, 3H), 3.79(s, 3H), 6.67(d, 1H), 7.05-7.10(m, 1H), 7.12(d, 1H), 7.17(d, 1H), 7.23(d, 1H), 7.25-7.30(m, 1H), 7.50(d, 1H), 7.70-7.73(m, 1H), 8.20(s, 1H), 8.67(d, 1H), 8.70–8.75(m, 1H), 9.17(s, 1H), 11.64(s, 1H) |
| 7-29 | 7-morpholino-1,4-dimethylindole | 492 [M + 1]+ | DMSO-d6: 2.80(d, 3H), 2.91-2.99(m, 4H), 3.65-3.81(m, 2H), 3.82-3.95(m, 2H), 4.12(s, 3H), 6.58(d, 1H), 6.90(d, 1H), 7.05-7.09(m, 1H), 7.14(d, 1H), 7.22-7.28(m, 1H), 7.30(d, 1H), 7.70(dd, 1H), 8.16(s, 1H), 8.63-8.67(m, 1H), 8.68-8.72(m, 1H), 9.06(s, 1H), 11.64(s, 1) |
| 7-30 | 4-(4-acetylpiperazin-1-yl)-2-methylanisole | MS m/z 510 | DMSO-d$_6$: 2.02(s, 3H), 2.80(d, 3H), 2.82-2.92(m, 2H), 2.92-3.01(m, 2H), 3.44-3.53(m, 4H), 3.76(s, 3H), 6.68(dd, 1H), 6.95(d, 1H), 7.09(dd, 1H), 7.35-7.40(m, 1H), 7.50(brs, 1H), 7.73(d, 1H), 8.15(s, 1H), 8.19(s, 1H), 8.59(d, 1H), 8.69-8.76(m, 1H), 11.66(s, 1H). |

The following 2-[5-Bromo-2-(substituted phenylamino)-pyrimidin-4-ylamino]-N-ethyl-benzamide are prepared from 2-(5-bromo-2-chloro-pyrimidin-4-ylamino)-N-ethyl-benzamide and the corresponding aniline following the procedure of Example 7A

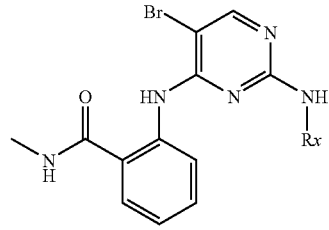

| Expl No. | Rx | Rf (solvent) or MS | NMR |
|---|---|---|---|
| 8-1 | | 0.27 (n-hexane: AcOEt = 1:2) | DMSO-d6: 2.80(d, 3H), 2.88(t, 4H), 3.65(m, 4H), 3.75 (s, 3H), 6.64(dd, 1H), 6.94(d, 1H), 7.11-7.08(m, 1H), 7.38-7.34(m, 1H), 7.47-7.46(m, 1H), 7.70(dd, 1H), 8.11(s, 1H), 8.26(s, 1H), 8.51-8.49(m, 1H), 8.72–8.71(m, 1H), 11.41(s, 1H) |
| 8-2 | | m/z 513, 515 (M + 1) | DMSO-d6: 2.79(d, 3H, J=4.04 Hz), 3.10-3.20(m, 4H), 3.77(s, 3H), 3.70-3.80(m, 4H), 6.45-6.55(m, 1H), 6.63-6.69(m, 1H), 7.05-7.10(m, 1H), 7.28-7.34 (m, 1H), 7.40-7.45(m, 1H), 7.65–7.70(m, 1H), 8.13 (s, 1H), 8.16(s, 1H), 8.50-8.56(m, 1H) 8.65-8.72(m, 1H), 11.40(s, 1H) |
| 8-3 | | 0.48 (n-Hexane: AcOEt = 4:1) | DMSO-d6: 2.80(d, 3H), 3.83(s, 3H), 4.11(t, 2H), 6.82(ddd, 1H), 7.03(dd, 1H), 7.15(dd, 1H), 7.44(dd, 1H), 7.73(d, 1H), 7.93(dd, 1H), 8.13(s, 1H), 8.33(s, 1H), 8.50(d, 1H), 8.70–8.77(m, 1H), 11.3(s, 1). |
| 8-4 | | MS 446, 448 | 2.79(d, 3H), 3.79(s, 3H), 6.75(ddd, 1H), 7.0(dd, 1H), 7.05-7.12(m, 1H), 7.3-7.36(m, 1H), 7.62(dd, 1H), 7.69(dd, 1H), 8.2(s, 1H), 8.29(s, 1H), 8.45(d, 1H), 8.66-8.73(m, 1H), 11.4(brs, 1H). |

The following 2-[5-Chloro-2-(substituted phenylamino)-pyrimidin-4-ylamino]-N-ethyl-benzamide are prepared from 2-(2,5-Dichloro-pyrimidin-4-ylamino)-N-ethyl-benzamide and the corresponding aniline following the procedure of Example 7A

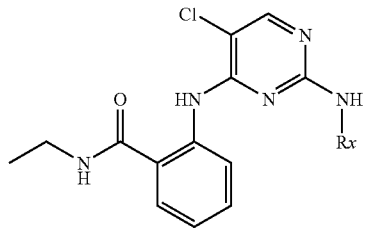

| Expl No. | Rx | Rf (solvent) or MS | NMR (400 MHz), δ (ppm) |
|---|---|---|---|
| 9-1 | | 0.35 (n-hexane: AcOEt = 1:2) | CDCl₃: 1.27(t, 3H), 3.10-3.15(m, 4H), 3.47-3.58(m, 2H), 3.85-3.93(m, 4H), 3.89(s, 3H), 6.08-6.17(m, 1H), 6.48(dd, 1H), 6.53(d, 1H), 7.05-7.11(m, 1H), 7.42-7.53(m, 2H), 8.08(s, 1H), 8.12(d, 1H), 8.67(d, 1H), 10.94(brs, 1H). |
| 9-2 | | MS (ESI) m/z 497, 499 (M + 1)⁺ | CDCl₃: 1.26(t, 3H, J=7.56 Hz), 2.37(s, 3H), 2.57-2.62(m, 4H), 3.15-3.20(m, 4H), 3.49(dq, 2H, J= 7.56, 1.52 Hz), 3.87(s, 3H), 6.11-6.16(m, 1H), 6.49 (dd, 1H, J=8.56, 2.52 Hz), 6.55(d, 1H, J=2.52 Hz), 7.05-7.10(m, 1H), 7.23(s, 1H), 7.41-7.50(m, 2H), 8.07(s, 1H), 8.08 (d, 1H, J=8.56 Hz), 8.65-8.69(m, 1H), 10.93(s, 1H) |
| 9-3 | | m/z 564, 566 (M + 1)⁺ | DMSO-d6: 1.26(t, 3H, J=7.56 Hz), 1.40-1.50(m, 2H), 1.56-1.64(m, 4H), 1.67-1.82(m, 2H), 1.88-1.97 2.73(m, 2H), 3.51(dq, 2H, J=7.56, 1.52 Hz), 3.62-3.69(m, 2H), 3.86(s, 3H), 6.10-6.15(m, 1H), 6.49 (dd, 1H, J=8.56, 2.52 Hz), 6.55(d, 1H, J=2.52 Hz), 7.05-7.10(m, 1H), 7.23(s, 1H), 7.43-7.50(m, 2H) 8.05-8.11(m, 1H), 8.07(s, 1H), 8.65-8.69(m, 1H), 10.91(s, 1 |

-continued
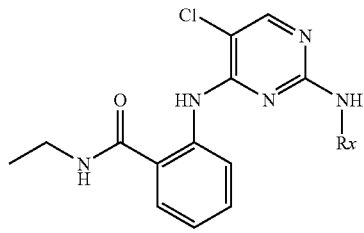
| Expl No. | Rx | Rf (solvent) or MS | NMR (400 MHz), δ (ppm) |
|---|---|---|---|
| 9-4 | | 0.39 (MeOH:CH$_2$Cl$_2$ = 1:4) | DMSO-d6: 1.19(t, 3H), 1.52-1.68(m, 2H), 1.71-1.79 (m, 4H), 1.92-2.05(m, 2H), 2.12-2.23(m, 1H), 2.76-2.85(m, 2H), 3.65-3.73(m, 2H), 3.82(s, 3H), 6.54 (dd, 1H), 6.69(d, 1H), 7.13(m, 1H), 7.45(d, 1H), 7.79 (dd, 1H), 8.15(s, 1H), 8.15-8.18(m, 1H), 8.60-8.68 (m, 1H), 8.74-8.83(m, 1H). |
| 9-5 | | Rf (Hexane:AcOEt = 1:2): 0.30 | CDCl3: 1.27(t, 3H), 3.08-3.14(m, 4H), 3.52(q, 2H), 3.71-3.90(m, 7H), 6.05-6.18(m, 1H), 6.47(dd, 1H), 6.53(dd, 1H), 7.08(dd, 1H), 7.41-7.53(m, 2H), 8.08 (s, 1H), 8.12(d, 1H), 8.67(d, 1H), 10.94(s, 1H). |
| 9-6 | | Rf (AcOEt:MeOH = 4:1) 0.050 | DMSO: 1.11(t, 3H), 1.60-1.69(m, 1H), 1.88-1.96(m, 2H), 2.19(s, 3H), 2.55-2.68(m, 2H), 3.30–3.45(m, 2H), 3.75(s, 3H), 4.33-4.43(m, 1H), 6.54(dd, 1H), 6.65(d, 1H), 7.07(dd, 1H), 7.30(dd, 1H), 7.43(d, 1H), 7.71(dd, 1H), 8.11(s, 1H), 8.20(s, 1H), 8.54 (br.d, 1H), 8.75(dd, 1H), 11.49(s, 1H). |
| 9-7 | | Rf (AcOEt:MeOH = 4:1) 0.050 | CDCl3: 1.34(t, 3H), 1.62-1.68(m, 2H), 1.93-2.18(m, 8H), 2.37-2.40(br, 2H), 2.74–2.86(br, 3H), 3.20-3.23 (m, 2H), 3.34(br, 2H), 3.53(q, 2H), 3.85(s, 3H), 6.47 (dd, 1H), 6.76(d, 1H), 7.04-7.08(m, 1H), 7.30(dd, 1H), 7.53(s, 1H), 8.00(d, 1H), 8.13-8.17(m, 1H), 8.22(d, 1H), 8.42-8.53(br, 1H), 10.91(s, 1H), 11.59-11.75(br, 1H) |

The following 2-[5-Chloro-2-(substituted phenylamino)-pyrimidin-4-ylamino]-6,N-dimethyl-benzamide are prepared from 2-(2,5-Dichloro-pyrimidin-4-ylamino)-6,N-dimethyl-benzamide and the corresponding aniline following the procedure of Example 7A

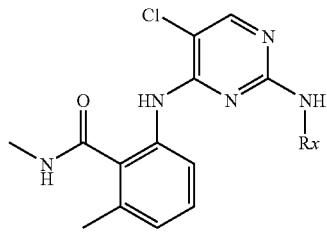

| Expl No. | Rx | Identification |
|---|---|---|
| 10-1 | 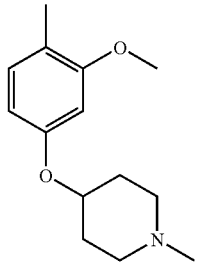 | NMR (400 MHz, DMSO-d6, δ): 1.58-1.68(m, 2H), 1.87-1.96(m, 2H), 2.13-2.22(m, 2H), 2.18(s, 3H), 2.18(s, 3H), 2.29(s, 3H), 2.57-2.65(m, 2H), 2.76(d, 3H), 3.75(s, 3H), 4.29-4.37(m, 1H), 6.45(dd, 1H), 6.61(d, 1H), 6.98(d, 1H), 7.18(dd, 1H), 7.47(d, 1H), 7.89(d, 1H), 8.02(s, 1H), 8.07(s, 1H), 8.37-8.43(m, 1H), 8.49(s, 1H). Rf: 0.39 (MeOH: CH$_2$Cl$_2$ = 1:4). |
| 10-2 | 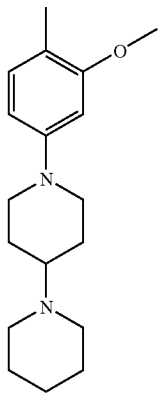 | NMR (400 MHz, DMSO-d6, δ): 1.35-1.42(m, 2H), 1.45-1.60(m, 6H), 1.75-1.85(m, 2H), 2.29(s, 3H), 2.30-2.35(m, 1H), 2.43-2.50 (m, 4H), 2.57-2.66(m, 2H), 2.76(d, 3H, J=5.0 Hz), 3.65-3.74(m, 2H), 3.76(s, 3H), 6.40(dd, 1H, J=9.0, 2.0 Hz), 6.59 (d, 1H, J= 2.0 Hz), 6.98(d, 1H, J=7.6 Hz), 7.20 (dd, 1H, J=7.6, 7.6 Hz), 7.43 (d, 1H, J=9.0 Hz), 7.91-7.94(m, 1H), 7.93(s, 1H), 8.06 (s, 1H), 8.36-8.42(m, 1H) 8.47(s, 1H). MS (ESI) m/z 564, 566 (M + 1)$^+$ |
| 10-3 | 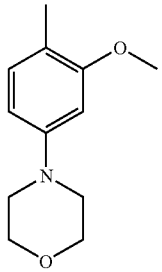 | DMSO-d6: 2.29(s, 3H), 2.77(d, 3H), 3.07-3.11(m, 4H), 3.73-3.76(m, 4H), 3.77(s, 3H), 6.41(dd, 1H), 6.63(d, 1H), 7.00(d, 1H), 7.21(dd, 1H), 7.49(d, 1H), 7.93(d, 1H), 7.96(s, 1H), 8.07(s, 1H), 8.37-8.42(m, 1H), 8.49(s, 1H). MS m/z 483 [M + 1]$^+$ |

The following 2-[5-Chloro-2-(substituted phenylamino)-pyrimidin-4-ylamino]-5-fluoro-N-methyl-benzamide are prepared from 2-(2,5-Dichloro-pyrimidin-4-ylamino)-5-fluoro-N-methyl-benzamide and the corresponding aniline following the procedure of Example 7A

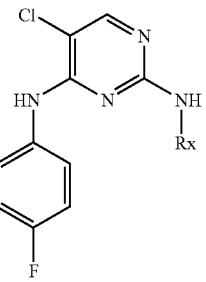

| Expl No. | Rx | Identification |
|---|---|---|
| 11-1 | 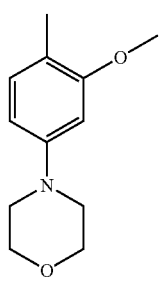 | NMR (400 MHz, DMSO-d$_6$, δ): 2.79(d, 3H), 3.10-3.15(m, 4H), 3.74-3.78(m, 7H), 6.50(dd, 1H), 6.66(d, 1H), 7.13-7.20 (m, 1H), 7.41(d, 1H), 7.57(dd, 1H), 8.09(s, 1H), 8.14(s, 1H), 8.55-8.65(m, 1H), 8.75-8.82(m, 1H), 11.39(s, 1H). MS (ESI): m/z 487, 489 (M + 1). |
| 11-2 | 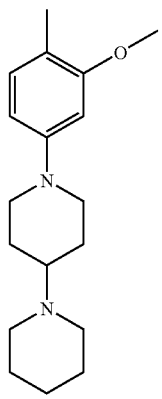 | NMR (400 MHz, DMSO-d$_6$, δ): 1.68-1.33 (m, 8H), 1.93-1.73 (m, 2H), 2.35-2.60 (m, 1H), 2.62-2.74 (m, 2H), 2.67 (t, 2H), 2.74 (d, 3H), 3.25-3.38 (m, 4H), 3.76 (s, 3H), 3.83-3.71 (m, 2H), 6.48 (dd, 1H), 6.49 (dd, 1H), 6.63 (d, 1H), 7.15 (dd, 1H), 7.36 (d, 1H), 7.57 (dd, 1H), 8.09(s, 1H), 8.12(s, 1H), 8.65-8.55 (m, 1H), 8.78(d, 1H), 11.39 (s, 1H) MS (ESI): m/z 568, 570 ( + 1) |
| 11-3 | 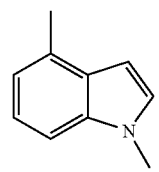 | DMSO-d6: 2.80(d, 3H), 3.79(s, 3H), 6.64(d, 1H), 7.05-7.20(m, 3H), 7.23(d, 1H), 7.42-7.49(d, 1H), 7.57(dd, 1H), 8.20(s, 1H), 8.62-8.69(m, 1H), 8.75-8.82(m, 1H), 9.17(s, 1H), 11.43(s, 1H). MS m/z 425 [M + 1]$^+$ |

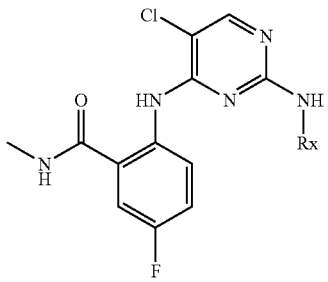

| Expl No. | Rx | Identification |
|---|---|---|
| 11-4 | 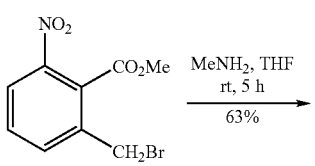 | DMSO-d6: 2.06(s, 3H), 2.79(d, 3H), 3.10-3.14(m, 2H), 3.15-3.19(m, 2H), 3.55-3.62(m, 4H), 3.77(s, 3H), 6.52(dd, 1H), 6.69(d, 1H), 7.15-7.23(m, 1H), 7.43(d, 1H), 7.58(dd, 1H), 8.10(s, 1H), 8.14(s, 1H), 8.56-8.65(m, 1H), 8.75-8.81(m, 1H), 11.39(s, 1H). MS m/z 528 [M + 1]$^+$ |

12-1 Preparation of 7-[5-Chloro-2-(2-methoxy-4-morpholin-4-yl-phenylamino)-pyrimidin-4-ylamino]-2-methyl-2,3-dihydro-isoindol-1-one Synthetic Procedure for 7-(2,5-Dichloro-pyrimidin-4-ylamino)-2-methyl-2,3-dihydro-isoindol-1-one N-Methyl-7-nirto-2,3-dihydroisoindole-1-one. At room temperature, a solution of methyl 2-bromomethyl-6-nitrobenzoate (1.26 g, 4.63 mmol) in THF (13 mL) is treated with 2M soln. of methylamine in THF (14 mL), stirred for 5 h, diluted with EtOAc (100 mL), washed with sat. aqueous solution of NaHCO$_3$ (15 mL) and brine (15 mL), dried (MgSO$_4$), and evaporated. A flash chromatography (30 g of silica gel; CH$_2$Cl$_2$/EtOAc 1:1) gives N-Methyl-7-nirto-2,3-dihydroisoindole-1-one (0.561 g, 2.92 mmol) in 63%. Yellow solid. Rf (CH$_2$Cl$_2$/EtOAc 1:1) 0.46. $^1$H-NMR (400 MHz, CDCl$_3$) 3.21 (s), 4.44 (s), 7.63-7.69 (m, 2H), 7.70-7.75 (m, 1H).

7-Amino-N-methyl-2,3-dihydroisoindole-1-one. At room temperature, a solution of N-Methyl-7-nirto-2,3-dihydroisoindole-1-one (561.0 mg, 2.92 mmol) in EtOAc (8.4 mL) is treated with SnCl$_2$.2H$_2$O (2.68 g), stirred at 80° C. under reflux for 5 h, and treated with 30 mL of 5N NaOH at 0° C. After the both layers are separated, the aqueous layer is extracted with EtOAc (2×8 mL), the combined extracts are washed with brine (5 mL), dried (MgSO$_4$), and evaporated to give 7-Amino-N-methyl-2,3-dihydroisoindole-1-one (455.9 g, 2.81 mmol) in 96%. Yellow solid. R$_f$(CH$_2$Cl$_2$/EtOAc 1:1) 0.53. $^1$H-NMR (400 MHz, CDCl$_3$) 3.12 (s), 4.28 (s), 5.20 (br. s), 6.56 (d, J=8.0), 6.68 (d, J=8.0), 7.21 (dd, J=8.0, 8.0).

7-(4-Amino-2,5-dichloropyrimidin-4-yl)amino-N-methyl-2,3-dihydroisoindole-1-one. At 0° C., a solution of 7-Amino-N-methyl-2,3-dihydroisoindole-1-one (232.6 mg, 1.43 mmol) in DMF (2.0 mL) is treated with 60% NaH (89.8 mg), stirred at the same temperature for 1.5 h, treated with a solution of 2,4,5-trichloropyrimidine (0.557 g) in DMF (3.5 mL), stirred for 1 h, and warmed to room temperature. After furthermore stirring for 13 h, the mixture is treated with sat. aqueous NH$_4$Cl (6 mL), and the resulting brown precipitates are collected by a filtration, followed by washing with H$_2$O, hexane, and CH$_3$CN to give 7-(4-Amino-2,5-dichloropyrimidin-4-yl)amino-N-methyl-2,3-dihydroisoindole-1-one (130.2 g, 0.416 mmol) in 26%. Brown solid. R$_f$ (CH$_2$Cl$_2$/EtOAc1:1) 0.50. $^1$H-NMR (400 MHz, CDCl$_3$): 3.22 (s), 4.43 (s), 7.15 (d, J=8.0), 7.59 (dd, J=8.0, 8.0), 8.24 (s), 8.71 (d, J=8.0), 11.05 (br. s).

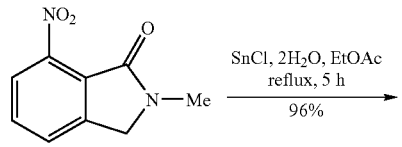

7-[5-Chloro-2-(2-methoxy-4-morpholin-4-yl-phenylamino)-pyrimidin-4-ylamino]-2-methyl-2,3-dihydro-isoindol-1-one

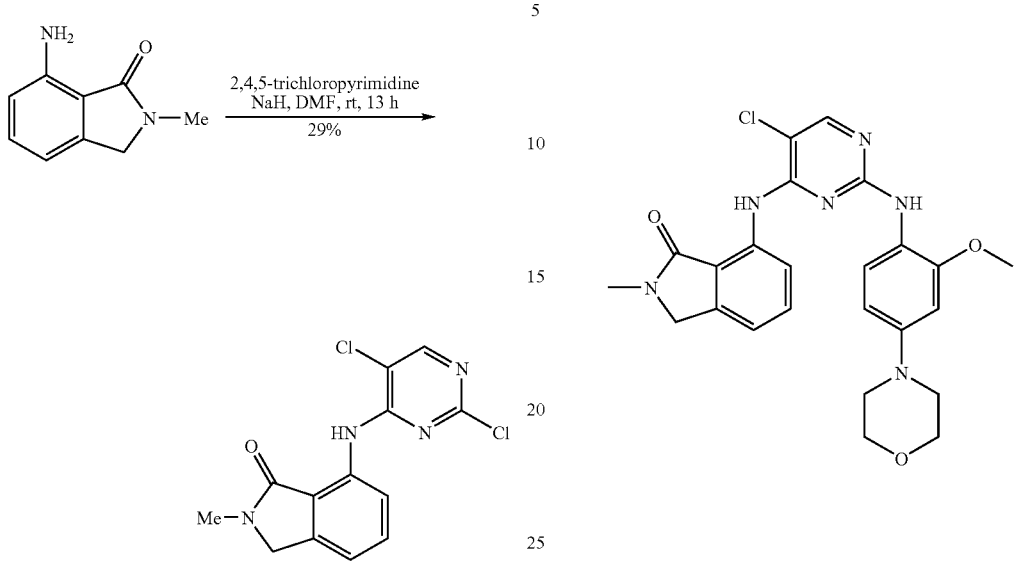

$^1$H-NMR (400 MHz, DMSO-d6, δ): 3.07 (s, 3H), 3.13-3.17 (m, 4H), 3.75 (s, 3H), 3.34-3.78 (m, 4H), 4.46 (s, 2H), 6.54 (dd, 1H, J=8.6, 2.5 Hz), 6.67 (d, 1H, J=2.5 Hz), 7.15 (d, 1H, J=7.6 Hz), 7.25-7.34 (m, 1H) 7.36 (d, 1H, J=8.6 Hz), 8.13 (s, 1H), 8.36 (s, 1H), 8.37-8.50 (m, 1H) 10.57 (s, 1H). MS (ESI) m/z 481. 483 (M+1)$^+$

The following 7-[5-Chloro-2-(substituted phenylamino)-pyrimidin-4-ylamino]-2-methyl-2,3-dihydro-isoindol-1-one are prepared from 7-(2,5-Dichloro-pyrimidin-4-ylamino)-2-methyl-2,3-dihydro-isoindol-1-one and the corresponding aniline following the procedure of Example 7A.

The following 7-(5-Chloro-2-(subst.phenylamino)-pyrimidin-4-ylamino)-2-methyl-2,3-dihydro-isoindol-1-ones are prepared from 7-(2,5-Dichloro-pyrimidin-4-ylamino)-2-methyl-2,3-dihydro-isoindol-1-one and the corresponding aniline following the procedure of Example 2:

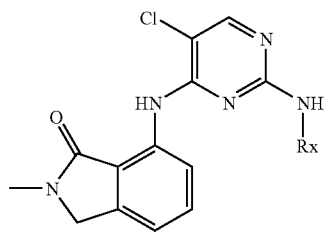

| Expl No. | Rx | Mass(m/z) | NMR (400 MHz) δ (ppm) |
|---|---|---|---|
| 12-2 | ![4-methyl-3-methoxy-phenyl with N-methylpiperazine] | 494 [M + 1]$^+$ | DMSO-d6: 2.24(s, 3H), 2.45-2.50(m, 4H), 3.07(s, 3H), 3.15-3.19(m, 4H), 3.74(s, 3H), 4.46(s, 2H), 6.52(dd, 1H), 6.66(d, 1H), 7.15 (d, 1H), 7.25-7.36(m, 2H), 8.12(s, 1H), 8.35(s, 1H), 8.35-8.45(m, 1H), 10.57(s, 1H) |

-continued

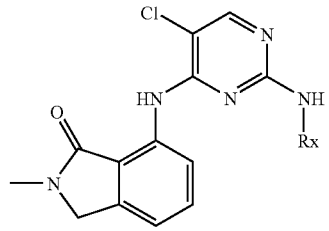

| Expl No. | Rx | Mass(m/z) | NMR (400 MHz) δ (ppm) |
|---|---|---|---|
| 12-3 | ![structure with 4-methyl-3-methoxyphenyl-piperidin-4-ol] | 495 [M + 1]⁺ | DMSO-d6: 1.48-1.57(m, 2H), 1.83-1.88(m, 2H), 2.83-2.90(m, 2H), 3.07(s, 3H), 3.51-3.60(m, 2H), 3.61-3.70(m, 2H), 3.73(s, 3H), 4.46(s, 2H), 4.69(d, 1H), 6.52(dd, 1H), 6.64(d, 1H), 7.14 (d, 1H), 7.25-7.35(m, 2H), 8.12(s, 1H), 8.33(s, 1H), 8.35-8.45(m, 1H), 10.57(s, 1H) |
| 12-4 | ![structure with 4-methyl-3-methoxyphenyl-piperidinyl-N-methylpiperazine] | 577 [M + 1]⁺ | DMSO-d6: 1.48-1.59(m, 2H), 1.83-1.88(m, 2H), 2.14(s, 3H), 2.25-2.39(m, 4H), 2.42-2.60(m, 5H), 2.66-2.73(m, 2H), 3.07(s, 3H), 3.73-3.77(m, 2H), 3.74(s, 3H), 4.46(s, 2H), 6.52(dd, 1H), 6.64(d, 1H), 7.14 (d, 1H), 7.25-7.34(m, 2H), 8.12(s, 1H), 8.34(s, 1H), 8.35-8.45(m, 1H), 10.57(s, 1) |
| 12-5 | ![structure with 3-methyl-4-methoxyphenyl-piperidinyl-piperidine] | 562 [M + 1]⁺ | DMSO-d6: 1.35-1.65(m, 8H), 1.73-1.85(m, 2H), 2.40-2.59(m, 7H), 3.08(s, 3H), 3.52-3.61(m,2H), 3.73(s, 3H), 4.47(s, 2H), 6.72(dd, 1H), 6.94(d, 1H), 7.17(d, 1H), 7.34-7.39(m, 2H), 8.21(s, 1H), 8.37(s, 1H), 8.45-8.53(m, 1H), 10.64(s, 1H) |

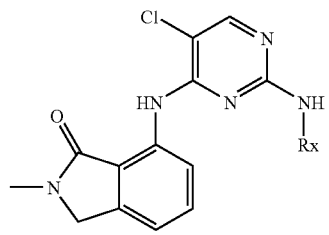

| Expl No. | Rx | Mass(m/z) | NMR (400 MHz) δ (ppm) |
|---|---|---|---|
| 12-6 | | MS m/z 536 | DMSO-d$_6$: 2.19-2.42 (m, 4H), 2.65-2.89 (m, 3H), 3.07 (s, 3H), 3.11-3.30 (m, 1H), 3.48-3.61 (m, 2H), 3.62-3.71 (m, 1H), 3.75 (s, 3H), 3.75-3.83 (m, 2H), 4.47 (s, 2H), 6.48-6.52 (m, 1H), 6.66 (d, 1H), 7.15 (d, 1H), 7.26-7.37 (m, 2H), 8.13 (s, 1H), 8.35 (s, 1H), 8.42 (brs, 1H), 10.57 (s, 1H). |

The following 7-(5-Chloro-2-(subst.phenylamino)-pyrimidin-4-ylamino)-2-ethyl-2,3-dihydroisoindol-1-ones are prepared from 7-(2,5-Dichloro-pyrimidin-4-ylamino)-2-ethyl-2,3-dihydro-isoindol-1-one and the corresponding aniline following the procedure of Example 2:

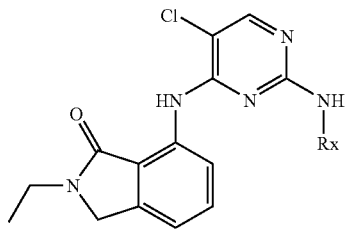

| Expl No. | Rx | Mass(m/z) | NMR (400 MHz) δ (ppm) |
|---|---|---|---|
| 13-1 | | 508 [M + 1]$^+$ | DMSO-d6: 1.19(t, 3H), 2.24(s, 3H), 2.47-2.51(m, 4H), 3.15-3.21(m, 4H), 3.54(q, 2H), 3.74(s, 3H), 4.48(s, 2H), 6.54(dd, 1H), 6.65(d, 1H), 7.15 (d, 1H), 7.26-7.36(m, 2H), 8.12(s, 1H), 8.34(s, 1H), 8.37-8.48(m, 1H), 10.58(s, 1H) |

Example 7B

2-[5-Chloro-2-(2-methoxy-4-morpholin-4-yl-phenylamino)-pyrimidin-4-ylamino]-N-methyl-benzamide (Alternative Synthesis to Example 7A)

To a suspension of 2-[5-chloro-2-(2-methoxy-4-morpholin-4-yl-phenylamino)-pyrimidin ylamino]-benzoic acid (5.5 g, 12.1 mmol) in 100 mL of THF are added Et$_3$N (2.06 mL, 14.8 mmol) and isobutyl chloroformate (1.7 mL, 12.8 mmol) at −5° C. After stirring at the same temperature for 30 min, the reaction mixture is further stirred at room temperature for 1 hour and then H$_2$O is added to the reaction mixture. The resulting precipitate is collected by filtration, washed with H$_2$O, and dried under reduced pressure to give an intermediate (4.80 g) (10.96 mmol, 91%) as yellow solid.

NMR (400 MHz, DMSO-d6, δ): 3.10-3.20 (m, 4H), 3.70-3.80 (m, 4H), 3.93 (s, 3H), 6.53 (dd, 1H, J=9.08, 2.0 Hz), 6.70 (d, 1H, J=2.0 Hz), 7.49-7.54 (m, 1H), 7.67 (d, 1H, J=8.56 Hz), 7.89 (s, 1H), 7.85-7.95 (m, 1H), 8.23 (d, 1H, J=9.08 Hz), 8.26 (d, 1H, J=8.56 Hz), 12.60 (s, 1H).

To a 1M solution of methylamine in THF (560 μl, 0.56 mmol) is added 82 mg of the obtained intermediate (0.187 mmol) followed by 1M solution of NaHMDS in THF (560 μl, 0.56 mmol) dropwise. After the reaction mixture is stirred for 10 minutes, 5 mL of H$_2$O is added and extraction is performed with AcOEt. The organic layer is washed with brine, dried over Na$_2$SO$_4$, concentrated under reduced pressure, and purified by silica gel column chromatography (Hexane: AcOEt=1:1 to AcOEt) to give the title compound as a pale yellow solid. Data are given in Example 7A.

By repeating the procedures described above using appropriate starting materials and conditions the following compounds are obtained as identified below.

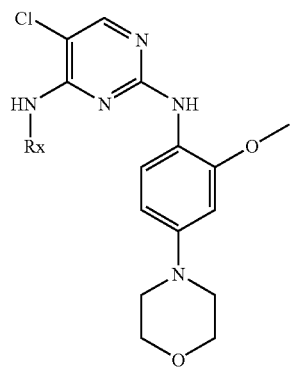

| Expl No. | Ry | Rf (solvent) or MS | NMR (400 MHz), δ (ppm) |
|---|---|---|---|
| 14-1 | N,N-dimethyl-2-methylbenzamide group | 0.10 (n-hexane: AcOEt = 1:1) | CDCl$_3$: 3.02-3.19 (m, 10H), 3.83-3.91 (m, 4H), 3.87 (s, 3H), 6.45 (dd, 1H), 6.52 (d, 1H), 7.09-7.14 (m, 1H), 7.29 (m, 1H), 7.31 (dd, 1H), 7.38-7.45 Cm, 1H), 8.06 (s, 1H), 8.14 (d, 1H), 8.39 (d, 1H), 8.97 (s, 1H). |
| 14-2 | N-isopropyl-2-methylbenzamide group | 0.36 (n-hexane: AcOEt = 1:2) | CDCl$_3$: 1.27 (d, 6H), 3.09-3.16 (m, 4H), 3.81-3.92 (m, 4H), 3.89 (s, 3H), 4.26-4.37 (m, 1H), 5.93-5.98 (m, 1H), 6.48 (dd, 1H), 6.53 (d, 1H), 7.05-7.11 (m, 1H), 7.42-7.49 (m, 2H), 8.08 (s, 1H), 8.12 (d, 1H), 8.65 (d, 1H), 10.88 (br.s, 1H). |
| 14-3 | N-methyl-4,5-difluoro-2-methylbenzamide group | 505 [M + 1]$^+$ | DMSO-d6: 2.79(d, 3H), 3.09-3.14(m, 4H), 3.74-3.77(m, 4H), 3.75(s, 3H), 6.49(dd, 1H), 6.65(d, 1H), 7.30 (d, 1H), 7.84(dd, 1H), 8.12(s, 1H), 8.40(s, 1H), 8.65-8.79(m, 2H), 11.39(s, 1H) |

-continued

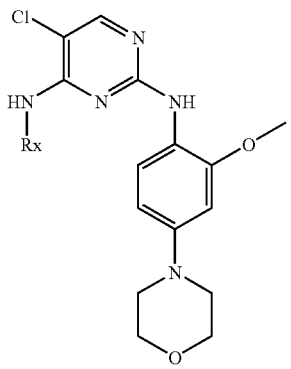

| Expl No. | Ry | Rf (solvent) or MS | NMR (400 MHz), δ (ppm) |
|---|---|---|---|
| 14-4 | (7-methyl-indan-1-one) | 466 [M + 1]⁺ | DMSO-d6: 2.70-2.75(m, 2H), 3.04-3.09(m, 2H), 3.12-3.18(m, 4H), 3.74-3.80(m, 4H), 3.75(s, 3H), 6.54(dd, 1H), 6.67(d, 1H), 7.14 (d, 1H), 7.34(d, 1H),7.37-7.44(m, 1H), 8.17(s, 1H), 8.35-8.50(m, 1H), 8.44(s, 1H), 10.59(s, 1H) |
| 14-5 | (N-ethyl-2-methyl-5-fluorobenzamide) | Rf (Hexane: AcOEt = 1:2): 0.31 | DMSO: 1.18 (t, 3H), 3.11-3.21 (4, 4H), 3.30-3.60 (m, 2H), 3.71-3.85 (m, 7H), 6.50-6.58 (m, 1H), 6.71 (d, 1H), 7.17-7.26 (m, 1H), 7.46 (d, 1H), 7.64 (dd, 1H), 8.14 (s, 1H), 8.19 (s, 1H), 8.57-8.68 (m, 1H), 8.80-8.87(m, 1H), 11.36 (s, 1H). |
| 14-6 | (pyrrolidin-1-yl-(2-methylphenyl)methanone) | Rf (Hexane: AcOEt = 1:1): 0.051 | DMSO: 1.71-1.92 (m, 2H), 1.92-2.06 (m, 2H), 3.08-3.14 (m, 4H), 3.48-3.57 (m, 2H), 3.63-3.75 (m, 2H), 3.84-3.90 (m, 7H), 6.47 (dd, 1H), 6.53 (d, 1H), 7.09 (ddd, 1H), 7.25-7.29 (m, 1H), 7.38-7.44 (m, 1H), 8.06 (s, 1H), 8.15 (d, 1H), 8.45 (dd, 1H), 9.60 (s, 1H). |
| 14-7 | (4-(2-methylphenylsulfonyl)morpholine) | | ¹H-NMR (400 MHz, δ ppm, CDCl₃): 3.04-3.10 (m, 4H), 3.10-3.16 (m, 4H), 3.63-3.68 (m, 4H), 3.85-3.90 (m, 7H), 6.46 (dd, 1H), 6.53 (d, 1H), 7.20-7.25 (m, 1H), 7.33 (brs, 1H), 7.56-7.62 (m, 1H), 7.85 (dd, 1H), 8.03 (d, 1H), 8.12 (s, 1H), 8.57-8.61 (m, 1H), 9.30 (s, 1H). |

The following 2-(5-Chloro-2-(subst. phenylamino)-pyrimidin-4-ylamino)-N-methyl-5-pyrrolidin-1-yl benzamides are prepared from 2-(5-Chloro-2-methyl-pyrimidin-4-ylamino)-N-methyl-5-pyrrolidin-1-yl-benzamide and the corresponding aniline following the procedure of Example 2:

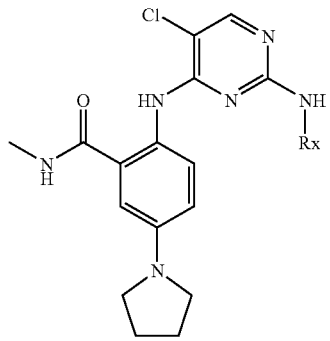

| Expl No. | Rx | Mass(m/z) | NMR (400 MHz) δ (ppm) |
|---|---|---|---|
| 15-1 | 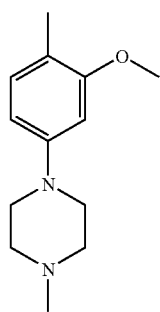 | 551 [M + 1]⁺ | DMSO-d6: 1.94-1.99(m, 4H), 2.23(s, 3H), 2.43-2.48(m, 4H), 2.78(d, 3H), 3.11-3.17(m, 4H), 3.22-3.29(m, 4H), 3.76(s, 3H), 6.46(dd, 1H), 6.48-6.53(m, 1H), 6.63(d, 1H), 6.79(d, 1H), 7.44(d, 1H), 7.89(s, 1H), 7.99(s, 1H), 8.24(d, 1H), 8.60(d, 1H), 10.88(s, 1H) |
| 15-2 | 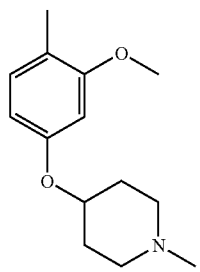 | 566 [M + 1]⁺ | DMSO-d6: 1.60-1.70(m, 2H), 1.90-2.00(m, 6H), 2.12-2.20(m, 2H), 2.18(s, 3H), 2.60-2.65(m, 2H), 2.78(d, 3H), 3.22-3.28(m, 4H), 3.75(s, 3H), 4.25-4.37(m, 1H), 6.49-6.55(m, 2H), 6.62(d, 1H), 6.80(d, 1H), 7.53(d, 1H), 7.90(s, 1H), 8.00(s, 1H), 8.24(d, 1H), 8.58-8.63(m, 1H), 10.88(s, 1H) |
| 15-3 | 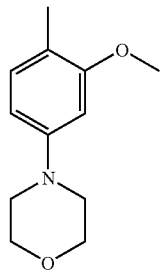 | 538 [M + 1]⁺ | DMSO-d6: 1.94-1.99(m, 4H), 2.78(d, 3H), 3.09-3.15(m, 4H), 3.22-3.27(m, 4H), 3.73-3.77(m, 4H), 3.76(s, 3H), 6.47(dd, 1H), 6.47-6.53(m, 1H), 6.65(d, 1H), 6.79(d, 1H), 7.47(d, 1H), 7.90(s, 1H), 7.99(s, 1H), 8.24(d, 1H), 8.60(d, 1H), 10.88(s, 1H) |

The following 2-[5-Chloro-2-(4-fluoro-2-methoxy-phenylamino)-pyrimidin-4-ylamino]-5-subst.-N-methyl-benzamide are prepared from the corresponding aniline following the procedure of Example 2:

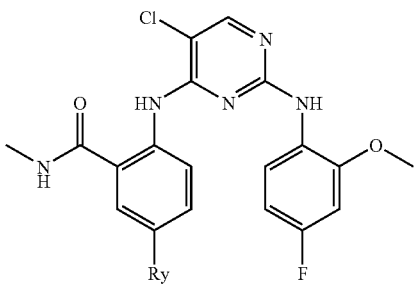

| Expl No. | Ry | Mass(m/z) | NMR (400 MHz) δ (ppm) |
|---|---|---|---|
| 16-1 | morpholinyl | 487 [M + 1]⁺ | DMSO-d6: 2.79(d, 3H), 3.11-3.15(m, 4H), 3.74-3.81(m, 4H), 3.81(s, 3H), 6.76(ddd, 1H), 6.95-7.05(m, 2H), 7.21(d, 1H), 7.72(dd, 1H), 8.08(s, 1H), 8.09(s, 1H), 8.33(d, 1H), 8.63-8.73(m, 1H), 11.17(s, 1H) |
| 16-2 | 4-methylpiperazinyl | 500 [M + 1]⁺ | DMSO-d6: 2.24(s, 3H), 2.45-2.52(m, 4H), 2.79(d, 3H), 3.13-3.18(m, 4H), 3.81(s, 3H), 6.75(ddd, 1H), 6.94-7.02(m, 2H), 7.20(d, 1H), 7.73(dd, 1H), 8.03-8.11(m, 2H), 8.30(d, 1H), 8.60-8.70(m, 1H), 11.14(s, 1H) |
| 16-3 | methoxy | 432 [M + 1]⁺ | DMSO-d6: 2.79(d, 3H), 3.80-3.81(m, 6H), 6.75(ddd, 1H), 6.90-7.02(m, 2H), 7.27(d, 1H), 7.67(dd, 1H), 8.10(s, 1H), 8.16(s, 1H), 8.39(d, 1H), 8.70-8.76(m, 1H), 11.20(s, 1H) |
| 16-4 | 1-methyl-4-piperidinyl-piperidinyl | 568 [M + 1]⁺ | DMSO-d6: 1.35-1.62(m, 8H), 1.78-1.85(m, 2H), 2.30-2.40(m, 1H), 2.41-2.52(m, 4H), 2.60-2.70(m, 2H), 2.78(d, 3H), 3.70-3.80(m, 2H), 3.81(s, 3H), 6.75(ddd, 1H), 6.95-7.02(m, 2H), 7.20(d, 1H), 7.72(dd, 1H), 8.05-8.08(m, 2H), 8.28(d, 1H), 8.63-8.69(m, 1H), 11.12(s, 1H) |

Example 16B

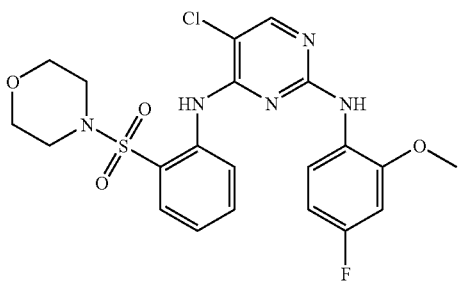

CDCl₃: 3.01-3.10 (m, 4H), 3.63-3.68 (m, 4H), 3.89 (s, 3H), 6.59 (ddd, 1H), 6.66 (dd, 1H), 7.20-7.26 (m, 1H), 7.36 (s, 1H), 7.57-7.63 (m, 1H), 7.84 (dd, 1H), 8.09-8.14 (m, 1H), 8.14 (s, 1H), 8.53 (d, 1H), 9.30 (s, 1H).

Example 16C

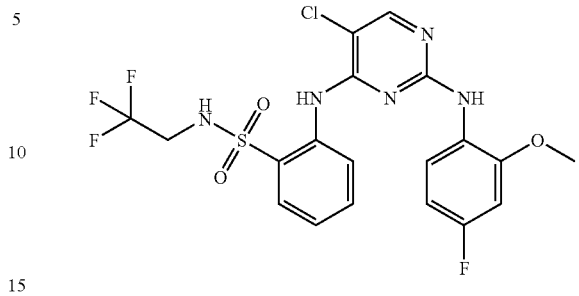

CDCl₃: 3.56-3.65 (m, 2H), 3.88 (s, 3H), 5.11-5.19 (m, 1H), 6.50-6.56 (m, 1H), 6.61-6.66 (m, 1H), 7.25-7.29 (m, 1H), 7.38 (brs, 1H), 7.58-7.62 (m, 1H), 7.97 (dd, 1H), 8.02-8.10 (m, 1H), 8.15 (s, 1H), 8.41 (dd, 1H), 8.81 (s, 1H).

The following 2-(5-Chloro-2-(subst.phenylamino)-pyrimidin-4-ylamino)-5-fluoro-N-methyl-benzamide are prepared from 2-(2,5-Dichloro-pyrimidin-4-ylamino)-5-fluoro-N-methyl-benzamide and the corresponding aniline following the procedure of Example 2:

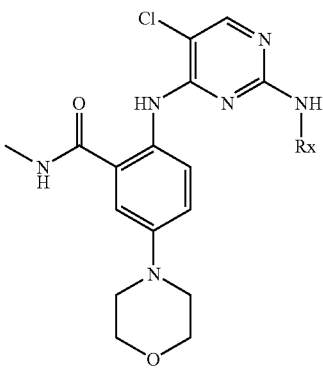

| Expl No. | Rx | Mass(m/z) | NMR (400 MHz) δ (ppm) |
|---|---|---|---|
| 18-1 | ![structure with methyl, methoxy, piperazine-acetyl] | 595 [M + 1]⁺ | DMSO-d6: 2.06 (s, 3H), 2.78 (d, 3H), 3.05-3.18 (m, 8H), 3.53-3.64 (m, 4H), 3.68-3.77 (m, 4H), 3.77 (s, 3H), 6.51 (dd, 1H), 6.69 (d, 1H), 6.88 (br.d, 1H), 7.20 (d, 1H), 7.43 (d, 1H), 7.99-8.03 (m, 2H), 8.34 (br.d, 1H), 8.63-8.71 (m, 1H), 11.15 (s, 1H). |

The following 2-[5-chloro-2-(subst.phenylamino)-pyrimidin-4-ylamino]-N-isopropyl-benzenesulfonamides are prepared from 2-(5-chloro-2-chloro-pyrimidin-4-ylamino)-N-isopropyl-benzenesulfonamide and the corresponding aniline following the procedure of Example 7A

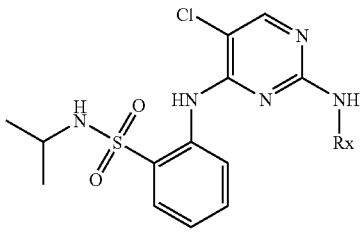

| ExplNo. | Rx | Rf (solvent) Or MS | NMR (400 MHz), δ (ppm) |
|---|---|---|---|
| 19-1 | 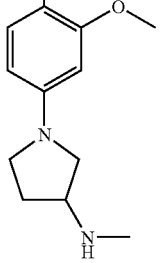 | 0.39 (MeOH: CH₂Cl₂ = 1:4) | DMSO-d6: 0.94(d, 6H), 1.75-1.84(m, 1H), 2.07-2.16(m, 1H), 2.33(s, 3H), 2.98-3.04(m, 1H), 3.22-3.36(m, 5H), 3.42-3.47(m, 1H), 3.74(s, 3H), 6.05(dd, 1H), 6.18(d, 1H), 7.18(dd, 1H), 7.25(d, 1H), 7.35-7.45(m, 1H), 7.77-7.82(m, 1H), 7.70-8.10(m, 1H), 8.09-8.17 (m, 2H), 8.45-8.63(m, 1H), 9.34(s, 1H) |
| 19-2 | 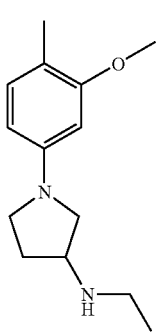 | 0.40 (n-hexane: AcOEt = 1:1) | CDCl₃: 1.00(d, 6H), 1.13(t, 3H), 1.83-1.92(m, 1H), 2.23-2.30(m, 1H), 2.70-2.78(m, 2H), 3.08-3.13(m, 1H), 3.27-3.54 (m, 5H), 3.85(s, 3H), 4.33(d, 1H), 6.05(d, 1H), 6.13(s, 1H), 7.13(bs, 1H), 7.18-7.22(m, 1H), 7.52-7.56(m, 1H), 7.83-7.86(m, 1H), 7.95-7.98(m, 1H), 8.09(s, 1H), 8.47-8.49(m, 1H), 8.89(s, 1H) |
| 19-3 | 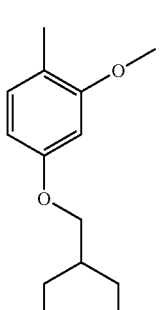 | 0.30 (n-hexane: AcOEt = 1:1) | CDCl₃: 0.93 (d, 6H), 1.05-1.09(m, 1H), 1.48-1.99(m, 6H), 2.16(s,3H), 2.61-2.67(m, 1H), 2.80-2.83(m, 1H), 3.75(s, 3H), 3.80-3.89(m, 2H), 6.44-6.47(m, 1H), 6.62-6.63(m, 1H), 7.18-7.22(m, 1H), 7.42-7.46(m, 1H), 7.80-7.89(m, 2H), 8.17(s, 1H), 8.23(s, 1H), 8.42-8.44(m, 1H), 8.89(s, 1H) |

-continued

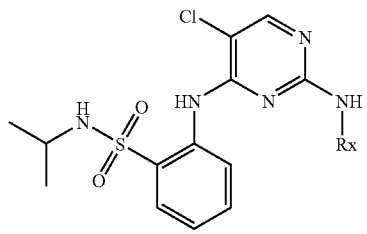

| ExplNo. | Rx | Rf (solvent) Or MS | NMR (400 MHz), δ (ppm) |
|---|---|---|---|
| 19-4 | 4-methyl-3-methoxyphenyl-piperidin-4-yl-(4-methylpiperazin-1-yl) | 0.69 (MeOH: $CH_2Cl_2$ = 1:3) | DMSO-d6: 0.94(d, 6H), 1.45-1.57(m, 2H), 1.80-1.88(m, 2H), 2.14(s, 3H), 2.25-2.35(m, 4H), 2.45-2.55(m, 4H), 2.62-2.70(m, 2H), 3.28-3.37(m, 1H), 3.68-3.74(m, 2H), 3.75(s, 3H), 6.44(dd, 1H, J=8.82, 2.0 Hz), 6.61(d, 1H, J=2.0 Hz), 7.21(dd, 1H), 7.37(d, 1H), 7.45(dd, 1H), 7.81 (dd, 1H, J=1.82, 1.52 Hz), 7.84-7.92(m, 1H), 8.12-8.20(m, 1H), 8.16(s, 1H), 8.43-8.51(m, 1H), 9.31(s, 1H) |
| 19-5 | 4-methyl-3-methoxyphenyl-(4-methylpiperazin-1-yl) | 0.35 (n-hexane: AcOEt = 1:1) | CDCl$_3$: 0.93(d, 6H), 2.23(s, 3H), 2.45-2.48(m, 4H), 3.12-3.15(m,4H), 3.75(s, 3H), 6.42-6.45(m, 1H), 6.63 (s, 1H), 7.19-7.23(m, 1H), 7.38-7.47(m, 2H), 7.80-7.89(m, 2H), 8.16(s, 1H), 8.46-8.48(m, 1H), 9.34(s, 1H) |
| 19-6 | 4-methyl-3-methoxy-6-fluorophenyl | 0.45 (n-hexane: AcOEt = 1:1) | CDCl$_3$: 0.99(d, 6H), 3.40-3.49(m, 1H), 3.88(s, 3H), 4.29-4.31(d, 1H), 6.51-6.56(m, 1H), 6.62-6.65 (m, 1H), 7.24-7.28(m, 1H), 7.37(s, 1H), 7.56-7.60(m, 1H), 7.98-8.15(m, 3H), 8.34-8.37(m, 1H), 8.89(s, 1H) |
| 19-7 | 4-methyl-3-methoxyphenyl-O-(1-methylpiperidin-4-yl) | 0.28 (n-hexane: AcOEt = 1:1) | DMSO-d6: 0.93(d, 6H), 1.59-1.67(m, 2H), 1.90-1.93(m, 2H), 2.10-2.24(m, 5H), 2.60-2.67(m, 2H), 3.74(s, 3H), 4.33-4.37(m, 1H), 6.47-6.50(m, 1H), 6.63(d, 1H), 7.18-7.22(m, 1H), 7.41-7.45(m, 2H), 7.79-7.87(m, 2H), 8.16(s, 1H), 8.21(s, 1H), 8.41-8.43(m, 1H), 9.29(s, 1H) |

-continued

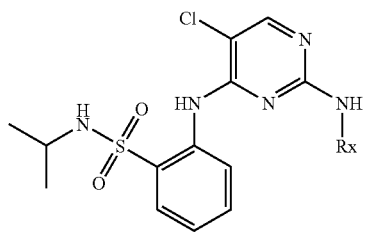

| ExplNo. | Rx | Rf (solvent) Or MS | NMR (400 MHz), δ (ppm) |
|---|---|---|---|
| 19-8 | 4-methyl-3-methoxyphenyl morpholine | 0.25 (n-hexane: AcOEt = 1:1) | DMSO-d6: 0.93(d, 6H), 3.09-3.12(m, 4H), 3.74-3.76(m, 7H), 6.43-6.46(m, 1H), 6.64(s, 1H), 7.19-7.23(m, 1H), 7.41-7.48(m, 2H), 7.80(d, 1H), 7.82(d, 1H), 8.17(s, 1H), 8.46-8.48(m, 1H), 9.31(s, 1H) |
| 19-9 | 4-methyl-3-methoxyphenyl 3-(dimethylamino)pyrrolidine | 0.56 (MeOH: $CH_2Cl_2$ = 1:4) | DMSO-d6: 0.93(d, 6H), 1.89-1.90(m, 1H), 2.30(bs, 6H), 3.13-3.50(m, 6H), 3.74(s, 3H), 6.10(d, 1H), 6.22(s, 1H), 7.16-7.20(m, 1H), 7.25-7.27(m, 1H), 7.40(bs, 1H), 7.79-7.81(m, 1H), 7.86-7.88(m, 1H), 8.12(s, 1H), 8.15(s, 1H), 8.51(s, 1H), 9.34(s, 1H) |
| 19-10 | 4-methyl-3-methoxyphenyl N-(3-dimethylamino-2,2-dimethylpropyl) | 0.45 (MeOH: $CH_2Cl_2$ = 1:4) | $CDCl_3$: 0.99(d, 12H), 2.27(s, 2H), 2.31(s, 6H), 2.96(s, 2H), 3.39-3.48(m, 1H), 3.83(s, 3H), 4.30(d, 1H), 6.09-6.12(m, 1H), 6.19(d, 1H), 7.11(s, 1H), 7.19-7.23(m, 1H), 7.51-7.57(m, 1H), 7.76-7.79(m, 1H), 7.95(d, 1H), 8.09(s, 1H), 8.46-8.49(m, 1H), 8.88(s, 1H) |
| 19-11 | 4-methyl-3-methoxy-2-fluorophenyl morpholine | 0.30 (n-hexane: AcOEt = 1:1) | DMSO-d6: 0.93(d, 6H), 2.96-2.99(m, 4H), 3.74-3.76(m, 7H), 6.67-6.72(m, 1H), 7.21-7.25(m, 1H), 7.31-7.34(m, 1H), 7.44-7.48(m, 1H), 7.80-7.83(m, 1H), 7.88(d, 1H), 8.21(s, 1H), 8.42(d, 1H), 8.58(s, 1H), 9.30 (s, 1H) |

-continued

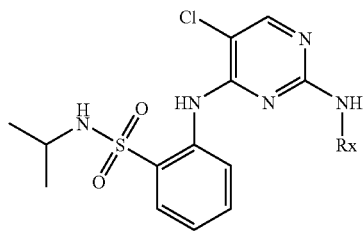

| ExplNo. | Rx | Rf (solvent) Or MS | NMR (400 MHz), δ (ppm) |
|---|---|---|---|
| 19-12 | (4-methyl-3-methoxy-2-fluorophenyl)-pyrrolidin-3-yl-methylamine | 0.42 (MeOH:CH₂Cl₂ = 1:4) | DMSO-d6: 0.94(d, 6H), 1.68-1.76(m, 1H), 1.99-2.07(m, 1H), 2.29(s, 3H), 3.05-3.49(m, 6H), 3.75(s, 3H), 6.36-6.40(m, 1H), 7.10-7.37(m, 3H), 7.70-7.80(m, 1H), 8.08-8.39(m, 3H), 9.24(s, 1H) |
| 19-13 | (4-methyl-3-methoxyphenyl)-pyrrolidin-3-yl-acetamide | 0.50 (MeOH:CH₂Cl₂ = 1:4) | CDCl₃: 1.01(d, 6H), 1.94-1.96(m, 1H), 2.01(s, 3H), 2.29-2.37(m, 1H), 3.19-3.58(m, 5H), 3.86(s, 3H), 4.42(d, 1H), 4.59-4.63(m, 1H), 5.70(d, 1H), 6.05-6.08(m, 1H), 6.15-6.16(m, 1H), 7.17-7.24(m, 2H), 7.53-7.57(m, 1H), 7.90(d, 1H), 7.91-7.98(m, 1H), 8.09(s, 1H), 8.47(d, 1H), 8.91(s, 1H) |
| 19-14 | (4-methyl-3-methoxyphenyl)-pyrrolidin-3-yl-N-methylacetamide | 0.53 (MeOH:CH₂Cl₂ = 1:4) | CDCl₃: 1.00(d, 6H), 2.04(s, 3H), 2.05-2.29(m, 2H), 2.96(s, 3H), 3.19-3.54(m, 5H), 3.86(s, 3H), 4.57-4.63(m, 1H), 5.39-5.46(m, 1H), 6.07-6.09(m, 1H), 6.16(d, 1H), 7.18-7.26(m, 2H), 7.53-7.57(m, 1H), 7.89-7.98(m, 2H), 8.08(s, 1H), 8.47(d, 1H), 8.94(d, 1H) |
| 19-15 | (4-methyl-3-methoxyphenyl)-piperidin-4-yl-pyrrolidine | 0.56 (MeOH:CH₂Cl₂ = 1:4) | DMSO-d6: 0.93(d, 6H), 1.48-1.56(m, 2H), 1.65-1.75(m, 4H), 1.90-1.93(m, 2H), 2.05-2.15(m, 1H), 2.45-2.55(m, 5H), 2.69-2.75(m, 2H), 3.61(d, 2H), 3.74(s, 1H), 6.42-6.51(m, 1H), 6.61(d, 1H), 7.18-7.22(m, 1H), 7.37(d, 1H), 7.43-7.47(m, 1H), 7.80(d, 1H), 7.81-7.89(m, 1H), 8.16(d, 1H), 8.46-8.48(m, 1H), 9.31(s, 1H) |

-continued

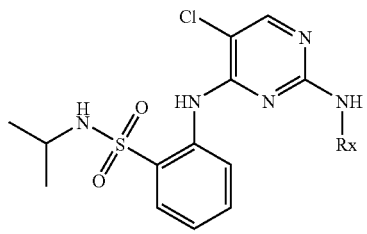

| ExplNo. | Rx | Rf (solvent) Or MS | NMR (400 MHz), δ (ppm) |
|---|---|---|---|
| 19-16 | 4-methyl-3-methoxyphenyl-N-(2-(pyrrolidin-1-ylmethyl)pyrrolidin-1-yl) | 0.56 (MeOH:CH₂Cl₂ = 1:4) | DMSO-d6: 0.92(d, 6H), 1.65-1.75(m, 4H), 1.88-2.00(m, 4H), 2.39-2.43(m, 2H), 2.60-2.65(m, 2H), 3.03-3.07(m, 1H), 3.03-3.40(m, 2H), 3.70(s, 3H), 3.77-3.78(m, 1H), 6.09(d, 1H), 6.23(s, 1H), 7.13-7.78(d, 1H), 7.86(d, 1H), 8.10(s, 1H), 8.13(s, 1H), 8.40-8.50(m, 1H), 9.31(s, 1H) |
| 19-17 | 4-methyl-3-methoxyphenyl-O-CH₂-(1-methylpiperidin-2-yl) | 0.23 (n-hexane:AcOEt = 1:1) | DMSO-d6: 0.93(d, 6H), 1.24.-1.57(m, 4H), 1.69-1.78(m, 2H), 1.98-2.04(m, 1H), 2.15-2.33(m, 5H), 2.70-2.80(m, 1H), 3.74(s, 3H), 3.91-3.94(m, 1H), 4.05-4.09(m, 1H), 6.46-6.49(m, 1H), 6.63(d, 1H), 7.18-7.22(m, 1H), 7.42-7.46(m, 2H), 7.80(d, 1H), 7.89(d, 1H), 8.17(s, 1H), 8.25(s, 1H), 8.42-8.44(m, 1H), 9.31(s, 1H) |
| 19-18 | 4-methyl-3-methoxyphenyl-N-(3-(N,N-diethylcarbamoyl)piperidin-1-yl) | 0.48 (n-hexane:AcOEt = 1:1) | DMSO-d6: 0.93(d, 6H), 1.03(t, 3H), 1.13(t, 3H), 1.42-1.81(m, 4H), 2.57-2.83(m, 4H), 3.17-3.41(m, 4H), 3.65-3.75(m, 1H), 3.80(s, 3H), 4.21(bs, 1H), 6.42-6.47(m, 2H), 6.51(d, 1H), 6.63(d, 1H), 7.18-7.22(m, 1H), 7.38-7.47(m, 2H), 7.80-7.82(m, 1H), 7.89(d, 1H), 8.16(s, 1H), 8.47-8.49(m, 1H), 9.31(s, 1H) |
| 19-19 | 4-methyl-3-methoxyphenyl-N-(3-carbamoylpiperidin-1-yl) | 0.44 (CH2Cl2:MeOH = 9:1) | CDCl₃: 1.45-1.62 (m, 2H), 1.72-1.78 (m, 1H), 1.82-1.90 (m, 1H), 2.40-2.46 (m, 1H), 2.61-2.75 (m, 2H), 3.75-3.70 (m, 2H), 3.76 (s, 3H), 6.45 (dd, 1H), 6.62 (d, 1H), 6.85 (s, 1H), 7.19-7.23 (m, 1H), 7.36-7.48 (m, 3H), 7.80-7.82 (m, 1H), 7.85-7.93 (br, 1H), 8.16 (s, 2H), 8.43-8.52 (m, 1H), 9.31 (s, 1H) |

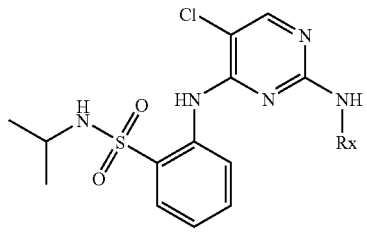

| ExplNo. | Rx | Rf (solvent) Or MS | NMR (400 MHz), δ (ppm) |
|---|---|---|---|
| 19-20 | 4-(1-methylpyrrolidin-3-yloxy)-3-methoxy-tolyl | Ms: 547 | DMSO-d6: 0.94 (d, 6H), 1.73-1.82 (m, 1H), 2.23-2.33 (m, 4H), 2.34-2.41 (m, 1H), 2.54-2.62 (m, 1H), 2.62-2.69 (m, 1H), 2.77-2.82 (m, 1H), 3.25-3.35 (m, 1H), 3.74 (s, 3H), 4.85-4.92 (m, 1H), 6.4 (dd, 1H), 6.57 (d, 1H), 7.16-7.24 (m, 1H), 7.38-7.51 (m, 1H), 7.81 (d, 1H), 7.82-7.94 (m, 1H), 8.16 (s, 1H), 8.22 (brs, 1H), 8.38-8.48 (m, 1H), 9.3 (brs, 1H) |
| 19-21 | 4-(1-methylpiperidin-4-yloxy)-3-fluoro-2-methoxy-tolyl | Ms: 579 | DMSO-d6: 0.92 (d, 6H), 1.61-1.71 (m, 2H), 1.86-1.96 (m, 2H), 2.12-2.22 (m, 5H), 2.57-2.64 (m, 2H), 3.2-3.4 (m, 1H), 3.77 (s, 3H), 4.27-4.35(m, 1H), 6.86 (dd, 1H), 7.19-7.27 (m, 1H), 7.39-7.46 (m, 1H), 7.81 (dd, 1H), 7.84-7.92 (m, 1H), 8.21 (s, 1H), 8.36-8.42 (m, 1H), 8.62 (s, 1H), 9.28 (s, 1H) |
| 19-22 | 3-methoxy-4-methyl-N-(3-hydroxy-2,2-dimethylpropyl)aniline | Ms: 549 | DMSO-d6: 0.90 (s, 6H), 0.94 (d, 6H), 2.9 (d, 2H), 3.24 (d, 2H), 3.25-3.35(m, 1H), 3.27-3.36 (m, 1H), 3.68 (s, 3H), 4.58 (t, 1H), 5.3 (t, 1H), 6.16 (dd, 1H), 6.39 (d, 1H), 7.13 (d, 1H), 7.15-7.21 (m, 1H), 7.35-7.45 (m, 1H), 7.8 (dd, 1H), 7.83-7.92 (m, 1H), 8.09 (s, 1H), 8.11 (s, 1H), 8.45-8.57 (m, 1H), 9.33 (s, 1H) |
| 19-23 | 3-methoxy-4-methyl-N-(1-hydroxy-2-methylpropan-2-yl)aniline | Rf: 0.51 (n-hexane: AcOEt = 1:1) | DMSO-d6: 0.94 (d, 6H), 1.22 (s, 6H), 3.25-3.35 (m, 1H), 3.36 (d, 2H), 3.68 (s, 3H), 4.73-4.79 (brs, 1H), 4.81 (t, 1H), 6.29 (dd, 1H), 6.44 (d, 1H), 7.14-7.22 (m, 2H), 7.38-7.46 (m, 1H), 7.8 (dd, 1H), 7.85-7.9 (m, 1H), 8.1 (s, 1H), 8.13 (s, 1H), 8.45-8.55 (m, 1H), 9.32 (s, 1H) |

-continued
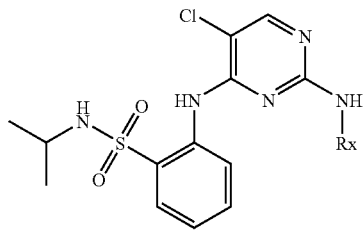
| ExplNo. | Rx | Rf (solvent) Or MS | NMR (400 MHz), δ (ppm) |
|---|---|---|---|
| 19-24 | | Ms: 577 | DMSO-d6: 0.93 (d, 6H), 0.96 (s, 6H), 2.22 (s, 6H), 3.25-3.35 (m, 1H), 3.7 (s, 3H), 3.75 (s, 3H), 6.46 (dd, 1H), 6.62 (d, 1H), 7.16-7.23 (m, 1H), 7.38-7.47 (m, 1H), 7.81 (dd, 1H), 7.85-7.9 (m, 1H), 8.17 (s, 1H), 8.23 (s, 1H), 8.38-8.48 (m, 1H), 9.31 (s, 1H) |
| 19-25 | | Ms: 521 | DMSO-d6: 0.94 (d, 6H), 3.12 (t, 4H), 3.25-3.35 (m, 1H), 3.75 (t, 4H), 6.73 (dd, 1H), 6.85 (dd, 1H), 7.16-7.24 (m, 1H), 7.25-7.32 (m, 1H), 7.38-7.47 (m, 1H), 7.8 (dd, 1H), 7.88 (d, 1H), 8.18 (s, 1H), 8.42-8.52 (m, 1H), 8.86 (s, 1H), 9.36 (s, 1H) |
| 19-26 | | Ms: 565 | DMSO-d6: 0.93 (d, 6H), 2.4-2.56 (m, 4H), 2.69 (t, 2H), 3.25-3.38 (m, 1H), 3.59 (t, 4H), 4.11 (t, 1H), 6.75 (dd, 1H), 6.93 (dd, 1H), 7.16-7.23 (m, 1H), 7.3-7.4 (m, 1H), 7.4-7.38 (m, 1H), 7.8 (dd, 1H), 7.88 (d, 1H), 8.19 (s, 1H), 8.36-8.5 (m, 1H), 8.92 (s, 1H), 9.34 (s, 1H) |
| 19-27 | | Ms: 614 | DMSO-d6: 0.93 (d, 6H), 1.3-1.62 (m, 8H), 1.75-1.85 (m, sH), 2.26-2.4 (m, 1H), 2.4-2.58 (m, 4H), 3.28-3.38 (m, 1H), 3.68-3.78 (m, 5H), 6.42 (dd, 1H), 6.64 (d, 1H), 7.18-7.24 (m, 1H), 7.42-7.5 (m, 2H), 7.77 (d, 1H), 7.82 (dd, 1H), 8.13 (s, 1H), 8.17 (s, 1H), 8.4-8.5 (m, 1H), 9.36 (s, 1H) |

-continued

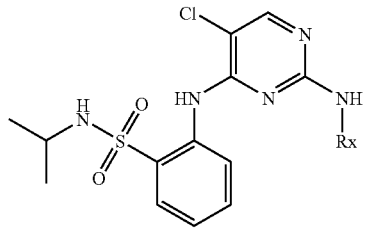

| ExplNo. | Rx | Rf (solvent) Or MS | NMR (400 MHz), δ (ppm) |
|---|---|---|---|
| 19-28 | 3-fluoro-4-methylphenyl-O-(1-methylpiperidin-4-yl) | Rf: 0.5 (MeOH:CH2Cl2 = 3:7) | DMSO-d6: 0.93 (d, 6H), 1.6-1.7 (m, 2H), 1.88-1.98 (m, 2H), 2.17-2.35 (m, 5H), 2.6-2.73 (m, 2H), 3.25-3.4 (m, 1H), 4.34-4.44 (m, 1H), 6.75 (dd, 1H), 6.93 (dd, 1H), 7.16-7.23 (m, 1H), 7.29-7.36 (m, 1H), 7.37-7.47 (m, 1H), 7.8 (dd, 1H), 7.89 (d, 1H), 8.19 (s, 1H), 8.36-8.46 (m, 1H), 8.92 (s, 1H), 9.31 (s, 1H) |
| 19-29 | 3-methoxy-4-methylphenyl-O-(2-morpholinoethyl) | Ms: 577 | DMSO-d6: 0.93 (d, 6H), 2.45-2.55 (m, 4H), 2.7 (t, 2H), 3.25-3.35 (m, 1H), 3.59 (t, 3H), 3.76 (s, 3H), 4.1 (t, 1H), 6.48 (dd, 1H), 6.65 (d, 1H), 7.18-7.24 (m, 1H), 7.4-7.5 (m, 2H), 7.82 (dd, 1H), 7.88 (d, 1H), 8.17 (s, 1H), 8.24 (s, 1H), 8.4-8.48 (m, 1H), 9.31 (s, 1H) |
| 19-30 | 3-methoxy-4-methylphenyl-O-(2-(4-methylpiperazin-1-yl)ethyl) | Ms: 590 | DMSO-d6: 0.93 (d, 6H), 2.15 (s, 3H), 2.2-2.4 (m, 4H), 2.4-2.6 (m, 4H), 2.69 (t, 2H), 3.25-3.35 (m, 1H), 3.75 (s, 3H), 4.08 (t, 2H), 6.47 (dd, 1H), 6.64 (d, 1H), 7.18-7.24 (m, 1H), 7.41-7.49 (m, 2H), 7.81 (dd, 1H), 7.86-7.91 (m, 1H), 8.17 (s, 1H), 8.24 (s, 1H), 8.39-8.46 (m, 1H), 9.31 (s, 1H) |
| 19-31 | 3-methoxy-4-methylphenyl-(hexahydropyrazino[2,1-c][1,4]oxazin-8(1H)-yl) | Ms: 588 | DMSO-d6: 0.94 (d, 6H), 2.19-2.36 (m, 4H), 2.66-2.85 (m, 3H), 3.15-3.21 (m, 1H), 3.73-3.8 (m, 5H), 6.43 (dd, 1H), 6.63 (d, 1H), 7.18-7.25 (m, 1H), 7.4 (d, 1H), 7.43-7.5 (m, 1H), 7.81 (dd, 1H), 7.89 (d, 1H), 8.16 (s, 1H), 8.17 (s, 1H), 8.42-8.52 (m, 1H), 9.32 (s, 1H) |

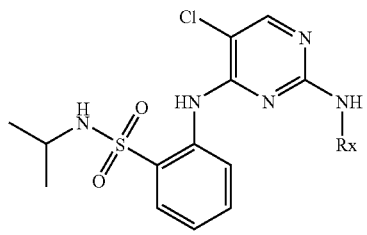

| ExplNo. | Rx | Rf (solvent) Or MS | NMR (400 MHz), δ (ppm) |
|---|---|---|---|
| 19-32 | (4-methyl-3-methoxyphenyl)-NH-(1-methylpiperidin-4-yl) | Ms: 560 | CDCl₃: 1.01(s, 6H), 1.45-1.56 (m, 2H), 2.03-2.11 (m, 2H), 2.11-2.2 (m, 2H), 2.31 (s, 3H), 2.78-2.87 (m, 2H), 3.22-3.31 (m, 1H), 3.39-3.5 (m, 1H), 3.82 (s, 3H), 4.5-4.6 (m, 1H), 6.13 (dd, 1H), 6.21 (d, 1H), 7.16 (s, 1H), 7.18-7.24 (m, 1H), 7.5-7.57 (m, 1H), 7.82 (d, 1H), 7.97 (dd, 1H), 8.16 (s, 1H), 8.08 (s, 1H), 8.46(d, 1H), 8.92 (s, 1H) |

The following 2-[5-chloro-2-(subst.phenylamino)-pyrimidin-4-ylamino]-N-methyl-benzenesulfonamides are prepared from 2-(5-chloro-2-chloro-pyrimidin-4-ylamino)-N-methyl-benzenesulfonamide and the corresponding aniline following the procedure of Example A

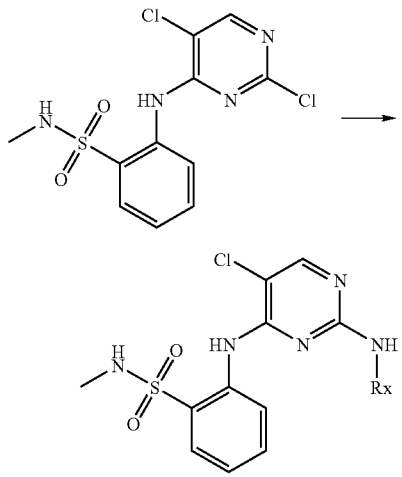

| ExplNo. | Rx | Rf (solvent) or MS | NMR (400 MHz), δ (ppm) |
|---|---|---|---|
| 20-1 | 4-methyl-3-methoxyphenyl-morpholine | 0.50 (AcOEt) | CDCl₃: 2.63(d, 3H), 3.14(t, 4H), 3.87-3.90(m, 7H), 4.64(m, 1H), 6.45(dd, 1H), 6.55(d, 1H), 7.23-7.26(m, 1H), 7.51-7.55(m, 1H), 7.91(d, 1H), 7.95(dd, 1H), 8.06(s, 1H), 8.47(d, 1H), 9.26(s, 1H) |

-continued

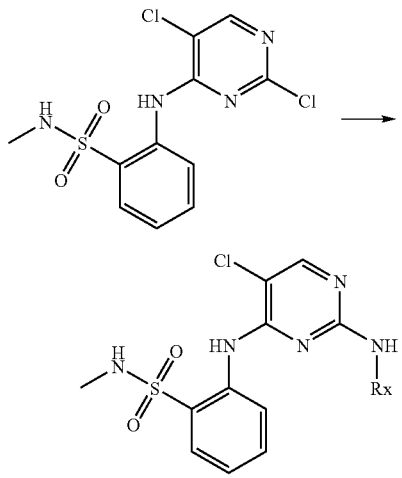

| ExplNo. | Rx | Rf (solvent) or MS | NMR (400 MHz), δ (ppm) |
|---|---|---|---|
| 20-2 | 4-(4-acetylpiperazin-1-yl)-2-methoxy-1-methylbenzene (3-methoxy-4-methylphenyl with 4-acetylpiperazinyl) | m/z 546, 548 (M + 1) | DMSO-d6: 2.06 (s, 3H), 2.43 (s, 3H), 3.10 (m, 2H), 3.16 (m, 2H), 3.59-3.62 (m, 4H), 3.77 (s, 3H), 6.49 (dd, 1H), 6.68 (d, 1H), 7.21-7.25 (m, 1H), 7.42 (d, 1H), 7.49 (dd, 1H), 7.75-7.77 (m, 1H), 7.78(s, 1H), 8.16(s, 1H), 8.21 (s, 1H), 8.50(d, 1H), 9.35 (s, 1H) |
| 20-3 | 2-methyl-1-(trifluoromethoxy)benzene | 0.27 (n-hexane: AcOEt = 3:1) | CDCl$_3$: 2.65(d, 3H), 4.45-4.49(m, 1H), 6.99-7.04(m, 1H), 7.17-7.28(m, 4H), 7.56-7.60(m, 1H), 7.96-7.98(m, 1H), 8.18(s, 1H), 8.31-8.34(m, 1H), 8.41-8.44(m, 1H), 9.14(s, 1H) |
| 20-4 | 2-methyl-1-(difluoromethoxy)benzene | 0.27 (n-hexane: AcOEt = 3:1) | CDCl$_3$: 2.65(d, 3H), 4.54-4.58(m, 1H), 6.53(dd, 1H), 6.98-7.02(m, 1H), 7.11-7.15(m, 2H), 7.24-7.28(m, 1H), 7.35(bs, 1H), 7.57-7.61(m, 1H), 7.95-7.98(m, 1H), 8.16(s, 1H), 8.29-8.32(m, 1H), 8.42-8.46(m, 1H), 9.14(s, 1H) |
| 20-5 | N-(1-(3-methoxy-4-methylphenyl)pyrrolidin-3-yl)acetamide | 0.46 (MeOH: CH$_2$Cl$_2$ = 1:4) | CDCl$_3$: 1.95-2.00(m, 5H), 2.29-2.37(m, 1H), 2.62(d, 3H), 3.20-3.78(m, 4H), 3.86(s, 3H), 4.60-4.64(m, 2H), 5.68-5.69(m, 1H), 6.09-6.16(m, 2H), 7.15(bs, 1H), 7.19-7.23(m, 1H), 7.54-7.58(m, 1H), 7.88-7.95(m, 2H), 8.06(s, 1H), 8.55-8.57(m, 1H), 9.08(s, 1H) |

-continued
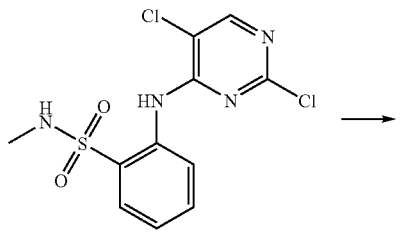
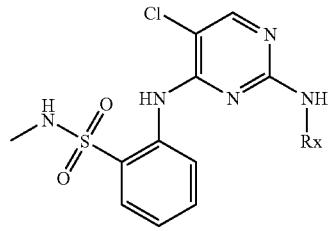
| ExplNo. | Rx | Rf (solvent) or MS | NMR (400 MHz), δ (ppm) |
|---|---|---|---|
| 20-6 | 4-(4-methylpiperazin-1-yl)-2-methoxy-1-methylphenyl | 518 [M + 1]+ | DMSO-d6: 2.23(s, 3H), 2.43(s, 3H), 2.45-2.50(m, 4H), 3.12-3.17(m, 4H), 3.76(s, 3H), 6.45(dd,1H), 6.63(d, 1H), 7.22(dd, 1H), 7.37(d, 1H), 7.45-7.50(m 1H), 7.74-7.78(m, 1H), 7.76(d, 1H), 8.15(s, 1H), 8.19(s, 1H), 8.46-8.53(m, 1H), 9.35(bs, 1H) |
| 20-7 | 4-(piperazin-1-yl)-2-methoxy-1-methylphenyl | 504 [M + 1]+ | DMSO-d6: 2.43(s, 3H), 2.80-2.89(m, 4H), 2.99-3.07(m, 4H), 3.76(s, 3H), 6.44(dd,1H), 6.61(d, 1H), 7.18-7.24(m, 1H), 7.37(d, 1H), 7.44-7.50(m, 1H), 7.76(dd, 1H), 8.15(s, 1H), 8.18(s, 1H), 8.45-8.55(m, 1H), 9.20-9.45(m, 1H) |
| 20-8 | 4-(4-piperidin-1-yl-piperidin-1-yl)-2-methoxy-1-methylphenyl | 586 [M + 1]+ | DMSO-d6: 1.35-1.43(m, 2H), 1.45-1.61 (m, 6H), 1.75-1.85(m,2H), 2.30-2.40(m, 1H), 2.43(d, 3H), 2.42-2.55(m, 4H), 2.60-2.70(m, 2H), 3.68-3.77(m, 2H), 3.75(s, 3H), 6.45(dd, 1H), 6.62(d, 1H), 7.21 (dd, 1H), 7.36(d, 1H), 7.43-7.51(m, 1H), 7.73-7.81(m, 1H), 7.75(dd, 1H), 8.15(s, 1H), 8.17(s, 1H), 8.45-8.52(m, 1H), 9.34(bs, 1H) |

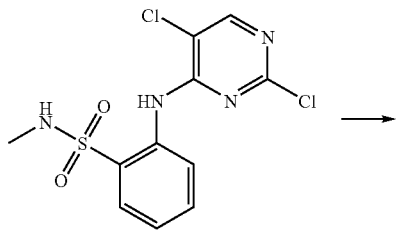
→
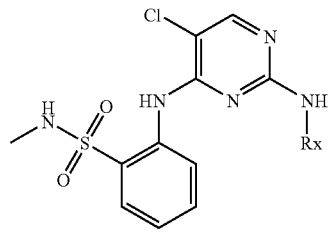
| ExplNo. | Rx | Rf (solvent) or MS | NMR (400 MHz), δ (ppm) |
|---|---|---|---|
| 20-9 | | 569 [M + 1]+ | DMSO-d6: 1.85-1.95(m, 2H), 2.15(s, 3H), 2.18(t, 2H), 2.22-2.40(m, 8H), 2.43(s, 3H), 4.17(t, 2H), 6.65(d, 1H), 7.06(dd, 1H), 7.20(d, 1H), 7.22(ddd, 1H), 7.25(d, 1H), 7.39-7.47(m, 2H), 7.72-7.82(m, 1H), 7.77(dd, 1H), 8.26(s, 1H), 8.52(d, 1H), 9.22(s, 1H), 9.36(s, 1H) |
| 20-10 | | 556 [M + 1]+ | DMSO-d6: 1.85-1.95(m, 2H), 2.19(t, 2H), 2.25-2.35(m, 4H), 2.43(s, 3H), 3.55-3.60(m, 4H), 4.19(t, 2H), 6.66(d, 1H), 7.06(dd, 1H), 7.17-7.24(m, 1H), 7.21(d, 1H), 7.27(d, 1H), 7.39-7.45(m, 1H), 7.44(d, 1H), 7.70-7.80(m, 1H), 7.76(dd, 1H), 8.26(s, 1H), 8.52(d, 1H), 9.21(s, 1H), 9.36(s, 1H) |
| 20-11 | | Rf (Hexane: AcOEt = 1:1) 0.29 | DMSO-d6: 2.64 (d, 3H), 2.87-2.96 (m, 4H), 3.65-3.74 (m, 4H), 3.86 (s, 3H), 4.41451 (m, 1H), 6.50 (dd, 1H), 6.81 (d, 1H), 7.55-7.64 (m, 2H), 7.96 (d, 1H), 8.01 (s, 1H), 8.19 (s, 1H), 8.49 (d, 1H), 9.07 (s, 1H). |

-continued
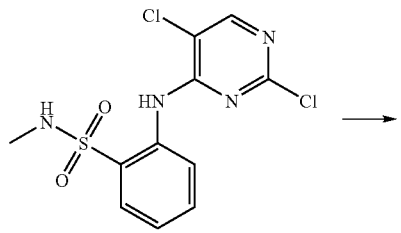
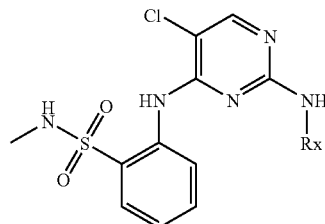
| ExplNo. | Rx | Rf (solvent) or MS | NMR (400 MHz), δ (ppm) |
|---|---|---|---|
| 20-12 | (2,5-dimethoxy-4-methyl-phenyl morpholine) | MS 535 | DMSO-d6: 2.64 (d, 3H), 3.05 (bs, 4H), 3.59 (bs, 3H), 3.87(bs, 3H), 3.89 (bs, 4H), 4.52-4.48 (m, 1H), 6.57(bs, 1H), 7.25-7.20(m, 1H), 7.44-7.32 (m, 1H), 7.63-7.52 (m, 1H), 7.94(bs, 1H), 8.06 (d, 1H), 8.25(s, 1H), 8.48(d, 1H), 9.06(bs, 1H) |
| 20-13 | (2,5-dimethoxy-4-methyl-phenyl 4-methylpiperazine) | MS 548 | DMSO-d6: 2.17 (bs, 3H), 2.63 (d, 3H), 2.68 (bs, 4H), 3.10(bs, 4H), 3.57 (s, 3H), 4.54-4.46 (m, 1H), 6.59(bs, 1H), 7.27-7.18(m, 1H), 7.37 (bs, 1H), 7.62-7.55 (m, 1H), 7.94(bs, 1H), 7.95 (d. 1H), 8.16(s, 1H), 8.48(d, 1H), 9.04(bs, 1H) |
| 20-14 | (4-methyl-3-propoxy-phenyl 4-methylpiperazine) | MS 546 | DMSO-d6: 1.06 (t, 3H), 1.86 (dd, 2H), 2.37 (s, 3H), 2.62-2.59 (m, 4H), 2.64(d, 3H), 4.00-3.97 (m, 4H), 4.62-4.54 (m, 1H), 6.44 (dd, 1H), 6.54(d, 1H), 7.27-7.22(m, 1H), 7.34(bs, 1H), 7.58-7.54(m, 1H), 7.95(dd, 1H), 8.02(d, 1H), 8.11(s, 1H), 8.53(d, 1H), 9.07(bs, 1H) |

-continued
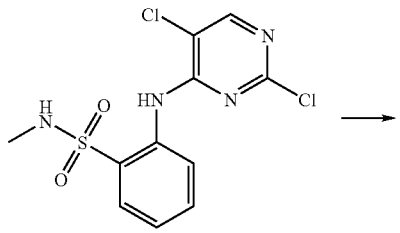
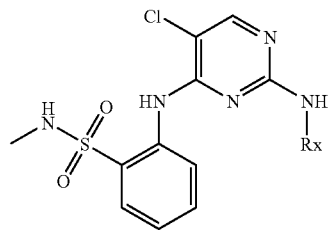
| ExplNo. | Rx | Rf (solvent) or MS | NMR (400 MHz), δ (ppm) |
|---|---|---|---|
| 20-15 | 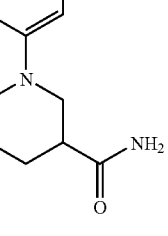 | LC-MS 535 | DMSO-d6: 1.46-1.62 (m, 2H), 1.72-1.79 (m, 1H), 1.82-1.90 (m, 1H), 2.38-2.46 (m, 1H), 2.43 (s, 3H), 2.62-2.76 (m, 2H), 3.59-3.69 (m, 2H), 3.43 (s, 3H), 6.47 (dd, 1H), 6.63 (d, 1H), 6.82-6.89 (br, 1H), 7.21 (dd, 1H), 7.32-7.41 (m, 2H), 7.44-7.52 (m, 1H), 7.71-7.82 (m, 2H), 8.15 (s, 1H), 8.15-8.20 (br, 1H), 8.44-8.53 (m, 1H), 9.28-9.38 (m, 1H) |
| 20-16 | 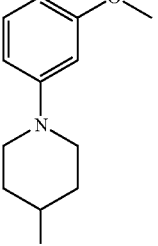 | 0.24 (CH2Cl2: MeOH = 8:2) | DMSO-d6: 1.47-1.55 (m, 2H), 1.80-1.91 (m, 2H), 2.16 (s, 3H), 2.25-2.41 (m, 5H), 2.42-2.48 (m, 3H), 2.61-2.73 (m, 2H), 3.68-3.79 (m, 5H), 6.45 (dd, 1H), 6.62 (d, 1H), 7.21 (dd, 1H), 7.34 (d, 1H), 7.45-7.49 (m, 1H), 7.73-7.80 (m, 2H), 8.15 (s, 1H), 8.20 (s, 1H), 8.45-8.54 (m, 1H), 9.34 (s, 1H) |
| 20-17 | 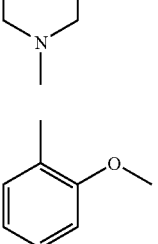 | LC-MS 535 | DMSO-d6: 1.76-1.84 (m, 1H), 2.08-2.16 (m, 1H), 2.33 (s, 3H), 2.42 (s, 3H), 3.00-3.03 (m, 1H), 3.23-3.27 (m, 3H), 3.42-3.46 (m, 1H), 3.74 (s, 3H), 6.06 (dd, 1H), 6.18-6.20 (m, 1H), 7.17-7.23 (m, 1H), 7.38-7.48 (br, 1H), 7.72-7.77 (m, 1H), 8.12 (s, 1H), 8.17-8.21 (br, 1H), 8.46-8.58 (br, 1H), 9.30-9.40 (br, 1H) |

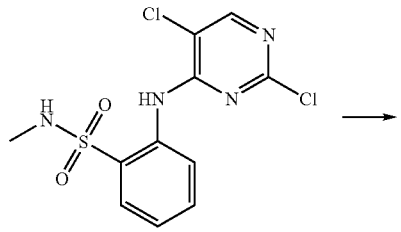
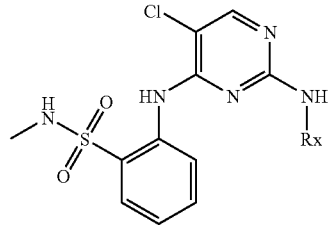
| ExplNo. | Rx | Rf (solvent) or MS | NMR (400 MHz), δ (ppm) |
|---|---|---|---|
| 20-18 | | LC-MS 601 | DMSO-d6: 1.36-1.49 (m, 2H), 1.69-1.76 (m, 2H), 2.13 (s, 3H), 2.15-2.23 (m, 1H), 2.24-2.36 (br, 4H), 2.39-2.48 (m, 5H), 2.43 (s, 3H), 3.27-3.40 (m, 2H), 3.74 (s, 3H), 6.62 (dd, 1H), 6.90 (d, 1H), 7.22-7.26 (m, 1H), 7.41-7.46 (m, 1H), 7.49-7.53 (m, 1H), 7.55-7.86 (br, 1H), 7.77 (dd, 1H), 8.16 (s, 1H), 8.25 (s, 1H), 8.42 (d, 1H), 9.28 (s, 1H) |
| 20-19 | | LC-MS 519 | DMSO-d6: 1.37-1.46 (m, 2H), 1.69-1.75 (m, 2H), 2.43 (s, 3H), 2.53-2.61 (m, 2H), 3.18-3.26 (m, 2H), 3.40-3.74 (m, 2H), 4.62 (d, 1H), 6.62 (dd, 1H), 6.90 (d, 1H), 7.22-7.26 (m, 1H), 7.42-7.46 (br, 1H), 7.48-7.55 (m, 1H), 7.77-7.80 (m, 2H), 8.13-8.18 (br, 1H), 8.25 (s, 1H), 8.40-8.45 (m, 1H), 9.25-9.30 (m, 1H) |
| 20-20 | | LC-MS 532 | DMSO-d6: 1.66-1.76 (m, 1H), 2.00-2.07 (m, 1H), 2.14 (s, 6H), 2.43 (s, 3H), 2.68-2.76 (m, 1H), 2.87-2.91 (m, 1H), 2.99-3.10 (m, 2H), 3.24-3.28 (m, 1H), 3.71 (s, 3H), 6.25 (dd, 1H), 6.90 (d, 1H), 7.00-7.03 (m, 1H), 7.21-7.24 (m, 1H), 7.40-7.45 (m, 1H), 7.78-7.83 (m, 2H), 8.19 (s, 1H), 8.24 (s, 1H), 8.46 (d, 1H), 9.27-9.36 (br, 1H) |

-continued

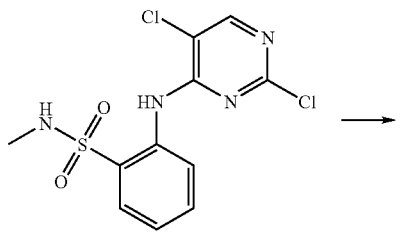

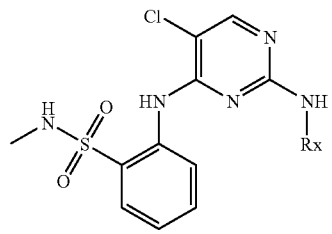

| ExplNo. | Rx | Rf (solvent) or MS | NMR (400 MHz), δ (ppm) |
|---|---|---|---|
| 20-21 | (3-methyl-4-methoxyphenoxy ethyl morpholine) | Me: 549 | DMSO-d6: 2.37-2.47 (m, 4H), 2.48-2.53 (m, 3H), 2.64 (t, 2H), 3.57 (t, 3H), 3.77 (s, 3H), 3.92 (t, 2H), 6.61 (dd, 1H), 6.93 (d, 1H), 7.28 (dd, 1H), 7.56-7.63 (m, 2H), 7.75-7.85 (m, 2H), 7.74-7.84 (m, 2H), 8.14 (s, 1H), 8.29 (s, 1H) 8.46 (d, 1H), 9.33(s, 1H) |
| 20-22 | (3-methyl-4-methoxyphenoxy ethyl N-methylpiperazine) | Ms: 562 | DMSO-d6: 2.20 (s, 3H), 2.3-2.5 (m, 11H), 2.64 (t, 2H), 3.77 (s, 3H), 3.91 (t, 2H), 6.61(dd, 1H), 6.94 (d, 1H), 7.25-7.31(m, 1H), 7.57 (d, 1H), 7.58-7.64 (m, 1H), 7.74-7.84 (m, 2H), 8.12 (brs, 1H), 8.28 (s, 1H) 8.46 (d, 1H), 9.33(brs, 1H) |
| 20-23 | (5-fluoro-2-methoxy-3-methylphenyl methylene) | Ms: 439 | DMSO-d6: 2.42-2.45 (m, 3H), 3.83 (s, 2H), 6.8 (ddd, 1H), 7.02 (dd, 1H), 7.3-7.36 (m, 1H), 7.58-7.64 (m, 1H), 7.74-7.8 (m, 1H), 7.82 (dd, 1H), 7.85 (dd, 1H), 8.18 (brs, 1H), 8.31 (s, 1H), 8.41 (d, 1H), 9.3 (brs, 1H) |
| 20-24 | (4-fluoro-2-methoxyphenyl methylene) | Ms: 438 | DMSO-d6: 2.41-2.45 (m, 3H), 3.79 (s, 2H), 6.74 (ddd, 1H), 7.0 (dd, 1H), 7.22-7.28 (m, 1H), 7.49-7.55 (m, 1H), 7.6 (dd, 1H), 7.75-7.8 (m, 2H), 8.21 (s, 1H), 8.37 (brs, 1H), 8.39-8.45 (m, 1H), 9.34 (brs, 1H) |

-continued

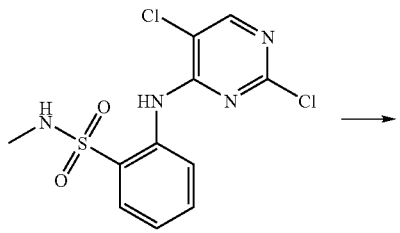

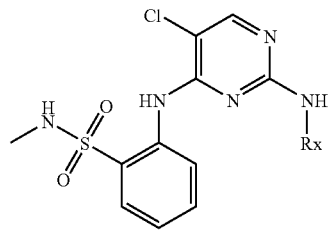

| ExplNo. | Rx | Rf (solvent) or MS | NMR (400 MHz), δ (ppm) |
|---|---|---|---|
| 20-25 | (4-methyl-3-methoxyphenoxy)methyl-1-methylpiperidine | Ms: 547 | DMSO-d6: 1.24-1.38 (m, 2H), 1.64-1.8 (m, 3H), 1.83-1.92 (m, 2H), 2.16 (s, 3H), 2.41-2.45(m, 3H), 2.76-2.83 (m, 2H), 3.75 (s, 3H), 3.84 (d, 2H), 6.48 (dd, 1H), 6.64 (d, 1H), 7.2-7.25 (m, 1H), 7.41 (d, 1H), 7.43-7.5 (m, 1H), 7.74-7.8 (m, 2H), 8.16 (s, 1H), 8.26 (brs, 1H) 8.44-8.5 (m, 1H), 9.34 (brs, 1H) |
| 20-26 | (3-methyl-4-methoxyphenoxy)methyl-1-methylpiperidine | Ms: 547 | DMSO-d6: 1.18-1.3 (m, 2H), 1.56-1.7 (m, 3H), 1.8-1.88 (m, 2H), 2.15 (s, 3H), 2.41-2.45(m, 3H), 2.73-2.8 (m, 2H), 3.75 (s, 3H), 3.65 (d, 2H), 3.77 (s, 3H), 6.57 (dd, 1H), 6.93 (d, 1H), 7.25 (dd, 1H), 7.51-7.6 (m, 2H), 7.7-7.9 (m, 2H), 8.09 (brs, 1H), 8.28 (s, 1H), 8.45 (d, 1H), 9.31 (brs, 1H) |
| 20-27 | (4-methyl-3-methoxyphenoxy)-1-methylpiperidine | Ms: 533 | DMSO-d6: 1.62-1.72 (m, 2H), 1.9-1.99 (m, 2H), 2.3-2.35 (m, 5H), 2.41-2.45(m, 3H), 2.64-2.74 (m, 2H), 3.75 (s, 3H), 4.35-4.43 (m, 1H), 6.52 (dd, 1H), 6.65 (d, 1H), 7.19-7.25 (m, 1H), 7.41 (d, 1H), 7.43-7.49 (m, 1H), 7.74-7.8 (m, 2H), 8.16 (s, 1H), 8.27 (brs, 1H), 8.42-8.5 (m, 1H), 9.34 (brs, 1H) |

-continued

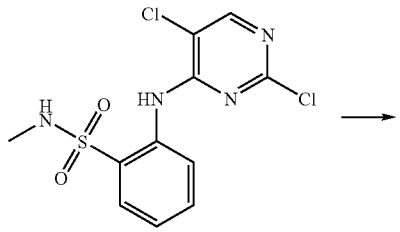

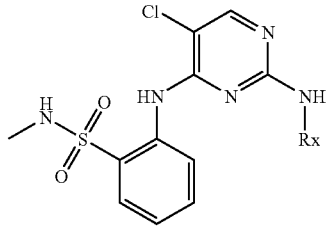

| ExplNo. | Rx | Rf (solvent) or MS | NMR (400 MHz), δ (ppm) |
|---|---|---|---|
| 20-28 | (4-methyl-3-methoxyphenoxy)-1-isopropylpyrrolidin-3-yl | Ms: 547 | DMSO-d6: 0.96-1.2 (m, 2H), 1.75-1.9 (m, 1H), 2.2-2.3 (m, 1H), 2.35-2.45 (m, 1H), 2.41-2.45(m, 2H), 2.43(d, 3H), 2.6-3.0 (m, 3H), 3.76 (s, 3H), 4.85-5.0 (m, 1H), 6.43-6.49 (m, 1H), 6.57-6.64 (m, 1H), 7.18-7.25 (m, 1H), 7.39-7.52 (m, 2H), 7.73-7.83 (m, 2H), 8.17 (s, 1H), 8.27 (brs, 1H), 8.44-8.51 (m, 1H), 9.35 (brs, 1H) |
| 20-29 | (4-methyl-3-methoxyphenoxy)-1-methylpyrrolidin-3-yl | Ms: 519 | DMSO-d6: 1.74-1.83 (m, 1H), 2.23-2.31 (m, 1H), 2.28 (s, 3H), 2.35-2.4 (m, 1H), 2.41-2.45(m, 3H), 2.58-2.63 (m, 1H), 2.63-2.7 (m, 1H), 2.78-2.83 (m, 1H), 3.75 (s, 3H), 4.86-4.92 (m, 1H), 6.43 (dd, 1H), 6.58 (d, 1H), 7.19-7.25 (m, 1H), 7.41 (d, 1H), 7.44-7.51 (m, 1H), 7.73-7.83 (m, 2H), 8.16 (s, 1H), 8.26 (brs, 1H), 8.43-8.52 (m, 1H), 9.34 (brs, 1H) |
| 20-30 | (4-methyl-3-methoxyphenoxy)-1-ethylpyrrolidin-3-yl | Ms: 533 | DMSO-d6: 1.04 (t, 3H), 1.74-1.82 (m, 1H), 2.23-2.33 (m, 1H), 2.47-2.5(m, 6H), 2.62-2.72 (m, 2H), 2.8-2.87 (m, 1H), 3.75 (s, 3H), 4.86-4.92 (m, 1H), 6.44 (dd, 1H), 6.59 (d, 1H), 7.19-7.25 (m, 1H), 7.41 (d, 1H), 7.44-7.51 (m, 1H), 7.73-7.8 (m, 2H), 8.16 (s, 1H), 8.26 (brs, 1H), 8.44-8.51 (m, 1H), 9.34 (brs, 1H) |

-continued

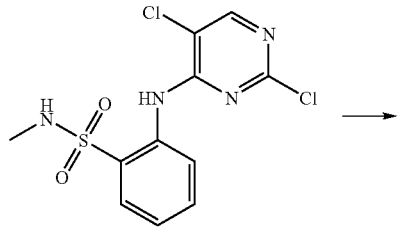

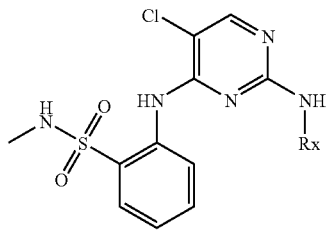

| ExplNo. | Rx | Rf (solvent) or MS | NMR (400 MHz), δ (ppm) |
|---|---|---|---|
| 20-31 | ![structure] 4-(4-methylpiperazin-1-yl)-2-methyl-1-methoxyphenyl | Ms: 518 | DMSO-d6: 2.23(s, 3H), 2.38-2.47 (m, 7H), 2.87-2.93 (m, 4H), 3.75 (s, 3H), 6.63 (dd, 1H), 6.93 (d, 1H), 7.22-7.28 (m, 1H), 7.42 (d, 1H), 7.48-7.54 (m, 1H), 7.76-7.84 (m, 1H), 8.2 (s, 1H), 8.25(s, 1H), 8.43 (dd, 1H) 9.29 (s, 1H) |
| 20-32 | ![structure] 4-(4-piperidin-1-yl-piperidin-1-yl)-2-methyl-1-methoxyphenyl | Ms: 586 | DMSO-d6: 1.35-1.55 (m, 8H), 1.66-1.75 (m, 2H), 2.23(s, 3H), 2.41-2.45 (m, 3H), 3.74 (s, 3H), 6.63 (dd, 1H), 6.91 (d, 1H), 7.21-7.28 (m, 1H), 7.44 (d, 1H), 7.48-7.54 (m, 1H), 7.76-7.87 (m, 1H), 8.16 (s, 1H), 8.25 (s, 1H), 8.43 (dd, 1H) 9.29 (s, 1H) |
| 20-33 | ![structure] 4-(3-methylaminopyrrolidin-1-yl)-2-methyl-1-methoxyphenyl | Ms: 518 | DMSO-d6: 1.62-1.71 (m, 1H), 1.95-2.04 (m, 1H), 2.23-2.27 (m, 3H), 2.39-2.43 (m, 3H), 2.93-3.1 (m, 2H), 3.13-3.26 (m, 2H), 3.71 (s, 3H), 6.19 (dd, 1H), 6.88 (d, 1H), 7.07-7.13 (m, 1H), 7.13-7.2 (m, 1H), 7.4-7.48 (m, 1H), 7.75 (dd, 1H), 8.06 (brs, 1H), 8.18 (s, 1H), 8.4 (d, 1H) |
| 20-34 | ![structure] 4-(4-acetylpiperazin-1-yl)-2-methyl-1-methoxyphenyl | Ms: 546 | DMSO-d6: 2.02 (m, 1H), 2.42-2.46 (m, 3H), 2.71-2.91 (m, 4H), 3.44-3.51 (m, 4H), 3.76 (s, 3H), 6.66 (dd, 1H), 6.94 (d, 1H), 7.21-7.27 (m, 1H), 7.75-7.85 (m, 2H), 8.19 (s, 1H), 8.26 (s, 1H), 8.41 (d, 1H), 9.28 (brs, 1H). |

-continued

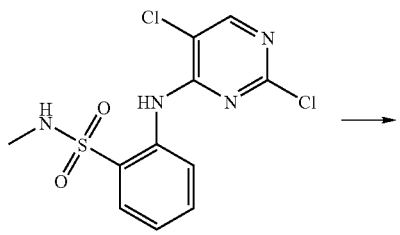

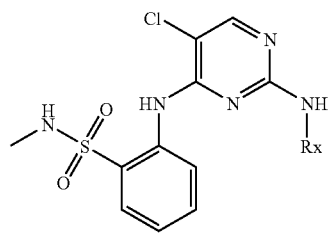

| ExplNo. | Rx | Rf (solvent) or MS | NMR (400 MHz), δ (ppm) |
|---|---|---|---|
| 20-35 | ![dimethoxy-dimethylbenzene] | MS (ESI) 464 (M + H) | HPLC Retention time (min) 2.68 |

The following 2-[5-chloro-2-(subst.phenylamino)-pyrimidin-4-ylamino]-N-sec-butyl-benzenesulfonamides are prepared from 2-(5-chloro-2-chloro-pyrimidin-4-ylamino)-N-sec-butyl-benzenesulfonamide and the corresponding aniline following the procedure of Example 7A

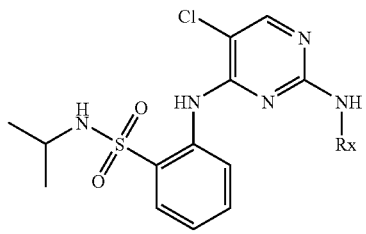

| ExplNo. | Rx | Rf (solvent) or MS | NMR (400 MHz), δ (ppm) |
|---|---|---|---|
| 21-1 | ![methyl-methoxy-(4-methylpiperazinyl)phenyl] | 0.35 (n-hexane: AcOEt = 1:1) | CDCl₃: 0.62(t, 3H), 0.88(d, 3H), 1.22-1.29(m, 2H), 2.23(s,3H), 2.45-2.47(m, 4H), 3.05-3.14(m, 5H), 3.75 (s, 3H), 6.40-6.43(m, 1H), 6.62(s, 1H), 7.18-7.22(m, 1H), 7.39-7.47(m, 2H), 7.80-7.82(m, 1H), 8.15-8.16(m, 2H), 8.44-8.46(m, 1H), 9.32(s |

-continued

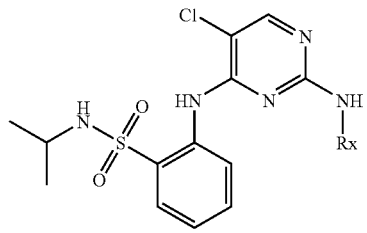

| ExplNo. | Rx | Rf (solvent) or MS | NMR (400 MHz), δ (ppm) |
|---|---|---|---|
| 21-2 | 2-methoxy-4-fluoro-toluene group | 0.30 (n-hexane: AcOEt = 3:1) | DMSO-d6: 0.62(t, 3H), 0.87(d, 3H), 1.17-1.26(m, 2H), 3.03-3.10(m, 1H), 3.79(s, 3H), 6.66-6.71(m, 1H), 6.96-7.00(m, 1H), 7.21-7.25(m, 1H), 7.47-7.51(m, 1H), 7.60-7.64(m, 1H), 7.79-7.83(m, 2H), 8.21(s, 1H), 8.31(s, 1H), 8.35-8.37(m, 1H), 9.29(s, 1H) |
| 21-3 | 4-(1-methylpiperidin-4-yloxy)-2-methoxy-toluene group | 0.30 (n-hexane: AcOEt = 1:1) | DMSO-d6: 0.61(t, 3H), O.87(d, 3H), 1.21-1.29(m, 2H), 1.58-1.67(m, 2H), 1.86-1.93(m, 2H), 2.14-2.20(m, 5H), 2.59-2.67(m, 2H), 3.06-3.08(m, 1H), 3.74(s, 3H), 4.32-4.36(m, 1H), 6.46-6.48(m, 1H), 6.63(d, 1H), 7.17-7.21 (m, 1H), 7.40-7.50(m, 2H), 7.79-7.81 (m, 2H), 8.16(s, 1H), 8.21(bs, 1H), 8.35-8.42(m, 1H), 9.29(s, 1H) |
| 21-4 | 4-(2-morpholinoethoxy)-2-methoxy-toluene group | 0.30 (n-hexane: AcOEt = 1:1) | DMSO-d6: 0.61 (t, 3H), 0.87(d, 3H), 1.22-1.29(m, 2H), 2.43-2.47(m, 2H), 2.61-2.63(m, 1H), 2.68-2.70(m, 2H), 3.04-3.11(m, 1H), 3.56-3.60(m, 5H), 3.75(s, 3H), 3.93-3.96(m, 1H), 4.08-4.11(m, 2H), 6.45-6.47(m, 1H), 6.64(d, 1H), 7.18-7.22(m, 1H), 7.43-7.46(m, 2H), 7.80-7.82(m, 2H), 8.17(s, 1H), 8.21(s, 1H), 8.42-8.44(m, 1H), 9.31(s, 1H) |

The following 2-[5-chloro-2-(subst.phenylamino)-pyrimidin-4-ylamino]-N-iso-butyl-benzenesulfonamides are prepared from 2-(5-chloro-2-chloro-pyrimidin-4-ylamino)-N-sec-butyl-benzenesulfonamide and the corresponding aniline following the procedure of Example 7A

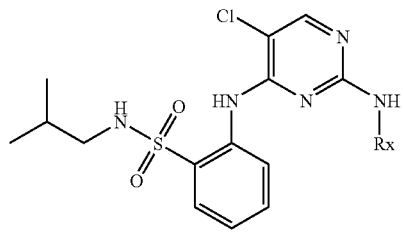

| Expl No. | Rx | Rf (solvent) or MS | NMR (400 MHz), δ (ppm) |
|---|---|---|---|
| 22-1 | 4-fluoro-2-methyl-1-methoxyphenyl | 0.30 (n-hexane:AcOEt = 3:1) | DMSO-d6: 0.69(d, 6H), 1.52-1.59(m, 1H), 2.57-2.58 (m, 2H), 3.82(s, 3H), 6.75-6.80(m, 1H), 6.99-7.02 (m, 1H), 7.29-7.33(m, 1H), 7.56-7.60(m, 1H), 7.82-7.93(m, 3H), 8.14(bs, 1H), 8.31(s, 1H), 8.33(s, 1H), 9.23(s, 1H) |
| 22-2 | 4-fluoro-2-methoxy-1-methylphenyl | 0.30 (n-hexane:AcOEt = 3:1) | CDCl₃: 0.74(d, 6H), 1.57-1.64(m, 1H), 2.72-2.76 (m, 2H), 3.88(s, 3H), 4.55-4.56(m, 1H), 6.52-6.57 (m, 1H), 6.62-6.65(m, 1H), 7.24-7.28(m, 2H), 7.36(bs, 1H), 7.56-7.60(m, 1H), 7.95-8.08(m, 1H), 8.10-8.14 (m, 2H), 8.36-8.39(m, 1H), 8.98(bs, 1H) |
| 22-3 | 2-methoxy-1-methyl-4-morpholinophenyl | 0.54 (AcOEt) | DMSO-d6: 0.73(d, 6H), 1.55-1.62(m, 1H), 2.56-2.59 (m, 2H), 3.10-3.12(m, 4H), 3.74-3.76(m, 7H), 6.43-6.46(m, 1H), 6.65(d, 1H), 7.20-7.24(m, 1H), 7.40-7.48(m, 2H), 7.76-7.78(m, 1H), 7.90-7.95(m, 1H), 8.16(s, 1H), 8.17(s, 1H), 8.43-8.45(m, 1H), 9.32(s, 1H) |

The following 2-[5-chloro-2-(subst.phenylamino)-pyrimidin-4-ylamino]-N-(1-ethyl-propyl)-benzenesulfonamides are prepared from 2-(5-chloro-2-chloro-pyrimidin-4-ylamino)-N-(1-ethyl-propyl)-benzenesulfonamide and the corresponding aniline following the procedure of Example 7A

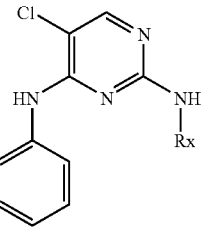

| Expl No. | Rx | Rf (solvent) or MS | NMR (400 MHz), δ (ppm) |
|---|---|---|---|
| 23-1 | | 0.46 (MeOH:CH₂Cl₂ = 3:7) | DMSO-d6: 0.58(t, 6H), 1.14-1.34(m, 4H), 1.58-1.68 (m, 2H), 1.87-1.96(m, 2H), 2.12-2.22(m, 2H), 2.18(s, 3H), 2.57-2.65(m, 2H), 2.86-2.96(m, 1H), 3.75(s, 3H), 4.30-4.39(m, 1H), 6.46(dd, 1H), 6.63(d, 1H), 7.19(dd, 1H), 7.39-7.48(m, 2H), 7.75-7.84(m, 2H), 8.18(s, 1H), 8.20(s, 1H), 8.39(m, 1H), 9.33(bs, 1H) |
| 23-2 | | 0.35 (n-hexane:AcOEt = 1:1) | CDCl₃: 0.59(t, 6H), 1.14-1.34(m, 4H), 2.23(s, 3H), 2.45-2.47(m, 4H), 2.90-2.95(m, 1H), 3.11-3.14(m, 4H), 3.76(s, 3H), 6.39-6.42(m, 1H), 6.62(s, 1H), 7.18-7.22 (m, 1H), 7.41-7.46(m, 2H), 7.76-7.82(m, 2H), 8.12(s, 1H), 8.16(s, 1H), 8.43-8.44(m, 1H), 9.35(s, 1H) |
| 23-3 | | 0.41 (MeOH:CH₂Cl₂ = 1:4) | DMSO-d6: 0.59(t, 6H), 1.16-1.35(m, 4H), 1.75-1.89 (m, 1H), 2.08-2.15(m, 1H), 2.32(s, 3H), 2.90-3.02 (m, 2H), 3.21-3.45(m, 4H), 3.73(s, 3H), 6.02(dd, 1H), 6.18(d, 1H), 7.16(dd, 1H), 7.27(d, 1H), 7.35-7.45 (m, 1H), 7.77-7.82(m, 2H), 8.10(s, 1H) 8.12(s, 1H), 8.45-8.55(m, 1H), 9.38(s, 1H) |
| 23-4 | | 0.41 (MeOH:CH₂Cl₂ = 1:4) | DMSO-d6: 0.60(t, 6H), 1.04(t, 3H), 1.17-1.35(m, 4H), 1.76-1.83(m, 1H), 2.10-2.15(m, 1H), 2.56-2.64(m, 2H), 2.91-3.01(m, 2H), 3.21-3.47(m, 4H), 3.74(s, 3H), 6.02(dd, 1H), 6.18(d, 1H), 7.14-7.17(m, 1H), 7.28(d, 1H), 7.35-7.45(m, 1H), 7.77-7.82(m, 2H), 8.11(s, 1H) 8.12(s, 1H), 8.45-8.55(m, 1H), 9.38(s, 1H) |

-continued

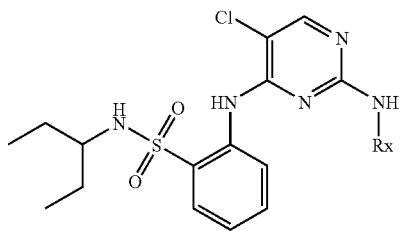

| Expl No. | Rx | Rf (solvent) or MS | NMR (400 MHz), δ (ppm) |
|---|---|---|---|
| 23-5 | (4-methyl-3-methoxyphenyl-O-CH2-N-methylpiperidin-3-yl) | 0.25 (n-hexane:AcOEt = 1:1) | DMSO-d6: 0.58(t, 6H), 1.06-2.16(m, 11H), 2.16(s, 3H), 2.62-2.67(m, 1H), 2.81-2.94(m, 2H), 3.75(s, 3H), 3.80-3.89(m, 2H), 6.41-6.44(m, 1H), 6.62(d, 1H), 7.17-7.21(m, 1H), 7.42-7.47(m, 2H), 7.77-7.82(m, 2H), 8.18(s, 1H), 8.19(s, 1H), 8.35-8.42(m, 1H), 9.35(s, 1H) |
| 23-6 | (4-methyl-3-methoxyphenyl-morpholin-4-yl) | Ms:561 | DMSO-d6: 0.59(t, 6H), 1.14-1.38(m, 4H), 2.87-2.98 (m, 1H), 3.1(t, 4H), 3.72-3.79(m, 7H), 6.42(dd, 1H), 6.64(d, 1H), 7.18-7.24(m, 1H), 7.42-7.5(m, 2H), 7.77(d, 1H), 7.81(dd, 1H), 8.13(s, 1H), 8.17(s, 1H), 8.4-8.5(m, 1H), 9.36(s, 1H) |
| 23-7 | (4-methyl-3-methoxyphenyl-O-N-methylpyrrolidin-3-yl) | Ms:575 | DMSO-d6: 0.58(t, 6H), 1.13-1.37(m, 4H), 1.72-1.82 (m, 1H), 2.21-2.31(m, 4H), 2.32-2.4(m, 1H), 2.54-2.61 (m, 1H), 2.62-2.68(m, 1H), 2.75-2.82(m, 1H), 2.87-2.97(m, 1H), 3.75(s, 3H), 4.84-4.91(m, 1H), 6.37(dd, 1H), 6.56(d, 1H), 7.14-7.24(m, 1H), 7.38-7.52 (m, 2H), 7.72-7.86(m, 1H), 8.12-8.25(m, 2H), 8.34-8.45(M, 1H), 9.33(brs, 1H) |
| 23-8 | (4-methyl-3-methoxyphenyl-O-CH2CH2-morpholin-4-yl) | Ms:605 | DMSO-d6: 0.58(t, 6H), 1.14-1.36(m, 4H), 2.43-2.53 (m, 4H), 2.69(t, 2H), 2.89-2.95(m, 1H), 3.59(t, 4H), 3.76(s, 3H), 4.09(t, 1H), 6.45(dd, 1H), 6.64(d, 1H), 7.17-7.23(m, 1H), 7.41-7.52(m, 2H), 7.78(d, 1H), 7.81(dd, 1H), 8.18(s, 1H), 8.19(s, 1H), 8.36-8.46(m, 1H), 9.35(s, 1H) |

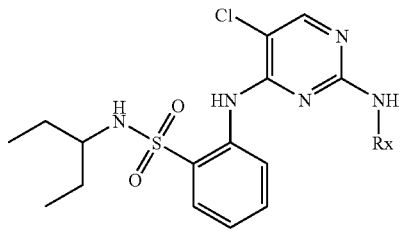

| Expl No. | Rx | Rf (solvent) or MS | NMR (400 MHz), δ (ppm) |
|---|---|---|---|
| 23-9 | ![structure] | Ms:618 | DMSO-d6: 0.58(t, 6H), 1.14-1.37(m, 4H), 2.15(s, 1H), 2.25-2.4(m, 4H), 2.45-2.55(m, 4H), 2.68(t, 2H), 2.88-2.97(m, 1H), 3.76(s, 3H), 4.07(t, 1H), 6.44(dd, 1H), 6.64(d, 1H), 7.15-7.23(m, 1H), 7.41-7.51(m, 2H), 7.7-7.84(m, 2H), 8.12-8.22(m, 1H), 8.34-8.44 (m, 1H), 9.34(s, 1H) |

The following 2-[chloro-2-(subst.phenylamino)-pyrimidin-4-ylamino]-N-iso-butyl-benzenesulfonamides are prepared from 2-(5-chloro-2-chloro-pyrimidin-4-ylamino)-N-cyclobutyl-benzenesulfonamide and the corresponding aniline following the procedure of Example 7A

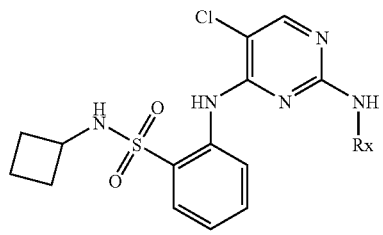

| Expl No. | Rx | Rf (solvent) or MS | NMR (400 MHz), δ (ppm) |
|---|---|---|---|
| 24-1 | ![structure] | 0.35 (n-hexane:AcOEt = 1:1) | DMSO-d6: 1.37-1.48(m, 2H), 1.69-1.91(m, 4H), 3.09-3.12 (m, 4H), 3.63-3.74(m, 1H), 3.76(s, 3H), 6.43-6.45 (m, 1H), 6.63(d, 1H), 7.18-7.22(m, 1H), 7.41-7.47 (m, 2H), 7.76-7.78(m, 1H), 8.17-8.24(m, 3H), 8.46(d, 1H), 9.33(s, 1H) |

-continued

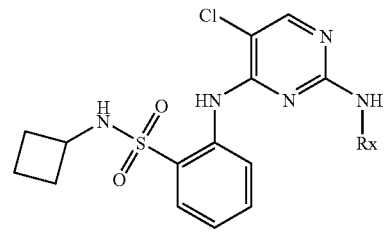

| Expl No. | Rx | Rf (solvent) or MS | NMR (400 MHz), δ (ppm) |
|---|---|---|---|
| 24-2 | (structure: 4-methyl-3-methoxyphenyl ether linked to 1-methylpiperidin-4-yl) | 0.46 (MeOH:CH₂Cl₂ = 3:7) | DMSO-d6: 1.37-1.93(m, 10H), 2.18(s, 3H), 2.59-2.62 (m, 1H), 3.60-3.74(m, 1H), 3.77(s, 3H), 4.32-4.36 (m, 1H), 6.46-6.49(m, 1H), 6.62(d, 1H), 7.16-7.20 (m, 1H), 7.41-7.44(m, 2H), 7.75-7.77(m, 1H), 8.16(s, 1H), 8.22(bs, 1H), 8.40-8.42(m, 1H), 9.30(bs, 1H) |
| 24-3 | (structure: 4-methyl-3-methoxyphenyl-pyrrolidin-3-yl acetamide) | 0.46 (MeOH:CH₂Cl₂ = 3:7) | CDCl₃: 1.45-1.75(m, 5H), 1.94-2.06(m, 6H), 2.29-2.37 (m, 1H), 3.21-3.56(m, 4H), 3.72-3.81(m, 1H), 3.86(s, 3H), 4.55-4.65(m, 1H), 4.90(d, 1H), 5.72(d, 1H), 6.07(bs, 1H), 6.15(bs, 1H), 7.18-7.22(m, 2H), 7.52-7.56(m, 1H), 7.89-7.94(m, 2H), 8.08(s, 1H), 8.50(d, 1H), 9.00(s, 1H) |

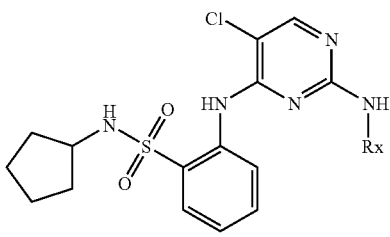

| Expl No. | Rx | Ms | NMR (400 MHz), δ (ppm) |
|---|---|---|---|
| 25-1 | (structure: 4-methyl-3-methoxyphenyl linked to morpholine) | Ms:559 | DMSO-d6: 1.2-1.38(m, 4H), 1.4-1.65(m, 4H), 3.11 (t, 4H), 3.42-3.5(m, 1H), 3.7-3.8(m, 7H), 6.44(dd, 1H), 6.64(d, 1H), 7.18-7.26(m, 1H), 7.38-7.5(m, 2H), 7.81(d, 1H), 7.88-7.96(m, 1H), 8.16(s, 1H), 8.17(s, 1H), 8.4-8.5(m, 1H), 9.34(s, 1H) |

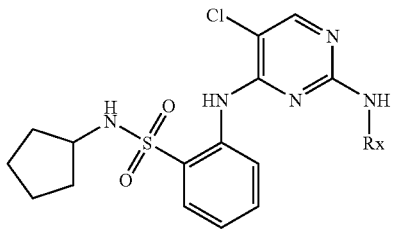

| Expl No. | Rx | Ms | NMR (400 MHz), δ (ppm) |
|---|---|---|---|
| 25-2 | | Ms:587 | DMSO-d6: 1.2-1.38(m, 4H), 1.42-1.6(m, 6H), 1.88-1.98 1.98(m, 2H), 2.1-2.25(m, 5H), 2.55-2.65(m, 2H), 3.4-3.5(m, 1H), 3.74(s, 3H), 4.3-4.4(m, 1H), 6.48 (dd, 1H), 6.63(d, 1H), 7.18-7.24(m, 1H), 7.38-7.47 (m, 1H), 7.77-7.82(m, 1H), 7.88-7.96(m, 1H), 8.17(s, 1H), 8.22(s, 1H), 8.36-8.46(m, 1H), 9.31(s, 1H) |

The following 5-Chloro-$N^2$-(substituted phenyl)-$N^4$-[2-(propane-1-sulfonyl)-phenyl]-pyrimidine-2,4-diamine are prepared from (2,5-Dichloro-pyrimidin-4-yl)-[2-(propane-1-sulfonyl)-phenyl]-amine and the corresponding aniline following the procedure of Example 7A

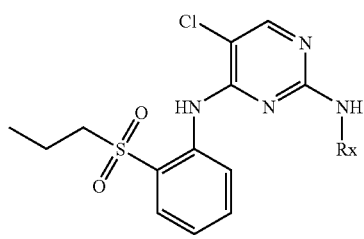

| Expl No. | Rx | Rf (solvent), MS or Mp | NMR (400 MHz), δ (ppm) |
|---|---|---|---|
| 26-1 | | 0.58 (AcOEt) | CDCl₃: 0.97(t, 3H), 1.72-1.82(m, 2H), 3.08-3.14(m, 6H), 3.87-3.89(m, 7H), 6.46(dd, 1H), 6.53(d, 1H), 7.24-7.28 (m, 1H), 7.30(s, 1H), 7.60-7.64(m, 1H), 7.94(dd, 1H), 8.05(d, 1H), 8.15(s, 1H), 8.59(d, 1H), 9.40(s, 1H) |

-continued

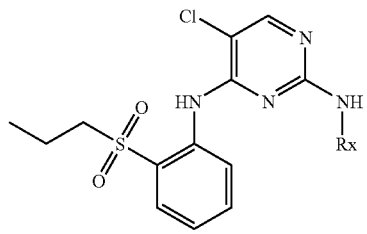

| Expl No. | Rx | Rf (solvent), MS or Mp | NMR (400 MHz), δ (ppm) |
|---|---|---|---|
| 26-2 | (4-methyl-3-methoxyphenyl)-piperazine-N-Ac | 0.57 (MeOH:AcOEt = 1:4) | CDCl$_3$: 0.98(t, 3H), 1.85-1.68(m, 2H), 2.15(s, 3H), 3.16-3.07(m, 6H), 3.67-3.62(m, 2H), 3.81-3.78(m, 2H), 3.89(s, 3H), 6.47(d, 1H), 6.55(d, 1H), 7.36-7.33 (m, 1H), 7.62(dd, 1H). 7.95(dd, 1H), 8.08(d, 1H), 8.15(s, 1H), 8.58(d, 1H), 9.41(s, 1) |
| 26-3 | (4-methyl-3-methoxyphenyl)-4-piperidinopiperidine | 0.13 (MeOH:AcOEt = 1:4) | CDCl$_3$: 0.97(t, 3H), 1.43-1.52(m, 2H), 1.52-1.67(m, 4H), 1.69-1.72(m, 4H), 1.90-1.98(m, 2H), 2.34-2.46 (m, 1H), 2.51-2.59(m, 4H), 2.64-2.74(m, 2H), 3.11(dd, 2H), 3.64-3.73(m, 2H), 3.87(s, 3H), 6.47(dd, 1H), 6.56(d, 1H), 7.24-7.33(m, 1H), 7.62(dd, 1H), 7.94(dd, 1H), 8.00(d, 1H), 8.14(s, 1H), 8.59(d, 1H), 9.39(bs, 1H). |
| 26-4 | (4-methyl-3-methoxyphenyl)-4-hydroxypiperidine | 0.22 (AcOEt) | CDCl$_3$: 0.97(t, 3H), 1.45(d, 1H), 1.68-1.82(m, 4H), 2.0-2.1 (m, 2H), 2.91(ddd, 2H), 3.10(ddd, 2H), 3.46-3.51 (m, 2H), 3.84-3.92(m, 1H), 3.88(s, 3H), 6.48(dd, 1H), 6.57(d, 1H), 7.23-7.32(m, 1H), 7.62(dd, 1H), 7.94(dd, 1H), 8.02(dd, 1H), 8.14(s, 1H), 8.59(d, 1H), 9.39(bs, 1H) |

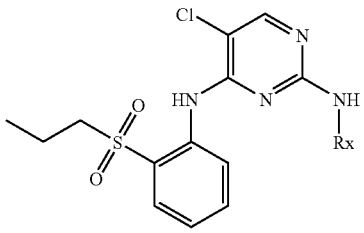

| Expl No. | Rx | Rf (solvent), MS or Mp | NMR (400 MHz), δ (ppm) |
|---|---|---|---|
| 26-5 | (4-methyl-3-methoxyphenyl)-piperidine-4-carboxamide | 0.1 (AcOEt) | CDCl$_3$: 0.97(t, 3H), 1.71-1.82(m, 2H), 1.86-1.98(m, 2H), 2.01-2.08(m, 2H), 2.25-2.37(m, 1H), 2.75(ddd, 2H), 3.10(ddd, 2H), 3.63-3.66(m, 2H), 3.88(s, 3H), 5.25-5.40(m, 1H), 5.40-5.58(m, 1H), 6.48(dd, 1H), 6.57(d, 1H), 7.22-7.34(m, 1H), 7.62(ddd, 1H), 7.93 (d, 1H), 7.94(dd, 1H), 8.02(d, 1H), 8.14(s, 1H), 8.59(d, 1H), 9.40(m, 1H) |
| 26-6 | N-methyl-(4-methyl-3-methoxyphenyl)-piperidine-4-carboxamide | MS 587 | CDCl$_3$: 0.97(t, 3H), 1.77(ddd, 2H), 2.00-1.85(m, 4H), 2.27-2.18(m, 1H), 2.72(ddd, 2H) 3.12-3.08(m, 2H), 3.69-3.61(m, 2H), 3.58-3.46(m, 1H), 3.64(t, 2H), 3.80(t, 2H), 3.88(s, 3H), 5.56-5.46(m, 1H), 6.47(dd, 1H), 6.55(d, 1H), 7.32-7.23(m, 1H), 7.30(bs, 1H), 7.64-7.60(m, 1H), 7.94(dd, 1H), 8.02(d, 1H), 8.14(s, 1H), 8.59(d, 1H), 9.40(s, 1H) |
| 26-7 | 1-acetyl-3,5-dimethyl-4-(4-methyl-3-methoxyphenyl)piperazine | MS 587 | CDCl$_3$: 0.98(t, 3H), 1.46(bs, 6H) 1.82-1.73 (m, 2H), 2.17(s, 3H), 3.58-3.46(m, 1H), 2.95-2.84(m, 2H), 3.12-3.08(m, 2H), 3.90(s, 3H), 6.48(dd, 1H), 6.52(d, 1H), 7.30-7.22(m, 1H), 7.31(bs, 1H), 7.66-7.60(m, 1H), 7.95(dd, 1H), 8.06(d, 1H), 8.15(s, 1H), 8.59(d, 1H), 9.43(s, 1H) |

-continued

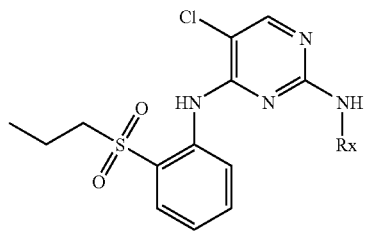

| Expl No. | Rx | Rf (solvent), MS or Mp | NMR (400 MHz), δ (ppm) |
|---|---|---|---|
| 26-8 | (4-methyl-3-methoxyphenyl)piperazine with propionyl | MS 573 | CDCl₃: 0.97(t, 3H), 1.19(t, 3H), 1.77(ddd, 2H), 2.41(m, 2H), 3.18-3.09(m, 6H), 3.68-3.64(m, 2H), 3.85-3.78 (m, 2H), 3.89(s, 3H), 6.47(dd, 1H), 6.55(d, 1H), 7.29-7.25 (m, 1H), 7.34(bs, 1H), 7.64-7.60(m, 1H), 7.95(dd, 1H), 8.07(d, 1H), 8.15(s, 1H), 8.58(d, 1H), 9.41(s, 1H) |
| 26-9 | (4-methyl-3-methoxyphenyl)piperazine with isobutyryl | MS 587 | CDCl₃: 0.97(t, 3H), 1.17(d, 3H) 1.76(ddd, 2H), 2.88-2.81 (m, 2H), 3.18-3.05(m, 6H), 3.74-3.67(m, 2H), 3.86-3.78(m, 2H), 3.89(s, 3H), 6.47(dd, 1H), 6.55(d, 1H), 7.29-7.20(m, 1H), 7.34(bs, 1H), 7.64-7.60(m, 1H), 7.95(dd, 1H), 8.07(d, 1H), 8.15(s, 1H), 8.58(d, 1H), 9.41(s, 1H) |
| 26-10 | (4-methyl-3-methoxyphenyl)piperazine with N-methylcarbamoyl | MS 517 | CDCl₃: 0.97(t, 3H), 1.76(ddd, 2H), 2.86(d, 3H), 3.14-3.08 (m, 2H), 3.13(t, 4H), 3.55 (t, 4H), 3.89(s, 3H), 4.48-4.39(m, 1H), 6.46(dd, 1H), 6.55(d, 1H), 7.29-7.21 (m, 1H), 7.34(bs, 1H), 7.64-7.60(m, 1H), 7.95(dd, 1H), 8.06(d, 1H), 8.15(s, 1H), 9.41(s, 1H) |

-continued

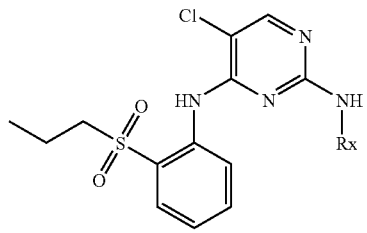

| Expl No. | Rx | Rf (solvent), MS or Mp | NMR (400 MHz), δ (ppm) |
|---|---|---|---|
| 26-11 | (4-methyl-3-methoxyphenyl)-(4-acetyl-2,2-dimethylpiperazin-1-yl) | MS 587 | CDCl₃: 0.98(t, 3H), 1.51(s, 6H), 1.82-1.72(m, 1H), 2.13(s, 3H), 3.12-3.08(m, 2H), 3.26(s, 2H), 3.44 (t, 2H), 3.74(t, 2H), 3.88(s, 3H), 5.56-5.46(m, 1H), 6.45(dd, 1H), 6.51(d, 1H), 7.00(bs, 1H), 7.62-7.58(m, 1H), 7.64-7.60(m, 1H), 7.93(d, 1H), 7.96(dd, 1H), 8.13(s, 1H), 8.62(d, 1H), 9.42(s, 1H) |
| 26-12 | (4-methyl-3-methoxyphenyl)-(3R)-piperidine-3-carboxamide | MS 559 | CDCl₃: 0.98(t, 3H), 1.81-1.71(m, 3H), 1.95-1.84(m, 3H), 2.68-2.63(m, 1H), 3.12-3.08(m, 4H), 3.28(d, 2H), 3.89(s, 3H), 5.45-5.38(m, 1H), 6.53(dd, 1H), 6.59(d, 1H), 6.71-6.62(m, 1H), 7.28-7.21(m, 1H), 7.35(bs, 1H), 7.65-7.61(m, 1H), 7.95(dd, 1H), 8.08(d, 1H), 8.15(s, 1H), 8.58(d, 1H), 9.41(s, 1H) |
| 26-13 | (4-methyl-3-methoxyphenyl)-(3S)-piperidine-3-carboxamide | MS 559 | CDCl₃: 0.98(t, 3H), 1.81-1.71(m, 3H), 1.95-1.84(m, 3H), 2.68-2.63(m, 1H), 3.12-3.08(m, 4H), 3.28(d, 2H), 3.89(s, 3H), 5.45-5.38(m, 1H), 6.53(dd, 1H), 6.59(d, 1H), 6.71-6.62(m, 1H), 7.28-7.21(m, 1H), 7.35(bs, 1H), 7.65-7.61(m, 1H), 7.95(dd, 1H), 8.08(d, 1H), 8.15(s, 1H), 8.58(d, 1H), 9.41(s, 1H) |
| 26-14 | (4-methyl-3-methoxyphenyl)-piperidine-3-carboxamide | MS 559 | CDCl₃: 0.98(t, 3H), 1.85-1.74(m, 3H), 2.00-1.86(m, 3H), 2.70-2.51(m, 1H), 3.13-3.08(m, 4H), 3.29-3.27(m, 2H), 3.89(s, 3H), 5.46-5.37(m, 1H), 6.53(dd, 1H), 6.59(d, 1H), 6.69-6.56(m, 1H), 7.29-7.19(m, 1H), 7.34(bs, 1H), 7.65-7.61(m, 1H), 7.95(dd, 1H), 8.08(d, 1H), 8.15(s, 1H), 8.58(d, 1H), 9.41(s, 1H) |

-continued

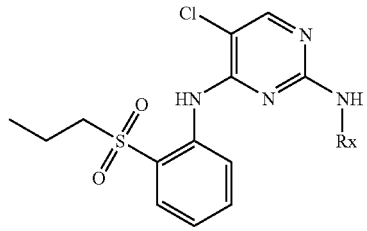

| Expl No. | Rx | Rf (solvent), MS or Mp | NMR (400 MHz), δ (ppm) |
|---|---|---|---|
| 26-15 | (3-methyl-4-methoxyphenyl)-piperazine-N-Ac | MS 559 | CDCl₃: 0.99(t, 3H), 1.79-1.72(m, 2H), 2.92(t, 2H), 2.98(t, 2H), 3.16-3.12(m, 2H), 3.53(t, 2H), 3.67(t, 2H), 3.87(s, 3H), 6.54(dd, 1H), 6.82(d, 1H), 7.29-7.19(m, 1H), 7.56(bs, 1H), 7.67-7.62(m, 1H), 7.96(dd, 1H), 8.07(d, 1H), 8.21(s, 1H), 8.59(dd, 1H), 9.46(s, 1H) |
| 26-16 | (4-methyl-3-methoxyphenyl)-NH-CH₂CH₂-morpholine | MS 561 | CDCl₃: 0.98(t, 3H), 1.81-1.72(m, 2H), 2.49(t, 4H), 2.66(t, 2H), 3.12-3.08(m, 2H), 3.18(t, 2H), 3.74(t, 4H), 3.86(s, 3H), 6.53(dd, 1H), 6.20(dd,1H), 6.26(d, 1H), 7.13(bs, 1H), 7.25-7.21(m, 1H), 7.62-7.57(m, 1H), 7.87(dd, 1H), 7.93(dd, 1H), 8.12(s, 1H), 8.62(d, 1H), 9.40(s, 1H) |
| 26-17 | (3-methyl-4-methoxyphenyl)-morpholine | MS 518 | CDCl₃: 0.98(t, 3H), 1.78-1.73(m, 2H), 2.49(t, 4H), 2.66(t, 2H), 2.94-2.92(m, 4H), 3.15-3.11(m, 2H), 3.76-3.73(m, 4H), 3.88(s, 3H), 6.52(dd, 1H), 6.82(d, 1H), 7.28-7.24(m, 1H), 7.57(bs, 1H), 7.25-7.21(m, 1H), 7.68-7.63(m, 1H), 7.95(dd, 1H), 8.02(d, 1H), 8.20(s, 1H), 8.56(d, 1H), 9.41(s, 1H) |
| 26-18 | (4-methyl-3-methoxyphenyl)-O-CH₂CH₂-pyrrolidinone | MS 559 | CDCl₃: 0.97(t, 3H), 1.81-1.72(m, 2H), 2.08-2.00(m, 2H), 2.49(t, 4H), 2.66(t, 2H), 2.40(t, 2H), 3.59(t, 2H), 3.69(t, 2H), 3.87(s, 3H), 6.41(dd, 1H), 6.51(d, 1H), 7.29-7.25(m, 2H), 7.65-7.60(m, 1H), 7.95(dd, 1H), 8.05(d, 1H), 8.15(s, 1H), 8.56(d, 1H), 9.41(s, 1H) |

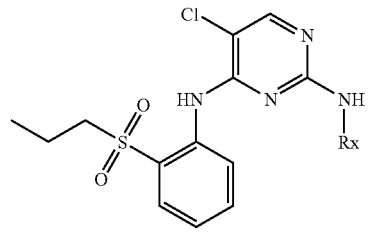
| Expl No. | Rx | Rf (solvent), MS or Mp | NMR (400 MHz), δ (ppm) |
|---|---|---|---|
| 26-19 | | MS 587 | CDCl$_3$: 0.98(t, 3H), 1.82-1.73(m, 2H), 2.14(s, 3H), 3.12-3.08(m, 2H), 3.55-3.45(m, 2H), 3.66-3.56(m, 4H), 3.79-3.68(m, 2H), 3.95(s, 3H), 6.95(dd, 1H), 7.03 (d, 1H), 7.32-7.28(m, 1H), 7.69-7.64(m, 1H), 7.71(s, 1H), 7.97(dd, 1H), 8.22(s, 1H), 8.39(d, 1H), 8.52(d, 1H), 9.46(s, 1H) |
| 26-20 | | MS 546 | CDCl$_3$: 0.97(t, 3H), 1.82-1.73(m, 2H), 3.12-3.08(m, 2H), 3.80-3.58(m, 8H), 3.94(s, 3H), 6.94(dd, 1H), 7.02 (d, 1H), 7.32-7.28(m, 1H), 7.69-7.64(m, 1H), 7.32-7.28 (m, 1H), 7.97(dd, 1H), 8.21(s, 1H), 8.34(d, 1H), 8.52(d, 1H), 9.45(s, 1H) |
| 26-21 | | MS 615 | CDCl$_3$: 0.97(t, 3H), 1.82-1.72(m, 2H), 2.71(t, 3H), 3.05(s, 2H), 3.10(m, 2H), 3.18(t, 4H), 3.88(s, 3H), 4.17-4.08(m, 1H), 6.47(dd, 1H), 6.54(d, 1H), 6.99-6.89 (m, 1H), 7.28-7.24(m, 1H), 7.31(bs, 1H), 7.65-7.60 (m, 1H), 7.32-7.28(m, 1H), 7.95(dd, 1H), 8.05 (d, 1H), 8.15(s, 1H), 8.59(d, 1H), 9.41(s, 1H) |

-continued
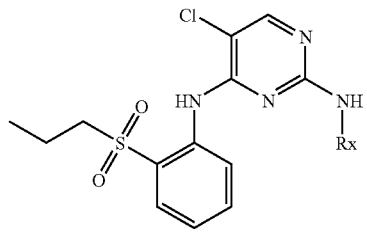
| Expl No. | Rx | Rf (solvent), MS or Mp | NMR (400 MHz), δ (ppm) |
|---|---|---|---|
| 26-22 | ![structure] | MS 530 | CDCl₃: 0.98(t, 3H), 1.80-1.74(m, 2H), 3.12-3.08(m, 2H), 3.45-3.42(m, 2H), 3.55-3.53(m, 2H), 3.87 (s, 2H), 3.89(s, 3H), 5.98-5.89(m, 1H), 6.44(dd, 1H), 6.50(d, 1H), 7.35-7.19(m, 2H), 7.62-7.58(m, 1H), 7.95(dd, 1H), 8.09(d, 1H), 8.15(s, 1H), 8.57(d, 1H), 9.43(s, 1H) |
| 26-23 | ![structure] | MS 558 | CDCl₃: 0.97(t, 3H), 1.10(s, 3H), 1.12(s, 3H), 1.80-1.74 (m, 2H), 2.80-2.63(m, 5H), 3.12-3.08(m, 2H), 3.19-3.17(m, 4H), 3.87(s, 3H), 6.48(dd, 1H), 6.56(d, 1H), 7.30-7.23(m, 2H), 7.62-7.58(m, 1H), 7.94(dd, 1H), 8.00(d, 1H), 8.14(s, 1H), 8.59(d, 1H), 9.40(s, 1H) |
| 26-24 | ![structure] | MS 544 | CDCl₃: 0.98(t, 3H), 1.81-1.72(m, 2H), 2.03-1.91(m, 1H), 2.28-2.19(m, 1H), 2.33(s, 6H), 2.92-2.84(m, 1H), 3.12-3.08(m, 2H), 3.17(t, 1H), 3.35(ddd, 1H), 3.51-3.42(m, 2H), 3.87(s, 3H), 6.11(dd, 1H), 6.14 (d, 1H), 7.09(s, 1H), 7.26-7.20(m, 1H), 7.60-7.56(m, 1H), 7.85(d, 1H), 7.92(dd, 1H), 8.11(s, 1H), 8.38(d, 1H), 9.41(s, 1H) |
| 26-25 | ![structure] | MS 530 | CDCl₃: 0.98(t, 3H), 1.82-1.71(m, 2H), 1.96-1.86(m, 1H), 2.33-2.20(m, 1H), 2.51(s, 1H), 3.17-3.08(m, 3H), 3.35-3.30(m, 1H), 3.54-3.30(m, 3H), 3.87(s, 3H), 6.12(dd, 1H), 6.16(d, 1H), 7.09(s, 1H), 7.32-7.21 (m, 1H), 7.58 (dd, 1H), 7.85(d, 1H), 7.92(dd, 1H), 8.11(s, 1H), 8.64(d, 1H), 9.40(s, 1H) |

-continued

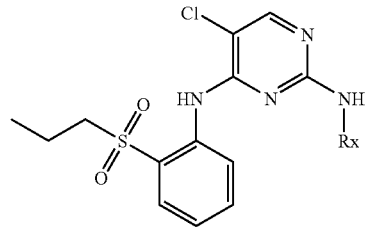

| Expl No. | Rx | Rf (solvent), MS or Mp | NMR (400 MHz), δ (ppm) |
|---|---|---|---|
| 26-26 | (3-methoxy-4-methylphenyl 4-oxy-1-methylpiperidine) | MS 546 | CDCl₃: 0.98(t, 3H), 1.83-1.71(m, 2H), 1.98-1.81(m, 2H), 2.16-2.02(m, 2H), 2.53-2.28(m, 5H), 2.87-2.72(m, 2H), 3.12-3.08(m, 2H), 3.88(s, 3H), 4.32(bs, 3H), 6.44(dd, 1H), 6.53(d, 1H), 7.32-7.25(m, 2H), 7.63-7.59(m, 2H), 7.94(dd, 1H), 8.04(d, 1H), 8.15(s, 1H), 8.57(d, 1H), 9.42(s, 1H) |
| 26-27 | (3-methoxy-4-methylphenyl 4-hydroxymethylpiperidine) | MS 545 | CDCl₃: 0.97(t, 3H), 1.38-1.30(m, 1H), 1.49-1.40(m, 2H), 1.70-1.62(m, 1H), 1.83-1.72(m, 2H), 1.89(d, 2H), 2.74-2.10(m, 2H), 3.12-3.08(m, 2H), 3.57(d, 2H), 3.63(d, 2H), 3.90(s, 3H), 6.50(d, 1H), 6.58(s, 1H), 7.34-7.24(m, 2H), 7.64-7.60(m, 1H), 7.94(dd, 1H), 8.02(d, 1H), 8.14(s, 1H), 8.60(dd, 1H), 9.40(s, 1H) |
| 26-28 | (3-methoxy-4-methylphenyl 3-hydroxypyrrolidine) | MS 517 | CDCl₃: 0.97(t, 3H), 1.88-1.65(m, 3H), 2.05-1.97(m, 2H), 2.21-2.08(m, 1H), 2.67-2.55(m, 4H), 2.78-2.71(m, 2H), 3.12-3.08(m, 2H), 3.61(d, 2H), 3.87(s, 3H), 6.47(dd, 1H), 6.56(d, 1H), 7.28-7.23(m, 2H), 7.64-7.60(m, 1H), 7.94(dd, 1H), 7.99(d, 1H), 8.13(s, 1H), 8.60(dd, 1H), 9.39(s, 1H) |

-continued

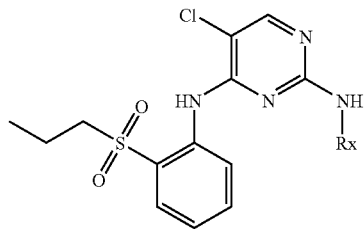

| Expl No. | Rx | Rf (solvent), MS or Mp | NMR (400 MHz), δ (ppm) |
| --- | --- | --- | --- |
| 26-29 | ![structure: 4-methyl-3-methoxyphenyl-piperidine-pyrrolidine] | MS 585 | CDCl₃: 0.97(t, 3H), 1.89-1.65(m, 8H), 2.03(d, 2H), 2.20-2.10(m, 1H), 2.68-2.58(m, 4H), 2.78-2.72(m, 2H), 3.12-3.08(m, 2H), 3.61(d, 2H), 3.87(s, 3H), 6.47 (dd, 1H), 6.56(d, 1H), 7.30-7.23(m, 2H), 7.64-7.60(m, 1H), 7.94(dd, 1H), 7.99(dd, 1H), 8.13(s, 1H), 8.60(dd, 1H), 9.39(s, 1H) |
| 26-30 | ![structure: 4-fluoro-2-methoxy-tolyl] | MS 451, 453 | 0.97(t, 3H), 1.71-1.82(m, 2H), 3.06-3.14(m, 2H), 3.89(s, 1H), 6.60(ddd, 1H), 6.66(dd, 1H), 7.25-7.30 (m, 1H), 7.35(br.s, 1H), 7.63(dd, 1H), 7.95(dd, 1H), 8.09-8.18(m, 1H), 8.17(s, 1H), 8.52(dd, 1H), 9.42(s, 1H). |
| 26-31 | ![structure: methoxy-methylphenyl-ethoxy-piperazine-acetyl] | MS 647, 649 | 0.98(t, 3H), 1.71-1.83(m, 2H), 2.18(s, 3H), 2.47-2.64 (m, 4H), 2.72-2.84(m, 2H), 3.08-3.15(m, 2H), 3.42-3.54 (m, 2H), 3.58-3.69(m, 2H), 3.84(s, 3H), 3.94-4.03 (m, 2H), 6.45-6.51(m, 1H), 6.78(d, 1H), 7.22-7.27 (m, 1H), 7.60(s, 1H), 7.67-7.74(m, 1H), 7.93-7.97 (m, 1H), 7.73(d, 1H), 8.02(s, 1H), 8.54(d, 1H), 9.33(s, 1H). |
| 26-32 | ![structure: methylpiperazine-piperidine-methoxy-methylphenyl] | m.p. 139.4 | 400 MHz, CDCl3, δ(ppm): 0.98(t; 3H), 1.55-1.90(m; 6H), 2.38(s; 3H), 2.45-2.80(m; 6H), 3.13(m; 2H), 3.47(m; 2H), 3.84(s; 3H), 6.54(dd; 1H), 6.79(d; 1H), 7.23(dd; 1H), 7.51(s; 1H), 7.64(dd: 1H), 7.92(d; 1H), 8.00(s; 1H), 8.19(s; 1H), 8.57(d; 1H), 9.41(s; 1H). |

-continued
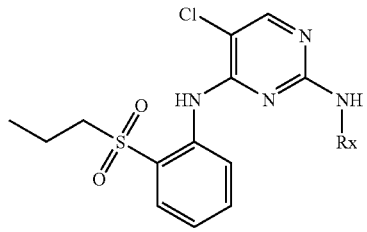
| Expl No. | Rx | Rf (solvent), MS or Mp | NMR (400 MHz), δ (ppm) |
|---|---|---|---|
| 26-33 | | m.p. 163.4 | 400 MHz, CDCl3, δ(ppm): 0.98(t; 3H), 1.50-1.90(m; 6H), 2.24(bs; 1H), 2.45-2.65(m; 6H), 3.12(m; 2H), 3.45(m; 2H), 3.77(m; 4H9, 3.85(s; 3H), 6.55(dd; 1H); 6.79(d; 1H), 7.24(dd; 1H). 7.52(s; 1H), 7.64 (dd; 1H), 7.93(d; 1H), 8.01(s; 1H), 8.20(s; 1H9, 9.42 (s; 1H). |
| 26-34 | | m.p. 232.9 | 400 MHz, CDCl3, δ(ppm): 1.00(s; 3H), 1.78(m; 2H), 2.83(s; 3H), 3.03(m; 2H), 3.12(m; 2H), 3.38-3.60(m; 8H), 3.88(s; 3H), 6.56(m; 1H), 6.82(d; 1H), 7.29(m; 1H), 7.60(s; 1H), 7.64(m; 1H), 7.95(d; 1H), 8.12(s; 1H), 8.20(s; 1H), 8.59(d; 1H), 9.50(s; 1H). |
| 26-35 | | m.p. 197.3 | 400 MHz, CDCl3, δ(ppm): 0.99(t; 3H), 1.43(m; 1H), 1.63(m; 2H), 1.77(m; 2H), 1.90(m; 2H), 2.70(m; 2H), 3.13(m; 2H), 3.28(m; 2H), 3.75(s; 1H), 3.84(s; 3H), 6.55(m; 1H), 6.80(d; 1H), 7.24(m; 1H), 7.53(s; 1H), 7.64(s; 1H), 7.93(d; 1H), 8.02(s; 1H), 8.20(s; 1H), 8.58(d; 1H), 9.41(s; 1H). |
| 26-36 | | m.p. 147.6 | 400 MHz, CDCl3, δ(ppm): 1.00(t; 3H), 1.78(m; 2H), 3.12(m; 2H), 3.56(m; 1H), 3.87(s; 3H), 6.53(dd; 1H), 6.80(d; 1H), 7.30(dd; 1H), 7.52(s; 1H), 7.64(m; 1H), 7.95(dd; 1H), 8.08(s; 1H), 8.20(s; 1H), 8.60(d; 1H), 9.48(s; 1H). |
| 26-37 | | m.p. 143.2 | 500 MHz, CDCl3, δ(ppm): 0.96(t; 3H), 1.70(m; 2H), 2.11(m; 1H), 2.39(m; 1H), 2.75(s; 3H), 3.02(m; 1H), 3.22(m; 2H), 3.43(d; 2H), 3.82(s; 3H), 3.86(m; 1H), 6.40(dd; 1H), 6.94(d; 1H), 7.34(ddd; 1H), 7.47(s; 1H), 7.63(ddd; 1H), 7.93(dd; 1H), 8.18(s; 1H), 8.51 (d; 1H). |

-continued

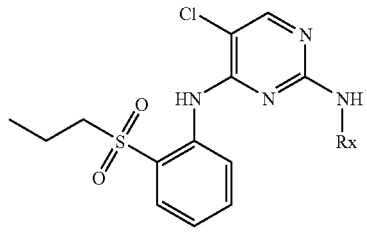

| Expl No. | Rx | Rf (solvent), MS or Mp | NMR (400 MHz), δ (ppm) |
|---|---|---|---|
| 26-38 | | m.p. 133.5 | 400 MHz, CDCl3, δ(ppm): 1.00(t; 3H), 1.70-1.95(m; 6H), 2.63(s; 1H), 2,92(s; 1H), 3.00-3.25(m; 5H), 3.89(s; 3H), 5.42(s; 1H), 6.70(s; 1H), 6.83(m; 2H), 7.25(m; 1H), 7.55(s; 1H), 7.63(m; 1H9, 8.95(m; 1H), 8.15(s; 1H), 8.23(s; 1H), 8.54(d; 1H), 9.45(s; 1H). |
| 26-39 | | m.p. 188.8 | 400 MHz, CDCl3, δ(ppm): 0.99(t; 3H), 1.70-1.90(m; 3H), 2.08(m; 1H), 2.28(s; 6H9, 2.83(s; 1H), 3.00-3.23 (m; 4H9, 3.37(m; 1H), 3.83(s; 3H), 6.19(dd; 1H), 6.83(d; 1H), 7.23(dd; 1H), 7.50(s; 1H), 7.59(m; 2H), 7.93(d; 1H), 8.19(s; 1H), 8.60(d; 1H), 9.42(s; 1H). |

The following 5-Chloro-N²-(substituted phenyl)-N⁴-[2-ethanesulfonyl-phenyl]-pyrimidine-2,4-diamine are prepared from (2,5-Dichloro-pyrimidin-4-yl)-[2-ethanesulfonyl-phenyl]-amine and the corresponding aniline following the procedure of Example 7A

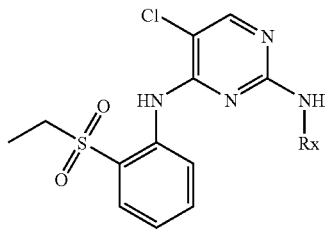

| Expl No. | Rx | Rf (solvent) or MS | NMR (400 MHz), δ (ppm) or Retention time min. (HPLC) |
|---|---|---|---|
| 27-1 | | 0.53 (AcOEt) | CDCl3: 1.28(t, 3H), 3.12-3.19(m, 6H), 3.87-3.89(m, 7H), 6.45(dd, 1H), 6.53(d, 1H), 7.24-7.28(m, 1H), 7.31(s, 1H), 7.60-7.64(m; 1H), 7.95(dd, 1H), 8.04(d, 1H), 8.14(s, 1H), 8.58(d, 1H), 9.39(s, 1H) |

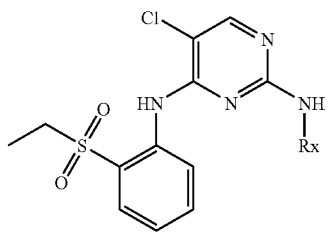
| Expl No. | Rx | Rf (solvent) or MS | NMR (400 MHz), δ (ppm) or Retention time min. (HPLC) |
|---|---|---|---|
| 27-2 | 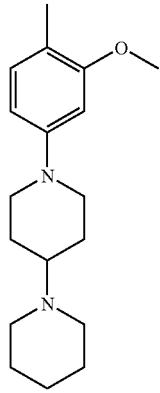 | 585 (M + H) | 2.38 |
| 27-3 | 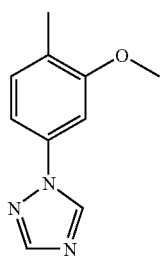 | 486 (M + H) | 3.07 |
| 27-4 | 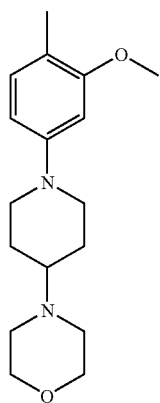 | 587 (M + H) | 2.29 |

-continued
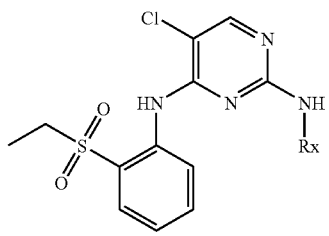
| Expl No. | Rx | Rf (solvent) or MS | NMR (400 MHz), δ (ppm) or Retention time min. (HPLC) |
|---|---|---|---|
| 27-5 | 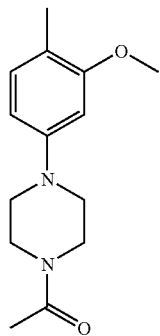 | 545 (M + H) | 2.59 |
| 27-6 | 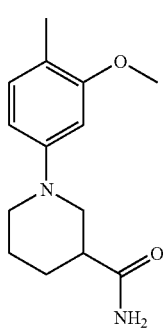 | 545 (M + H) | 2.45 |
| 27-7 | 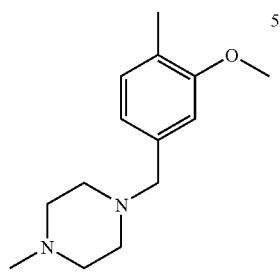 | 531 (M + H) | 2.25 |

-continued
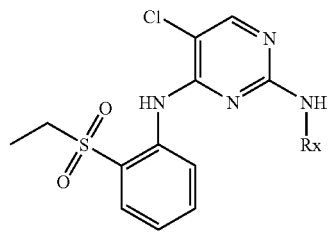
| Expl No. | Rx | Rf (solvent) or MS | NMR (400 MHz), δ (ppm) or Retention time min. (HPLC) |
|---|---|---|---|
| 27-8 | 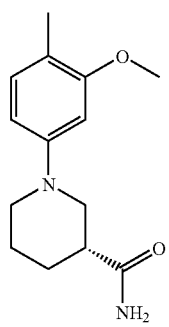 | 545 (M + H) | 2.45 |
| 27-9 | 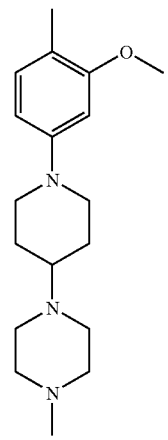 | 600 (M + H) | 2.17 |
HPLC condition
Column: YMC CombiScreen ODS-A (5 um, 12 nm), 50 × 4.6 mm I.D.
Flow rate: 2.0 ml/min
Eluent: A) TFA/water (0.1/100), B) TFA/acetonitrile (0.1/100)
Gradient 5-100% B (0-5 min)
Detection: UV at 215 nm The following 5-Chloro-N²-(substituted phenyl)-N⁴-[2-(propane-2-sulfonyl)-phenyl]-pyrimidine-2,4-diamine are prepared from (2,5-Dichloro-pyrimidin-4-yl)-[2-(propane-2-sulfonyl)-phenyl]-amine and the corresponding aniline following the procedure of Example 7A

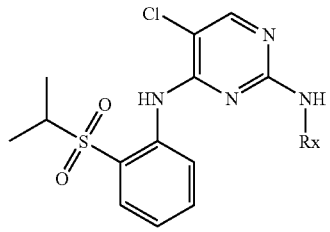

| Expl No. | Rx | Rf (solvent) or MS | NMR (400 MHz), δ (ppm) or Retention time min. (HPLC) |
|---|---|---|---|
| 28-1 | (1-(4-methyl-3-methoxyphenyl)piperidine-3-carboxamide) | 0.2 (AcOEt) | CDCl₃: 1.31(d, 6H), 1.85-1.73(m, 1H), 1.86-1.98(m, 3H), 2.62-2.70(m, 1H), 3.11-3.13(m, 2H), 3.21-8.28 (m, 1H), 3.28(m, 2H), 3.88 8s, 3H), 5.41(brs, 1H), 6.53(d, 1H), 6.59(d, 1H), 6.64(brs, 1H), 7.28-7.34 (m, 1H), 7.34(s, 1H), 7.60-7.67(m, 1H), 7.91(dd, 1H), 8.08(d, 1H), 8.13(s, 1H), 8.60(d, 1H), 9.55(s, 1H). |
| 28-2 | (1-(2-hydroxyethyl)-4-(4-methyl-3-methoxyphenyl)piperazine) | MS m/z 561, 563 (M + 1). | CDCl₃: 1.31(d, 6H), 2.64(t, 2H), 2.68-2.77(m, 4H), 3.19(t, 4H), 3.17-3.28(m, 1H), 3.68(t, 2H), 3.88(s, 3H), 6.48(dd, 1H), 6.55(d, 1H), 7.23-7.32(m, 1H), 7.62(ddd, 1H), 7.91(dd, 1H), 8.04(dd, 1H), 8.12(s, 1H), 8.60(d, 1H), 9.54(bs, 1H) |
| 28-3 | (4-(4-methyl-3-methoxyphenyl)morpholine) | 0.55 (AcOEt) | CDCl₃: 1.31(d, 6H), 3.12-3.14(m, 4H), 3.21-3.27(m, 1H), 3.87-3.89(m, 7H), 6.46(dd, 1H), 6.53(d, 1H), 7.23-7.27 (m, 1H), 7.30(s, 1H), 7.59-7.64(m, 1H), 7.91(dd, 1H), 8.05(d, 1H), 8.14(s, 1H), 8.60(d, 1H), 9.55(s, 1H) |

-continued
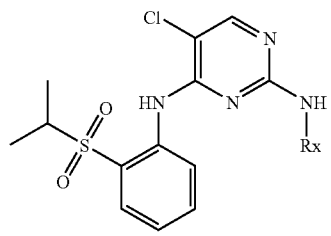
| Expl No. | Rx | Rf (solvent) or MS | NMR (400 MHz), δ (ppm) or Retention time min. (HPLC) |
|---|---|---|---|
| 28-4 | (4-methyl-3-methoxyphenyl)-1H-1,2,4-triazole | 0.37 (AcOEt) | CDCl$_3$: 1.32(d, 6H), 3.21-3.27(m, 1H), 4.00(s, 1H), 7.11(dd, 1H), 7.26-7.27(m, 1H), 7.29-7.33(m, 1H), 7.64(s, 1H), 7.66-7.71(m, 1H), 7.95(dd, 1H), 8.10(s, 1H), 8.21(s, 1H), 8.46(d, 1H), 8.50(s, 1H), 8.54(d, 1H), 9.59(s, 1H) |
| 28-5 | 4-[4-(4-methyl-3-methoxyphenyl)piperidin-1-yl]-1-methylpiperazine | 0.03 (AcOEt) | CDCl$_3$: 1.31(d, 6H), 1.67-1.77(m, 2H), 1.95-2.05(m, 2H), 2.39-2.48(m, 1H), 2.48-2.61(m, 2H), 2.63-2.78 (m, 8H), 3.24(sept, 1H), 3.71-3.63(m, 2H), 3.87(s, 3H), 6.47(dd, 1H), 6.55(d, 1H), 7.21-7.28(m, 1H), 7.61(ddd, 1H), 7.91(dd, 1H), 8.00(dd, 1H), 8.12(s, 1H), 8.60(d, 1H), 9.53(bs, 1H) |
| 28-6 | 4-(3,4-dimethylphenyl)morpholine | 502 (M + H) | 2.84 |
| 28-7 | 4-methyl-3-methoxy-nitrobenzene | 478 (M + H) | 4.53 |

-continued

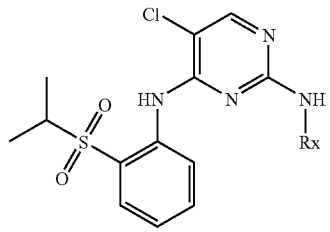

| Expl No. | Rx | Rf (solvent) or MS | NMR (400 MHz), δ (ppm) or Retention time min. (HPLC) |
|---|---|---|---|
| 28-8 | (4-methyl-3-methoxyphenyl)-piperidin-4-yl-piperidine | MS 599 | CDCl₃: 1.31(d, 6H), 1.51-1.42(m, 2H), 1.67-1.53(m, 4H), 1.81-1.68(m, 2H), 1.96-1.89(m, 2H), 2.47-2.36 (m, 1H), 2.57-2.54(m, 4H), 2.69(dd, 2H) 3.24(sept, 1H), 3.67(d, 1H), 3.87(s, 1H), 6.48(dd, 1H), 6.56(d, 1H), 7.31-7.21(m, 1H), 7.63-7.59(m, 1H), 8.00(d, 1H), 8.12(s, 1H), 8.60(d, 1H), 9.55(s, 1H) |
| 28-9 | (4-methyl-3-methoxyphenyl)-piperidin-4-yl-pyrrolidine | MS 585 | CDCl₃: 1.26(t, 3H), 1.31(d, 6H), 1.74-1.68(m, 2H), 1.85-1.76(m, 4H), 2.08-1.98(m, 2H), 2.19-2.10(m, 2H), 2.67-2.58(m, 4H), 2.79-2.72(m, 2H), 3.24(sept, 1H) 3.61(d, 2H), 3.87(s, 3H), 6.48(dd, 1H), 6.56(d, 1H), 7.29-7.22(m, 1H), 7.62(dd, 1H), 7.90(dd, 1H), 7.99(d, 1H), 8.12(s, 1H), 8.60(d, 1H), 9.53(s, 1H) |
| 28-10 | (4-methyl-3-methoxyphenyl)-4-(methoxymethyl)piperidine | MS 559 | CDCl₃: 1.31(d, 6H), 1.59-1.37(m, 2H), 1.81-1.69(m, 1H), 1.87(d, 2H), 2.73-2.67(m, 2H), 3.28-3.21(m, 1H), 3.37(s, 3H), 3.61(d, 1H), 3.87(s, 3H), 6.49(dd, 1H), 6.57(s, 1H), 7.31-7.21(m, 1H), 7.64-7.60(m, 1H), 7.91(dd, 1H), 8.00(d, 1H), 8.60(d, 1H) 9.53(s, 1H) |

-continued

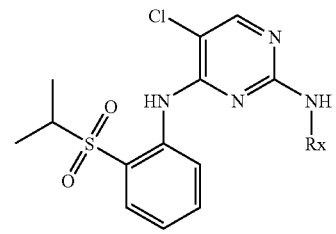

| Expl No. | Rx | Rf (solvent) or MS | NMR (400 MHz), δ (ppm) or Retention time min. (HPLC) |
|---|---|---|---|
| 28-11 | (4-methyl-3-methoxyphenyl)-piperazine-N-Ac | MS 558 | CDCl$_3$: 1.31(d, 6H), 2.15(s, 3H), 3.12(ddd, 4H), 3.24(sept, 1H), 3.64(t, 2H), 3.80(t, 2H), 3.89(s, 3H), 6.47(dd, 1H), 6.55(d, 1H), 7.29-7.24(m, 1H), 7.33(bs, 1H), 7.62(m, 1H), 7.92(dd, 1H), 8.08(d, 1H), 8.14(s, 1H), 8.60(d, 1H) 9.55(s, 1H) |
| 28-12 | (4-methyl-3-methoxyphenyl)-piperazine-N-Et | MS 544 | CDCl$_3$: 1.16,(t, 3H), 1.31(d, 6H), 2.56-2.44(b, 2H), 2.71-2.60(m, 4H), 3.28-3.17(m, 5H), 3.88(s, 3H), 6.48(dd, 1H), 6.58(d, 1H), 7.30-7.22(m, 1H), 7.63-7.58 (m, 1H), 7.90(dd, 1H), 8.01(d, 1H), 8.12(s, 1H), 8.60(d, 1H) 9.54(s, 1H) |
| 28-13 | (4-methyl-3-methoxyphenyl)-piperidine-morpholine | MS 601 | CDCl$_3$: 1.31(d, 6H, J=6.55), 1.75-1.63(m, 2H), 2.00-1.91 (m, 2H), 2.37-2.27(m, 1H), 2.60(t, 4H, J=4.79), 2.74-2.59(m, 2H), 3.24(sept, 1H), 3.66(d, 2H, J=12.1), 3.75(t, 4H, J=4.53), 3.88(s, 3H), 6.48(dd, 1H, J=2.52, 8.56), 6.56(d, 1H, J=2.52), 7.33-7.22(m, 1H), 7.64-7.59(m, 1H), 7.91(dd, 1H, J=8.05, 1.51), 8.01(d, 1H, J=8.56), 8.12(s, 1H), 8.61(d, 1H, J=7.55) 9.54(s, 1H) |

-continued

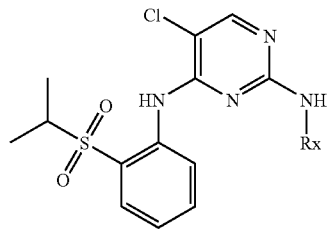

| Expl No. | Rx | Rf (solvent) or MS | NMR (400 MHz), δ (ppm) or Retention time min. (HPLC) |
|---|---|---|---|
| 28-14 | 4-(4-isopropylpiperazin-1-yl)-2-methoxy-1-methylphenyl | MS 559 | CDCl$_3$: 1.11(d, 6H, J=6.55), 1.31(d, 6H, J=7.05), 2.82-2.68(m, 5H), 3.20-3.17(m, 4H), 3.28-3.17(m, 1H), 3.87(s, 3H), 6.48(dd, 1H, J=2.52, 8.56), 6.56(d, 1H, J=2.52), 7.33-7.24(m, 1H), 7.62-7.58(m, 1H), 7.90(dd, 1H, J=), 8.01(d, 1H, J=8.56), 8.12(s, 1H), 8.60(d, 1H, J=8.56) 9.54(s, 1H) |
| 28-15 | 1-(4-carbamoylpiperidin-1-yl)-3-methoxy-4-methylphenyl | MS 559 | CDCl$_3$: 1.31(d, 6H, J=7.05), 1.97-1.85(m, 2H), 2.17-1.98(m, 2H), 2.35-2.25(m, 1H), 2.75(m, 2H), 3.24(sept, 1H), 3.65(d, 2H), 3.88(s, 3H), 5.30(bs, 1H), 5.48(bs, 1H), 6.48(dd, 1H, J=2.51, 8.56), 6.56(d, 1H, J=2.52), 7.33-7.21(m, 1H), 7.62(m, 1H), 7.91(dd, 1H, J=1.51, 8.06), 8.03(dd, 1H, J=3.02, 8.56), 8.13(s, 1H), 8.60(d, 1H, J=8.57), 9.54(s, 1H) |
| 28-16 | 1-(4-hydroxypiperidin-1-yl)-3-methoxy-4-methylphenyl | MS 532 | CDCl$_3$: 1.31(d, 6H, J=7.06), 1.46-1.43(m, 1H), 1.79-1.68(m, 2H), 2.08-1.99(m, 2H), 2.99-2.88(m, 2H), 3.24(sept, 1H), 3.51-3.45(m, 2H), 3.91-3.80(m, 1H), 3.88(s, 3H), 6.49(dd, 1H, J=2.52, 8.56), 6.57(d, 1H, J=2.52), 7.34-7.23(m, 1H), 7.64-7.60(m, 1H), 7.91(dd, 1H, J=1.51, 8.06), 8.02(dd, 1H, J=3.02, 9.06), 8.13(s, 1H), 8.60(d, 1H, J=8.06) 9.53(s, 1H) |
| 28-17 | 1-(3-methoxypyrrolidin-1-yl)-3-methoxy-4-methylphenyl | MS 532 | CDCl$_3$: 1.31(d, 6H, J=6.96), 2.18-2.12(m, 2H), 3.24(sept, 1H), 3.37-3.32(m, 2H), 3.39(s, 3H), 3.43(d, 1H, J=8.56), 3.51(dd, 1H, J=5.04, 10.6), 3.87(s, 3H), 4.17-4.09(m, 1H) 6.13(dd, 1H, J=2.51, 8.56), 6.16(d, 1H, J=2.52), 7.09(bs, 1H), 7.31-7.21(m, 1H), 7.60-7.56(m, 1H), 7.85(d, 1H, J=8.56), 7.89(dd, 1H, J=1.51, 8.06), 8.10(s, 1H), 8.65(d, 1H, J=9.06) 9.54(s, 1H) |

-continued
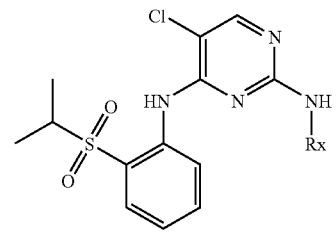
| Expl No. | Rx | Rf (solvent) or MS | NMR (400 MHz), δ (ppm) or Retention time min. (HPLC) |
|---|---|---|---|
| 28-18 | ![structure] | MS 546 | CDCl₃: 1.31(d, 6H, J=7.05), 1.82-1.70(m, 2H), 2.08-1.99 (m, 2H), 2.96-2.87(m, 2H), 3.24(sept, 1H), 3.41-3.33 (m, 1H), 3.40(s, 3H), 3.51-3.42(m, 2H), 3.87(s, 3H), 6.49(dd, 1H, J=2.52, 9.07), 6.57(d, 1H, J=2.52), 7.32-7.22(m, 1H), 7.64-7.60(m, 1H), 7.91(dd, 1H,), 8.00(dd, 1H, J=3.02, 9.06), 8.12(s, 1H), 8.60(d, 1H, J=8.56) 9.53(s, 1H) |
| 28-19 | ![structure] | 0.33 (AcOEt) | CDCl₃: 1.31(d, 6H, J=7.05), 1.82-1.70(m, 2H), 2.08-1.99 (m, 2H), 2.96-2.87(m, 2H), 3.24(sept, 1H), 3.41-3.33 (m, 1H), 3.40(s, 3H), 3.51-3.42(m, 2H), 3.87(s, 3H), 6.49(dd, 1H, J=2.52, 9.07), 6.57(d, 1H, J=2.52), 7.32-7.22(m, 1H), 7.62(m, 1H), 7.91(dd, 1H,), 8.00(dd, 1H, J=3.02, 9.06), 8.12(s, 1H), 8.60(d, 1H, J=8.56) 9.53(s, 1H) |
| 28-20 | ![structure] | MS 544 | CDCl₃: 1.31(d, 6H), 1.66-1.53(m, 2H), 2.10-2.01(m, 2H), 2.51(s, 3H), 2.70-2.13(m, 1H), 2.83-2.74(m, 2H), 3.24(Sept, 1H), 3.63-3.55(m, 2H), 3.87(s, 3H), 4.34-4.25 (m, 1H), 6.48(dd, 1H), 6.56(d, 1H), 7.34-7.24(m, 1H), 7.64-7.60(m, 1H), 7.90(dd, 1H), 8.00(d, 1H), 8.12(s, 1H), 8.60(dd, 1H), 9.53(s, 1H) |

-continued

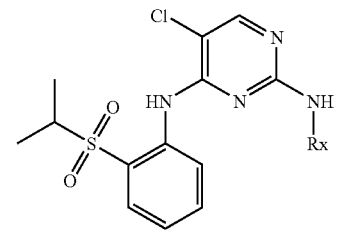

| Expl No. | Rx | Rf (solvent) or MS | NMR (400 MHz), δ (ppm) or Retention time min. (HPLC) |
|---|---|---|---|
| 28-21 | (4-methyl-3-methoxyphenyl)-pyrrolidin-3-yl-methylamine | MS 531 | CDCl₃: 1.30(s, 3H), 1.32(s, 3H), 2.33-2.22(m, 1H), 2.54(s, 3H), 3.37-3.20(m, 3H), 3.57-3.44(m, 3H), 3.86(s, 3H), 6.12(dd, 1H), 6.16(d, 1H), 7.14-7.08(m, 1H), 7.30-7.20(m, 1H), 7.65-7.58(m, 1H), 7.93-7.87(m, 1H,), 8.10(s, 1H), 8.64(d, 1H) 9.54(s, 1H) |
| 28-22 | (4-methyl-3-methoxyphenyl)-pyrrolidin-3-yl-dimethylamine | MS 545 | CDCl₃: 1.30(s, 3H), 1.32(s, 3H), 2.03-1.89(m, 1H), 2.30-2.18(m, 1H), 2.34(s, 6H), 2.96-2.83(m, 1H), 3.29-3.16(m, 2H), 3.40-3.34(m, 1H), 3.53-3.43(m, 2H), 3.87(s, 3H), 6.11(dd, 1H,) 6.13(dd, 1H), 7.08(bs, 1H), 7.31-7.21(m, 1H), 7.60-7.56(m, 1H), 7.85(d, 1H), 7.89(dd, 1H), 8.10(s, 1H), 8.66(d, 1H) 9.54(s, 1H) |
| 28-23 | (4-methyl-3-methoxyphenyl)-4-methyl-piperazin-2-one | MS 545 | CDCl₃: 1.31(s, 3H), 1.32(s, 3H), 3.05(s, 3H), 3.24(sept, 1H), 3.50-3.43(m, 4H), 3.85(s, 2H), 3.89(s, 3H), 6.11(dd, 1H,) 6.43(dd, 1H), 6.50(d, 1H), 7.31-7.28(m, 1H), 7.64-7.60(m, 1H), 7.92(dd, 1H), 8.09(d, 1H), 8.13(s, 1H), 8.58(d, 1H) 9.55(s, 1H) |

-continued

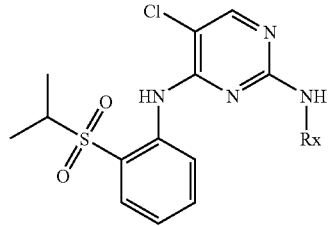

| Expl No. | Rx | Rf (solvent) or MS | NMR (400 MHz), δ (ppm) or Retention time min. (HPLC) |
|---|---|---|---|
| 28-24 | (4-methyl-3-methoxyphenyl)-piperazinyl-(1-methylpiperidin-4-yl) | 0.05 (AcOEt/ MeOH = 4/1) | CDCl$_3$: 1.30(s, 3H), 1.32(s, 3H), 1.92-1.83(m, 1H), 2.17-1.95(m, 1H), 2.43-2.27(m, 2H), 2.79-2.71(m, 4H), 3.15-2.97(m, 4H), 3.23-3.16(m, 4H), 3.24(sept, 1H), 3.87(s, 3H), 6.11(dd, 1H,) 6.47(dd, 1H), 6.55(d, 1H), 7.33-7.23(m, 1H), 7.63-7.59(m, 1H), 7.95(dd, 1H), 8.01(dd, 1H), 8.12(s, 1H), 8.60(d, 1H) 9.54(s, 1H) |
| 28-25 | (4-methyl-3-methoxyphenyl)-piperazinyl-piperidin-4-yl | MS 600 | CDCl$_3$: 1.30(s, 3H), 1.32(s, 3H), 1.80-1.70(m, 2H), 2.01-1.93(m, 2H), 2.49-2.28(m, 12H), 2.76-2.62 (m, 4H), 3.04-2.96(m, 4H), 3.16-3.05(m, 2H), 3.24(sept, 1H), 3.72-3.63(m, 2H), 3.87(s, 3H), 6.48(dd, 1H), 6.55(d, 1H), 7.31-7.23(m, 1H), 7.66-7.589 (m, 1H), 7.91(dd, 1H), 8.01(d, 1H), 8.12(s, 1H), 8.60(d, 1H) 9.53(s, 1H) |
| 28-26 | (4-methyl-3-methoxyphenyl)-hexahydropyrazino-oxazine | MS 573 | CDCl$_3$: 1.30(s, 3H), 1.32(s, 3H), 2.59-2.43(m, 4H), 2.78-2.73(m, 1H), 3.00-2.86(m, 2H), 3.38-3.20(m, 3H), 3.54-2.45(m, 1H), 3.73(dd, 1H), 3.84-3.77(m, 1H), 3.94-3.87(m, 1H), 3.88(s, 3H), 6.46(dd, 1H), 6.53(d, 1H), 7.32-7.23(m, 1H), 7.31(bs, 1H), 7.63-7.52(m, 1H), 7.91(dd, 1H), 8.04(d, 1H), 8.13(s, 1H), 8.60(d, 1H) 9.54(s, 1H) |

-continued

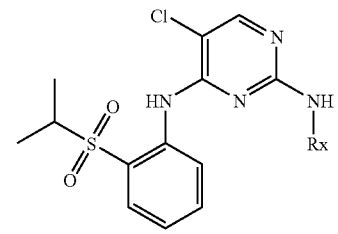

| Expl No. | Rx | Rf (solvent) or MS | NMR (400 MHz), δ (ppm) or Retention time min. (HPLC) |
|---|---|---|---|
| 28-27 | (3-methoxy-4-methylphenyl piperidine-3-carboxamide, one stereoisomer) | MS 559 | CDCl$_3$: 1.30(s, 3H), 1.32(s, 3H), 1.82-1.73(m, 1H), 1.97-1.84(m, 3H), 2.73-2.51(m, 1H), 3.12(t, 2H), 3.31-3.20(m, 3H), 3.90(s, 3H), 5.46-5.37(m, 1H), 6.53(dd, 1H), 6.59(d, 1H), 6.68-6.62(m, 1H), 7.28-7.21 (m, 1H), 7.33(bs, 1H), 7.65-7.61(m, 1H), 7.92(dd, 1H), 8.08(d, 1H), 8.14(s, 1H), 8.60(d, 1H), 9.55(s, 1H) |
| 28-28 | (3-methoxy-4-methylphenyl piperidine-3-carboxamide, other stereoisomer) | MS 559 | CDCl$_3$: 1.30(s, 3H), 1.32(s, 3H), 1.82-1.73(m, 1H), 1.97-1.84(m, 3H), 2.73-2.51(m, 1H), 3.12(t, 2H), 3.31-3.20(m, 3H), 3.90(s, 3H), 5.46-5.37(m, 1H), 6.53(dd, 1H), 6.59(d, 1H), 6.68-6.62(m, 1H), 7.28-7.21 (m, 1H), 7.33(bs, 1H), 7.65-7.61(m, 1H), 7.92(dd, 1H), 8.08(d, 1H), 8.14(s, 1H), 8.60(d, 1H), 9.55(s, 1H) |
| 28-29 | (4-methoxy-3-methylphenyl morpholine) | MS 413 | CDCl$_3$: 1.31(s, 3H), 1.33(s, 3H), 2.92(t, 4H), 3.28(sept, 1H) 3.73(t, 4H), 3.87(s, 3H), 6.51(dd, 1H), 6.82(d, 1H), 7.32-7.23(m, 1H), 7.57(bs, 1H), 7.70-7.64 (m, 1H), 7.92(dd, 1H), 8.01(bs, 1H), 8.12(s, 1H), 8.60(d, 1H), 9.53(s, 1H) |
| 28-30 | (2,4,5-trimethoxy-methylphenyl) | MS 493 | CDCl$_3$: 1.30(s, 3H), 1.33(s, 3H), 3.25(sept, 1H) 3.60 (bs, 3H), 3.89(s, 3H), 6.59(s, 1H), 7.27-7.18(m, 1H), 7.61(dd, 1H), 7.83(bs, 1H), 7.90(dd, 1H), 8.15 (s, 1H), 8.55(d, 1H), 9.55(s, 1H) |
| 28-31 | (7-methyl-2,3-dihydrobenzofuran) | MS 445 | CDCl$_3$: 1.31(d, 6H), 1.59-1.37(m, 2H), 1.81-1.69(m, 1H), 1.87(d, 2H), 2.73-2.67(m, 2H), 3.28-3.21(m, 1H), 3.37(s, 3H), 3.61(d, 1H), 3.87(s, 3H), 6.49(dd, 1H), 7.025(bs, 1H), 7.28-7.23(m, 1H), 7.64-7.59(m, 1H), 7.93-7.89(m, 2H), 8.15(s, 1H), 8.57(dd, 1H) 9.56(s, 1H) |

| 201 | | | | 202 | | | |
|---|---|---|---|---|---|---|---|

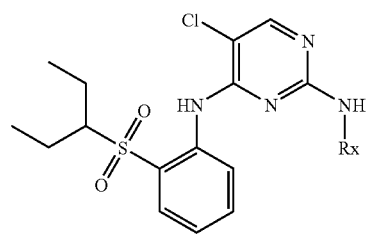

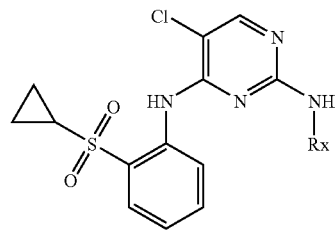

| Expl No. | Rx | HPLC Retention time (min) | Mass (ESI) m/z | Expl No. | Rx | HPLC Retention time (min) | Mass (ESI) m/z |
|---|---|---|---|---|---|---|---|
| 29-1 | ![Rx structure: 4-methyl-3-methoxyphenyl-morpholine] | 3.30 | 546 (M + H) | 30-1 | ![Rx structure: 4-methyl-3-methoxyphenyl-morpholine] | 2.82 | 516 (M + H) |
| 29-2 | ![Rx structure: 4-methyl-3-methoxyphenyl-piperidinyl-piperidine] | 2.82 | 627 (M + H) | 30-2 | ![Rx structure: 4-methyl-3-methoxyphenyl-acetylpiperazine] | 2.65 | 557 (M + H) |
| 29-3 | ![Rx structure: 4-methyl-3-methoxyphenyl-acetylpiperazine] | 3.07 | 587 (M + H) | 30-3 | ![Rx structure: 4-methyl-3-methoxyphenyl-piperidine-3-carboxamide] | 2.50 | 557 (M + H) |

203
-continued
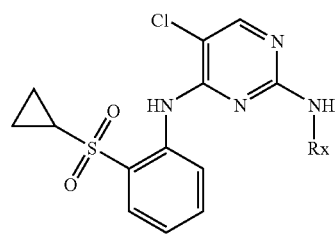
| Expl No. | Rx | HPLC Retention time (min) | Mass (ESI) m/z |
|---|---|---|---|
| 30-4 | 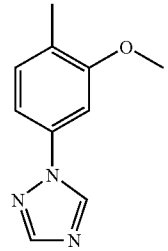 | 3.10 | 498 (M + H) |
| 30-5 | 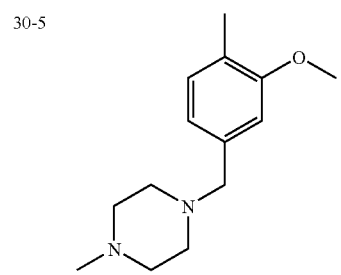 | 2.30 | 543 (M + H) |
| 30-6 | 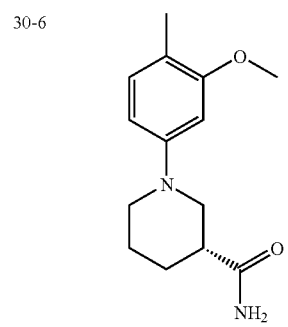 | 2.52 | 557 (M + H) |
204
-continued
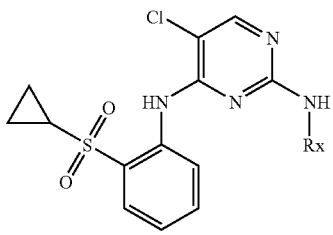
| Expl No. | Rx | HPLC Retention time (min) | Mass (ESI) m/z |
|---|---|---|---|
| 30-7 | 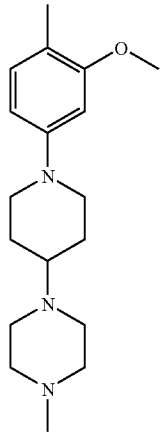 | 2.23 | 612 (M + H) |
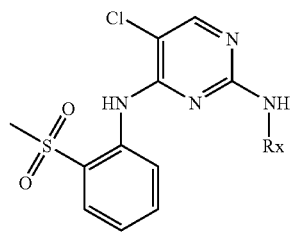
| Expl No. | Rx | HPLC Retention time (min) | Mass (ESI) m/z |
|---|---|---|---|
| 31-1 | 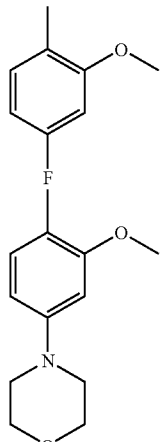 | 3.15 | 423 (M + H) |
| 31-2 | 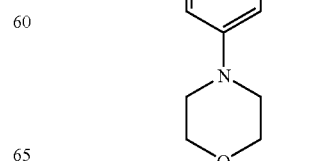 | 2.62 | 490 (M + H) |

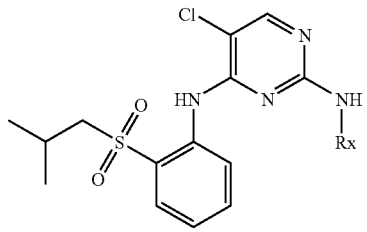
| Expl No. | Rx | MS | NMR (400 MHz) in CDCl₃, δ (ppm) |
|---|---|---|---|
| 32-1 | ![Rx structure with methyl, methoxy phenyl, piperazine-Ac] | 585.3 | 1.03(s, 3H), 1.04(s, 3H), 2.15(s, 3H), 2.32(sept, 1H) 3.00(d, 2H) 3.10(t, 2H), 3.13(t, 2H), 3.64(t, 2H), 3.79(t, 2H), 3.89(s, 3H), 6.45(dd, 1H), 6.55(d, 1H), 7.34-7.26 (m, 1H), 7.52(bs, 1H), 7.64-7.60(m, 1H), 7.97(dd, 1H), 8.07(d, 1H), 8.15(s, 1H), 8.54(d, 1H), 9.32(s, 1H) |
| 32-2 | ![Rx structure with methyl, methoxy phenyl, morpholine] | 532 (M + H) | 3.17 |
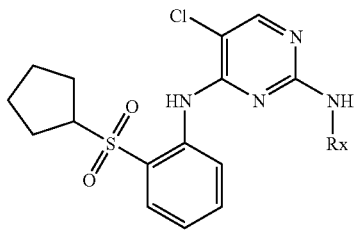
| Expl No. | Rx | MS | NMR (400 MHz) in CDCl₃, δ (ppm) |
|---|---|---|---|
| 33-1 | ![Rx structure with methyl, methoxy phenyl, piperazine-Ac] | 585.3 | 1.66-1.52(m, 2H), 1.92-1.73(m, 4H), 2.12-2.03(m, 2H), 2.15(s, 3H), 3.00(d, 2H) 3.11(t, 2H), 3.14(t, 2H), 3.58-3.46(m, 1H), 3.64(t, 2H), 3.80(t, 2H), 3.89(s, 3H), 6.48(dd, 1H), 6.55(d, 1H), 7.30-7.24(m, 1H), 7.52(bs, 1H), 7.63-7.58(m, 1H), 7.94(dd, 1H), 8.08(d, 1H), 8.14(s, 1H), 8.60(d, 1H), 9.54(s, 1H) |

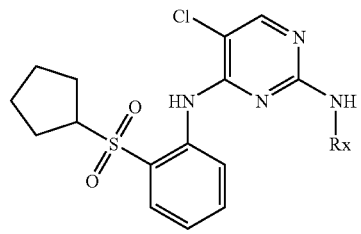
| Expl No. | Rx | MS | NMR (400 MHz) in CDCl₃, δ (ppm) |
|---|---|---|---|
| 33-2 | 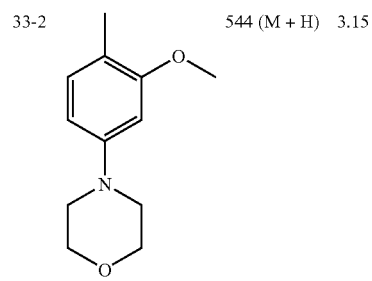 | 544 (M + H) | 3.15 |
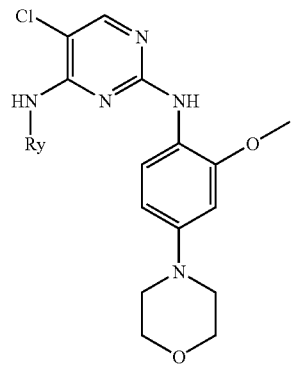
| Expl No. | Rx | HPLC Retention time (min) | Mass (ESI) m/z |
|---|---|---|---|
| 34-1 | 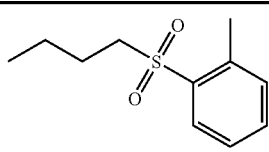 | 3.15 | 532 (M + H) |
| 34-2 | 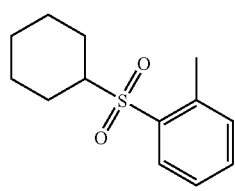 | 3.34 | 558 (M + H) |

-continued
| | | | |
|---|---|---|---|
| 34-3 | 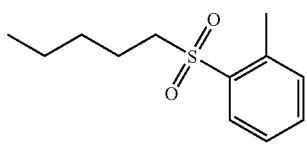 | 3.35 | 546 (M + H) |
| 34-4 | 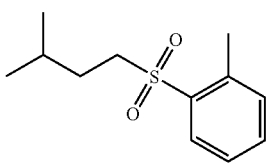 | 3.32 | 546 (M + H) |
| 34-5 | 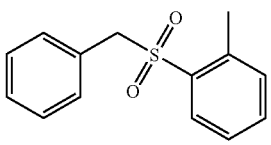 | 3.09 | 566 (M + H) |
| 34-6 | 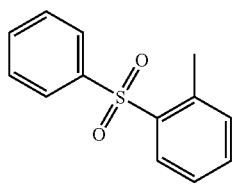 | 2.87 | 552 (M + H) |
| Ex No | | MS | NMR (400 MHz), CDCl$_3$, δ ppm |
|---|---|---|---|
| 34-7 | 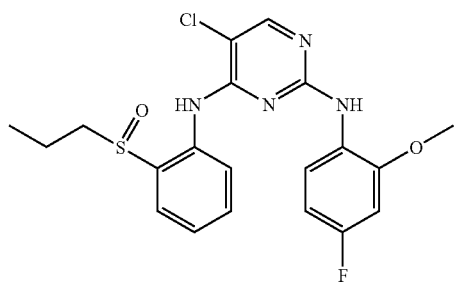 | MS 435, 436 | 1.05(t, 3H), 1.69-1.78(m, 2H), 2.86-2.95(m, 1H), 3.16-3.25(m, 1H), 6.57-6.68(m, 2H), 7.17(dd, 1H), 7.35-7.39(m, 1H), 7.50(dd, 1H), 8.13(s, 1H), 8.16-8.21 (m, 1H), 8.48(d, 1H), 10.14(s, 1H) |
| 34-8 | 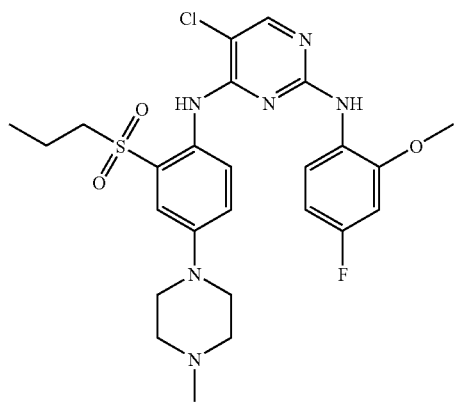 | MS 549, 551 | 0.94(t, 3H), 1.69-1.80(m, 2H), 2.38(s, 3H), 2.55-2.64 (m, 4H), 3.02-3.08(m, 2H), 3.22-3.29(m, 4H), 3.88(s, 3H), 6.55(ddd, 1H), 6.60-6.66(m, 1H), 7.13-7.18(m, 1H), 7.34(br.s, 1H), 7.44(d, 1H), 8.10(s, 1H), 8.10-8.23 (m, 2H), 8.88(s, 1H). |

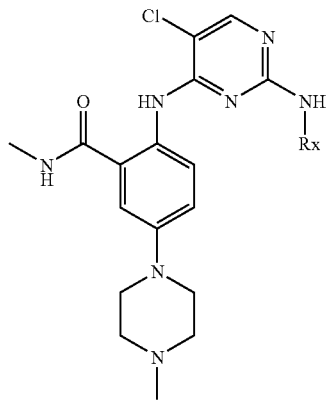

| | | | |
|---|---|---|---|
| 35-1 |  | 567 [M+1]+ | DMSO-d6: 2.24(s, 3H), 2.45-2.50(m, 4H), 2.78(d, 3H), 3.10-3.17(m, 8H), 3.74-3.79(m, 7H), 6.49(dd, 1H), 6.66(d, 1H), 6.85-6.89(m, 1H), 7.18(d, 1H), 7.40(d, 1H), 7.98-8.02(m, 2H), 8.29(br.d, 1H), 8.60-8.66 (m, 1H), 11.17(s, 1H). |
| 35-2 | | 505 [M+1]+ | DMSO-d6: 2.24(s, 3H), 2.46-2.50(m, 4H), 2.79(d, 3H), 3.13-3.17(m, 4H), 3.78(s, 3H), 6.69(d, 1H), 6.87(dd, 1H), 7.07-7.17(m, 2H), 7.19-7.23(m, 2H), 7.54(d, 1H), 8.13(s, 1H), 8.45(s, 1H), 8.65-8.75(m, 1H), 9.04(s, 1H), 11.19(s, 1H) |

Example 36

Intermediates for Left Anilines

36-1 Preparation of 2-amino-N-methyl-benzamide

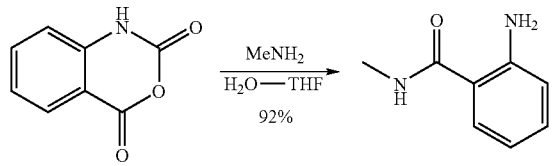

To a suspension of 16.3 g (100 mmol) of isatoic anhydride in 100 mL of H$_2$O is added portionwise 100 mL of 2N methylamine-tetrahydrofuran solution (200 mmol) at room temperature. The reaction mixture is stirred for 1 hour and then extracted with AcOEt. The organic layer is washed with H$_2$O and brine, dried over Na$_2$SO$_4$, and concentrated under reduced pressure to give 13.79 g of desired product, 2-amino-N-methyl-benzamide (92 mmol, 92%) as colorless solid.

NMR (400 MHz, CDCl3, δ): 2.97 (d, 3H, J=4.52 Hz), 5.49 (bs, 1H), 6.07 (bs, 1H), 6.64 (ddd, 1H, J=8.04, 7.56, 1.0 Hz), 6.68 (dd, 1H, J=8.32, 1.0 Hz), 7.20 (ddd, 1H, J=8.32, 7.56, 1.52 Hz), 7.29 (dd, 1H, J=8.04, 1.52 Hz).

36-2

2-(2,5-Dichloro-pyrimidin-4-ylamino)-N-methyl-benzamide

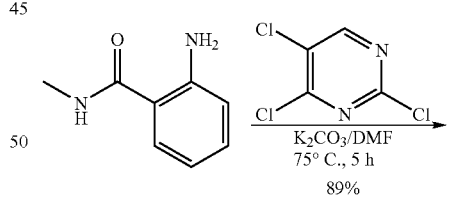

To a solution of 15.0 g (99.8 mmol) of 2-amino-N-methyl-benzamide in DMF (300 mL) are added 2,4,5-trichloropyrimidine (23.8 g, 130 mmol) and potassium carbonate (17.9 g, 130 mmol). The reaction mixture is stirred at 75° C. for 5 hours, cooled to room temperature, and then poured into H$_2$O (600 mL). The resulting precipitate is collected by a filtration followed by washing with 50% aqueous CH₃CN (200 mL) and dried under reduced pressure (40° C., 10 hours) to give desired 2-(2,5-dichloro-pyrimidin-4-yl-amino)-N-methyl-benzamide as ivory solid (26.4 g, 88.9 mmol, 89%).

NMR (400 MHz, DMSO-d6, δ): 2.81 (d, 3H, J=4.52 Hz), 7.22 (dd, 1H, J=8.56, 8.04 Hz), 7.60 (ddd, 1H, J=8.56, 8.56, 1.0 Hz), 7.81 (dd, 1H, J=8.04, 1.0 Hz), 8.48 (s, 1H), 8.52 (d, 1H, J=8.56 Hz) 8.80-8.90 (m, 1H), 12.18 (s, 1H).

According the manner described above, the following compounds are prepared.

36-3

2-(5-Bromo-2-chloro-pyrimidin-4-ylamino)-N-methyl-benzamide

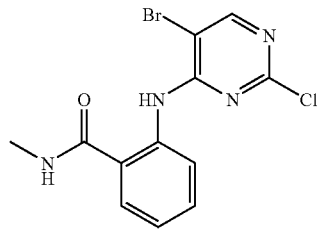

NMR (400 MHz, DMSO-d₆, δ): 2.81(d, 3H), 7.23(ddd, 1H, J=7.54, 7.54, 1.0 Hz), 7.59(ddd, 1H, J=7.93, 8.06, 1.52 Hz),7.79(dd, 1H, J=7.8, 1.52 Hz), 8.47(dd, 1H J=8.06, 1.0 Hz), 8.55(s, 1H), 8.81-8.87(m, 1H), 12.0(brs, 1H). Rf: 0.46 (n-Hexane:AcOEt=7:3).

36-4

2-(2,5-Dichloro-pyrimidin-4-ylamino)-N-ethyl-benzamide

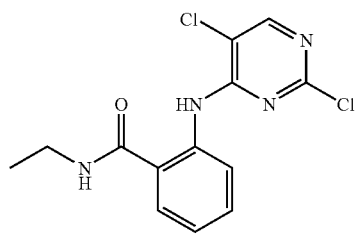

NMR (400 MHz, CDCl₃, δ): 1.28 (t, d=7.04, 3H), 3.48-3.57 (m, 2H), 6.22 (br. s, 1H), 7.11-7.17 (m, 1H), 7.51 (dd, J=1.0, 8.04, 1H), 7.53-7.61 (m, 1H), 8.22 (s, 1H), 8.69-8.74 (m, 1H), 11.66 (br. s, 1H). Rf: 0.60 (Hexane:AcOEt=1:1).

36-5

Preparation of 2-(5-bromo-2-chloro-pyrimidin-4-ylamino)-N-methyl-benzenesulfonamide

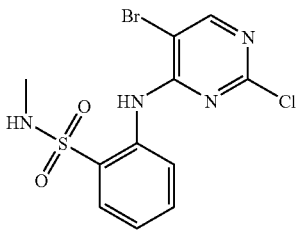

A suspension of 5-bromo-2,4-dichloropyrimidine (684 mg, 3.0 mmol) and 2-amino-N-methyl-benzenesulfonamide (559 mg, 3.0 mmol) in N,N-dimethylformamide (10 mL) containing potassium carbonate (830 mg, 6.0 mmol) is stirred at room temperature for 23 hours. Saturated aqueous ammonium chloride is added and the mixture is poured into water and extracted twice with ethyl acetate. The organic layer is washed with brine, dried over sodium sulfate, and evaporated in vacuo. The residue is purified by silica gel column chromatography (n-hexane-ethyl acetate gradient) to afford the title compound as a slightly yellow solid.

¹H-NMR (CDCl₃), δ(ppm): 2.67 (d, 3H), 4.79 (q, 1H), 7.26 (s, 1H), 7.29 (ddd, 1H), 7.66 (ddd, 1H), 7.95 (dd, 1H), 8.37 (s, 1H), 8.48 (d, 1H), 9.52 (s, 1H). Rf (n-hexane:ethyl acetate=10:3): 0.33.

According to the manner described above, the following compound is prepared.

36-6

2-(2,5-Dichloro-pyrimidin-4-ylamino)-N-methyl-benzenesulfonamide

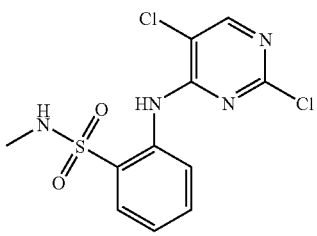

¹H-NMR (400 MHz, CDCl₃, δ):2.67(d, 3H),4.97-5.04(m, 1H), 7.29(ddd, 1H, J=7.54, 7.54, 1.0 Hz), 7.66(ddd, 1H, J=7.93, 8.08, 1.48 Hz),7.94(dd, 1H, J=8.04, 1.52 Hz), 8.24(s, 1H), 8.51(dd, 1H J=8.06, 1.0 Hz), 9.64(brs, 1H). Rf: 0.45 (n-Hexane:AcOEt=4:1).

36-7

2-(2,5-Dichloro-pyrimidin-4-ylamino)-N-isopropyl-benzenesulfonamide

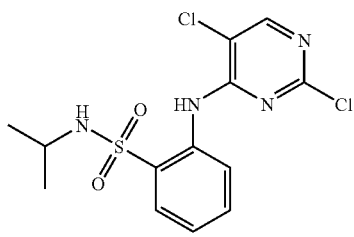

To a solution of 2-amino-N-isopropyl-benzenesulfonamide (16.1 g, 75.1 mmol) in DMI (150 mL) is added sodium hydride (6.6 g, 165.3 mmol) portionwise at 0° C. After the mixture is stirred at room temperature for one hour, 2,4,5-trichloropyrimidine (20.7 g, 112.7 mmol) is added at 0° C. After further stirring at room temperature for 5 hrs, water is added and the mixture is extracted with AcOEt three times. Organic layer is washed with brine, dried over sodium sulfate and evaporated under reduced pressure. The residue is purified by silica gel column chromatography (Hexane to Hexane:AcOEt=4:1) to afford the title compound as pale brown solid (10.2 g, 38%).

$^1$H-NMR (400 MHz, CDCl$_3$, δ);1.06(d, 6H), 3.43-3.53(m, 1H), 4.38(d, 1H), 7.29(dd, 1H), 7.66(dd, 1H), 7.98(d, 1H), 8.29(s, 1H), 8.51 (d, 1H), 9.51 (brs, 1H). Rf: 0.45 (n-Hexane:AcOEt=4:1)

The following compounds are prepared in the same manner described above.

36-10

Preparation of 2-(2-chloro-5-nitro-pyrimidin-4-ylamino)-N-methyl-benzenesulfonamide

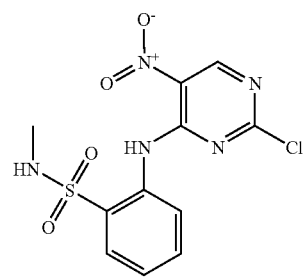

2,4-Dichloro-5-nitro-pyrimidine (1.94 g, 10 mmol) and 2-amino-N-methyl-benzenesulfonamide (1.86 g, 10 mmol) are dissolved in CHCl$_3$ (30 mL). The reaction mixture is heated at 61° C. for 2 h. The solvent is evaporated and the residue is washed with ether to give the title product. Rf=0.5 (n-hexane:ethyl acetate=1:1). $^1$H-NMR (400 MHz, CDCl$_3$), δ (ppm): 2.67 (d, 3H), 4.6-4.7 (m, 2H), 7.41 (t 1H), 7.7 (t, 1H), 8.04 (d, 1H), 8.15 (d, 1H), 9.21 (s, 1H), 11.2 (s, 1H).

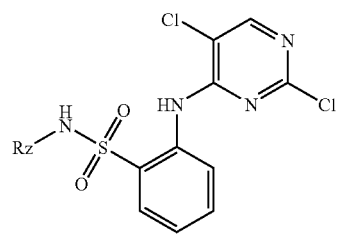

| Expl No. | Rz | Rf (solvent) or MS | NMR (400 MHz), δ (ppm) |
|---|---|---|---|
| 36-8 | (sec-butyl-like group) | 0.45 (n-Hexane:AcOEt = 4:1) | DMSO-d$_6$; 0.63(t, 6H), 0.86(d, 3H), 1.21-1.31(m, 2H), 3.02-3.12(m, 1H), 7.37(dd, 1H), 7.71(dd, 1H), 7.85(d, 1H), 7.89(d, 1H), 8.20(d, 1H), 8.56(s, 1H), 9.51(brs, 1H) |
| 36-9 | (3-pentyl-methyl group) | 0.46 (n-Hexane:AcOEt = 7:3) | CDCl$_3$; 0.70(t, 6H), 1.23-1.45(m, 4H), 3.03-3.13(m, 1H), 4.27(d, 1H), 7.27(dd, 1H), 7.65(dd, 1H), 7.98(d, 1H), 8.29(s, 1H), 8.52(d, 1H), 9.59(brs, 1H) |

36-11

Preparation of (2,5-Dichloro-pyrimidin-4-yl)-[2-(propane-1-sulfonyl)-phenyl]-amine

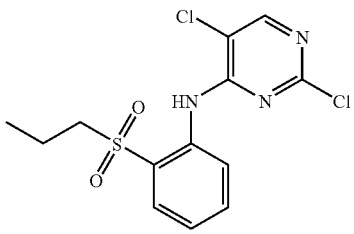

To a solution of 2-(Propane-1-sulfonyl)-phenylamine (3.69 g, 18.5 mmol) of N,N-dimethylformamide (40 mL), sodium hydride (1.48 g, 37 mmol) is added portionwise at 0° C. After stirring, 2,4,5-trichloropyrimidine (2.1 mL, 18.5 mmol) is added. The mixture is stirred at 0° C. for 30 minutes and is further stirred at room temperature for 7 hrs. After adding saturated aqueous ammonium chloride, the mixture is poured into water and extracted twice with ethyl acetate. The organic layer is washed with brine, dried over sodium sulfate, and evaporated in vacuo. The residue is purified by silica gel column chromatography (n-hexane-ethyl acetate gradient) to afford the title compound as colorless solids.

$^1$H-NMR (CDCl$_3$), δ (ppm): 0.99 (t, 3H), 1.77 (d, 2H), 3.07-3.11 (m, 2H), 7.26 (s, 1H), 7.32 (ddd, 1H), 7.73 (ddd, 1H), 7.95 (dd, 1H), 8.31 (s, 1H), 8.61 (dd, 1H), 9.94 (bs, 1H). Rf (n-hexane ethyl acetate=3:1): 0.63

According to the manner described above, the following compounds are prepared.

Example 36-16

Synthesis of substituted amines which are commercially not available:

Preparation of 3-amino-4'-methoxy-4-methylbiphenyl

To a solution of 4-methoxyphenyl-boronic acid (500 mg, 3.29 mmol) in toluene (5.2 mL) and ethanol (1.3 mL), potassium carbonate (910 mg, 6.58 mmol), tetrakis(triphenylphosphine) palladium (228.1 mg, 0.099 mmol) and 4-bromo-1-methyl-2-nitrobenzene (711 mg, 3.29 mmol) are added and stirred at 100° C. for 7 hours. The mixture is poured into water and extracted with ethyl acetate two times. The organic layer is washed with water and then brine, dried over magnesium sulfate, and evaporated in vacuo. The residue is purified with silica gel column chromatography (n-hexane:ethyl acetate=5:1) to afford the 4'-methoxy-4-methyl-3-nitro-biphenyl as a yellow solid.

$^1$H-NMR (δ, ppm): 2.62 (s, 3H), 3.86 (s, 3H), 7.02-6.98 (m, 2H), 7.37 (d, 1H), 7.54 (dd, 2H), 7.68 (dd, 1H), 8.18 (d, 1H). Rf (hexane:ethyl acetate=3:1): 0.40.

A suspension of 4'-methoxy-4-methyl-3-nitrobiphenyl (630 mg, 2.95 mmol) and 10% palladium on charcoal (63 mg, 0.059 mmol) in methanol (6 mL) is stirred under hydrogen atmosphere for 12 hours. Palladium catalyst is removed by filtration and the resulting solution is evaporated in vacuo to afford the title compound.

$^1$H-NMR (δ, ppm): 2.20 (s, 3H), 3.84 (s, 3H), 6.87 (d, 1H), 6.89 (dd, 1H), 6.95 (d, 2H), 7.09 (d, 1H), 7.48 (d, 2H). Rf (n-hexane:ethyl acetate=1:1): 0.50.

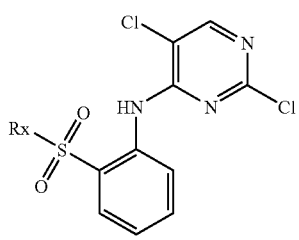

| Expl No. | Rx | Identification |
| --- | --- | --- |
| 36-12 | isopropyl | $^1$H-NMR(CDCl$_3$), δ(ppm): 1.35(d, 6H), 3.18-3.24(m, 1H), 7.30-7.34(m, 1H), 7.70-7.75(m, 1H), 7.92(dd, 1H), 8.30(s, 1H), 8.63(d, 1H), 10.06(s, 1H). Rf 0.70:(AcOEt) |
| 36-13 | ethyl | NMR(400 MHz) in CDCl$_3$, δ(ppm): 1.29(t, 3H), 3.15(q, 1H), 7.31-7.35(m, 1H), 7.71-7.75(m, 1H), 7.96(dd, 1H), 8.31(s, 1H), 8.60(d, 1H), 9.92(s, 1H). Rf: 0.67 (AcOEt). |
| 36-14 | cyclopropylmethyl | 1.01-1.06(m, 2H), 1.32-1.37(m, 2H), 2.49-2.55(m, 1H), 7.29-7.33(m, 1H), 7.69-7.73(m, 1H), 7.91(dd, 1H), 8.31(s, 1H), 8.58(d, 1H), 9.90(s, 1H). Rf 0.69 (AcOEt) |
| 36-15 | 2-ethylbutyl | 0.99(t, 6H), 1.72-1.90(m, 4H), 2.76-2.82(m, 1H), 7.26-7.34 (m, 1H), 7.69-7.74(m, 1H), 7.92(dd, 1H), 8.30(s, 1H), 8.62(d, 1H), 10.02(s, 1H). Rf: 0.73(AcOEt) |

Preparation of 4-(3-amino-4-methylbenzoyl)-piperazine-1-carboxylic acid tert-butyl ester To a solution of 4-methyl-3-nitro-benzoic acid (300 mg, 2.76 mmol), N -butoxycarbonyl-piperazine (340 mg, 1.83 mmol) in DMF (3.0 mL), triethylamine (300 μL, 3.59 mmol), TBTU (800 mg, 2.49 mmol) and HOAt (270.5 mg, 1.99 mmol) are added and stirred at room temperature for 24 hours. The mixture is poured into water and extracted twice with ethyl acetate. The organic layer is washed with water and then brine, dried over magnesium sulfate, and evaporated in vacuo. The residue is purified with silica gel column chromatography (n -hexane:ethyl acetate=5:1) to afford 4-(4-methyl-3-nitrobenzoyl)-piperazine-1-carboxylic acid tert-butyl ester as a colorless solid.

$^1$H-NMR (δ, ppm): 1.47 (s, 9H), 2.64 (s, 3H), 3.28-3.88 (m, 8H), 7.42 (d, 1H), 7.56 (dd, 1H), 8.03 (d, 1H). Rf (hexane:ethyl acetate=10:1): 0.13.

The title compound is obtained by reduction with hydrogen over 10% palladium on charcoal in methanol solution.

Preparation of 4-(3-amino-4-methylphenyl)-morpholine

To a solution of 4-bromo-1-methyl-2-nitrobenzene (225 mg, 1.04 mmol), morpholine (125 μL, 1.25 mmol), and cesium carbonate (474.4 mg, 1.46 mmol) in toluene, palladium diacetate (31.2 mg, 0,139 mmol) and 2-(di-t-butylphosphino)biphenyl (125 mg, 0.403 mmol) are added and stirred at 100° C. for 5 hours. After cooling, the mixture is filtered to remove insoluble material. The filtrate is poured into water and extracted with ethyl acetate twice. The organic layer is washed with water and then brine, dried over magnesium sulfate, and evaporated in vacuo. The residue is purified with silica gel column chromatography (n-hexane:ethyl acetate=5:1) to afford 4-(4-methyl-3-nitrophenyl)morpholine as a yellow solid.

$^1$H-NMR (δ, ppm): 2.50 (s, 3H), 3.17-3.19 (m, 4H), 3.86-3.88(m, 4H), 7.04 (dd, 1H), 7.21 (d, 1H), 7.47 (d, 1H). Rf (hexane:ethyl acetate=5:1): 0.20.

The title compound is obtained by reduction with hydrogen over 10% palladium on charcoal in methanol solution.

Example 37

Synthesis of Substituted Amines Which are Commercially not Available 37-1

Preparation of 1-(3-Methoxy-4-nitro-phenyl)-piperdin-4-ol

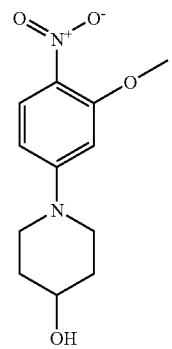

To a suspension of piperidin-4-ol (2.79 g, 28 mmol) and potassium carbonate (3.88 g, 28 mmol) in N,N-dimethylformamide (40 mL), 4-Fluoro-2-methoxy-1-nitro-benzene (4.0 g, 23 mmol) is added and stirred at room temperature for 24 hours. The mixture is poured into water and the precipitate is collected by a filtration. The resulting solid is dried in vacuo at 50° C. to afford 1-(3-methoxy-4-nitro-phenyl)-piperidin-4-ol (5.23 g) as yellow solids in 89% yield.

$^1$H-NMR (400 MHz, CDCl$_3$, δ, ppm):1.54(d, 1H), 1.62-1.71(m, 2H), 1.98-2.04(m, 2H), 3.22(ddd, 4H), 3.73-3.80(m, 2H), 3.95(s, 3H), 3.98-4.02(m, 1H), 6.33(d, 1H), 6.43(dd, 1H), 8.00(d, 1H).

By repeating the procedures described above using appropriate starting materials and conditions the following compounds are obtained.

| Ex-No | Rx | Identification |
|---|---|---|
| 37-2 | (structure shown: 2-methoxy-4-(4-pyrrolidin-1-yl-piperidin-1-yl)-1-nitrobenzene) | $^1$H-NMR(400 MHz, CDCl$_3$, δ, ppm): 1.53-1.72(m, 2H), 1.80-1.83 (m, 4H), 1.99-2.04(m, 2H), 2.24-2.31(m, 1H), 2.54-2.67 (m, 4H), 3.03(dt, 2H), 3.84-3.89(m, 2H), 3.95(s, 3H), 6.31(d, 1H), 6.42(dd, 1H), 8.01(d, 1H). Rf 0.54(AcOEt) |

| Ex-No | Rx | Identification |
|---|---|---|
| 37-3 | (3-nitro-2-methoxy-phenyl piperidine-3-carboxamide) | $^1$H-NMR(400 MHz, CDCl$_3$, δ, ppm): 1.81-1.91(m, 2H), 1.99-2.04 (m, 2H), 2.38-2.48(m, 1H), 3.03(ddd, 2H), 3.91-3.96(m, 2H), 3.95(s, 3H), 5.22-5.41(m, 1H), 5.40-5.53(m, 1H), 6.36(d, 1H), 6.43(dd, 1H), 8.00(d, 1H). Rf 0.15(AcOEt) |
| 37-4 | Ethyl-[1-(3-methyoxy-4-nitro-pheny-pyrrolidin-3-yl]-amine | $^1$H-NMR(400 MHz, CDCl$_3$, δ, ppm): 1.15(t, 3H), 1.88-1.96(m, 1H), 2.22-2.30(m, 1H), 2.68-2.77(m, 2H), 3.15-3.18(m, 1H), 3.38-3.44(m, 1H), 3.52-3.62(m, 2H), 3.93(s, 3H), 5.92(d, 1H), 6.07-6.10(m, 1H), 8.00-8.02(m, 1H). Rf 0.65(n-hexane:AcOEt = 1:1). |
| 37-5 | 1-(3-Methoxy-4-nitro-phenyl)-4-methyl-piperazine | $^1$H-NMR(400 MHz, CDCl$_3$, δ, ppm): 2.36(s, 3H), 2.52-2.57(m, 4H), 3.40-3.43(m, 4H), 3.95(s, 3H), 6.32(d, 1H, J=2.52 Hz), 6.43(dd, 1H, J=9.56, 2.52 Hz), 7.99(d, 1H, J=9.08 Hz). Rf 0.60 (MeOH:CH$_2$Cl$_2$ = 4:1). |
| 37-6 | 3-(3-Methoxy-4-nitro-phenoxymethy-1-methyl-piperidine | $^1$H-NMR(400 MHz, CDCl$_3$, δ, ppm): 1.10-1.19(m, 1H), 1.59-2.18 (m, 6H), 2.28(s, 3H), 2.71-2.74(m, 1H), 2.88-2.91(m, 1H), 3.86.-3.95(m, 5H), 6.47-6.52(m, 2H), 7.97-8.00(m, 1H). Rf 0.65(n-hexane:AcOEt = 1:1) |

| Ex-No | Rx | Identification |
|---|---|---|
| 37-7 | | ¹H-NMR(400 MHz, CDCl₃, δ, ppm): 4.08(s, 3H), 7.30(dd, 1H), 7.58(d, 1H), 8.05(d, 1H), 8.15(s, 1H), 8.67(s, 1H). Rf: 0.42 (AcOEt) |
| 37-8 | | ¹H-NMR(400 MHz, CDCl₃, δ, ppm): 1.40-1.50(m, 2H), 1.55-1.69 (m, 6H), 1.90-1.96(m, 2H), 2.45-2.53(m, 5H), 2.90-2.99 (m, 2H), 3.90-4.00(m, 2H), 3.94(s, 3H), 6.30(d, 1H, J=, 2.5 Hz), 6.41(dd, 1H, J=9.0, 2.5 Hz), 7.99(d, 1H, J=9.0 Hz) |
| 37-9 | | ¹H-NMR(400 MHz, DMSO-d6, δ, ppm): 1.95-1.82(m, 2H), 2.15-2.06(m, 1H), 2.30(s, 3H), 3.17(dd, 1H), 3.32-3.23(m, 1H), 3.56-3.34(m, 3H), 3.96(s, 1H), 6.09(d, 1H), 6.21(dd, 1H), 7.91(d, 1H) |
| 37-10 | | ¹H-NMR(400 MHz, CDCl₃, δ, ppm): 2.30-2.48(m, 3H), 2.59-2.66 (m, 1H), 2.70-2.76(m, 1H), 2.85-2.92(m, 1H), 3.09-3.17 (m, 1H), 3.30-3.34(m, 1H), 3.52-3.58(m, 1H), 3.68-3.84 (m, 3H), 3.87-3.91(m, 1H), 3.96(s, 3H), 6.32(d, 1H, J=2.5 Hz), 6.42(dd, 1H, J=9.6, 2.5 Hz), 8.00(d, 1H, J=9.6 Hz) |

-continued

| Ex-No | Rx | Identification |
|---|---|---|
| 37-11 | (structure: 4-nitro-3-methoxyphenyl attached to N of pyrrolidine bearing 3-dimethylamino) | ¹H-NMR(400 MHz, DMSO-d6, CDCl₃, δ, ppm): 1.90-1.79(m, 1H), 2.25-2.15(m, 1H), 2.21(s, 3H), 2.87-2.77(m, 1H), 3.16 (dd, 1H), 3.42-3.32(m, 1H), 3.59-3.52(m, 1H), 3.67-3.61(m, 1H), 3.91(s, 3H), 6.13(d, 1H), 6.24(dd, 1H)), 7.91(dd, 1H) |
| 37-12 | (structure: 4-nitro-3-methoxyphenyl attached to N of piperidine bearing 4-methoxymethyl) | ¹H-NMR(400 MHz, CDCl₃): 1.43-1.00(m, 2H), 1.95-1.81(m, 2H), 2.94-2.17(m, 2H), 2.96(s, 3H), 3.27(d, 2H), 3.35(s, 3H), 3.97-3.90(m, 2H), 3.95(s, 3H), 6.30(d, 1H), 6.42(dd, 1H) 8.00(d, 1H). Rf: 0.25 (AcOEt) |
| 37-13 | (structure: 4-nitro-3-methoxyphenyl attached to N of 4-ethylpiperazine) | ¹H-NMR(400 MHz, CDCl₃): 1.14(t, 3H), 2.48(dd, 2H), 2.59(t, 4H), 3.42(t, 4H), 3.95(s, 3H), 6.32(d, 1H), 6.43(dd, 1H) 8.01(d, 1H). Rf 0.15(AcOEt) |
| 37-14 | (structure: 4-nitro-3-methoxyphenyl attached to N of piperidine bearing 4-morpholino) | ¹H-NMR(400 MHz, CDCl₃): 1.02-0.89(m, 2H), 2.01-1.94(m, 2H), 2.52-2.38(m, 1H), 2.65-2.53(m, 4H), 3.04-2.94(m, 2H), 3.79-3.69(m, 4H), 3.97-3.88(m, 2H), 3.95(s, 3H), 6.32(d, 1H), 6.42(dd, 1H) 8.00(d, 1H). Rf 0.10(AcOE |

| Ex-No | Rx | Identification |
|---|---|---|
| 37-15 | (4-isopropylpiperazin-1-yl)-(3-methoxy-4-nitrophenyl) | ¹H-NMR(400 MHz, CDCl₃): 1.08(s, 3H), 1.09(s, 3H), 2.66(t, 4H), 2.74(sept, 1H), 3.41(t, 4H), 3.95(s, 3H), 6.32(d, 1H), 6.42(dd, 1H) 8.00(d, 1H). Rf 0.15(AcOEt) |
| 37-16 | 1-(3-methoxy-4-nitrophenyl)piperidine-4-carboxamide | ¹H-NMR(400 MHz, CDCl₃): 1.91-1.81(m, 2H), 2.06-1.97(m, 2H), 2.48-2.40(m, 1H), 3.07-2.98(m, 2H), 3.97-3.93(m, 2H), 3.93(s, 3H), 5.37-5.30(m, 1H), 5.55-5.43(m, 1H), 6.33(d, 1H), 6.43(dd, 1H) 8.00(d, 1H). Rf 0.10(AcOEt) |
| 37-17 | 3-methoxy-1-(3-methoxy-4-nitrophenyl)pyrrolidine | ¹H-NMR(400 MHz, CDCl₃): 2.18-2.07(m, 1H), 2.30-2.22(m, 1H), 3.38(s, 3H), 3.56-3.44(m, 4H), 3.95(s, 3H), 4.13(ddd, 1H), 5.96(d, 1H), 6.12(dd, 1H) 8.03(d, 1H). Rf 0.30(AcOEt) |
| 37-18 | tert-butyl (1-(3-methoxy-4-nitrophenyl)piperidin-4-yl)(methyl)carbamate | ¹H-NMR(400 MHz, CDCl₃): 1.46(s, 9H), 1.81-1.68(m, 4H), 2.73(bs, 3H), 3.07-2.97(m, 2H), 3.95(s, 3H), 4.03-3.94(m, 2H), 6.32(d, 1H), 6.43(dd, 1H) 8.00(d, 1H). Rf 0.55 (Hexane:AcOEt) |

-continued
| Ex-No | Rx | Identification |
|---|---|---|
| 37-19 | 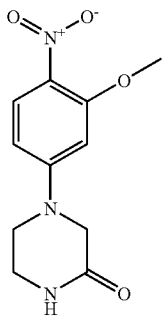 | $^1$H-NMR(400 MHz, CDCl$_3$): 3.60-3.57(m, 2H), 3.68-3.65(m, 2H), 3.97(s, 3H), 4.07(s, 2H), 6.17(bs, 1H), 6.26(d, 1H), 6.39(dd, 1H) 8.04(d, 1H). Rf 0.85(AcOEt) |
| 37-20 | 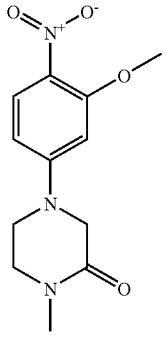 | $^1$H-NMR(400 MHz, CDCl$_3$): 3.08(s, 3H), 3.54(dd, 2H), 3.67(dd, 2H), 3.96(s, 3H), 4.05(s, 2H), 6.25(d, 1H), 6.38(dd, 1H) 8.03(d, 1H). Rf 0.30(AcOEt) |
| 37-21 | 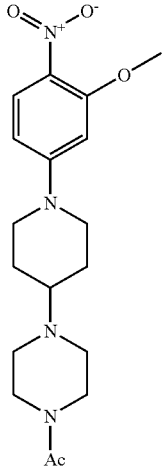 | $^1$H-NMR(400 MHz, CDCl$_3$): 1.73-1.55(m, 2H), 1.99-1.91(m, 2H), 2.09(s, 3H), 2.61-2.49(m, 5H), 3.47(t, 2H), 3.63(t, 2H), 3.99-3.89(m, 3H), 3.95(s, 3H), 6.32(d, 1H), 6.42(dd, 1H) 8.01(d, 1H). Rf 0.10(AcOEt:MeOH = 4:1) |
| 37-22 | 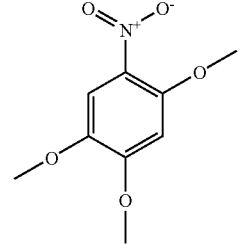 | $^1$H-NMR(400 MHz, CDCl$_3$): 3.90(s, 3H), 3.98(s, 3H), 3.98(s, 3H), 6.56(s, 1H), 7.59(s, 1H). Rf 0.605(AcOEt) |

-continued

| Ex-No | Rx | Identification |
|---|---|---|
| 37-23 | (2,5-dimethoxy-4-nitrophenyl morpholine) | ¹H-NMR(400 MHz, CDCl₃): 3.25-3.22(m, 4H), 3.90-3.87(m, 4H), 3.95(s, 3H), 6.48(s, 1H), 7.57(s, 1H). Rf 0.060 (Hexane:AcOEt = 5:1) |
| 37-24 | (1-(2,5-dimethoxy-4-nitrophenyl)-4-methylpiperazine) | ¹H-NMR(400 MHz, CDCl₃): 2.37(s, 3H), 2.61(bs, 4H), 3.27 (bs, 4H), 3.88(s, 3H), 3.95(s, 3H), 6.48(s, 1H), 7.56(s, 1H). Rf 0.10(AcOEt:MeOH = :1) |
| 37-25 | (4-methyl-1-(4-nitro-3-propoxyphenyl)piperazine) | ¹H-NMR(400 MHz, CDCl₃): 1.09(t, 3H), 1.89(dd, 2H), 2.36(s, 3H), 2.55(t, 4H), 3.39(t, 4H), 4.03(t, 2H), 6.32(d, 1H), 6.42(dd, 1H), 7.98(d, 1H). Rf 0.12(AcOEt:MeOH = 9:1) |
| 37-26 | (1-acetyl-4-(3-methoxy-4-nitrophenyl)-3,5-dimethylpiperazine) | ¹H-NMR(400 MHz, CDCl₃): 1.36(s, 3H), 1.38(s, 3H), 2.10(s, 2H), 2.17(s, 3H), 3.27-2.96(m, 2H), 3.71(d, 2H), 3.96(s, 3H), 6.33(d, 1H), 6.43(dd, 1H), 8.02(d, 1H). Rf 0.10(AcOEt) |

-continued

| Ex-No | Rx | Identification |
|---|---|---|
| 37-27 | (3,5-dimethylpiperazin-1-yl on 3-methoxy-4-nitrophenyl) | ¹H-NMR(400 MHz, CDCl₃): 1.16(s, 3H), 1.18(s, 3H), 2.50(dd, 2H), 3.02-2.47(m, 2H), 3.69(dd, 2H), 3.96(s, 3H), 6.31(d, 1H), 6.43(dd, 1H), 8.00(d, 1H). Rf 0.070(AcOEt) |
| 37-28 | (3-methylpiperazin-1-yl on 3-methoxy-4-nitrophenyl) | ¹H-NMR(400 MHz, CDCl₃): 1.16(d, 3H), 2.57(dd, 1H), 3.00-2.89 (m, 4H), 3.18-3.11(m, 1H), 3.75-3.68(m, 2H), 3.96(s, 3H), 6.31(d, 1H), 6.43(dd, 1H), 8.01(d, 1H). Rf 0.070(AcOEt) |
| 37-29 | (4-propanoylpiperazin-1-yl on 3-methoxy-4-nitrophenyl) | ¹H-NMR(400 MHz, CDCl₃): 1.18(t, 3H), 2.40(dd, 2H), 3.47-3.38 (m, 4H), 3.71-3.63(m, 2H), 3.85-3.79(m, 2H), 3.96(s, 3H), 6.32(d, 1H), 6.42(dd, 1H), 8.01(d, 1H). Rf 0.20(AcOEt) |
| 37-30 | (4-isobutanoylpiperazin-1-yl on 3-methoxy-4-nitrophenyl) | ¹H-NMR(400 MHz, CDCl₃): 1.16(s, 3H), 1.18(s, 3H), 2.82(sept, 1H), 3.50-3.37(m, 4H), 3.77-3.65(m, 2H), 3.86-3.78(m, 2H), 3.96(s, 3H), 6.33(d, 1H), 6.43(dd, 1H), 8.01(d, 1H). Rf 0.48 (AcOEt) |

-continued

| Ex-No | Rx | Identification |
|---|---|---|
| 37-31 | | ¹H-NMR(400 MHz, CDCl₃): 2.86(d, 3H), 3.48-3.45(m, 4H), 3.61-3.58(m, 4H), 3.96(s, 3H), 4.48-4.37(m, 1H), 6.29(d, 1H), 6.40(dd, 1H), 8.01(d, 1H). Rf 0.20(AcOEt) |
| 37-32 | | ¹H-NMR(400 MHz, CDCl₃): 1.72-1.60(m, 2H), 2.06-1.97(m, 2H), 3.25-3.17(d, 3H), 3.78-3.70(m, 2H), 3.95(s, 3H), 4.04-3.99 (m, 1H), 6.33(d, 1H), 6.43(dd, 1H), 8.00(d, 1H). Rf 0.20 (AcOEt) |
| 37-33 | | ¹H-NMR(400 MHz, CDCl₃): 1.53(s, 6H), 2.14(s, 3H), 3.50(s, 2H), 3.61-3.58(m, 2H), 3.97-3.81(m, 2H), 3.97(s, 3H), 6.10(d, 1H), 6.26(dd, 1H), 8.05(d, 1H). Rf 0.030(AcOEt) |
| 37-34 | | ¹H-NMR(400 MHz, CDCl₃): 2.54-2.23(m, 4H), 2.67(t, 2H), 3.29-3.23(m, 2H), 3.74(t, 4H), 3.94(s, 3H), 6.07(d, 1H), 6.16 (dd, 1H), 8.00(d, 1H). Rf 0.15(AcO |

-continued

| Ex-No | Rx | Identification |
|---|---|---|
| 37-35 | (4-nitro-3-methoxyphenoxy)ethyl-pyrrolidin-2-one | ¹H-NMR(400 MHz, CDCl₃): 2.10-2.02(m, 2H), 2.41(t, 2H), 3.56(dd, 2H), 3.71(t, 2H), 3.95(s, 3H), 4.19(t, 2H), 6.49(dd, 1H), 6.55(d, 1H), 7.99(d, 1H). Rf 0.10(AcOEt) |
| 37-36 | (4-acetylpiperazin-1-yl)(4-nitro-3-methoxyphenyl)methanone | ¹H-NMR(400 MHz, CDCl₃): 2.14(s, 3H), 3.87-3.34(m, 8H), 3.99 (s, 3H), 7.01(dd, 1H), 7.16(d, 1H), 7.88(d, 1H). Rf 0.25 (AcOEt) |
| 37-37 | morpholino(4-nitro-3-methoxyphenyl)methanone | ¹H-NMR(400 MHz, CDCl₃): 3.49-3.37(m, 2H), 3.88-3.55(m, 6H), 3.99(s, 3H), 7.00(dd, 1H), 7.16(d, 1H), 7.87(d, 1H). Rf 0.50(AcOEt) |
| 37-38 | N-isopropyl-2-(4-(4-nitro-3-methoxyphenyl)piperazin-1-yl)acetamide | ¹H-NMR(400 MHz, CDCl₃): 1.17(s, 3H), 1.19(s, 3H), 2.69(t, 4H), 3.06(s, 2H), 3.42(t, 4H), 3.96(s, 3H), 4.13(sept, 1H), 6.34 (d, 1H), 6.44(dd, 1H), 6.90-6.79(m, 1H), 8.00(d 1H). Rf 0.20 (AcOEt) |

US 7,964,592 B2
239                                                                                         240
-continued
| Ex-No | Rx | Identification |
|---|---|---|
| 37-39 | 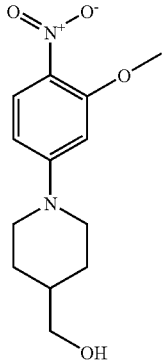 | ¹H-NMR(400 MHz, CDCl₃): 1.44-1.34(m, 2H), 1.84-1.77(m, 1H), 1.94-1.85(m, 2H), 3.04-2.94(m, 2H), 3.55(t, 2H), 3.96-3.57 (m, 2H), 3.95(s, 3H), 6.31(d, 1H), 6.42(dd, 1H), 8.00(d, 1H). Rf 0.30(AcOEt) |
| 37-40 | 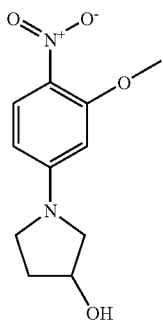 | ¹H-NMR(400 MHz, CDCl₃): 1.44-1.34(m, 2H), 1.84-1.77(m, 1H), 1.94-1.85(m, 2H), 3.04-2.94(m, 2H), 3.55(t, 2H), 3.96-3.57 (m, 2H), 3.95(s, 3H), 6.31(d, 1H), 6.42(dd, 1H), 8.04(d, 1H). Rf 0.45(AcOEt) |
| 37-41 | 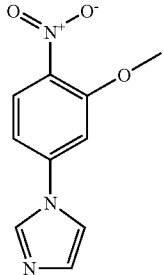 | ¹H-NMR(400 MHz, CDCl₃): 4.05(s, 3H), 7.07(d, 1H), 7.08(d, 1H), 7.27-7.26(m, 1H), 7.33(t, 1H), 7.92(s, 1H), 8.04(d, 1H). Rf: 0.20(AcOEt) |
| 37-42 | 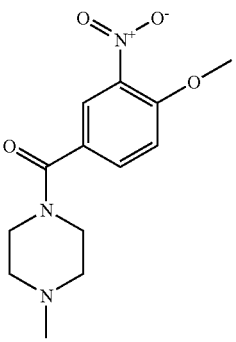 | ¹H-NMR(400 MHz, CDCl₃): 2.34(s, 3H), 2.55-2.37(m, 4H), 3.86-3.38(m, 4H), 4.00(s, 3H), 7.13(d, 1H). 7.66(dd, 1H). 7.93(d, 1H). Rf: 0.30(AcOEt:MeOH = 4:1) |
| 37-43 | 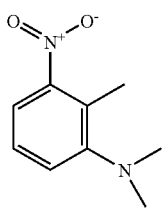 | ¹H-NMR(400 MHz, CDCl₃): 2.43(s, 3H), 2.74(s, 6H), 7.91(dd, 1H), 7.23(d, 1H), 7.24(d, 1H), 7.46(dd, 1H). Rf: 0.70(Hexane:AcOEt = 5:1) |

| Ex-No | Rx | Identification |
|---|---|---|
| 37-44 | 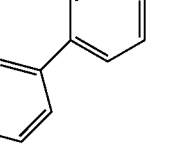 | ¹H-NMR(400 MHz, CDCl₃): 2.15(s, 3H), 3.80-3.48(m, 2H), 6.87(dd, 1H), 6.92(dd, 1H), 7.09(d, 1H), 7.40 (dd, 2H), 8.54(dd, 2H). |
| 37-45 | 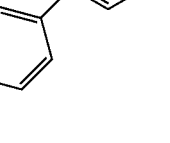 | ¹H-NMR(400 MHz, CDCl₃): 3.86(s, 3H), 4.00(s, 3H), 6.78(d, 1H), 6.99(dd, 2H), 7.14(d, 1H), 7.48(dd, 2H), 7.71(dd, 1H), 8.03(d, 1H). Rf: 0.30 (Hexane:AcOEt = 3:1) |
| 37-46 | 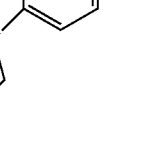 | ¹H-NMR(400 MHz, CDCl₃): 1.44(t, 3H), 3.10(t, 4H), 3.86(t, 4H), 4.13(q, 2H), 7.01(dd, 1H), 7.08(dd, 1H), 7.35(d, 1H). Rf: 0.25(Hexane:AcOEt = 3:1) |
| 37-47 | 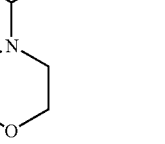 | ¹H-NMR(400 MHz, CDCl₃): 1.26(t, 3H), 3.32(t, 4H), 3.85(t, 4H), 4.15(q, 2H), 6.34(d, 1H), 6.42(dd, 1H), 7.98(d, 1H). Rf: 0.45(Hexane:AcOEt = 5:1) |
| 37-48 | 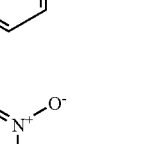 | ¹H-NMR(400 MHz, CDCl₃): 3.45(s, 3H), 3.77(dd, 2H), 3.81(s, 3H), 4.06(t, 2H), 7.08—7.08(m, 2H), 7.37(t, 1H). Rf: 0.45(Hexane:AcOEt = 3:1) |
| 37-49 | 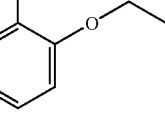 | ¹H-NMR(400 MHz, CDCl₃): 2.44(t, 1H), 3.53(s, 3H), 3.96(ddd, 2H), 4.20(t, 2H), 7.06(d, 1H), 7.12(dd, 1H), 7.40(d, 1H). Rf: 0.10(Hexane:AcOEt = 3:1) |

| Ex-No | Rx | Identification |
|---|---|---|
| 37-50 | | ¹H-NMR(400 MHz, CDCl₃): 1.45(t, 3H), 3.81(s, 3H), 4.13(q, 2H), 7.01(d, 1H), 7.08(dd, 1H), 7.36(d, 1H). Rf: 0.20(Hexane:AcOEt = 3:1) |
| 37-51 | | ¹H-NMR(400 MHz, CDCl₃): 1.35(s, 3H), 1.36(s, 3H), 3.81(s, 3H), 4.52(sept, 1H), 7.08-7.01(m, 2H), 7.31(d, 1H). Rf: 0.30(Hexane:AcOEt = 3:1) |
| 37-52 | | ¹H-NMR(400 MHz, CDCl₃): 1.05(t, 3H), 1.83(ddd, 2H), 3.81(s, 3H), 4.01(t, 2H), 7.01(d, 1H), 7.08(dd, 1H), 7.36(d, 1H). Rf: 0.35(Hexane:AcOEt = 3:1) |
| 37-53 | | ¹H-NMR(400 MHz, CDCl₃): 3.86(s, 6H), 3.79(s, 3H), 6.91(dd, 1H), 7.00(d, 1H), 7.18(d, 1H). Rf: 0.5 (Hexane:AcOEt = 9:1) |
| 37-54 | | ¹H-NMR(400 MHz, CDCl₃): 4.04(s, 3H), 7.22(d, 1H), 7.48(dd, 2H), 7.83(dd, 1H), 8.16(d, 1H), 8.69(dd, 2H). Rf: 0.12(Hexane:AcOEt = 1:1) |
| 37-55 | | ¹H-NMR(400 MHz, CDCl₃): 4.02(s, 3H), 7.22(d, 1H), 7.39(ddd, 1H), 7.77(dd, 1H), 7.85(ddd, 1H), 8.08(d, 1H), 8.63(dd, 1H), 8.83(d, 1H). Rf: 0.55 (Hexane:AcOEt = 2:1) |
| 37-56 | | ¹H-NMR(400 MHz, CDCl₃): 4.03(s, 3H), 7.19(d, 1H), 7.28-7.24(m, 1H), 7.72(dd, 1H), 7.80-7.76(m, 1H), 8.25(dd, 1H), 8.52(d, 1H), 8.69(ddd, 1H). Rf: 0.55 (Hexane:AcOEt = 2:1) |

| Ex-No | Rx | Identification |
|---|---|---|
| 37-57 | 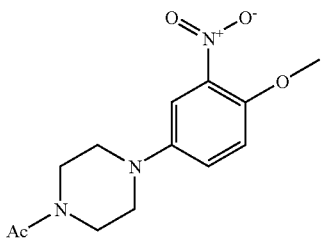 | mp 90.7° C.; $^1$H-NMR(400 MHz, CDCl$_3$)δ(ppm): 1.68 (m; 2H), 2.00(m; 2H), 2.36(s; 1H), 2.62(bs; 4H), 2.72(m; 2H), 3.62(m; 2H), 3.78(bs; 4H), 3.90(s; 3H), 6.99(d; 1H); 7.13(dd; 1H); 7.26(s; 1H); 7.40(s; 1H). |

Preparation of 1-[4-(4-Methoxy-3-nitro-phenyl)-piperazin-1-yl]-ethanone

To a solution of 5-bromo-1-methoxy-2-nitrobenzene (300 mg, 1.29 mmol) in dioxane, 1-acetyl piperazine (400 mg, 3.12 mmol), cesium carbonate (1.0 g, 3.07 mmol), palladium diacetate (29.0 mg, 0.129 mmol) and 2-(di-t-butylphosphino)biphenyl (77 mg, 0.258 mmol) are added and stirred at 100° C. for 8 hours. After cooling, the mixture is filtered to remove insoluble material. The filtrate is poured into water and extracted with ethyl acetate twice. The organic layer is washed with water and then brine, dried over magnesium sulfate, and evaporated in vacuo. The residue is purified by silica gel column chromatography (n-hexane:ethyl acetate gradient) to afford 1-[4-(4-Methoxy-3-nitro-phenyl)-piperazin-1-yl]-ethanone (319 mg, 44%) as yellow solids.

$^1$H-NMR (400 MHz, CDCl$_3$, δ, ppm): 2.14 (s, 3H), 3.63 (ddd, 4H), 3.63 (t, 2H), 3.78 (t, 2H), 3.92 (s, 3H), 7.03 (d, 1H), 7.12 (d, 1H), 7.41 (d, 1H). Rf (ethyl acetate): 0.18

39

Preparation of 1-(3-Methoxy-4-nitro-phenyl)-piperidin-4-one

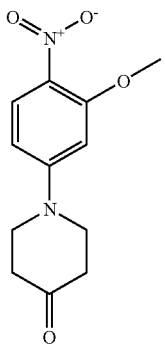

To a solution of 4-piperidone hydrochloride monohydrate (10.0 g, 0.065 mol) in DMF (80 mL) are added 4-Fluoro-2-methoxy-1-nitro-benzene (10.0 g, 0.058 mol) and potassium carbonate (20.2 g), and the mixture is stirred at 70° C. for 20 h. After a filtration, the filtrate is poured into H$_2$O (ca. 300 mL), and the resulting precipitates are collected by a filtration followed by washing with H$_2$O for several times to give title compound (8.98 g) in 61% yield. Orange solid. $^1$H-NMR (400 MHz, CDCl$_3$, δ): 2.65-2.62 (4H, m), 3.81-3.78 (4H, m), 3.98 (3H, s), 6.34 (1H, d), 6.45 (1H, dd), 8.05 (1H, d).

40

Preparation of 1-[1-(3-Methoxy-4-nitro-phenyl)-piperidin-4-yl]-4-methyl-piperazine

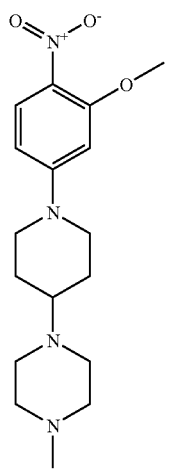

To a solution of 1-(3-Methoxy-4-nitro-phenyl)-piperidin-4-one (4.96 g, 0.020 mol) in dichloroethane (50 ml) is added N-methylpiperazine (2.7 ml, 0.024 mol) at 0° C. and the mixture is stirred at room temperature. After 4 h, sodium triacetoxy-borohydride (5.04 g, 0.024 mol) is added and the mixture is further stirred at room temperature for 24 h. After addition of 1N sodium hydroxide at 0° C., the mixture is poured into water and extracted three times with dichloromethane. The organic layer is combined and extracted three times with 1N hydrochloride. The water layer is basified with 2N sodium hydroxide and extracted three times with dichloromethane. The organic layer is washed with brine, dried over sodium sulfate, and evaporated in vacuo to give the title compound as yellow solids (6.04 g) in 91% yield.

$^1$H-NMR (400 MHz, CDCl$_3$, δ): 1.70-1.57 (2H, m), 2.03-1.93 (2H, m), 2.29 (3H, s), 2.55-2.38 (5H, m), 2.70-2.56 (4H, m), 2.97 (2H, ddd), 3.97-3.92 (2H, m), 3.95 (3H, s), 6.31 (1H, d,), 6.42 (1H, dd), 8.00 (1H, d).

41

Preparation of
4'-Methoxy-4-methyl-3-nitro-biphenyl

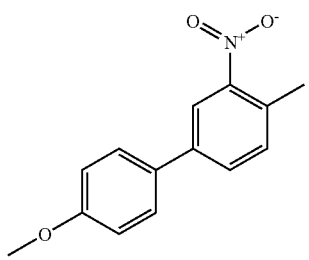

To a solution of 4-methoxyphenyl-boronic acid (500 mg, 3.29 mmol) in toluene (5.2 mL) and ethanol (1.3 mL), potassium carbonate (910 mg, 6.58 mmol), tetrakis(triphenylphosphine)-palladium (228.1 mg, 0.099 mmol) and 4-bromo-1-methyl-2-nitrobenzene (711 mg, 3.29 mmol) are added and stirred at 100° C. for 7 hours. The mixture is poured into water and extracted with ethyl acetate two times. The organic layer is washed with water and then brine, dried over magnesium sulfate, and evaporated in vacuo. The residue is purified with silica gel column chromatography (n-hexane:ethyl acetate=5:1) to afford the 4'-methoxy-4-methyl-3-nitro-biphenyl (630 mg, 79%) as a yellow solid.

$^1$H-NMR (400 MHz, CDCl$_3$, δ, ppm): 2.62 (s, 3H), 3.86 (s, 3H), 7.02-6.98 (m,2H), 7.37 (d, 1H), 7.54 (dd, 2H), 7.68 (dd, 1H), 8.18 (d, 1H). Rf (hexane:ethyl acetate=3:1): 0.40.

42

Preparation of 4-(2-Ethoxy-ethoxy)-1-(3-methoxy-4-nitro-phenyl)-piperidine

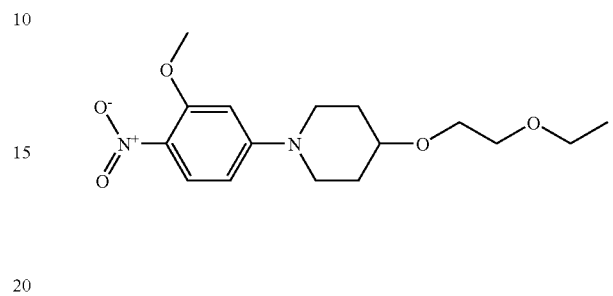

To a solution of 1-(3-Methoxy-4-nitro-phenyl)-piperidin-4-ol (300 mg, 1.2 mmol) in N,N-dimethylformamide (3.0 mL), sodium hydride (1.52 g, 3.8 mmol) is added. After stirring, 2-bromoethyl methyl ether (150 µl, 1.6 mmol) is added and the mixture is further stirred at 70° C. for 15 hours. After addition of saturated aqueous ammonium chloride, the mixture is poured into water and extracted twice with ethyl acetate. The organic layer is washed with brine, dried over sodium sulfate, and evaporated in vacuo. The residue is purified by silica gel column chromatography (n-hexane-ethyl acetate gradient) to afford 4-(2-Methoxy-ethoxy)-1-(3-methoxy-4-nitro-phenyl)-piperidine (111 mg, 29%) as a yellow oil.

$^1$H-NMR (400 MHz, CDCl$_3$, δ, ppm): 1.52(t, 3H), 1.95-2.00(m, 2H), 1.70-1.79(m, 2H), 3.23(ddd, 2H), 3.58-3.64(m, 2H), 3.65-3.68(m, 2H), 3.64-3.72(m, 2H), 3.95(s, 3H), 6.31 (d, 1H), 6.42(dd, 1H), 8.00(d, 1H). Rf 0.53 (n-hexane:AcOEt=1:1).

According the procedure described above using appropriate alkyl halides, the following compounds are prepared.

| Ex-No. | Rx | Identification |
|---|---|---|
| 42-1 | ![structure] | $^1$H-NMR(400 MHz, CDCl$_3$, δ, ppm): 2.04-2.21(m, 1H), 2.63(t, 2H), 2.68(t, 2H), 3.42(t, 4H), 3.87(t, 4H), 3.96(s, 3H), 6.33(d, 1H), 6.44(dd, 1H), 8.02(d, 1H). Rf 0.09(AcOEt). |

-continued

| Ex-No. | Rx | Identification |
|---|---|---|
| 42-2 | 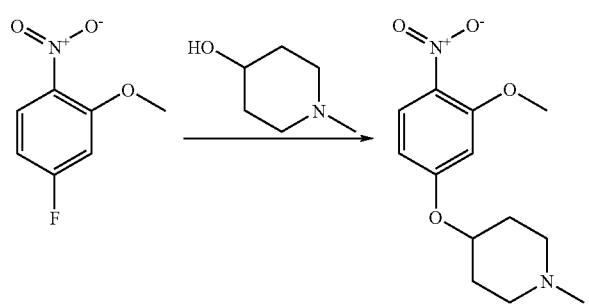 | $^1$H-NMR(400 MHz, CDCl$_3$, δ, ppm): 1.71-1.79(m, 2H), 1.95-2.02 (m, 2H), 3.22(ddd, 2H), 3.40(s, 3H), 3.55-3.57(m, 2H), 3.59-3.73(m, 3H), 3.65-3.67(m, 2H), 3.95(s, 3H), 6.31(d, 1H), 6.42(dd, 1H), 8.00(d, 1H). Rf 0.35(n-hexane:AcOEt = 1:1) |

Example: 43

2-Methoxy-4-(1-methyl-piperidin-4-yloxy)-phenylamine 4-(3-Methoxy-4-nitro-Phenoxy)-1-methyl-piperidine

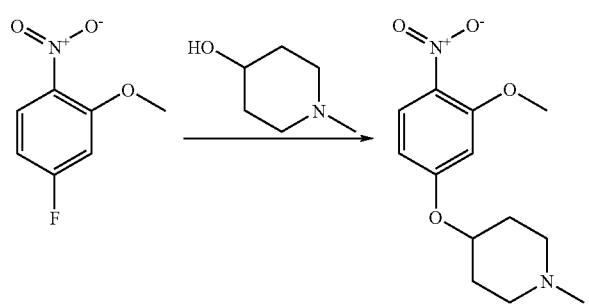

To a solution of 4-Fluoro-2-methoxy-1-nitro-benzene (10.3 g, 60 mmol) in toluene (50 mL) and 25% KOH aq. (50 mL), 4-hydroxy-1-methylpiperidine (13.8 g, 120 mmol) and tetra-n-butyl ammonium bromide (3.87 g, 12 mmol) are added at room temperature. The mixture is heated at 60° C. for 1 day. The reaction mixture is cooled to room temperature, poured into ice water and extracted twice with ethyl acetate. The organic layer is successively washed with dil.HCl and brine, dried over sodium sulfate, and evaporated in vacuo to afford the crude compound in quantitative yield (13.4 g).

Rf=0.22 (methanol:dichloromethane=1:4). $^1$H-NMR (400 MHz, CDCl$_3$, δ, ppm): 1.84-1.92(m, 2H), 2.0-2.1(m, 2H), 2.3-2.4 (m, 2H), 2.33 (s, 3H), 2.65-2.75(m, 2H), 3.94(s, 3H), 4.39-4.46(m, 1H), 6.49 (dd, 1H), 6.99 (d, 1H), 6.54 (d, 1H), 7.99 (d, 1H).

Example: 44

2-Methoxy-4-(2-morpholin-4-yl-ethoxy)-phenylamine

3-Methoxy-4-nitro-phenol

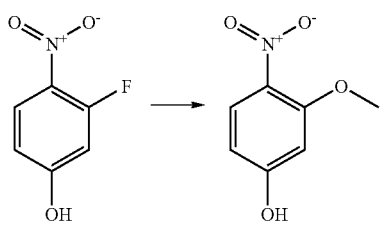

To a solution of 3-Fluoro-4-nitro-phenol (15.7 g, 100 mmol) in THF (300 mL), 30% KOMe in Methanol (49 mL, 210 mmol) is added at 0° C. The mixture is heated to gentle reflux for 18 hours.

4-[2-(3-Methoxy-4-nitro-phenoxy)-ethyl]-morpholine

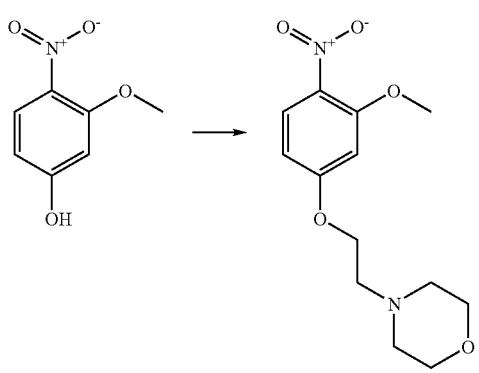

To a solution of 3-Methoxy-4-nitro-phenol (1.69 g, 10 mmol) in DMF (25 mL), 4-(2-Chloroethyl)morpholine hydrochloride (2.05 g, 11 mmol), K2CO3 (1.52 g, 11 mmol), KI (332 mg, 2 mmol) are added at room temperature. The mixture is heated to gentle reflux for 4 hours. The reaction mixture is cooled to room temperature and quenched with water. The resulting mixture is extracted twice with ethyl acetate and then the organic layer is successively washed with water and brine, dried over sodium sulfate, filtered and evaporated in vacuo to afford the crude compound in 90% yield (2.55 g).

Rf=0.11 (AcOEt only). $^1$H-NMR (400 MHz, CDCl$_3$), δ (ppm): 2.56-2.61(m, 4H), 2.83(t, The reaction mixture is cooled to room temperature and quenched slowly with 1NHCl aq at 0° C. The resulting mixture is extracted twice with ethyl acetate and then the organic layer is successively washed with brine, dried over sodium sulfate, filtered and evaporated in vacuo to afford the crude compound in 94% yield (15.9 g).

Rf=0.22 (methanol:dichloromethane=1:4). $^1$H-NMR (400 MHz, CDCl$_3$), δ (ppm): 3.95(s, 3H), 5.49(s, 1H), 6.44 (dd, 1H, J=8.8, 2.52 Hz), 6.54 (d, 1H, J=2.52 Hz), 7.96 (d, 1H J=8.6 Hz). 3.72-3.76(m, 4H), 3.94(s, 3H), 4.18(t, 2H), 6.51 (dd, 1H, J=9.08, 2.52 Hz), 6.56 (d, 1H, J=2.48 Hz), 8.00 (d, 1H J=9.08 Hz). 2H), Example: 45

2-Methoxy(2-morpholin-4-yl-ethoxy)-phenylamine

Acetic acid 4-methoxy-3-nitro-phenyl ester

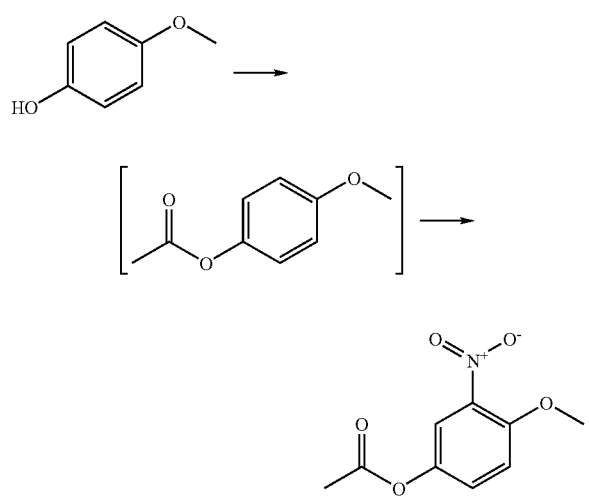

To a solution of 4-Methoxyphenol (12.4 g, 100 mmol) in AcOH (50 mL), Ac$_2$O (50 mL) is added at room temperature. The mixture is heated to gentle reflux for 1.5 hour. The reaction mixture is cooled to room temperature and c.HNO$_3$ (d=1.38, 10 mL) is added slowly at 0° C. The mixture is heated to 55° C. for 1.5 h. The reaction mixture is cooled to room temperature and quenched with water at 0° C. The resulting solid is filtered on Buchner funnel to afford the crude compound in 76% yield (16.0 g).

Rf=0.59 (AcOEt:n-Hexane=3:7). $^1$H-NMR (400 MHz, CDCl$_3$), δ (ppm): 2.31(s, 3H), 3.96(s, 3H), 7.08 (d, 1H, J=9.04 Hz), 7.31 (dd, 1H, J=9.04, 3.04 Hz), 7.96 (d, 1H J=3.04 Hz).

4-Methoxy-3-nitro-phenol

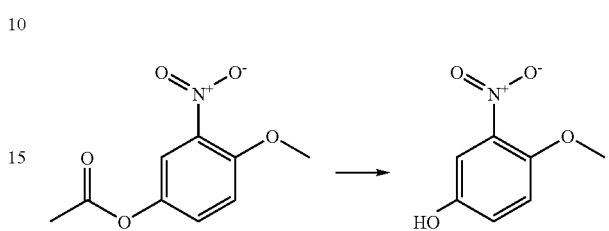

To a solution of Acetic acid 4-methoxy-3-nitro-phenyl ester (1.06 g, 5 mmol) in EtOH (20 mL), 1N NaOH aq (5.5 mL) is added at 0° C. The mixture is stirred at room temperature for 2 hours. The reaction mixture is quenched with AcOH and extracted twice with ethyl acetate. The organic layer is successively washed with water and brine, dried over sodium sulfate, filtered and evaporated in vacuo to afford the crude compound in quantitative yield (840 mg).

Rf=0.59 (AcOEt:n-Hexane=3:7). $^1$H-NMR (400 MHz, CDCl$_3$), δ (ppm): 3.91 (s, 3H), 6.99 (d, 1H, J=9.04 Hz), 7.17 (dd, 1H, J=9.04, 3.00 Hz), 7.38 (d, 1H J=3.04 Hz).

4-[2-(4-Methoxy-3-nitro-phenoxy)-ethyl]-morpholine

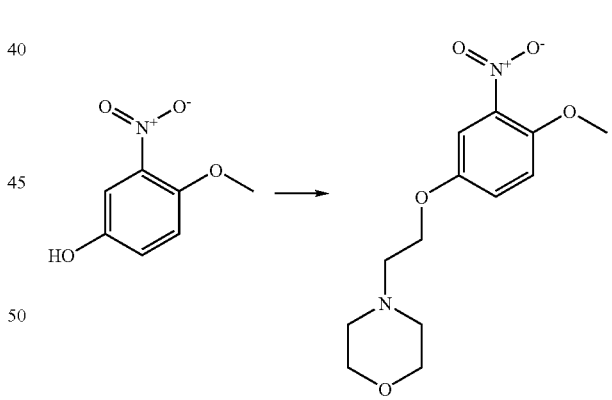

To a solution of 4-Methoxy-3-nitro-phenol (1.01 g, 6 mmol) in DMF (15 mL) 4-(2-Chloroethyl)morpholine hydrochloride (1.34 g, 7.2 mmol), K2CO3 (2.49 g, 18 mmol), KI (2.99 g, 18 mmol) are added at room temperature. The mixture is heated to 80° C. for 4 hours. The reaction mixture is cooled to room temperature and quenched with saturated NH4Cl solution in water. The resulting mixture is extracted twice with ethyl acetate and then the organic layer is successively washed with water and brine, dried over sodium sulfate, filtered and evaporated in vacuo to afford the crude compound in quantitative yield (1.70 g). Rf=0.14 (AcOEt only). $^1$H-NMR (400 MHz, DMSO, δ, ppm): 2.36-2.51 (m, 4H), 2.67 (t, J=5.5, 2H), 3.52-3.60 (m, 4H), 3.86 (s, 3H), 4.11 (t, J=6.0, 2H), 7.25-7.29 (m, 2H), 7.46-7.49 (m, 1H).

Preparation of 2-Methoxy-4-(1-methyl-piperidin-4-yloxy)-phenylamine

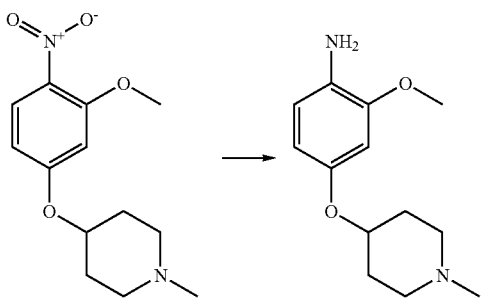

To a solution of 4-(3-Methoxy-4-nitro-phenoxy)-1-methyl-piperidine (3.0 g, 11.3 mmol) in ethanol (50 mL), 5% palladium on carbon (300 mg) is added under a nitrogen atmosphere. The reaction vessel is fitted with a balloon adapter and charged with hydrogen and evacuated three times until the reaction is under a hydrogen atmosphere. The reaction is allowed to stir overnight. The reaction mixture is filtered through a pad of Celite and washed with methanol. The filtrate is concentrated in vacuo to afford 2-Methoxy-4-(1-methyl-piperidin-4-yloxy)-phenylamine in quantitative yield (2.7 g).

Rf=0.41 (methanol:dichloromethane=1:1). $^1$H-NMR (400 MHz, CDCl$_3$), δ (ppm): 1.75-1.86(m, 2H), 1.92-2.05(m, 2H), 2.2-2.32 (m, 2H), 2.30 (s, 3H), 3.4-3.7(brs, 2H), 3.82(s, 3H), 4.14.2(m, 1H), 6.37(dd, 1H), 6.46 (d, 1H), 6.61 (d, 1H).

By repeating the procedures described above using appropriate starting materials and conditions the following compounds are obtained.

| Ex-No. | Rx | Identification |
|---|---|---|
| 46-1 | (4-amino-3-methoxyphenyl-1,2,4-triazole structure) | $^1$H-NMR(400 MHz, CDCl$_3$, δ, ppm): 3.92(s, 3H), 3.97(br,H), 6.75(d, 1H), 7.00(dd, 1H), 7.12(d, 1H), 8.06(s, 1H), 8.41(s, 1H). Rf 0.32(AcOEt) |
| 46-2 | [1-(4-Amino-3-methoxy-phenyl)-pyrrolidin-3-yl]-ethyl-amine | $^1$H-NMR(400 MHz, CDCl$_3$, δ, ppm): 1.13(t, 3H), 1.77-1.86(m, 1H), 2.19-2.27(m, 1H), 2.67-2.75(m, 2H), 3.01-3.06(m, 1H), 3.20-3.26(m, 1H), 3.33-3.38(m, 1H), 3.42-3.49(m, 2H), 3.84(s, 3H), 6.04-6.07(m, 1H), 6.14-6.15(m, 1H), 6.64-6.66(m, 1H). Rf 0.2(AcOEt only) |
| 46-3 | 2-Methoxy-4-(4-methyl-piperazin-1-l)-phenylamine | $^1$H-NMR(400 MHz, CDCl$_3$, δ, ppm): 2.44(s, 3H), 2.70-2.73(m, 4H), 3.13-3.17(m, 4H), 3.48(brs, 2H), 3.84(s, 3H), 6.41(dd, 1H, J=8.5, 2.52 Hz), 6.51(d, 1H, J=2.52 Hz), 6.64(d, 1H, J=8.5 Hz). Rf 0.2(AcOEt only). |

-continued

| Ex-No. | Rx | Identification |
| --- | --- | --- |
| 46-4 | 2-Methoxy-4-(1-methyl-piperidin-3-lmethoxy)-phenylamine | ¹H-NMR(400 MHz, CDCl$_3$, δ, ppm): 1.01-1.12(m, 1H), 1.57-2.13 (m, 6H), 2.26(s, 3H), 2.74-2.77(m, 1H), 2.93-2.96(m, 1H), 3.47(bs, 2H), 3.70-3.80(m, 2H), 3.82(s, 3H), 6.31-6.34(m, 1H), 6.44-6.45(m, 1H), 6.60-6.62(m, 1H). Rf 0.2(AcOEt only) |
| 46-5 | | ¹H-NMR(400 MHz, CDCl$_3$) 1.80-1.67(2H, m), 1.99-1.90 (2H, m), 2.42-2.27(1H, m), 2.56-2.43(4H, m), 2.68-2.58(2H, m), 2.76-2.58(4H, m), 3.57-3.48(2H, m), 3.83(3H. s), 6.41 (1H, dd), 6.52(1H, d), 6.63(1H, d). R$_f$(hexane/acetone 1:1) 0.44. |
| 46-6 | | ¹H-NMR(400 MHz, CDCl$_3$, δ, ppm): 1.83-1.95(m, 2H), 1.97-2.08 (m, 2H), 2.20-2.31(m, 1H), 2.60-2.72(m, 2H), 3.46-3.53 (m, 2H), 3.84(s, 3H), 5.42-5.60(m, 1H), 6.43(dd, 1H), 6.53 (d, 1H), 6.64(d, 1H). |
| 46-7 | | ¹H-NMR(400 MHz, CDCl$_3$, δ, ppm): 2.13(s, 3H), 3.01-3.05 (m, 4H), 3.59(t, 2H), 3.75(t, 2H), 3.81(s, 3H), 6.30(dd, 1H), 6.39(bs, 1H), 6.71(d, 1H). |

| Ex-No. | Rx | Identification |
|---|---|---|
| 46-8 | | ¹H-NMR(400 MHz, CDCl₃, δ, ppm): 1.84-1.97(m, 2H), 1.98-2.07 (m, 2H), 2.20-2.32(m, 1H), 2.61-2.72(m, 2H), 3.47-3.55 (m, 2H), 3.95(s, 3H), 5.20-5.38(m, 1H), 5.40-5.56(m, 2H), 6.43(d, 1H), 6.53(bs, 1H), 6.64(d, 1H). |
| 46-9 | | ¹H-NMR(400 MHz, CDCl₃, δ, ppm): 2.59-2.67(m, 2H), 2.77-2.68 (m, 4H), 3.08-3.15(m, 4H), 3.49-3.56(m, 1H), 3.67-3.77 (m, 2H), 3.98(s, 3H), 6.41-6.43(m, 1H), 6.52(bs, 1H), 6.65 (d,1H). |
| 46-10 | | ¹H-NMR(400 MHz, CDCl₃, δ, ppm): 1.72-1.96(m, 2H), 1.98-2.10 (m, 2H), 2.63(s, 3H), 2.73-2.84(m, 2H), 3.40(s, 3H), 3.34-3.42(m, 2H), 3.44-3.49(m, 1H), 3.55-3.57(m, 2H), 3.64-3.66 (m, 2H), 3.83(s, 3H), 6.41-6.43(m, 1H), 6.53(bs, 1H), 6.63(d, 1H). |

| Ex-No. | Rx | Identification |
|---|---|---|
| 46-11 | (structure) | ¹H-NMR(400 MHz, CDCl₃, δ, ppm): 1.22(t, 3H), 1.72-1.84(m, 2H), 2.00-2.10(m, 2H), 2.72-2.82(m, 2H), 3.33-3.38(m, 2H), 3.43-3.49(m, 1H), 3.55(q, 2H), 3.58-3.61(m, 2H), 3.64-3.66 (m, 2H), 3.83(s, 3H), 6.41-6.43(m, 1H), 6.53(bs, 1H), 6.63 (d, 1H). |
| 46-12 | (structure) | ¹H-NMR(400 MHz, CDCl₃, δ, ppm): 2.20(s, 3H), 3.84(s, 3H), 6.87(d, 1H), 6.89(dd, 1H), 6.95(d, 2H), 7.09(d, 1H), 7.48(d, 2H). Rf (n-hexane:ethyl acetate = 1:1):0.50. |
| 46-13 | (structure) | ¹H-NMR(400 MHz, CDCl₃, δ, ppm): 1.49-1.59(m, 3H), 1.70-1.95 (m, 6H), 2.00-2.20(m, 2H), 2.60-2.90(m, 7H), 3.50-3.60 (m, 3H), 3.83(s, 3H), 3.85-3.91(m, 1H), 6.41(dd, 1H, J=8.0, 2.5 Hz), 6.50(d, 1H, J=2.5 Hz), 6.63(d, 1H, J=8.0 Hz) |
| 46-14 | (structure) | ¹H-NMR(400 MHz, DMSO-d6, δ, ppm): 1.87-1.79(m, 1H), 2.22(ddd, 1H), 2.48(s, 3H), 3.05(dd, 1H), 3.28-3.21(m, 1H), 3.40-3.32(m, 2H), 3.45(dd, 1H), 3.84(s, 3H), 6.06(dd, 1H), 6.15(d, 1H)), 6.66(d, 1H) |

-continued
| Ex-No. | Rx | Identification |
|---|---|---|
| 46-15 | 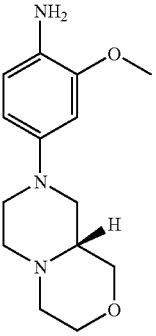 | ¹H-NMR(400 MHz, CDCl₃, δ, ppm): 2.35-2.73(m, 4H), 2.68-2.75 (m, 1H), 2.82-2.93(m, 2H), 3.14-3.19(m, 1H), 3.29-3.40 (m, 2H), 3.50-3.60(bs, 2H), 3.69-3.78(m, 2H), 3.84(s, 3H), 3.85-3.91(m, 1H), 6.40(dd, 1H, J=8.0, 2.5 Hz), 6.50 (d, 1H, J=2.5 Hz), 6.64(d, 1H, J=8.0 Hz) |
| 46-16 | 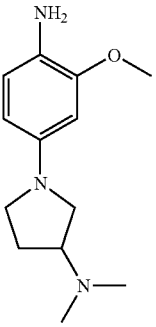 | ¹H-NMR(400 MHz, DMSO-d6, δ, ppm): 1.95-1.85(m, 1H), 2.22-2.14(m, 1H), 2.31(s, 3H), 2.89-2.79(m, 1H), 3.10(t, 1H), 3.39-3.25(m, 3H), 3.42(t, 1H), 3.85(s, 3H), 6.05(dd, 1H), 6.14(d, 1H), 6.67(d, H) |
| 46-17 | 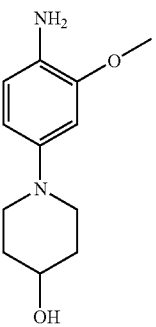 | ¹H-NMR(400 MHz, CDCl₃, δ, ppm): 1.68-1.81(m, 2H), 1.97-2.09 (m, 2H), 2.74-2.87(m, 2H), 3.31-3.41(m, 2H), 3.77-3.88 (m, 1H), 3.84(s, 3H), 6.40-6.48(m, 1H), 6.65(bs, 1H), 6.64 (d, 1H). |
| 46-18 | 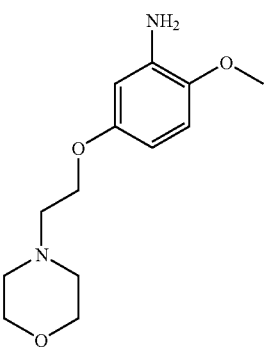 | ¹H-NMR(400 MHz, CDCl₃), δ(ppm): 2.55-2.61(m, 4H), 2.80(t, 2H), 3.72-3.77(m, 4H), 3.81(s, 3H), 4.05(t, 2H), 6.24(dd, 1H, J=8.56, 2.52 Hz), 6.34(d, 1H, J=2.52 Hz), 6.68(d, 1H J=8.56 Hz). Rf = 0.31(methanol:dichloromethane = 1:9). |

| Ex-No. | Rx | Identification |
|---|---|---|
| 46-19 | (structure: 4-(2-morpholinoethoxy)-2-methoxyaniline) | ¹H-NMR(400 MHz, CDCl₃), δ(ppm): 2.55-2.61(m, 4H), 2.78(t, 2H), 3.72-3.77(m, 4H), 3.82(s, 3H), 4.05(t, 2H), 6.35(dd, 1H, J=8.56, 2.52 Hz), 6.47(d, 1H, J=2.52 Hz), 6.63(d, 1H J=8.56 Hz). Rf = 0.61(methanol:dichloromethane = 1:4). |
| 46-20 | (structure: 4-methoxybenzene-1,3-diamine) | ¹H-NMR(DMSO), δ(ppm): 3.84(s, 3H), 6.95-7.00(m, 1H), 7.08-7.12(m, 2H). |
| 46-21 | (structure: 2-methoxy-4-(4-(methoxymethyl)piperidin-1-yl)aniline) | ¹H-NMR(400 MHz, CDCl₃): 1.47-1.34(m, 2H), 1.75-1.63(m, 1H), 1.86-1.79(m, 2H), 2.64-2.58(m, 2H), 3.28(d, 2H), 3.61(d, 3H), 3.87(s, 3H), 3.36(s, 1H), 3.49-3.45(m, 2H), 3.84(s, 3H), 6.43(dd, 1H), 6.53(d, 1H) 6.64(d, 1H) |
| 46-22 | (structure: 4-(4-ethylpiperazin-1-yl)-2-methoxyaniline) | ¹H-NMR(400 MHz, CDCl₃): 1.13(t, 3H), 2.49(dd, 2H), 2.68-2.59 (m, 4H), 3.10(t, 4H), 3.84(s, 3H), 6.43(dd, 1H), 6.53(d, 1H) 6.65(d, 1H) |

| Ex-No. | Rx | Identification |
|---|---|---|
| 46-23 | (structure: 4-amino-3-methoxyphenyl-piperidin-4-yl-morpholine) | $^1$H-NMR(400 MHz, CDCl$_3$): 1.78-1.68(m, 2H), 1.99-1.89(m, 2H), 2.36-2.20(m, 1H), 2.67-2.50(m, 6H), 3.56-3.48(m, 2H), 3.79-3.69(m, 4H), 3.84(s, 3H), 6.42(dd, 1H), 6.52(d, 1H) 6.64(d, 1H) |
| 46-24 | (structure: 4-amino-3-methoxyphenyl-4-isopropylpiperazine) | $^1$H-NMR(400 MHz, CDCl$_3$): 1.08(s, 3H), 1.10(s, 3H), 2.69(t, 4H), 2.72-2.68(m, 1H), 3.08(t, 4H), 3.83(s, 3H), 6.42(dd, 1H), 6.53(d, 1H) 6.64(d, 1H) |
| 46-25 | (structure: 4-amino-3-methoxyphenyl-piperidine-4-carboxamide) | $^1$H-NMR(400 MHz, CDCl$_3$): 1.96-1.84(m, 2H), 2.07-1.99(m, 2H), 2.32-2.28(m, 1H), 2.70-2.60(m, 2H), 3.54-3.47(m, 2H), 3.84(s, 3H), 5.35-5.24(m, 1H), 5.50-5.45(m, 1H), 6.42(dd, 1H), 6.52(d, 1H) 6.64(d, 1H) |
| 46-26 | (structure: 4-amino-3-methoxyphenyl-3-methoxypyrrolidine) | $^1$H-NMR(400 MHz, CDCl$_3$): 2.18-2.03(m, 2H), 3.28-3.19(m, 2H), 3.39-3.31(m, 1H), 3.36(s, 3H), 3.49-3.42(m, 1H), 3.85 (s, 3H), 6.07(dd, 1H), 6.16(d, 1H), 6.66(d, 1H) |

| Ex-No. | Rx | Identification |
|---|---|---|
| 46-27 | (4-amino-3-methoxyphenyl)-piperidine with N-methyl-N-boc substituent | $^1$H-NMR(400 MHz, CDCl$_3$): 1.48(s, 9H), 1.88-1.71(m, 2H), 1.97-1.82(m, 2H), 2.78(s, 3H), 2.84-2.64(m, 2H), 3.55-3.48 (m, 2H), 3.95(s, 3H), 3.84(s, 3H), 6.43(d, 1H), 6.52(bs, 1H), 6.64(d, 1H) |
| 46-28 | 4-(4-amino-3-methoxyphenyl)-1-methylpiperazin-2-one | $^1$H-NMR(400 MHz, CDCl$_3$): 3.02(s, 3H), 3.33(dd, 2H), 3.44(t, 2H), 3.74(s, 2H), 3.83(s, 3H), 6.38(dd, 1H), 6.47(d 1H), 6.66(d, 1H) |
| 46-29 | 1-(4-(4-(4-amino-3-methoxyphenyl)piperidin-1-yl)piperazin-1-yl)ethanone | $^1$H-NMR(400 MHz, CDCl$_3$): 1.78-1.38(m, 2H), 1.98-1.89(m, 2H), 2.30(s, 3H), 2.39-2.31(m, 1H), 2.55-2.42(m, 4H), 2.71-2.56 (m, 6H), 3.35-3.49(m, 2H), 3.83(s, 3H), 6.41(dd, 1H), 6.52(d, 1H) 6.63(d, 1H) |
| 46-30 | 2,4,5-trimethoxyaniline | $^1$H-NMR(400 MHz, CDCl$_3$): 3.80(s, 3H), 3.82(s, 3H), 3.82(s, 3H), 6.40(s, 1H), 6.54(s, 1H) |
| 46-31 | 2,3-dihydrobenzofuran-7-amine | $^1$H-NMR(400 MHz, CDCl$_3$): 3.20(t, 2H), 4.57(t, 2H), 6.55(dd, 1H), 6.70-6.65(m, 1H), 6.68(d, 1H). Rf 040(AcOEt) |

-continued

| Ex-No. | Rx | Identification |
| --- | --- | --- |
| 46-32 | [structure: 2,5-dimethoxy-4-morpholinoaniline] | ¹H-NMR(400 MHz, CDCl₃): 2.98(t, 4H), 3.62(bs, 2H), 3.79(s, 3H), 3.81(s, 3H), 3.87(t, 4H), 6.36(s, 1H), 6.53(s, 1H) |
| 46-33 | [structure: 2,5-dimethoxy-4-(4-methylpiperazin-1-yl)aniline] | ¹H-NMR(400 MHz, CDCl₃): 2.37(s, 3H), 2.61(t, 4H), 3.27(t, 4H), 3.88(s, 3H), 3.95(s, 3H), 6.48(s, 1H), 7.56(s, 1H) |
| 46-34 | [structure: 2-propoxy-4-(4-methylpiperazin-1-yl)aniline] | ¹H-NMR(400 MHz, CDCl₃): 1.05(t, 3H), 1.83(ddd, 2H), 2.35(s, 3H), 2.58(t, 4H), 3.07(t, 4H), 3.94(t, 2H), 6.41(dd, 1H), 6.51(d, 1H), 6.65(d, 1H) |
| 46-35 | [structure: 2-methoxy-4-(4-acetyl-3,5-dimethylpiperazin-1-yl)aniline] | ¹H-NMR(400 MHz, CDCl₃): 1.28(s, 3H), 1.30(s, 3H), 2.04(s, 2H), 2.17(s, 3H), 2.84–2.72(m, 2H), 3.20(d, 2H), 3.86(s, 3H), 6.41(d, 1H), 6.46(dd, 1H), 6.66(d, 1H). |

| Ex-No. | Rx | Identification |
|---|---|---|
| 46-36 | 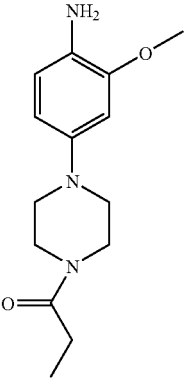 | $^1$H-NMR(400 MHz, CDCl$_3$): 1.18(t, 3H), 2.39(dd, 2H), 3.07-2.98 (m, 4H), 3.61(t, 2H), 3.78(t, 2H), 3.88(s, 3H), 6.41(dd, 1H), 6.51(d, 1H), 6.65(d, 1H) |
| 46-37 | 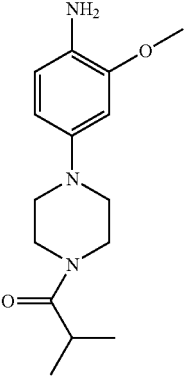 | $^1$H-NMR(400 MHz, CDCl$_3$): 1.15(s, 3H), 1.16(s, 3H), 2.83(sept, 1H), 3.07-2.98(m, 4H), 3.73-3.64(m, 2H), 3.83-3.76(m, 2H), 3.84(s, 3H), 6.41(dd, 1H), 6.51(d, 1H), 6.65(d, 1H) |
| 46-38 | 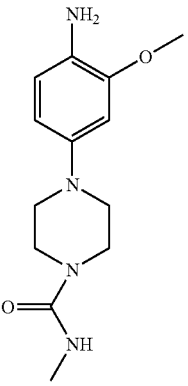 | $^1$H-NMR(400 MHz, CDCl$_3$): 2.84(d, 3H), 3.02(t, 4H), 3.51(t, 4H), 3.84(s, 3H), 4.48-4.38(m, 1H), 6.41(dd, 1H), 6.51(d, 1H), 6.65(d, 1H) |
| 46-39 | 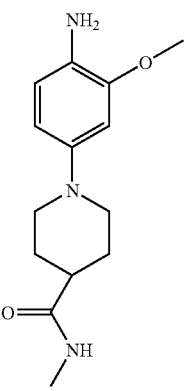 | $^1$H-NMR(400 MHz, CDCl$_3$): 1.99-1.81(m, 2H), 2.23-2.12(m, 2H), 2.69-2.58(m, 2H), 2.84(d, 3H), 3.54-3.45(m, 2H), 3.84(s, 3H), 5.55-5.45(m, 1H), 6.42(dd, 1H), 6.52(d, 1H), 6.64(d, 1H) |

-continued
| Ex-No. | Rx | Identification |
|---|---|---|
| 46-40 | 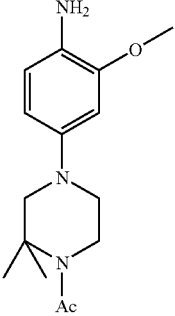 | $^1$H-NMR(400 MHz, CDCl$_3$): 1.53(s, 6H), 2.11(s, 3H), 3.05(s, 2H), 3.28(t, 2H), 3.64(t, 2H), 3.86(s, 3H), 6.26(dd, 1H), 6.33(d, 1H), 6.67(d, 1H) |
| 46-41 | 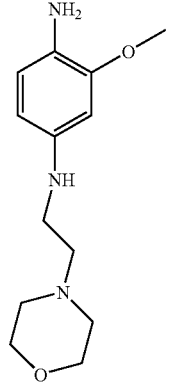 | $^1$H-NMR(400 MHz, CDCl$_3$): 2.55-2.41(m, 4H), 2.63(t, 2H), 3.13(t, 2H), 3.77-3.68(m, 4H), 3.83(s, 3H), 6.15(dd, 1H), 6.25(d, 1H), 6.62(d, 1H) |
| 46-42 | 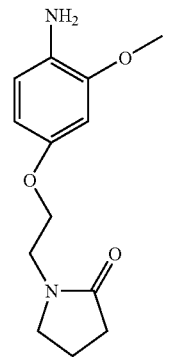 | $^1$H-NMR(400 MHz, CDCl$_3$): 2.05-2.00(m, 2H), 2.39(t, 2H), 3.57(t, 2H), 3.64(t, 2H), 3.83(s, 3H), 4.04(t, 2H), 6.32(dd, 1H), 6.44(d, 1H), 6.63(d, 1H) |
| 46-43 | 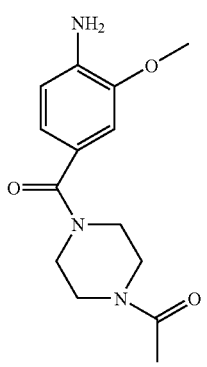 | $^1$H-NMR(400 MHz, CDCl$_3$): 2.13(s, 3H), 3.53-3.46(m, 2H), 3.65-3.55(m, 4H), 3.71-3.66(m, 2H), 3.88(s, 3H), 6.67(d, 1H), 6.87(dd, 1H), 6.95(d, 1H) |

-continued
| Ex-No. | Rx | Identification |
|---|---|---|
| 46-44 | 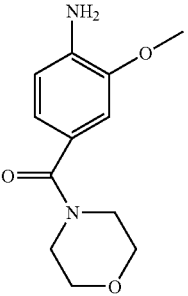 | ¹H-NMR(400 MHz, CDCl₃): 3.73-3.61(m, 8H), 3.87(s, 3H), 6.65(d, 1H), 6.86(dd, 1H), 6.95(d, 1H) |
| 46-46 | 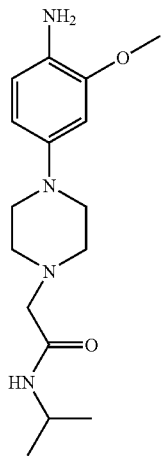 | ¹H-NMR(400 MHz, CDCl₃): 1.17(s, 3H), 1.19(s, 3H), 2.69(t, 4H), 3.04(s, 2H), 3.08(t, 4H), 4.15-4.07(m, 1H), 6.41(dd, 1H), 6.51(d, 1H), 6.65(d, 1H), 7.01-6.94(m 1H) |
| 46-47 | 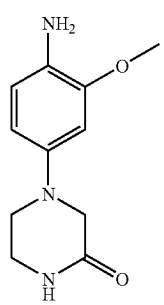 | ¹H-NMR(400 MHz, CDCl₃): 3.35-3.28(m, 2H), 3.53-3.46(m, 2H), 3.76(s, 2H), 3.84(s, 3H), 5.92-5.83(m, 1H), 6.40(dd, 1H), 6.48(d, 1H), 6.67(d, 1H) |
| 46-48 | 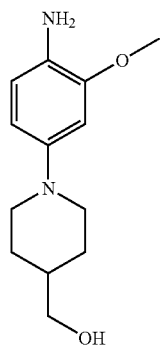 | ¹H-NMR(400 MHz, CDCl₃): 2.09-2.00(m, 2H), 2.25-2.15(m, 2H), 3.29-3.20(m, 2H), 3.51-3.40(m, 4H), 3.85(s, 3H), 4.62-4.55(m, 1H), 6.08(d, 1H), 6.18(d, 1H), 6.67(d, 1H) |

-continued

| Ex-No. | Rx | Identification |
|---|---|---|
| 46-49 | (4-amino-3-methoxyphenyl)-pyrrolidin-3-ol structure | ¹H-NMR(400 MHz, CDCl₃): 1.52-1.40(m, 2H), 1.90-1.84(m, 2H), 2.68-2.59(m, 2H), 3.51-3.45(m, 2H), 3.84(s, 3H), 6.44(dd, 1H), 6.54(d, 1H), 6.64(d, 1H) |
| 46-50 | 2-methyl-N1,N1-dimethyl-benzene-1,3-diamine structure | ¹H-NMR(400 MHz, CDCl₃): 2.14(s, 3H), 2.66(s, 6H), 6.44(d, 1H), 6.54(d, 1H), 6.98(t, 1H). |
| 46-51 | 2-methyl-5-(pyridin-4-yl)aniline structure | ¹H-NMR(400 MHz, CDCl₃): 2.63(s, 3H), 7.49-7.45(m, 1H), 7.74-7.62(m, 2H), 7.76(dd, 1H), 8.24(d, 1H), 8.77-8.64(m, 2H). |
| 46-52 | 4-methoxy-5-(4-methoxyphenyl)aniline structure | ¹H-NMR(400 MHz, CDCl₃): 3.84(s, 3H), 3.88(s, 3H), 6.78(d, 1H), 6.83(d, 1H), 7.00-6.89(m, 3H), 7.45(d, 1H). |
| 46-53 | 2-ethoxy-5-morpholinoaniline structure | ¹H-NMR(400 MHz, CDCl₃): 1.40(t, 3H), 3.03(t, 4H), 3.84(t, 4H), 4.00(q, 2H), 6.27(dd, 1H), 6.38(d, 1H), 6.71(dd, 1H), |
| 46-54 | 2-ethoxy-4-morpholinoaniline structure | ¹H-NMR(400 MHz, CDCl₃): 1.26(t, 3H), 3.02(t, 4H), 3.85(t, 4H), 4.05(q, 2H), 6.40(dd, 1H), 6.49(d, 1H), 6.66(d, 1H), |

| Ex-No. | Rx | Identification |
|---|---|---|
| 46-55 | (2-amino-4-methoxyphenyl 2-methoxyethyl ether) | ¹H-NMR(400 MHz, CDCl₃): 3.44(s, 3H), 3.73(s, 3H), 3.74-3.68 (m, 2H), 3.95-3.85(m, 2H), 4.10-4.05(m, 2H), 6.21(dd, 1H), 6.32(d, 1H), 6.75(d, 1H). |
| 46-56 | (2-amino-4-methoxyphenoxy ethanol) | ¹H-NMR(400 MHz, CDCl₃): 2.35-2.26(m, 1H), 3.74(s, 3H), 3.93-3.86(m, 2H), 4.09-4.07(m, 2H), 6.25(dd, 1H), 6.34(d, 1H), 6.76(d, 1H). |
| 46-57 | (2-ethoxy-5-methoxyaniline) | ¹H-NMR(400 MHz, CDCl₃): 1.40(t, 3H), 3.71(s, 3H), 4.00(q, 2H), 6.22(dd, 1H), 6.33(d, 1H), 6.69(d, 1H). |
| 46-58 | (2-isopropoxy-5-methoxyaniline) | ¹H-NMR(400 MHz, CDCl₃): 1.32(d, 6H), 3.73(s, 3H), 3.85-3.71 (m, 2H), 4.37(sept, 1H), 6.22(dd, 1H), 6.32(d, 1H), 6.72(d, 1H). |
| 46-59 | (5-methoxy-2-propoxyaniline) | ¹H-NMR(400 MHz, CDCl₃): 1.04(t, 3H), 1.80(ddd, 2H), 3.72 (s, 3H), 3.85-3.75(m, 2H), 3.90(t, 2H), 6.22(dd, 1H), 6.33(d, 1H), 6.69(d, 1H). |
| 46-60 | (N,N-dimethyl-4-methoxybenzene-1,3-diamine) | ¹H-NMR(400 MHz, CDCl₃): 2.94(s, 6H), 3.89(s, 3H), 6.16(dd, 1H), 6.25(d, 1H), 6.72(d, 1H). |
| 46-61 | (2-methoxy-5-(pyridin-4-yl)aniline) | ¹H-NMR(400 MHz, CDCl₃): 3.91(s, 3H), 6.87(d, 1H), 7.02(dd, 1H), 7.05(d, 1H), 7.44(dd, 2H), 8.59(dd, 2H). |
| 46-62 | (2-methoxy-5-(pyridin-3-yl)aniline) | ¹H-NMR(400 MHz, CDCl₃): 3.91(s, 3H), 6.88(d, 1H), 6.96-6.93 (m, 1H), 7.31(ddd, 1H), 7.83-7.80(m, 1H), 8.51(dd, 1H), 8.78(dd, 1H). |

| Ex-No. | Rx | Identification |
|---|---|---|
| 46-63 | | $^1$H-NMR(400 MHz, CDCl$_3$): 3.91(s, 3H), 6.87(dd, 1H), 7.16(ddd, 1H), 7.34(dd, 1H), 7.43(d, 1H), 7.72-7.64(m, 2H), 8.63-8.61(m, 1H). |
| 46-64 | | mp 148.6° C.; $^1$H-NMR(500 MHz, CDCl$_3$)δ(ppm): 1.63(m; 2H), 1.99(m; 2H), 2.27(m; 1H), 2.60(m; 6H), 3.52(m; 2H), 3.71 (m; 4H), 3.78(s; 3H), 6.36(dd; 1H); 6.52(d; 1H), 6.73(d; 1H). |

Preparation of 4-(3-amino-4-methylbenzoyl)-piperazine-1-carboxylic acid tert-butyl ester

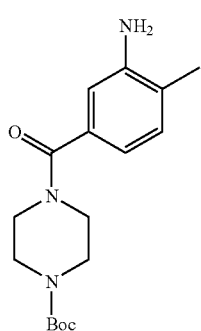

To a solution of 4-methyl-3-nitro-benzoic acid (300 mg, 2.76 mmol), N-butoxycarbonyl-piperazine (340 mg, 1.83 mmol) in DMF (3.0 mL), triethylamine (300 μL, 3.59 mmol), TBTU (800 mg, 2.49 mmol) and HOAt (270.5 mg, 1.99 mmol) are added and stirred at room temperature for 24 hours. The mixture is poured into water and extracted twice with ethyl acetate. The organic layer is washed with water and then brine, dried over magnesium sulfate, and evaporated in vacuo. The residue is purified with silica gel column chromatography (n-hexane:ethyl acetate=5:1) to afford 4-(4-methyl-3-nitrobenzoyl)-piperazine-1-carboxylic acid tert-butyl ester as a colorless solid.

$^1$H-NMR (δ, ppm): 1.47 (s,9H), 2.64 (s, 3H), 3.88-3.28 (m, 8H), 7.42 (d, 1H), 7.56 (dd, 1H), 8.03 (d, 1H). Rf (hexane:ethyl acetate=10:1): 0.13.

The title compound is obtained by reduction with hydrogen over 10% palladium on charcoal in methanol solution.

Preparation of 4-(3-amino-4-methylphenyl)-morpholine

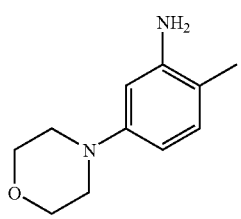

To a suspension of 4-bromo-1-methyl-2-nitrobenzene (225 mg, 1.04 mmol), morpholine (125 μL, 1.25 mmol), and cesium carbonate (474.4 mg, 1.46 mmol) in toluene, palladium diacetate (31.2 mg, 0.139 mmol) and 2-(di-t-butylphosphino)biphenyl (125 mg, 0.403 mmol) are added and stirred at 100° C. for 5 hours. After cooling, the mixture is filtered to remove insoluble material. The filtrate is poured into water and extracted with ethyl acetate twice. The organic layer is washed with water and then brine, dried over magnesium sulfate, and evaporated in vacuo. The residue is purified with silica gel column chromatography (n-hexane:ethyl acetate=5:1) to afford 4-(4-methyl-3-nitrophenyl)-morpholine as a yellow solid.

$^1$H-NMR (δ, ppm): 2.50 (s, 3H), 3.19-3.17 (m, 4H), 3.88-3.86 (m, 4H), 7.04 (dd, 1H), 7.21 (d, 1H), 7.47 (d, 1H). Rf (hexane:ethyl acetate=5:1): 0.20.

The title compound is obtained by reduction with hydrogen over 10% palladium on charcoal in methanol solution.

Preparation of 2-[5-chloro-2-(2-methoxy-4-morpholin-4-yl-phenylamino)-pyrimidin-4-ylamino]-benzoic acid

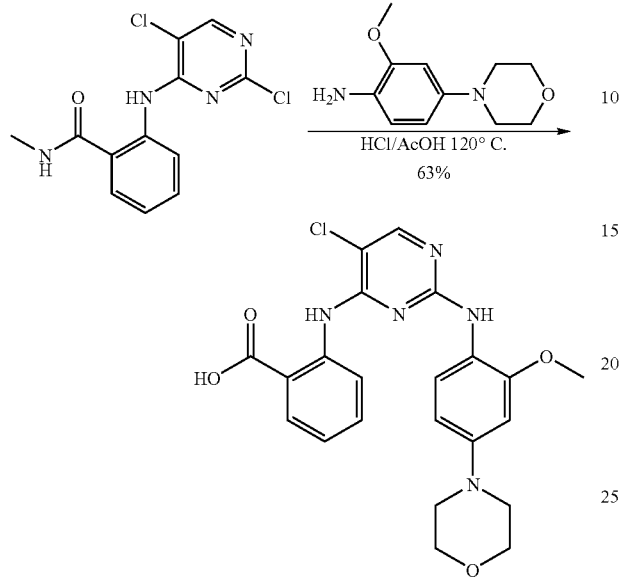

To a solution of 1.0 g (3.37 mmol) of 2-(2,5-dichloro-pyrimidin-4-ylamino)-N-methyl-benzamide in 15 mL of acetic acid are added 2-methoxy-4-morpholinoaniline dihydrochloride (1.9 g, 6.73 mmol) and 6.0 mL of 1N ethanolic solution of hydrogen chloride (6.0 mmol). After the reaction mixture is stirred at 120° C. for 16 hours and cooled to mom temperature, aqueous NaHCO₃ solution is added to adjust the acidity between pH 5 and pH 6. The resulting precipitate is collected by a filtration and dried under reduced pressure to give 2-[5-chloro-2-(2-methoxy-4-morpholin-4-yl-phenylamino)-pyrimidin-4-ylamino]-benzoic acid (970 mg, 2.12 mmol, 63%) as ivory solid.

NMR (400 MHz, DMSO-d6, δ): 3.10-3.20 (m, 4H), 3.78 (s, 3H), 3.70-3.80 (m, 4H), 6.52 (dd, 1H, J=8.56, 2.52 Hz), 6.67 (d, 1H, J=2.52 Hz), 7.08 (dd, 1H, J=8.04, 8.04 Hz), 7.39 (d, 1H, J=8.56 Hz), 7.35-7.45 (m, 1H), 7.99 (dd, 1H, J=8.04, 1.52 Hz), 8.14 (s, 1H), 8.28 (s, 1H) 8.70-8.80 (m, 1H).

Example 50

Sulfonamide Moieties are Prepared as Follows

Preparation of 2-amino-4-chloro-5-methyl-benzenesulfonyl chloride

To a solution of 2-amino-5-chloro-4-methyl-benzene-sulfonic acid (3.0 g, 1.35 mmol) in dichloroethane (10 mL) is added sulfuryl chloride (4.4 mL, 3.83 mmol) and stirred at 60° C. After one hour, thionyl chloride (1.3 mL) is added and the mixture is further stirred at 100° C. for 7.0 hours. The mixture is poured into iced water and extracted with ether three times. The organic layer is washed with water and then brine, dried over sodium sulfate, and evaporated in vacuo.

¹H-NMR (δ, ppm): 2.35 (s, 3H), 6.68 (s, 1H), 7.75 (s, 1H).

This substituted sulfonyl chloride is reacted with a suitable amine. On reaction e.g. with methylamine, 2-amino-5-chloro-4,N-dimethylbenzenesulfonamide is formed.

Example 51

Preparation of 2-[5-bromo-2-(2-methoxy-4-morpholin-4-yl-phenylamino)-pyrimidin-4-ylamino]-N,N-dimethyl-benznensulfonamide

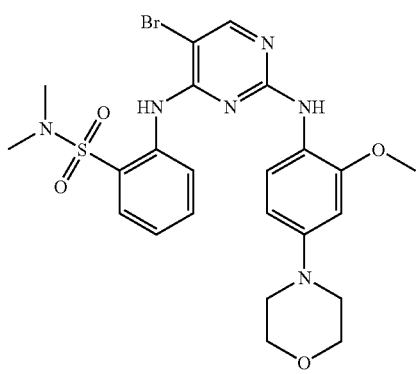

To a solution of 2-[5-Bromo-2-(2-methoxy-4-morpholin-4-yl-phenylamino)-pyrimidin-4-ylamino]-N-methyl-benzenesulfonamide (Ex 3-19) (1.0 g, 1.82 mmol) in DMF (10 mL), potassium carbonate (300 mg, 2.17 mmol) and iodomethane (116 µl, 1.86 mmol) are added. The resulting suspension is stirred at 50° C. for 1 h. To the reaction mixture, water is added and extracted with ethyl acetate three times. The organic layer is washed with water, dried over sodium sulfate, and concentrated in vacuo. The residue is purified by aluminum oxide column chromatography (AcOEt) to afford the title compound (728 mg, 71% yield).

NMR (400 MHz, CDCl₃, δ): 2.74 ((s, 6H), 3.05-3.18 (m, 4H), 3.84-3.93 (m, 4H), 3.88 (s, 3H), 6.43 (dd, 1H), 6.53 (d, 1H), 7.24 (m, 1H), 7.31 (s, 1H), 7.56 (m, 1H), 7.87 (dd, 1H), 8.05 (d, 1H), 8.21 (s, 1H), 8.49 (d, 1H), 8.49 (d, 1H), 9.27 (s, 1H). Rf: 0.23 (AcOEt:Hexane=1:1).

Example 52

Preparation of 2-[5-Bromo-2-(2-methoxy-4-morpholin-4-yl-phenylamino)-pyrimidin-4-ylamino]-5-fluoro-N-methyl-benzenesulfonamide

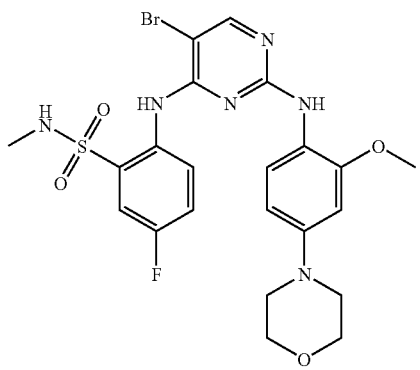

Preparation of 7-Fluoro-1,1-dioxo-1,4-dihydro-2H-1λ⁶-benzo[1,2,4]thiadiazin-3-one To a solution of chlorosulfonylisocyanate (1.2 mL, 13.5 mmol) in nitroethane (10 mL), 4-fluoroaniline (1.0 g, 8.97 mmol) is added dropwise at 0° C. and the reaction mixture is stirred for 30 min. To the solution, aluminum chloride (1.3 g, 9.87 mmol) is added at 0° C. and the mixture is stirred at 100° C. for 1 hour. After cooling to room temperature, water is added and the mixture is extracted with ethyl acetate twice. The organic layer is washed with brine, dried over sodium sulfate, and concentrated under reduced pressure. The resulting solids are collected by a filtration and wahed with ether to give slightly gray solids (803.9 mg, 41%).

NMR (400 MHz, DMSO-d6, δ): 7.22-7.28 (m, 1H), 7.45-7.57 (m, 1H), 7.60 (m, 1H), 11.15-11.30 (m, 1H). Rf: 0.43 (MeOH:AcOEt=1:5).

Preparation of 7-Fluoro-2-methyl-1,1-dioxo-1,4-dihydro-2H-1λ⁶-benzo[1,2,4]thiadiazin-3-one To a solution of 7-Fluoro-1,1-dioxo-1,4-dihydro-2H-1-λ⁶-benzo[1,2,4]thiadiazin-3-one (5.19 g, 24.0 mmol) in DMF (50 mL), sodium hydride (1.04 g, 26.0 mmol) and iodomethane (1.5 mL, 24.0 mmol) are added successively and the mixture is stirred for 1 hour at 70° C. After cooling to room temperature, the mixture is poured into water and the precipitate is collected by a filtration and washed with water and hexane, successively, to give slightly gray solids (5.38 g, 94%).

NMR (400 MHz, DMSO-d6, δ): 3.32 (s, 3H), 7.44 (dd, 1H), 7.75 (ddd, 1H), 7.94 (dd, 1H).

Rf (MeOH:AcOEt=1:5): 0.21. Rf: 0.39 (Hexane:AcOEt=1:1).

Preparation of 2-Amino-5-fluoro-N-methyl-benzenesulfonamide 6.79 g of 7-Fluoro-2-methyl-1,1-dioxo-1,4-dihydro-2H-1λ⁶-benzo[1,2,4]thiadiazin-3-one (29.5 mmol) is dissolved in 20% aq. sodium hydroxide and the resulting solution is stirred at 100° C. for 13.5 hours. The mixture is cooled to room temperature and poured into water. 78 mL of 5M HCl aq. is added and the precipitate is collected by a filtration and washed with water to afford slightly purple solids (3.96 g, 65%).

NMR (400 MHz, CDCl₃, δ): 2.60 (d, 3H), 4.55-4.82 (m, 3H), 6.74 (dd, 1H), 7.05-7.12 (m, 1H), 7.45 (dd, 1H). Rf: 0.41 (Hexane:AcOEt-1:1).

2-(5-Bromo-2-chloro-pyrimidin-4-ylamino)-5-fluoro-N-methyl-benzenesulfonamide

The reaction of pyrimidine with 2-Amino-5-fluoro-N-methyl-benzenesulfonamide is performed in the same manner described in example B.

NMR (400 MHz, CDCl₃, δ): 2.67 (d, 3H), 4.56 (m, 1H), 7.36-7.45 (m, 1H), 7.68 (dd, 1H), 8.39 (s, 1H), 8.42 (dd, 1H), 9.26 (s, 1H). Rf 0.59 (Hexane:AcOEt=1:1).

2-[5-Bromo-2-(2-methoxy-4-morpholin-4-yl-phenylamino)-pyrimidin-4-ylamino]-5-fluoro-N-methyl-benzenesulfonamide The introduction of substituted aniline is performed according to the manner described in Example A.

NMR (400 MHz, CDCl₃, δ): 2.65 (d, 3H), 3.09-3.16 (m, 4H), 3.87 (s, 3H), 4.50 (q, 1H), 6.41 (dd, 1H), 6.52 (d, 1H), 7.25-7.33 (m, 2H), 7.69 (dd, 1H), 7.95 (d, 1H), 8.20 (s, 1H), 8.37 (dd, 1H), 8.70 (s, 1H). Rf 0.30 (Hexane:AcOEt=1:1)

Example 53

FAK Assay

All steps are performed in a 96-well black microtiter plate. Purified recombinant hexahistidine-tagged human FAK kinase domain is diluted with dilution buffer (50 mM HEPES, pH 7.5, 0.01% BSA, 0.05% Tween-20 in water) to a concentration of 94 ng/mL (2.5 nM). The reaction mixture is prepared by mixing 10 μL 5× kinase buffer (250 mM HEPES, pH 7.5, 50 μM Na₃VO₄, 5 mM DTT, 10 mM MgCl₂, 50 mM MnCl₂, 0.05% BSA, 0.25% Tween-20 in water), 20 μL water, 5 μL of 4 μM biotinylated peptide substrate (Biot-Y397) in aqueous solution, 5 μL of test compound in DMSO, and 5 μL of recombinant enzyme solution and incubated for 30 min at room temperature. The enzyme reaction is started by addition of 5 μL of 5 μM ATP in water and the mixture is incubated for 3 hours at 37° C. The reaction is terminated by addition of 200 μL of detection mixture (1 nM Eu-PT66, 2.5 μg/mL SA-(SL) APC, 6.25 mM EDTA in dilution buffer), and the FRET signal from europium to allophycocyanin is measured by ARVOsx+L (Perkin Elmer) after 30 min of incubation at room temperature. The ratio of fluorescence intensity of 665 nm to 615 nm is used as a FRET signal for data analysis in order to cancel the colour quenching effect by a test compound. The results are shown as percent inhibition of enzyme activity. DMSO and 0.5 M EDTA are used as a control of 0% and 100% inhibition, respectively. $IC_{50}$ values are determined by non-linear curve fit analysis using the OriginPro 6.1 program (OriginLab).

The Biot-Y397 peptide (Biotin-SETDDYAEIID ammonium salt) is designed to have the same amino acid sequence as the region from S392 to D402 of human (GenBank Accession Number L13616) and is prepared by standard methods.

Purified recombinant hexahistidine-tagged human FAK kinase domain is obtained in the following way: Full-length human FAK cDNA is isolated by PCR amplification from human placenta Marathon-Ready™ cDNA (Clontech, No. 7411-1) with the 5' PCR primer (ATGGCAGCTGCTTAC-CTTGAC) and the 3' PCR primer (TCAGTGTG-GTCTCGTCTGCCC) and subcloned into a pGEM-T vector (Promega, No. A3600). After digestion with AccIII, the purified DNA fragment is treated with Klenow fragment. The cDNA fragment is digested with BamHI and cloned into pFastBacHTb plasmid (Invitrogen Japan K.K., Tokyo) previously cut with BamHI and Stu I. The resultant plasmid, hFAK KD (M384-G706)/pFastBacHTb, is sequenced to confirm its structure. The resulting DNA encodes a 364 amino acid protein containing a hexahistidine tag, a spacer region and a rTEV protease cleavage site at the N-terminal and the kinase domain of FAK (Met384-Gly706) from position 29 to 351.

Donor plasmid is transposed into the baculovirus genome, using MaxEfficacy DH10Bac E.coli cells. Bacmid DNA is prepared by a simple alkaline lysis protocol described in the Bac-to-Bac® Baculovirus Expression system (Invitrogen). Sf9 insect cells are transfected based on the protocol provided by the vendor (CellFECTIN®, Invitrogen). The expression of FAK in each lysate is analysed by SDS-PAGE and Western blotting with anti-human FAK monoclonal antibody (clone #77 from Transduction Laboratories).

The virus clone that shows the highest expression is further amplified by infection to Sf9 cells. Expression in ExpresSF+® cells (Protein Sciences Corp., Meriden, Conn., USA) gives high level of protein with little degradation. Cell lysates are loaded onto a column of HiTrap™ Chelating Sepharose HP (Amersham Biosciences) charged with nickel sulfate and equilibrated with 50 mM HEPES pH 7.5, 0.5 M NaCl and 10 mM imidazole. Captured protein is eluted with increasing amounts of imidazole in HEPES buffer/NaCl, and further purified by dialysis in 50 mM HEPES pH 7.5, 10% glycerol and 1 mM DTT.

Example 54

Cell-Free ZAP-70 Kinase Assay

The ZAP-70 kinase assay is based on time-resolved fluorescence resonance energy transfer (FRET). 80 nM ZAP-70 are incubated with 80 nM Lck (lymphoid T-cell protein tyrosine kinase) and 4 µM ATP in ZAP-70 kinase buffer (20 mM Tris, pH 7.5, 10 µM $Na_3VO_4$, 1 mM DTT, 1 mM $MnCl_2$, 0.01% BSA, 0.05% Tween-20) for 1 hour at room temperature in a siliconized polypropylene tube. Then, the selective Lck inhibitor PP2 (1-tert-butyl-3-(4-chloro-phenyl)-1H-pyrazolo[3,4-d]pyrimidin-4-ylamine; Alexis Biochemicals) is added (final concentration 1.2 µM) and incubated for further 10 min. 10 µL of this solution is mixed with the 10 µL biotinylated peptide LAT-11 (1 µM) as substrate and 20 µL of serial dilutions of inhibitors and incubated for 4 hours at room temperature. The kinase reaction is terminated with 10 µL of a 10 mM EDTA solution in detection buffer (20 mM Tris, pH 7.5, 0.01% BSA, 0.05% Tween-20). 50 µL europium-labelled anti-phosphotyrosine antibody (Eu-PT66; final concentration 0.125 nM); and 50 µL streptavidin-allophycocyanine (SA-APC; final concentration 40 nM) in detection buffer are added. After 1 hour incubation at room temperature fluorescence is measured on the Victor2 Multilabel Counter (Wallac) at 665 nm. Background values (low control) are obtained in the absence of test samples and ATP and are subtracted from all values. Signals obtained in the absence of test samples are taken as 100% (high control). The inhibition obtained in the presence of test compounds is calculated as percent inhibition of the high control. The concentration of test compounds resulting in 50% inhibition ($IC_{50}$) is determined from the dose-response curves. In this assay, the agents of the invention have $IC_{50}$ values in the range of 10 nM to 2 µM, preferably from 10 nM to 100 nM.

Recombinant ZAP-70 kinase is obtained as follows: A nucleic acid encoding full-length human ZAP-70 (GenBank #L05148) is amplified from a Jurkat cDNA library by RT-PCR and cloned into the pBluescript KS vector (Stratagene, California, USA). The authenticity of the ZAP-70 cDNA insert is validated by complete sequence analysis. This donor plasmid is then used to construct a recombinant baculovirus transfer vector based on the plasmid pVL1392 (Pharmingen, California, USA) featuring in addition an N-terminal hexahistidine tag. Following co-transfection with AcNPV viral DNA, 10 independent viral isolates are derived via plaque-purification, amplified on small scale and subsequently analyzed for recombinant ZAP-70 expression by Western Blot using a commercially available anti-ZAP-70 antibody (Clone 2F3.1, Upstate Biotechnology, Lake Placid, N.Y., USA). Upon further amplification of one positive recombinant plaque, titrated virus stocks are prepared and used for infection of Sf9 cells grown in serum-free SF900 II medium (Life Technologies, Basel, Switzerland) under defined, optimized conditions. ZAP-70 protein is isolated from the lysate of infected Sf9 cells by affinity chromatography on a Ni-NTA column (Qiagen, Basel, Switzerland).

Recombinant His-tagged ZAP-70 is also available from PanVera LLC, Madison, Wis., USA.

LAT-11 (linker for activation of T cell): The biotinylated peptide LAT-11 (Biotin -EEGAPDYENLQELN) used as a substrate in the ZAP-70 kinase assay is prepared in analogy to known methods of peptide synthesis. The N-α Fmoc group of Fmoc-Asn(Trt)-oxymethyl-4-phenoxymethyl-co(polystyrene-1%-divnyl-benzene), content of Asn approx. 0.5 mmol/g, is cleaved using piperidine, 20% in DMF. Four equivalents per amino-group of Fmoc-amino acid protected in their side chains [Asp(OtBu), Glu(OtBu), Asn(Trt), Gln(Trt) and Tyr (tBu)] are coupled using DIPCDI and HOBt in DMF. After complete assembly of the peptide chain the terminal Fmoc-protecting group is removed with piperidine in DMF as before. L(+)-biotinyl -aminohexanoic acid is then coupled to the terminal amino group using DIPCDI and HOBt in DMF using four equivalents of the reagents for four days at RT. The peptide is cleaved from the resin support and all side-chain protecting groups are simultaneously removed by using a reagent consisting of 5% dodecylmethylsulfide and 5% water in TFA for two hours at RT. Resin particles are filtered off, washed with TFA and the product is precipitated from the combined filtrates by the addition of 10 to 20 volumes of diethyl ether, washed with ether and dried. The product is purified by chromatography on a C-18 wide-pore silica column using a gradient of acetonitrile in 2% aqueous phosphoric acid. Fractions containing the pure compound are collected, filtered through an anion-exchange resin (Biorad, AG4-X4 acetate form) and lyophilized to give the title compound. MS: 1958.0 $(M-H)^{-1}$ Example 55

Phosphorylation Levels of FAK

Phosphorylation levels of FAK at Tyr397 is quantified by the sandwich ELISA. Mouse mammary carcinoma 4T1 cells ($1 \times 10^5$) are plated in wells of 96-well culture plates and incubated with or without various concentrations of inhibitors for 1 h in Dulbecco's modified eagle medium containing 0.5% BSA. The medium is removed and cells are lysed in 200 AIL 50 mM Tris-HCl, pH 7.4, containing 1% NP-40, 0.25% sodium deoxycholate, 150 mM NaCl, 1 mM EDTA, 1 mM PMSF, 1 mM $Na_3VO_4$, 1 mM NaF, 1 µg/mL aprotinin, 1 µg/mL leupeptin and 1 µg/mL pepstatin. After centrifugation, the supernatants are subjected to a sandwich ELISA to quantify the phosphorylated FAK and total FAK. Cell lysates are applied to 96-well flat-bottom ELISA plates which have been pre-coated with 100 µL/well of 4 µg/mL mouse monoclonal anti -FAK antibody (clone 77, Becton Dickinson Transduction Laboratories) in 50 mM Tris-HCl, pH 9.5, containing 150 mM NaCl for 18 h at 4° C. and blocked with 300 µL of BlockAce (Dainippon Pharmaceuticals Co.) diluted at 1:4 with $H_2O$ at room temperature for 2 h. After washing with TBSN (20 mM Tris-HCl, pH 8.3, containing 300 mM NaCl, 0.1% SDS and 0.05% NP-40), total FAK is detected with 100 µL of 1 µg/ml anti-FAK polyclonal antibody (#65-6140, Upstate Biology Inc.), and phosphorylated FAK is detected with 100 µL of 0.25 µg/µL anti-phosphorylated FAK (Y397) antibody (Affinity BioReagents, #OPA1-03071) in BlockAce diluted at 1:10 with $H_2O$. After 1 h incubation at room temperature, plates are washed with TBSN and 100 µL of biotinylated anti-rabbit IgG (#65-6140, Zymed Laboratolies Inc.) diluted at 1:2000 with BlockAce diluted at 1:10 with $H_2O$ is incubated at room temperature for 1 h. After washing with TBSN, ABTS solution substrate kit (#00-2011, Zymed Lobolatories Inc.) is used for color development. Absorbance at 405 nm is measured after 20 min incubation at room temparature. The concentration of compound causing 50% reduction of phosphorylation level of FAK is determined.

Example 56

Anchorage-Independent Tumor Cell Growth Assay

Mouse mammary carcinoma 4T1 cells ($5 \times 10^3$) are plated in 96-well Ultra low Attachment plates (#3474, Corning Inc.) in 100 μL of Dulbecco's modified eagle medium containing 10% FBS. Cells are cultured for 2 h and inhibitors are added at various concentrations in a final concentration of 0.1% DMSO. After 48 h, cell growth is assayed with the cell counting kit-8 (Wako Pure Chemical), which uses a water soluble tetrazolium salt WST8. Twenty μL of the reagent is added into each well and cells are further cultured for 2 h. The optical density is measured at 450 nm. The concentration of compound causing 50% inhibition of growth is determined.

Example 57

In Vitro T Cell Migration Assay

Inhibitory activities of FAK inhibitors on the mobility of immune cells are secured by the following in vitro study. That is, Jurkat T human leukemic cell line are placed at $1 \times 10^5$ cells in the upper chamber of Fluoroblok with 8 μm pores (Beckton Dickinson, UK), and are allowed to migrate by four hours cultivation at 37° C., in 95% air-5% $CO_2$ depending on a concentration gradient of fetal bovine serum (10% FBS). Cell mobility is appraised through the number of cells migrated into lower chamber by labeling with calcein-AM (Molecular Probes, Netherlands) at 8 μg/ml in HBSS for 1 h. For evaluation of FAK inhibitors, both the upper and lower chambers are added with various concentrations of FAK inhibitors (0.03-1 μM). IC50 values are calculated by the decrement of those fluorescent intensity compared to that in vehicle-treated group measured with Ascent (Ex: 485 nm, Em: 538 nm).

Example 58

Test for Activity Against IGF-I Induced IGF-IR Autophosphorylation Using the Cellular "Capture ELISA" Test The assay is conducted as follows:
For the assay NIH-3T3 mouse fibroblasts transfected with human IGF-R cDNA (complete human IGF-R cDNA: GenBank Acc. No. NM_000875), prepared as described in Kato et al., J. Biol. Chem. 268, 2655-61, 1993, are used. The cells which overexpress human IGF-R are cultured in Dulbecco's minimal essential (DMEM) medium, containing 10% Fetal Calf Serum (FCS). For the assay 5,000 cells/well are plated on day 1 on 96-well plates (Costar #3595) in normal growth medium and incubated for 2 days at 37° C. in a standard $CO_2$ cell incubator. The density of the cells does not exceed 70-80% at day 3. On day 3 the medium is discarded and the cells are incubated for 24 h in minimal medium (DMEM, containing 0.5% FCS). Compounds of formula I [starting from 10 mM dimethyl sulfoxide (DMSO) stock solutions] are added to produce final concentrations of 0.01, 0.03, 0.1, 0.3, 1, 3 and 10 μM to determine the $IC_{50}$ value. The cells are incubated for 90 min in the presence of a compound of formula I. Thereafter the cells are stimulated with 50 μl IGF-I (final concentration of IGF-I in the well=10 ng/ml; IGF-I is obtained from Sigma; Product Code: 13769) and incubated for 10 min at 37° C.

The medium is discarded and the cells are washed twice with PBS/O (=Phosphate-Buffered Saline without $CaCl_2$) and lysed for 15 min on ice with 50 μl/well RIPA -buffer [50 mM Tris-HCl, pH=7.2, 120 mM NaCl, 1 mM EDTA, 6 mM EGTA, 1% NP40, 20 mM NaF, 1 mM benzamidine, 15 mM sodium pyrophosphate, 1 mM Phenyl methyl sulphonyl fluoride (PMSF) and 0.5 mM $Na_3VO_4$] and shaken for 10 min using a 96-well plate shaker (=cellular extracts).

Packard HTRF-96 black plates are coated with 50 μl IGF-IR monoclonal Antibody (mAB) (Santa Cruz; Cat. No.: SC-462) in a concentration of 5 μg/ml at 4° C. overnight. The plates are washed twice with 0.05% (v/v) Tween-20 in Phosphate-Buffered Saline (PBS) and once with nanopure $H_2O$. Blocking is done for 2 h at room temperature (RT) with 3% Bovine Serum Albumin (BSA) in TBS-T buffer (20 mM Tris-HCl, pH=7.6, 137 mM NaCl, 0.05% Tween-20). After blocking, the plates are washed once with nanopure $H_2O$.

Cellular extracts (40 μl/well) are pipetted onto the precoated Packard plates, together with 40 μl of the anti-phosphotyrosine mouse mAB PY-20 conjugated with Alkaline Phosphatase (AP) (1:1000 diluted in RIPA buffer; the antibody is obtained from Transduction Labs; Cat. No.: P11120).

After incubating the extracts and the secondary antibody for 2 h at 4° C., the extracts are discarded, the plates are washed twice with 0.05% (v/v) Tween-20 in PBS and once with nanopure water.

90 μl/well AP substrate (CDP-Star; obtained from Tropix; Cat. No.: MS100RY) are then added and the plates are incubated for 45 min at RT in the dark, followed by measuring AP activity in a Packard Top Count Microplate Scintillation Counter. The $IC_{50}$ values for the compounds of formula I are calculated via linear regression analysis using the GraphPad Instat program (GraphPad Software, USA). $IC_{50}$ values in the range of 5 nM to 1 μM, especially in the range of 5 nM to 300 nM are found.

Example 59

In Vivo Activity in the Nude Mouse Xenograft Model female or male BALB/c nude mice (5-8 weeks old, Charles River Japan, Inc., Yokohama, Japan) are kept under sterile conditions with water and feed ad libitum. Tumours are induced by subcutaneous injection of tumour cells (human epithelial cell line MIA PaCa-2; European Collection of Cell Cultures (ECACC), Salisbury, Wiltshire, UK, Catalogue Number 85062806; cell line from a 65 year old Caucasian male; undifferentiated human pancreatic carcinoma cell line) into left or right flank of mice under Forene® anaesthesia (Abbott Japan Co., Ltd., Tokyo, Japan). Treatment with the test compound is started when the mean tumor volumes reached approximately 100 mm³. Tumour growth is measured two times per week and 1 day after the last treatment by determining the length of two perpendicular axis. The tumour volumes are calculated in accordance with published methods (see Evans et al., Brit. J. Cancer 45, 466-8, 1982). The anti-tumour efficacy is determined as the mean increase in tumour volume of the treated animals divided by the mean increase in tumour volume of the untreated animals (controls) and, after multiplication by 100, is expressed as delta T/C [%]. Tumour regression is reported as the mean changes of tumor volume of the treated animals divided by the mean tumor volume at start of treatment and, after multiplication by 100, is expressed as regression [%]. The test compound is orally administered daily with or without drug holidays.

As an alternative to cell line MIA PaCa-2, another cell line may also be used in the same manner, for example:
the 4T1 breast carcinoma cell line (ATCC Number CRL-2539; see also Cancer. 88(12 Supple), 2979-2988, 2000) with female BALB/c mice (injection into mammary fat pad).

On the basis of these studies, a compound of formula I according to the invention shows therapeutic efficacy especially against proliferative diseases responsive to an inhibition of a tyrosine kinase.

Example 60

Tablets

Tablets comprising 50 mg of active ingredient, for example one of the compounds of formula I described in Examples 1 to 131, and having the following composition are prepared in customary manner
Composition:

| active ingredient | 50 mg |
|---|---|
| wheat starch | 150 mg |
| lactose | 125 mg |
| colloidal silicic acid | 12.5 mg |
| talc | 22.5 mg |
| magnesium stearate | 2.5 mg |
| Total: | 362.5 mg |

Preparation: The active ingredient is mixed with a portion of the wheat starch, with the lactose and the colloidal silicic acid and the mixture is forced through a sieve. A further portion of the wheat starch is made into a paste, on a water bath, with five times the amount of water and the powder mixture is kneaded with the paste until a slightly plastic mass is obtained.

The plastic mass is pressed through a sieve of about 3 mm mesh size and dried, and the resulting dry granules are again forced through a sieve. Then the remainder of the wheat starch, the talc and the magnesium stearate are mixed in and the mixture is compressed to form tablets weighing 145 mg and having a breaking notch.

Example 61

Soft Capsules 5000 soft gelatin capsules comprising each 50 mg of active ingredient, for example one of the compounds of formula I described in Examples 1 to 131, are prepared in customary manner
Composition:

| active ingredient | 250 g |
|---|---|
| Lauroglykol | 2 litres |

Preparation: The pulverized active ingredient is suspended in Lauroglykol® (propylene glycol laurate, Gattefossé S.A., Saint Priest, France) and ground in a wet pulverizer to a particle size of approx. 1 to 3 μm. 0.419 g portions of the mixture are then dispensed into soft gelatin capsules using a capsule-filling machine.

Biological Results:

| Example | FAK IC50 (nM) | Phos IC50 (μM) | Growth IC50 (μM) | T Cell Migration IC50 (μM) | IGF-1R IC50 (μM) |
|---|---|---|---|---|---|
| 1.00 | 140 | 0.7 | >10 | | |
| 2.00 | 13 | 1.2 | | | |
| 3.01 | 44 | 0.34 | >10 | | |
| 3.02 | 36 | 0.85 | 4 | | |
| 3.03 | 9.1 | 0.14 | 0.8 | | |
| 3.04 | 32 | 0.53 | 2 | | |
| 3.05 | 21 | 0.17 | 2 | | >10 |
| 3.06 | 13 | 0.11 | 2 | | |
| 3.07 | 16 | 0.45 | 2 | | |
| 3.08 | 74 | 0.3 | 6 | | |
| 3.09 | 48 | 0.5 | 0.7 | | |
| 3.10 | 52 | 0.95 | >10 | | |
| 3.11 | 9 | 0.04 | 0.3 | | 0.2 |
| 3.12 | 5.4 | 0.01 | 1 | | |
| 3.13 | 58 | 1.7 | 0.6 | | 0.74 |
| 3.14 | 54 | 0.4 | 5 | | |
| 3.15 | 7 | 0.02 | 0.8 | | 0.94 |
| 3.16 | 48 | 1.1 | 3 | | |
| 3.17 | 2.8 | 0.03 | 0.2 | | <0.08 |
| 3.18 | 130 | 1.5 | 9 | | |
| 3.19 | 6.8 | 0.35 | 0.8 | | 0.1 |
| 3.20 | 16 | 0.22 | 0.3 | | |
| 3.22 | 120 | 0.9 | 2 | | |
| 3.23 | 38 | 0.39 | 0.5 | | |
| 3.24 | 64 | 3.5 | 5 | | |
| 3.25 | 22 | 0.3 | 0.3 | | 0.81 |
| 3.26 | 50 | 0.79 | 2 | | |
| 3.28 | 43 | 0.71 | 0.7 | | |
| 3.29 | 89 | 0.6 | >10 | | |
| 3.30 | 69 | 0.6 | 3 | | |
| 3.31 | 13 | 1.1 | 5 | | |
| 3.32 | 14 | 0.18 | 0.49 | 0.28 | 0.12 |
| 3.33 | 2.9 | 0.03 | 0.05 | 0.09 | 0.13 |
| 3.34 | 7 | 0.1 | 0.24 | 0.13 | <0.08 |
| 3.35 | 13 | 0.02 | 0.17 | 0.8 | 3.55 |
| 3.36 | 43 | 1.8 | 2.8 | | |
| 3.37 | 39 | 1.1 | 2.6 | | |
| 3.38 | 64 | 1.7 | 3.8 | | |
| 3.39 | 2 | 0.02 | 0.03 | 1 | 0.09 |
| 3.40 | 9 | >10 | 0.9 | | |
| 3.41 | 22 | >10 | 0.43 | | |
| 3.42 | 29 | 0.35 | 0.3 | | |
| 3.43 | 5.6 | 0.2 | 0.11 | | 0.27 |
| 3.44 | 11 | 0.05 | 0.09 | | 0.09 |
| 3.45 | 0.9 | 0.02 | 0.02 | | |
| 3.46 | 4 | 0.1 | 0.18 | 0.3 | |
| 3.47 | 1 | 0.1 | 0.06 | | |
| 3.48 | 7 | 0.07 | 0.3 | | 0.21 |
| 3.49 | 39 | 10 | 0.39 | | |
| 3.50 | 13 | 0.12 | 1 | | 1.19 |
| 3.51 | 29 | 0.2 | 0.4 | | 0.41 |
| 3.52 | 29 | 0.42 | 2 | | |
| 3.53 | 6 | 0.07 | 0.21 | | |
| 3.54 | 0.9 | 0.01 | 0.07 | | <0.08 |
| 3.55 | 34 | >10 | 3 | | |
| 3.56 | 28 | 0.53 | 0.15 | | |
| 3.57 | 28 | 0.61 | 3 | | |
| 3.58 | 21 | 0.08 | 0.3 | | 0.14 |
| 3.59 | 95 | 1.2 | >10 | | |
| 3.60 | 90 | 0.93 | 2 | | |
| 3.61 | 12 | 10 | >10 | | |
| 3.62 | 63 | >10 | >10 | | |
| 3.63 | 27 | >10 | >10 | | |
| 3.64 | 5 | 0.13 | 0.7 | 0.21 | |
| 3.65 | 8 | 0.08 | 0.1 | | 0.15 |
| 3.66 | 1 | 0.08 | 0.07 | | 0.25 |
| 3.67 | 6 | 0.38 | 0.39 | | |
| 3.68 | 5.5 | 0.2 | 0.63 | 1 | |
| 3.69 | 4 | 0.2 | 0.11 | 0.58 | |
| 3.70 | 3.5 | 0.02 | 0.13 | | |
| 3.71 | 11 | 0.05 | 0.08 | | |
| 3.72 | 2.1 | 0.11 | 0.06 | | |
| 3.73 | 11 | 0.03 | 0.29 | | 1.63 |

| Example | FAK IC50 (nM) | Phos IC50 (μM) | Growth IC50 (μM) | T Cell Migration IC50 (μM) | IGF-1R IC50 (μM) |
|---|---|---|---|---|---|
| 3.74 | 15 | 0.1 | 0.15 | | |
| 3.75 | 72 | 0.5 | 1.3 | | |
| 3.76 | 15 | 0.29 | 1.3 | 0.7 | |
| 3.77 | 65 | >10 | 3 | | |
| 3.78 | 10 | >10 | 0.22 | | |
| 3.79 | 5 | 1.3 | 0.12 | | |
| 3.80 | 12 | 0.22 | 0.45 | | 5 |
| 3.81 | 21 | 0.52 | 0.98 | | >10 |
| 3.82 | 4.8 | 0.2 | 0.07 | | |
| 3.83 | 20 | 0.08 | 0.32 | | 0.68 |
| 3.84 | 10 | 1 | 0.08 | | |
| 6.00 | 110 | 0.35 | 5 | | |
| 7.00 | 5.3 | 0.21 | 0.47 | 0.04 | 0.19 |
| 7.01 | 4.7 | 0.6 | 0.54 | | 0.19 |
| 7.02 | 7.5 | 0.1 | 0.36 | | 0.77 |
| 7.03 | 2.9 | 0.3 | 0.39 | | 0.27 |
| 7.04 | 5.2 | 1 | 0.29 | | |
| 7.05 | 6.2 | 0.3 | 0.2 | | 0.25 |
| 7.06 | 17 | 0.8 | 1.09 | 0.25 | |
| 7.07 | 4.1 | 0.9 | 0.18 | | |
| 7.08 | 8.7 | 0.8 | 1 | | |
| 7.09 | 8.2 | 1 | 0.85 | | |
| 7.10 | 6.6 | 1 | 0.98 | | |
| 7.11 | 2.5 | 0.6 | 1.2 | | 0.77 |
| 7.12 | 1.9 | 0.9 | 1 | 0.31 | 0.62 |
| 7.13 | 5.5 | 0.8 | 1.22 | | |
| 7.14 | 7.6 | 0.3 | 0.36 | | 0.33 |
| 7.15 | 4.5 | 0.06 | 0.19 | | 0.26 |
| 7.16 | 6.4 | 0.2 | 0.42 | | |
| 7.17 | 4.3 | 0.7 | 0.69 | | |
| 7.18 | 6.2 | 0.5 | 0.7 | | |
| 7.19 | 13 | | 0.33 | | |
| 7.20 | 2.5 | >10 | 0.11 | | |
| 7.21 | 3.3 | >10 | 0.46 | | |
| 7.22 | 25 | | 0.48 | | |
| 7.23 | 1.4 | | 0.25 | | |
| 7.24 | 5.1 | | 0.09 | | |
| 7.25 | 13 | 0.2 | 0.73 | | |
| 7.25 | 2 | >10 | 0.57 | | |
| 7.26 | 4.1 | | 0.15 | | |
| 7.27 | 21 | 0.5 | 0.22 | | |
| 7.28 | 34 | 1 | 0.15 | | |
| 7.29 | 57 | 2 | 0.48 | | |
| 7.30 | 2.1 | | 0.3 | 1 | |
| 8.01 | 6.6 | 0.6 | 0.33 | | |
| 8.02 | 2.4 | 0.5 | 0.99 | | |
| 8.03 | 13 | 0.22 | 1 | | >10 |
| 8.04 | 8 | >10 | 1.1 | | |
| 9.01 | 22 | 0.36 | 1 | 0.6 | |
| 9.02 | 15 | 0.5 | 0.81 | | |
| 9.03 | 18 | 0.1 | 0.37 | | |
| 9.04 | 13 | 0.2 | 0.73 | | |
| 9.05 | 22 | 0.36 | 1.6 | | 0.6 |
| 9.06 | 23 | 3 | 0.4 | 0.3 | |
| 9.07 | 17 | >10 | 0.26 | | |
| 10.01 | 39 | 1 | 0.44 | | |
| 10.02 | 26 | 0.9 | 1.06 | | |
| 10.03 | 23 | 0.9 | 2.4 | | |
| 11.01 | 9 | 0.7 | 0.85 | | |
| 11.02 | 4.1 | 0.8 | 0.69 | | |
| 11.03 | 26 | 0.41 | 0.1 | | |
| 11.04 | 4.3 | >10 | 3.2 | | |
| 12.01 | 2.5 | 0.09 | 0.4 | 0.22 | |
| 12.02 | 1.6 | | 0.05 | | |
| 12.03 | 2.3 | | 0.25 | | |
| 12.04 | 1.1 | | 0.14 | | |
| 12.06 | 2.6 | | | | |
| 13.01 | 65 | | 0.81 | | |
| 14.01 | 19 | 0.2 | 1.47 | 0.28 | |
| 14.02 | 190 | 2 | 1.1 | 1 | |
| 14.03 | 30 | 10 | 1.01 | | |
| 14.04 | 18 | | 0.54 | | |
| 14.05 | 37 | >10 | 1 | | |
| 14.06 | 63 | 10 | 1.11 | | |
| 14.07 | 7.5 | 0.2 | 1.4 | | |
| 15.01 | 15 | 10 | 0.47 | | |
| 15.02 | 21 | >10 | 0.66 | | |
| 15.03 | 44 | 2 | 1.67 | | |
| 16.01 | 44 | >10 | 4 | | |
| 16.02 | 6 | >10 | 0.6 | | |
| 16.03 | 21 | 3 | >10 | | |
| 16.04 | 9.5 | >10 | 0.92 | | |
| 16B | 11 | 3 | 7 | | |
| 16.C | 28 | 0.9 | >10 | | |
| 18.01 | 19 | >10 | 1.29 | | |
| 19.01 | <1 | 0.2 | 0.3 | 0.29 | 1.41 |
| 19.02 | 1.6 | 0.13 | 0.38 | | 0.91 |
| 19.03 | <1 | 0.3 | 0.09 | | 0.64 |
| 19.04 | 1.6 | 0.2 | 0.34 | | 0.14 |
| 19.05 | 1.8 | 0.2 | 0.67 | 0.07 | 0.47 |
| 19.06 | 5 | 1 | 0.7 | | |
| 19.07 | 2.1 | 0.3 | 0.11 | | |
| 19.08 | 3.2 | 0.03 | 0.4 | 0.29 | 0.13 |
| 19.09 | 1.3 | 0.17 | 0.39 | 0.3 | 0.48 |
| 19.10 | 1.3 | 0.06 | 0.56 | | 1.02 |
| 19.11 | 38 | >10 | 2 | | |
| 19.12 | 9 | >10 | 0.7 | | 0.63 |
| 19.13 | 2.5 | 0.3 | 1.1 | | |
| 19.14 | 2.6 | 0.4 | 1.13 | | 0.44 |
| 19.15 | 3.1 | 0.5 | 0.36 | | |
| 19.16 | 2.3 | 0.7 | 1.1 | | |
| 19.17 | 1 | >10 | 0.17 | | |
| 19.18 | 7 | 0.13 | 0.87 | | |
| 19.19 | 5.7 | | 0.4 | | |
| 19.20 | 1.6 | 0.03 | 0.07 | | 0.23 |
| 19.21 | 84 | >10 | 1.71 | | |
| 19.22 | 3.4 | 0.12 | 0.51 | | |
| 19.23 | 6.4 | 0.7 | 0.71 | | |
| 19.24 | 1.8 | 0.05 | 0.12 | | |
| 19.25 | 7.2 | 1 | 0.49 | | 0.24 |
| 19.26 | 6.1 | 0.1 | 0.3 | | |
| 19.27 | 1.5 | 0.3 | 0.4 | | |
| 19.28 | 4.8 | 0.1 | 0.12 | 0.3 | 0.46 |
| 19.29 | 1.9 | | | | |
| 19.30 | <1 | 0.06 | 0.1 | | |
| 19.31 | 1.8 | 0.4 | 0.38 | | |
| 19.32 | 1.4 | 0.2 | 0.31 | | |
| 20.01 | 10 | 0.3 | 0.18 | 0.25 | 0.7 |
| 20.02 | 9 | 0.12 | 0.17 | 0.75 | 0.52 |
| 20.03 | 42 | 0.4 | 2.5 | | 2.78 |
| 20.04 | 23 | 0.58 | 1.9 | | |
| 20.05 | 6.8 | 0.87 | 1.46 | | |
| 20.06 | 5 | 0.36 | 0.14 | 49 | |
| 20.07 | 3 | 0.1 | 0.05 | | 0.38 |
| 20.08 | 6.8 | 0.17 | 0.05 | 0.29 | |
| 20.09 | 2 | 0.3 | 0.01 | | |
| 20.10 | 2 | 0.1 | 0.02 | | |
| 20.11 | 26 | 2 | 0.4 | | |
| 20.12 | 9.5 | | | | |
| 20.13 | 6.3 | | 0.04 | | |
| 20.14 | 33 | | 0.32 | | |
| 20.15 | 14 | 0.4 | 0.97 | 0.3 | |
| 20.16 | 7.5 | | 0.06 | | |
| 20.17 | 2 | | 0.14 | | |
| 20.18 | 15 | | 0.81 | | |
| 20.19 | 28 | | 0.21 | | |
| 20.20 | 3.12 | | | | 0.1 |
| 20.21 | 26 | 3 | 0.68 | | |
| 20.22 | 8 | >10 | 0.19 | | |
| 20.23 | 30 | 0.49 | 3 | | |
| 20.24 | 19 | 0.48 | 2 | | |
| 20.25 | 6.2 | 0.21 | 0.06 | | |
| 20.26 | 5.3 | 0.76 | 0.27 | | |
| 20.27 | 12 | 0.85 | 0.05 | | 0.29 |
| 20.28 | 9.2 | 0.17 | 0.08 | | 0.42 |
| 20.29 | 6.1 | 0.2 | 0.05 | | 0.31 |
| 20.30 | 7.6 | 0.3 | 0.08 | | 0.67 |
| 20.31 | 39 | | 0.5 | | |
| 20.32 | 13 | | 0.11 | | |
| 20.33 | 2.5 | | 0.38 | | |
| 20.34 | 13 | 1 | 0.12 | | |
| 20.35 | 8.7 | 0.09 | 0.09 | | 0.15 |

| Example | FAK IC50 (nM) | Phos IC50 (μM) | Growth IC50 (μM) | T Cell Migration IC50 (μM) | IGF-1R IC50 (μM) |
|---|---|---|---|---|---|
| 21.01 | 1 | 0.07 | 0.19 | | 0.47 |
| 21.02 | 8.5 | 0.33 | >10 | | |
| 21.03 | 1.7 | 0.3 | 0.3 | | |
| 21.04 | 1.8 | 0.05 | 0.3 | | |
| 22.01 | 43 | >10 | >10 | | |
| 22.02 | 26 | 1 | 3 | | |
| 22.03 | 6.6 | 0.09 | 0.15 | | 0.26 |
| 23.01 | 3.4 | 0.6 | 0.2 | 0.63 | 0.53 |
| 23.02 | 1.5 | 0.2 | 0.4 | | 0.8 |
| 23.03 | 1.7 | 1 | 1.12 | | 0.82 |
| 23.04 | 1.2 | 0.9 | 1.07 | | 0.6 |
| 23.05 | 1.9 | >10 | 0.59 | | |
| 23.06 | 16 | 1 | 0.57 | | |
| 23.07 | 2.1 | 3 | 0.84 | | |
| 23.08 | 6.7 | 0.3 | 0.49 | | |
| 23.09 | 2.1 | 0.2 | 0.28 | | |
| 24.01 | 3.6 | 0.11 | 0.44 | | 0.05 |
| 24.02 | 2.1 | 0.5 | 0.11 | | 0.39 |
| 24.03 | 1 | 0.3 | 1.08 | | |
| 25.01 | 8.5 | 3 | 1 | | |
| 25.02 | 3 | 0.4 | 0.13 | | 0.64 |
| 26.01 | 4.4 | 0.05 | 0.35 | | 0.29 |
| 26.02 | 1.9 | 0.03 | 0.12 | 0.09 | 0.39 |
| 26.03 | 1.4 | 0.1 | 0.13 | | 0.23 |
| 26.04 | 4.9 | 0.05 | 0.43 | 0.29 | 1.16 |
| 26.05 | 2.1 | 0.09 | 0.23 | | 1.5 |
| 26.06 | 4.4 | 0.1 | 0.35 | | |
| 26.07 | 11 | 0.5 | 0.95 | | |
| 26.08 | 2.9 | 0.01 | 0.18 | | |
| 26.09 | 2.3 | 0.04 | 0.22 | | |
| 26.10 | 2 | 0.01 | 0.14 | | |
| 26.11 | 4.4 | 0.4 | 0.78 | 0.5 | |
| 26.12 | 3.7 | 0.2 | 0.19 | | |
| 26.13 | 1.6 | 0.2 | 0.44 | | |
| 26.14 | 5 | | 0.19 | | |
| 26.15 | 6.9 | 1.2 | 0.08 | | 0.07 |
| 26.16 | 9 | 0.32 | 2 | | |
| 26.17 | 17 | 0.3 | 0.1 | 0.26 | |
| 26.18 | 1.3 | 6 | 1.17 | | |
| 26.19 | 9.2 | 0.43 | 0.79 | | |
| 26.20 | 10 | 0.14 | 0.22 | 0.6 | 0.49 |
| 26.21 | 1.1 | 0.1 | 0.49 | | |
| 26.22 | <1 | 0.1 | 0.28 | | |
| 26.23 | 1.4 | 0.3 | 0.09 | 0.3 | 0.18 |
| 26.24 | 1 | 0.5 | 0.48 | 0.9 | |
| 26.25 | <1 | 0.6 | 0.73 | 0.3 | |
| 26.26 | 1.9 | 0.2 | 0.07 | | 0.34 |
| 26.27 | 4.8 | 0.6 | 1.49 | | |
| 26.28 | 2.1 | 0.5 | 1.52 | | |
| 26.29 | <1 | 0.31 | 0.26 | | |
| 26.30 | 4.4 | 1 | 0.76 | | |
| 26.31 | 2 | 0.3 | 0.16 | | |
| 26.32 | 1.6 | | 0.05 | 0.6 | |
| 26.33 | 4 | | 0.06 | 0.23 | |
| 26.34 | 7 | | 0.1 | 0.25 | |
| 26.35 | 4.5 | | 0.05 | 0.3 | |
| 26.36 | 1.9 | | 0.07 | 0.09 | |
| 26.37 | <1 | | | | |
| 26.38 | <1 | | | | |
| 26.39 | 3.1 | | | | |
| 27.01 | 14 | 0.06 | 0.47 | | |
| 27.02 | 5.1 | 0.5 | 1.1 | | |
| 27.03 | 6.3 | >10 | 0.56 | | |
| 27.04 | 11 | 0.1 | 0.27 | | |
| 27.05 | 8.2 | 0.04 | 0.3 | | |
| 27.06 | 1 | 0.08 | 0.31 | | |
| 27.07 | 5.5 | 2 | 0.57 | | |
| 27.08 | 9.3 | 0.6 | 0.75 | | |
| 27.09 | 4.2 | 0.5 | 0.36 | | |
| 28.01 | 12 | 0.3 | 0.46 | | 0.3 |
| 28.02 | 1.9 | 0.08 | 0.44 | | 3.71 |
| 28.03 | 7.4 | 0.07 | 0.29 | | |
| 28.04 | 7.5 | 0.3 | 0.3 | | |
| 28.05 | 6.7 | 0.1 | 0.12 | | 1.39 |
| 28.06 | 17 | 0.6 | 0.56 | | |
| 28.07 | 47 | 3 | >10 | | |
| 28.08 | 4.6 | 0.4 | 0.37 | | |
| 28.09 | 3.1 | 0.5 | 0.36 | | |
| 28.10 | 20 | 3 | 1.85 | | |
| 28.11 | 4.2 | 0.5 | 0.63 | | |
| 28.12 | 3.2 | 0.3 | 0.43 | | 0.1 |
| 28.13 | 7.8 | 0.1 | 0.55 | 0.29 | |
| 28.14 | 3 | 0.1 | 1.44 | | |
| 28.15 | 10 | 0.5 | 0.69 | | |
| 28.16 | 11 | 0.11 | 1 | 0.6 | |
| 28.17 | 15 | 0.16 | 1.9 | | |
| 28.18 | 9.1 | >10 | 2.03 | | |
| 28.19 | 3.7 | 0.5 | 0.14 | | |
| 28.20 | 4.4 | 2 | 0.4 | | |
| 28.21 | 1.3 | 0.1 | 0.23 | | |
| 28.22 | 1.3 | 0.1 | 0.3 | | |
| 28.23 | 5.9 | 0.5 | 0.28 | | |
| 28.24 | 2.9 | 0.2 | 0.09 | | 2.57 |
| 28.25 | 3.9 | 0.04 | 0.13 | | |
| 28.26 | 6.6 | 0.2 | 0.57 | | |
| 28.27 | 2.4 | 0.3 | 0.42 | 0.5 | |
| 28.28 | 5.2 | 0.4 | 0.52 | 1 | |
| 28.29 | 11 | 0.4 | 0.36 | | |
| 28.30 | 2.3 | 0.9 | 0.11 | | |
| 28.31 | 7.4 | 0.06 | 1.06 | | |
| 29.01 | 13 | 0.7 | 2.2 | | 0.09 |
| 29.02 | 3.3 | 0.7 | 1.1 | | |
| 29.03 | 5.6 | 0.1 | 0.99 | | |
| 30.01 | 22 | 0.2 | 0.89 | | |
| 30.02 | 12 | 0.2 | 0.47 | | |
| 30.03 | 19 | 0.5 | 0.68 | | |
| 30.04 | 25 | 0.3 | 0.99 | | |
| 30.05 | 8.5 | 2 | 0.29 | | |
| 30.06 | 15 | 1 | 1.03 | | |
| 30.07 | 8.8 | 0.6 | 0.47 | | |
| 31.01 | 30 | >10 | 1.6 | | |
| 31.02 | 31 | 0.28 | 0.29 | | 0.42 |
| 32.01 | 4.1 | 0.1 | 0.29 | | |
| 32.02 | 5.9 | 0.05 | 0.37 | | 0.12 |
| 33.01 | 2.5 | 0.08 | 0.25 | | |
| 33.02 | 5.2 | 0.06 | 0.25 | | 0.1 |
| 34.01 | 8 | 0.1 | 0.37 | | 0.28 |
| 34.02 | 11 | 0.08 | 1.17 | | |
| 34.03 | 33 | 0.19 | 2.25 | | |
| 34.04 | 13 | >10 | 1.22 | | |
| 34.05 | 51 | 0.36 | 5.1 | | |
| 34.06 | 14 | >10 | 3 | | |
| 34.07 | 27 | >10 | 2.7 | | |
| 34.08 | 8.7 | >10 | 1.9 | | |
| 35.01 | 6.8 | >10 | 1.43 | | |
| 35.02 | 6.1 | 0.7 | 0.23 | | |
| 51.00 | 8.1 | 0.013 | 0.19 | | 0.2 |
| 52.00 | 13 | 0.2 | 0.41 | | <0.08 |

SEQUENCE LISTING

<160> NUMBER OF SEQ ID NOS: 3

<210> SEQ ID NO 1
<211> LENGTH: 11
<212> TYPE: PRT
<213> ORGANISM: artificial
<220> FEATURE:
<223> OTHER INFORMATION: synthetic

<400> SEQUENCE: 1

Ser Glu Thr Asp Asp Tyr Ala Glu Ile Ile Asp
1               5                   10

<210> SEQ ID NO 2
<211> LENGTH: 21
<212> TYPE: DNA
<213> ORGANISM: artificial
<220> FEATURE:
<223> OTHER INFORMATION: synthetic

<400> SEQUENCE: 2
atggcagctg cttaccttga c                                             21

<210> SEQ ID NO 3
<211> LENGTH: 21
<212> TYPE: DNA
<213> ORGANISM: artificial
<220> FEATURE:
<223> OTHER INFORMATION: synthetic

<400> SEQUENCE: 3
tcagtgtggt ctcgtctgcc c                                             21

The invention claimed is:

1. A compound of formula I

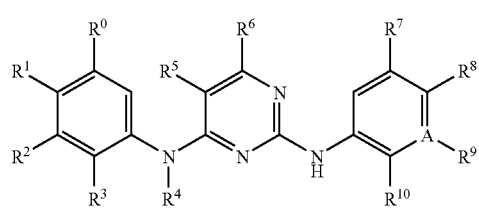

(I)

each of $R^0$ or $R^2$ independently is hydrogen, $C_1$-$C_8$alkyl, unsubstituted or substituted 5 or 6 membered heterocyclyl comprising 1 or 2 hetero atoms selected from N, O and S, $C_1$-$C_8$alkoxy, unsubstituted or substituted heterocyclyloxy, unsubstituted or substituted heterocyclyl$C_1$-$C_8$alkoxy, unsubstituted or substituted amino, or halogen;

$R^1$ is hydrogen, $C_1$-$C_8$alkyl, halo$C_1$-$C_8$alkyl, unsubstituted or substituted 5 or 6 membered heterocyclyl comprising 1 or 2 hetero atoms selected from N, O and S, $C_1$-$C_8$alkoxy, unsubstituted or substituted heterocyclyloxy, unsubstituted or substituted Heterocyclyl$C_1$-$C_8$alkoxy, unsubstituted or substituted amino, halogen;

$R^3$ is $C_1$-$C_8$alkylsulfinyl, $C_1$-$C_8$alkylsulfonyl, $C_5$-$C_{10}$ arylsulfonyl, or unsubstituted or substituted carbamoyl;

$R^4$ is hydrogen;

$R^5$ is chloro or bromo;

$R^6$ is hydrogen;

each of $R^7$ and $R^9$ independently is hydrogen, $C_1$-$C_8$alkyl, halo$C_1$-$C_8$alkyl, unsubstituted or substituted $C_5$-$C_{10}$aryl, unsubstituted or substituted 5 or 6 membered heterocyclyl comprising 1 or 2 hetero atoms selected from N, O and S, $C_1$-$C_8$alkoxy, unsubstituted or substituted heterocyclyloxy, unsubstituted or substituted heterocyclyl$C_1$-$C_8$alkoxy, unsubstituted or substituted amino, halogen, unsubstituted or substituted carbamoyl, or unsubstituted or substituted sulfamoyl;

$R^8$ is $C_5$-$C_{10}$aryl; unsubstituted or substituted 5 or 6 membered heterocyclyl comprising 1 or 2 hetero atoms selected from N, O and S; $C_5$-$C_{10}$aryloxy; unsubstituted or substituted heterocyclyloxy; or unsubstituted or substituted heterocyclyl$C_1$-$C_8$alkoxy; and $R^{10}$ is $C_1$-$C_8$alkyl, halo$C_1$-$C_8$alkyl, $C_1$-$C_8$alkoxy, unsubstituted or substituted heterocyclyl$C_1$-$C_8$alkoxy, unsubstituted or substituted amino, or halogen; and A is C;

or salts thereof.

2. The compound of claim 1, wherein each of $R^0$, $R^1$ or $R^2$ is hydrogen.

3. The compound of claim 1, wherein $R^3$ is $C_1$-$C_8$alkylsulfonyl, $C_5$-$C_{10}$arylsulfonyl or unsubstituted or substituted carbamoyl.

4. The compound of claim 1, wherein $R^3$ is $C_1$-$C_8$alkylsulfonyl.

5. The compound of claim 1, wherein $R^3$ is $C_5$-$C_{10}$arylsulfonyl.

6. The compound of claim 1, wherein $R^3$ is unsubstituted or substituted carbamoyl.

7. The compound of claim 1, wherein $R^8$ is piperidino, piperazino, N-methylpiperazino, morpholino, phenoxy, 1-methyl-4-piperidyloxy, 3-morpholinopropoxy, 2-morpholinoethoxy or 3-(N-methylpiperazino)-propoxy.

8. The compound of claim 1, wherein $R^8$ is unsubstituted or substituted 5 or 6 membered heterocyclyl comprising 1 or 2 hetero atoms selected from N, O and S.

9. The compound of claim 1, wherein $R^0$, $R^1$ or $R^2$ is hydrogen; $R^3$ is $C_1$-$C_8$alkylsulfonyl; and $R^8$ is unsubstituted or substituted 5 or 6 membered heterocyclyl comprising 1 or 2 hetero atoms selected from N, O and S.

10. The compound of claim 9, wherein $R^8$ is piperidino, piperazino, N-methylpiperazino or morpholino.

11. The compound of claim 1, wherein said compound is selected from the group of compounds with the following names or formulae: 2-[5-chloro-2-(2-methoxy-4-morpholin-4-yl-phenylamino)-pyrimidin-4-ylamino]-N-methyl-benzamide;

a compound of the formula

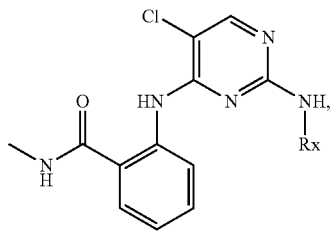

wherein Rx has one of the meanings given in the following table:

| Compound No. | Rx |
|---|---|
| 7-1 | 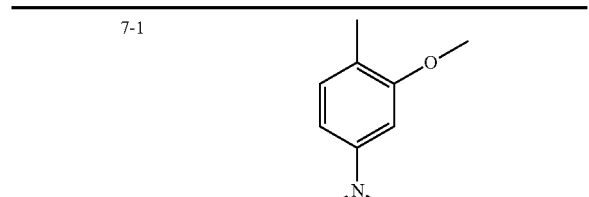 |
| 7-2 | 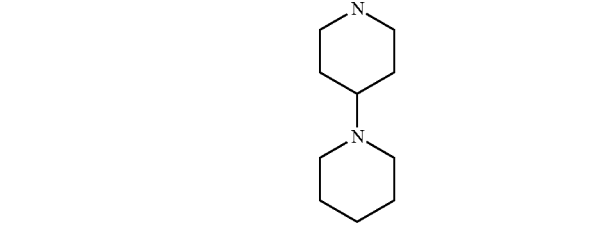 |

-continued

| Compound No. | Rx |
|---|---|
| 7-3 | |
| 7-4 | |
| 7-5 | |
| 7-7 | |
| 7-8 | |

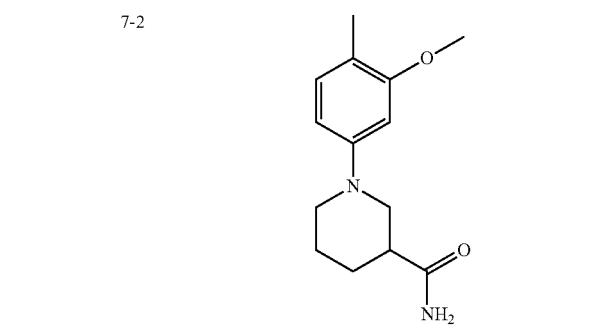

| Compound No. | Rx |
|---|---|
| 7-9 | 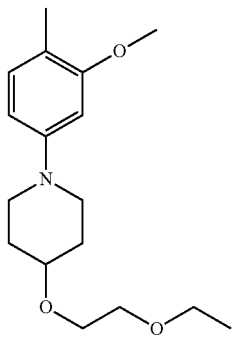 |
| 7-10 | 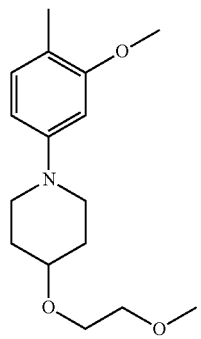 |
| 7-11 | 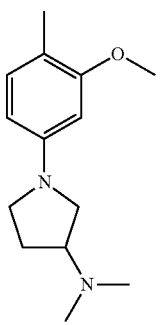 |
| 7-12 | 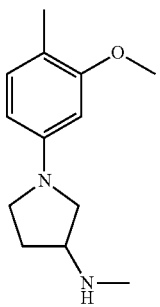 |
| Compound No. | Rx |
|---|---|
| 7-13 | 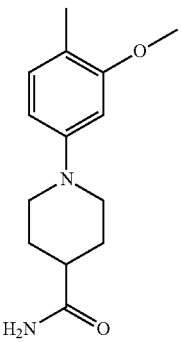 |
| 7-14 | 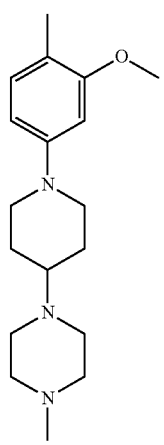 |
| 7-17 | 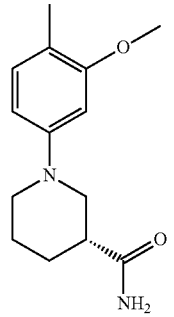 |
| 7-18 | 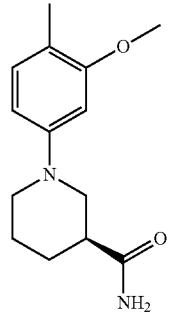 |

| Compound No. | Rx |
|---|---|
| 7-20 | 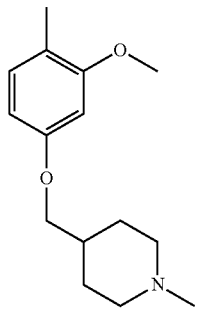 |
| 7-21 | 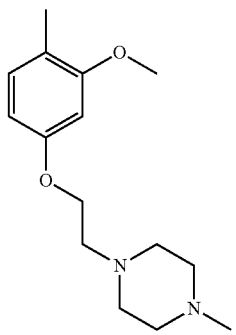 |
| 7-25 | 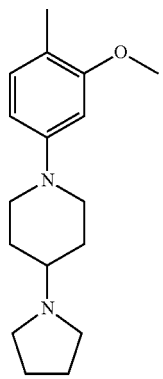 |
| 7-26 | 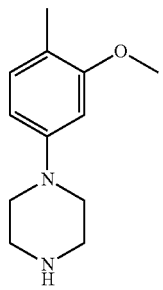 |
a compound of the formula
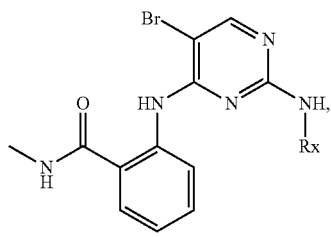
wherein Rx has one of the meanings given in the following table:
| Compound | Rx |
|---|---|
| 8-2 | 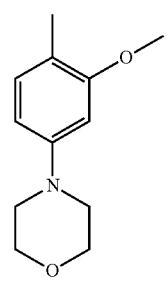 |
a compound of the formula
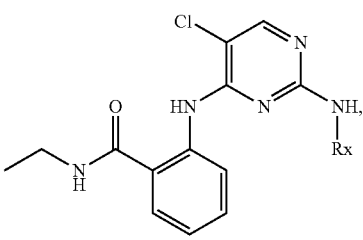
wherein Rx has one of the meanings given in the following table:
| Compound | Rx |
|---|---|
| 9-1 | 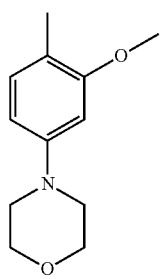 |

| Compound | Rx |
|---|---|
| 9-2 | 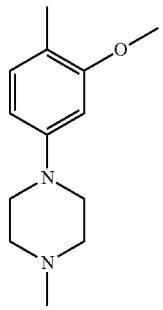 |
| 9-3 | 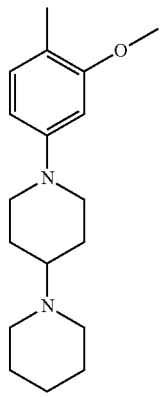 |
| 9-4 | 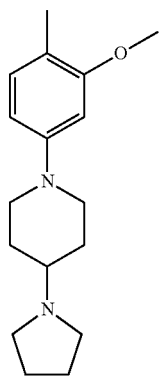 |
| 9-5 | 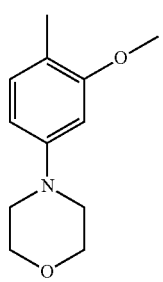 |
| Compound | Rx |
|---|---|
| 9-6 | 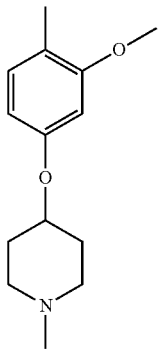 |
a compound of the formula
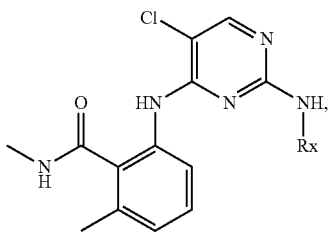
wherein Rx has one of the meanings given in the following table:
| Compound | Rx |
|---|---|
| 10-1 | 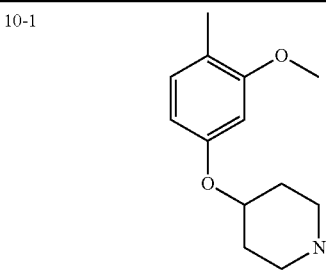 |
| 10-2 | 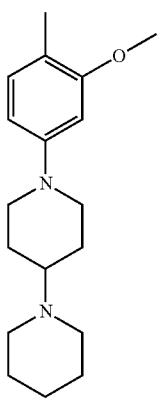 |

| Compound | Rx |
|---|---|
| 10-3 | 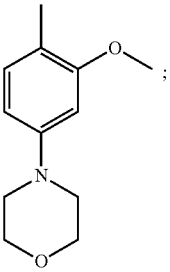 |
a compound of the formula
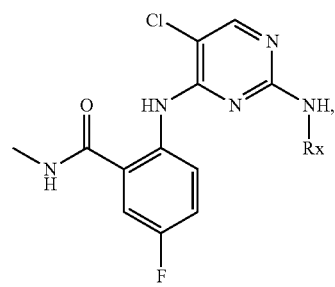
wherein Rx has one of the meanings given in the following table:
| Compound | Rx |
|---|---|
| 11-1 | 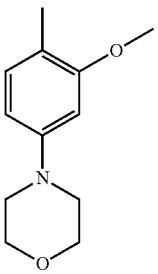 |
| 11-2 | 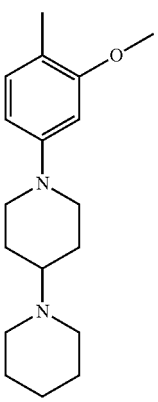 |
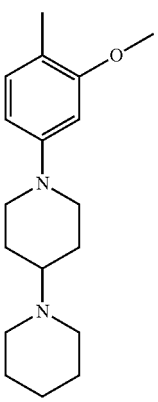
| Compound | Rx |
|---|---|
| 11-4 | 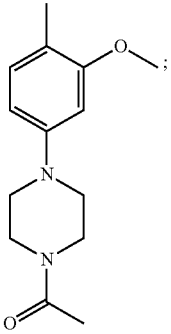 |
a compound of the formula
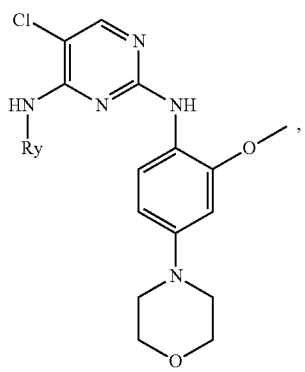
wherein Ry has one of the meanings given in the following table:
| Compound | R |
|---|---|
| 14-1 | 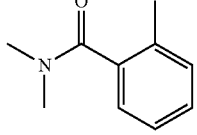 |
| 14-2 | 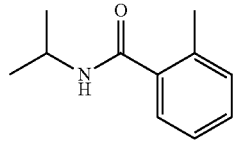 |
| 14-3 | 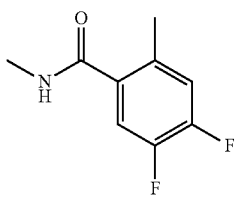 |

-continued
| Compound | R |
|---|---|
| 14-5 | 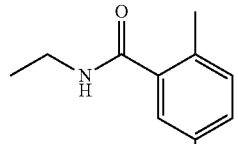 |
| 14-6 | 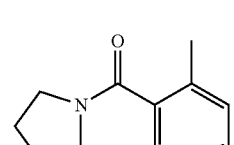 |
a compound of the formula
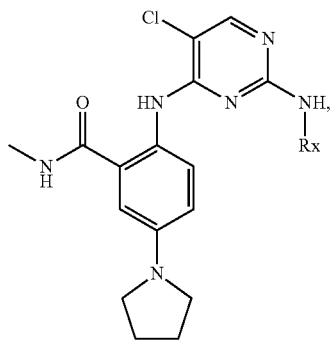
wherein Rx has one of the meanings given in the following table:
| Compound | Rx |
|---|---|
| 15-1 | 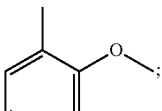 |
| 15-2 | 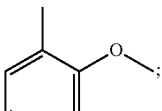 |
-continued
| Compound | Rx |
|---|---|
| 15-3 | 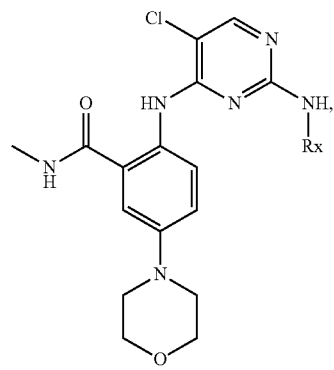 |
a compound of the formula
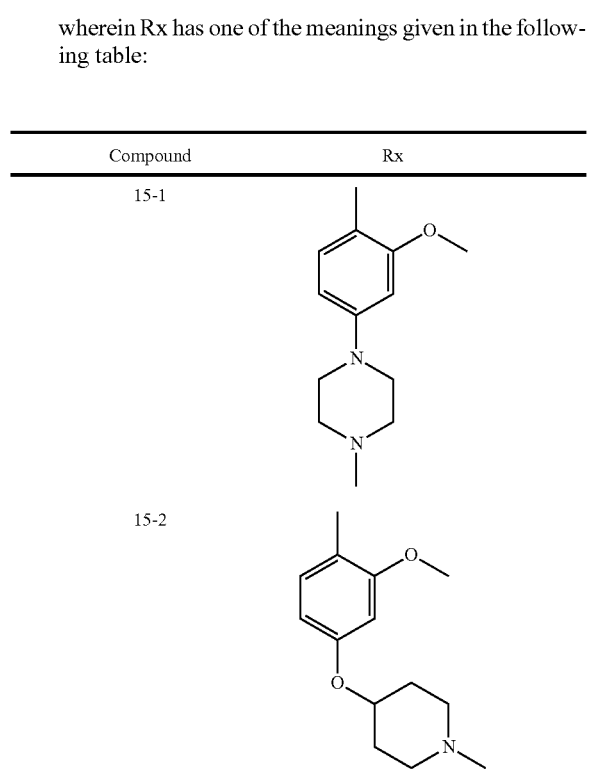
wherein Rx has one of the meanings given in the following table:
| Compound | Rx |
|---|---|
| 18-1 | 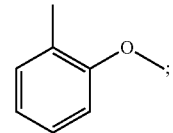 |
a compound of the formula
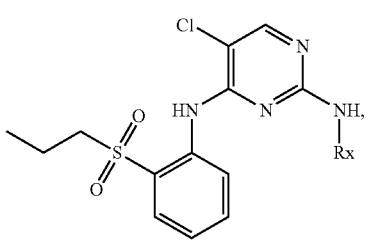

311
wherein Rx has one of the meanings given in the following table:
| Compound | Rx |
|---|---|
| 26-1 | 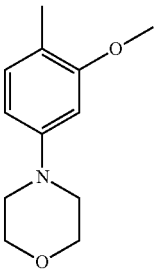 |
| 26-2 | 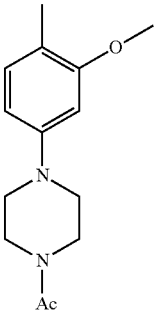 |
| 26-3 | 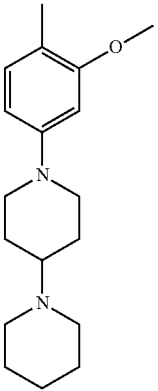 |
| 26-4 | 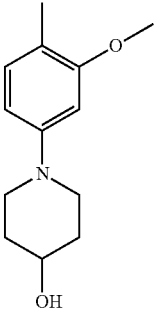 |
312
-continued
| Compound | Rx |
|---|---|
| 26-5 | 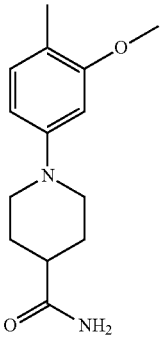 |
| 26-6 | 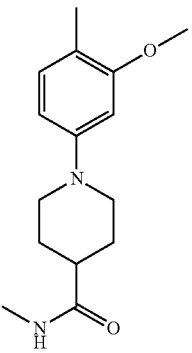 |
| 26-7 | 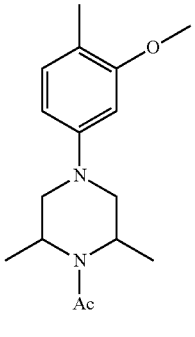 |
| 26-8 | 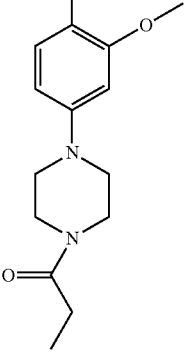 |

| Compound | Rx |
|---|---|
| 26-9 | 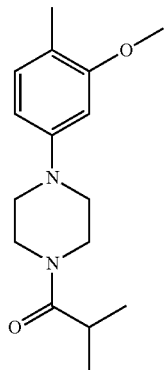 |
| 26-10 | 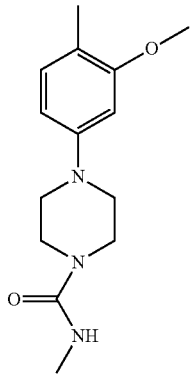 |
| 26-11 | 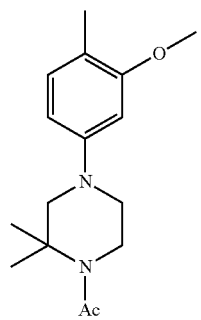 |
| 26-12 | 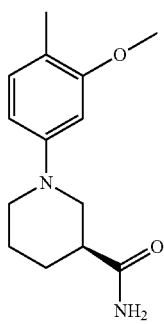 |
| Compound | Rx |
|---|---|
| 26-13 | 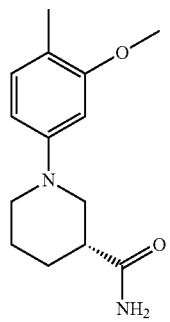 |
| 26-14 | 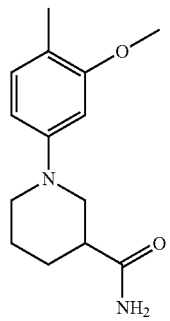 |
| 26-18 | 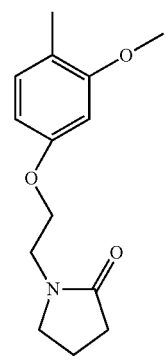 |
| 26-21 | 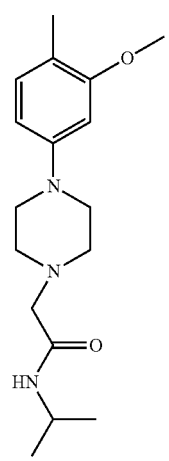 |

315
-continued
| Compound | Rx |
|---|---|
| 26-22 | 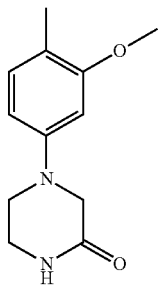 |
| 26-23 | 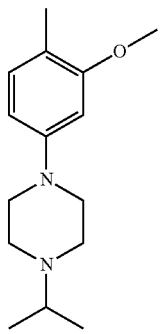 |
| 26-24 | 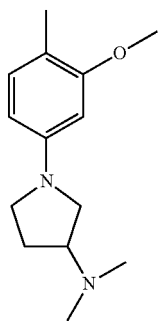 |
| 26-25 | 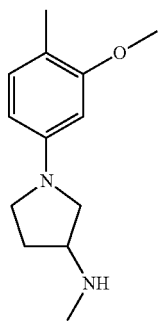 |
316
-continued
| Compound | Rx |
|---|---|
| 26-26 | 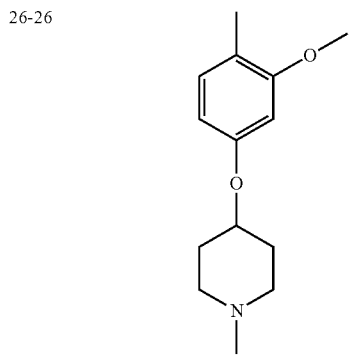 |
| 26-27 | |
| 26-28 | |
| 26-29 | | a compound of the formula
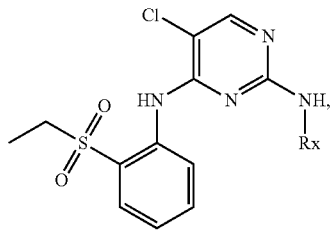
wherein Rx has one of the meanings given in the following table:
| Compound | Rx |
|---|---|
| 27-1 | 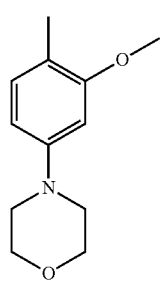 |
| 27-2 | 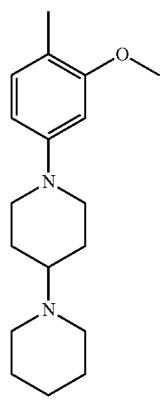 |
| 27-3 | 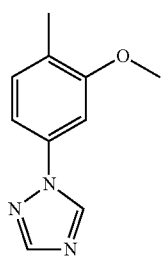 |
| 27-4 | 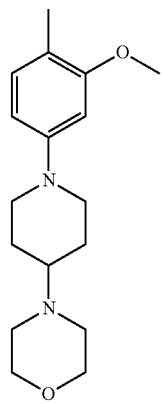 |
| 27-5 | 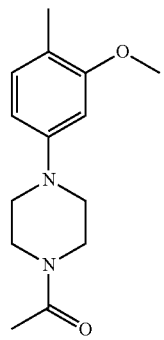 |
| 27-6 | 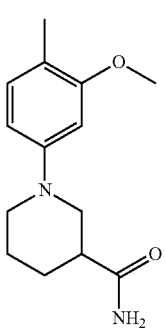 |
| 27-8 | 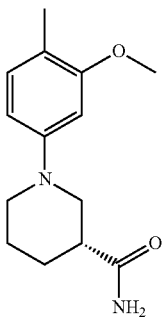 |

| Compound | Rx |
|---|---|
| 27-9 | 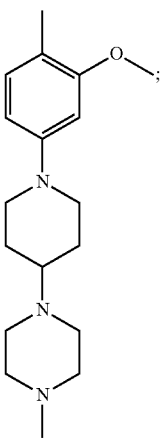 |
a compound of the formula
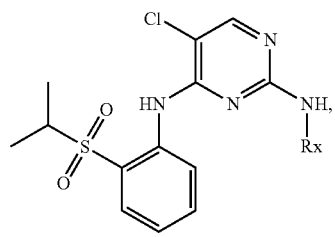
wherein Rx has one of the meanings given in the following table:
| Compound | Rx |
|---|---|
| 28-1 | 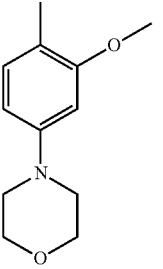 |
| 28-2 | 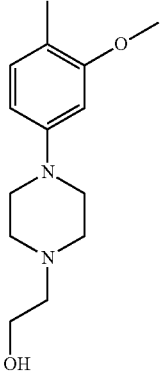 |
| 28-3 | 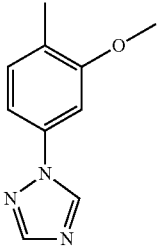 |
| 28-4 | 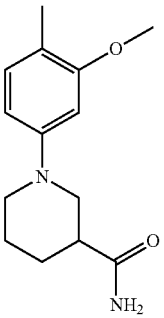 |
| 28-5 | 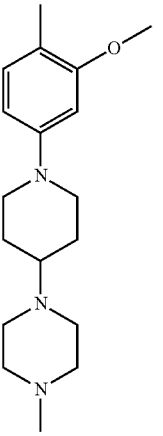 |

| Compound | Rx |
|---|---|
| 28-6 | 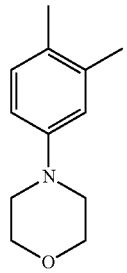 |
| 28-8 | 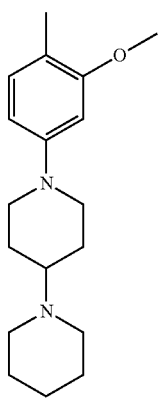 |
| 28-9 | 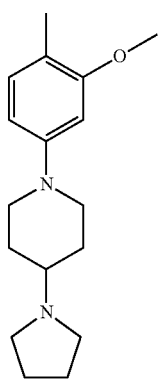 |
| 28-10 | 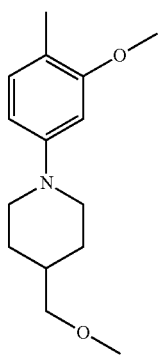 |
| Compound | Rx |
|---|---|
| 28-11 | 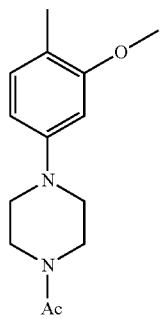 |
| 28-12 | 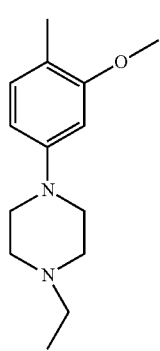 |
| 28-13 | 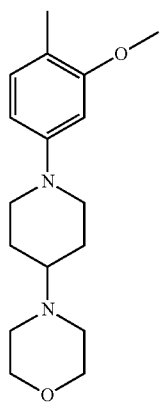 |
| 28-14 | 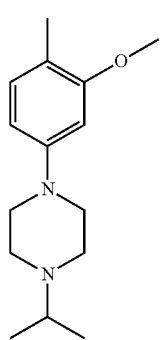 |

| Compound | Rx |
|---|---|
| 28-15 | 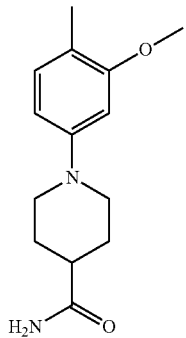 |
| 28-16 | 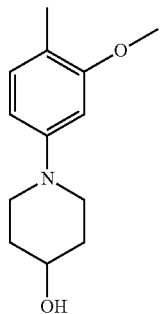 |
| 28-17 | 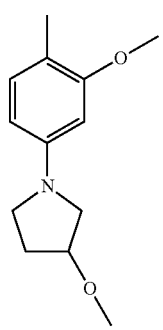 |
| 28-18 | 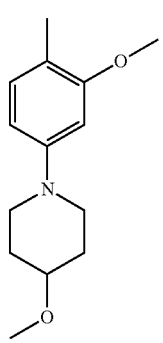 |
| Compound | Rx |
|---|---|
| 28-19 | 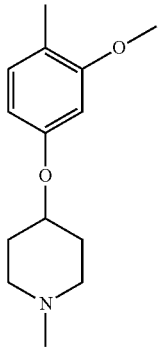 |
| 28-20 | 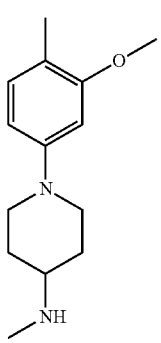 |
| 28-21 | 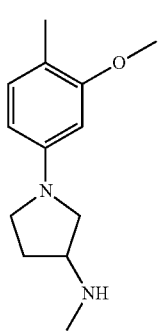 |
| 28-22 | 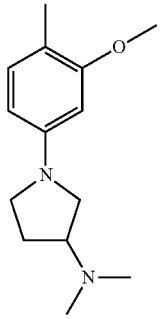 |

| Compound | Rx |
|---|---|
| 28-23 | 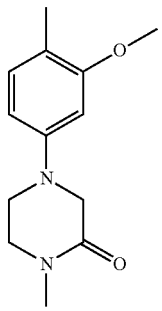 |
| 28-24 | 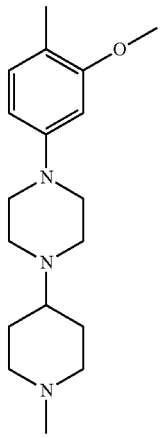 |
| 28-25 | 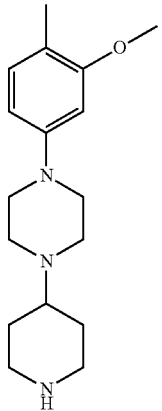 |
| 28-27 | 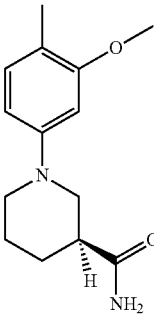 |
| Compound | Rx |
|---|---|
| 28-28 | 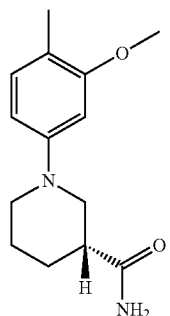 |
a compound of the formula
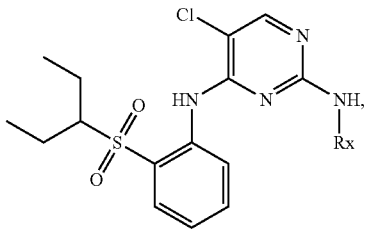
wherein Rx has one of the meanings given in the following table:
| Compound | Rx |
|---|---|
| 29-1 | 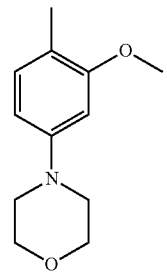 |
| 29-2 | 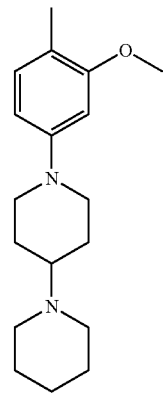 |

-continued

| Compound | Rx |
|---|---|
| 29-3 | 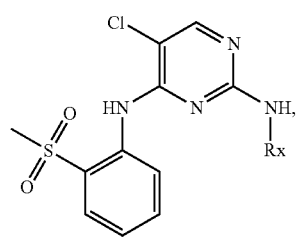 | a compound of the formula

[structure]

wherein Rx has one of the meanings given in the following table:

| Compound | Rx |
|---|---|
| 31-2 | 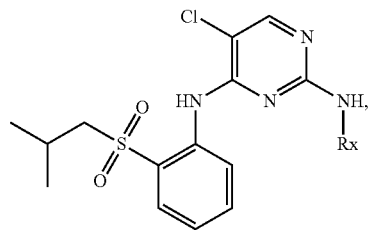 | a compound of the formula

[structure]

wherein Rx has one of the meanings given in the following table:

| Compound | Rx |
|---|---|
| 32-1 | [structure with methyl, methoxy phenyl, piperazine, Ac] |
| 32-2 | [structure with methyl, methoxy phenyl, morpholine] | a compound of the formula

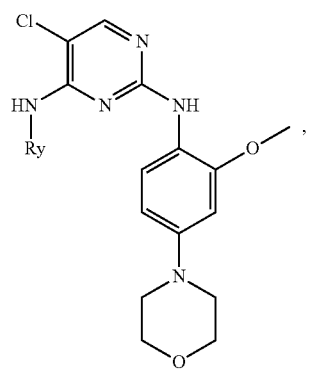

wherein Ry has one of the meanings given in the following table:

| Compound | Ry |
|---|---|
| 34-1 | [butyl sulfonyl tolyl structure] |
| 34-3 | [pentyl sulfonyl tolyl structure] |

-continued

| Compound | Ry |
|---|---|
| 34-4 | 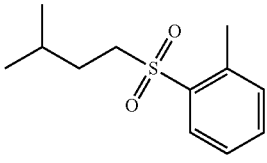 |
| 34-6 | 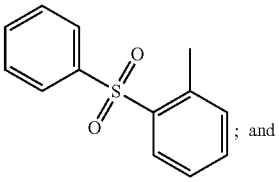; and | a compound of the formula

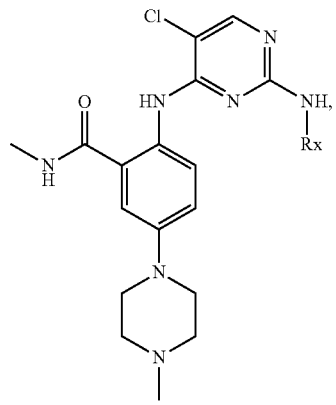

wherein Rx has one of the meanings given in the following table:

| Compound | Rx |
|---|---|
| 35-1 | 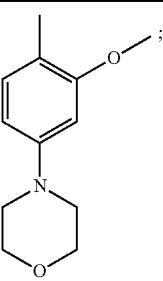; | or a pharmaceutically acceptable salt thereof.

12. The compound of claim 1, wherein said compound is 2-[5-chloro-2-(2-methoxy-4-morpholin-4-yl-phenylamino)-pyrimidin-4-ylamino]-N-methyl-benzamide, or $N^2$-(4-[1,4']Bipiperidinyl-1'-yl-2-methoxy-phenyl)-5-chloro-$N^4$-[2-(propane-1-sulfonyl)-phenyl]-pyrimidine-2,4-diamine, or a pharmaceutically acceptable salt thereof.

13. A process for the production of a compound of formula I according to claim 1, comprising reacting a compound of formula II

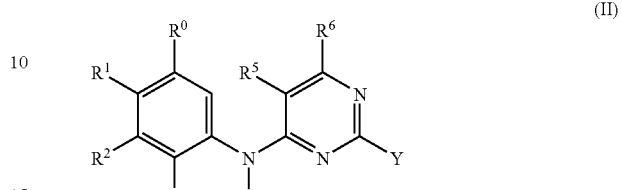

(II)

wherein $R^0$, $R^1$, $R^2$, $R^3$, $R^4$, $R^5$, and $R^6$ are as defined in claim 1, and Y is a leaving group, with a compound of formula III

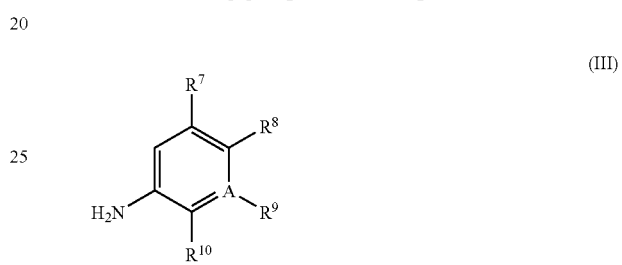

(III)

wherein A, $R^7$, $R^8$, $R^9$ and $R^{10}$ are as defined in claim 1;
and, if desired, converting a compound of formula I, wherein the substituents have the meaning as defined in claim 1, into another compound of formula I as defined in claim 1;
and recovering the resulting compound of formula I in free from or as a salt, and, when required, converting the compound of formula I obtained in free form into the desired salt, or an obtained salt into the free form.

14. A pharmaceutical composition comprising a compound according to claim 1, as active ingredient together with one or more pharmaceutically acceptable diluents or carriers.

15. A combination comprising a therapeutically effective amount of a compound according to claim 1 and one or more known drug substances, said further drug substance being useful in the treatment of neoplastic diseases or immune system disorders.

16. A method for the treatment of breast tumors in a subject in need thereof which comprises administering an effective amount of a compound according to claim 1 or a pharmaceutical composition comprising same.

17. The method of claim 16, wherein said compound is 2-[5-chloro-2-(2-methoxy-4-morpholin-4-yl-phenylamino)-pyrimidin-4-ylamino]-N-methyl-benzamide, or $N^2$-(4-[1,4']Bipiperidinyl-1'-yl-2-methoxy-phenyl)-5-chloro-$N^4$-[2-(propane-1-sulfonyl)-phenyl]-pyrimidine-2,4-diamine, or a pharmaceutically acceptable salt thereof.

* * * * *

UNITED STATES PATENT AND TRADEMARK OFFICE
CERTIFICATE OF CORRECTION

PATENT NO. : 7,964,592 B2  Page 1 of 3
APPLICATION NO. : 10/549250
DATED : June 21, 2011
INVENTOR(S) : Garcia-Echeverria et al.

It is certified that error appears in the above-identified patent and that said Letters Patent is hereby corrected as shown below:

In the Specification

In column 286, lines 36-37 following the sequence "(Biotin-SETDDYAEIID ammonium salt)", please insert --SEQ ID NO.: 1--.

In column 286, lines 44-45 following the sequence "(ATGGCAGCTGCTTACCTTGAC)", please insert --SEQ ID NO.: 2--.

In column 286, lines 45-46 following the sequence "(TCAGTGTGGTCTCGTCTGCCC)", please insert --SEQ ID NO.: 3--.

In column 288, line 4, following the sequence "(Biotin-EEGAPDYENLQELN)", please insert --SEQ ID NO.: 4--.

In columns 297 and 298, lines 1-31, please replace the SEQUENCE LISTING with the following:
--SEQUENCE LISTING <110>  NovartisAG
       Garcia-Echeverria, Carlos <120>  Pyrimidine Derivatives

<130>  PAT032910A-US-PCT

<140>  US 10/549,250
<141>  2006-05-18

<160>  4

Signed and Sealed this
Sixteenth Day of December, 2014

Michelle K. Lee
*Deputy Director of the United States Patent and Trademark Office*

Cont'd Columns 297 & 298

<170> Patentin version 3.5

<210> 1
<211> 11
<212> PRT
<213> Artificial

<220>
<223> Y397 peptide construct

<400> 1

Ser Glu Thr Asp Asp Tyr Ala Glu Ile Ile Asp
1               5                   10

<210> 2
<211> 21
<212> DNA
<213> Artificial

<220>
<223> Primer

<400> 2
atggcagctg cttaccttga c					21

<210> 3
<211> 21
<212> DNA
<213> Artificial

<220>
<223> Primer

<400> 3
tcagtgtggt ctcgtctgcc c					21

<210> 4
<211> 14
<212> PRT
<213> Artificial

CERTIFICATE OF CORRECTION (continued)
U.S. Pat. No. 7,964,592 B2

Cont'd Columns 297 & 298

<220>
<223> LAT-11 peptide construct

<400> 4

Glu Glu Gly Ala Pro Asp Tyr Glu Asn Leu Gln Glu Leu Asn--.
1               5                    10